US007045605B2

(12) United States Patent
Bander et al.

(10) Patent No.: US 7,045,605 B2
(45) Date of Patent: May 16, 2006

(54) MODIFIED ANTIBODIES TO PROSTATE-SPECIFIC MEMBRANE ANTIGEN AND USES THEREOF

(75) Inventors: Neil Bander, New York, NY (US); Francis J. Carr, Aberdeen (GB); Anita Hamilton, Aberdeen (GB)

(73) Assignee: Cornell Research Foundation, Inc., Ithaca, NY (US)

( * ) Notice: Subject to any disclaimer, the term of this patent is extended or adjusted under 35 U.S.C. 154(b) by 241 days.

(21) Appl. No.: 10/160,505

(22) Filed: May 30, 2002

(65) Prior Publication Data

US 2004/0213791 A1   Oct. 28, 2004

Related U.S. Application Data

(60) Provisional application No. 60/295,214, filed on Jun. 1, 2001, provisional application No. 60/323,585, filed on Sep. 20, 2001, provisional application No. 60/362,810, filed on Mar. 8, 2002.

(51) Int. Cl.
  *C07K 16/00* (2006.01)
  *A61K 39/395* (2006.01)
  *C12P 21/00* (2006.01)
  *C12N 15/02* (2006.01)

(52) U.S. Cl. .................. 530/388.8; 530/387.1; 530/387.3; 530/388.1; 530/391.5; 530/391.7; 424/130.1; 424/133.1; 424/141.1; 424/156.1; 424/179.1; 424/181.1; 435/70.21; 435/449

(58) Field of Classification Search ............ 424/133.1, 424/155.1, 181.1; 530/387.3, 388.8, 387.1, 530/388.1, 388.22, 388.85, 391.7, 391.9, 530/391.5; 435/70.21, 449
See application file for complete search history.

(56) References Cited

U.S. PATENT DOCUMENTS

| | | | |
|---|---|---|---|
| 4,454,106 A | 6/1984 | Gansow et al. |
| 4,472,509 A | 9/1984 | Gansow et al. |
| 4,814,275 A | 3/1989 | Durda et al. |
| 4,855,353 A | 8/1989 | Kurami et al. |
| 4,863,851 A | 9/1989 | McEwan et al. |
| 4,863,854 A | 9/1989 | Mattes et al. |
| 4,885,363 A | 12/1989 | Tweedle et al. |
| 5,013,645 A | 5/1991 | Kim |
| 5,053,503 A | 10/1991 | Dean et al. |
| 5,057,302 A | 10/1991 | Johnson et al. |
| 5,118,611 A | 6/1992 | Smith et al. |
| 5,130,118 A | 7/1992 | Johnson et al. |
| 5,162,504 A | 11/1992 | Horoszewicz |
| 5,198,208 A | 3/1993 | Berg et al. |
| 5,208,324 A | 5/1993 | Klaveness et al. |
| 5,217,704 A | 6/1993 | Johnson et al. |
| 5,227,471 A | 7/1993 | Wright, Jr. |
| 5,229,289 A | 7/1993 | Kjeldsen et al. |
| 5,314,996 A | 5/1994 | Wright, Jr. |
| 5,342,924 A | 8/1994 | Chang |
| 5,419,893 A | 5/1995 | Berg et al. |
| 5,474,756 A | 12/1995 | Tweedle et al. |
| 5,489,525 A | 2/1996 | Pastan |
| 5,530,101 A * | 6/1996 | Queen et al. |
| 5,531,978 A | 7/1996 | Berg et al. |
| 5,538,866 A | 7/1996 | Israeli et al. |
| 5,565,562 A | 10/1996 | Parker et al. |
| 5,578,484 A | 11/1996 | Horoszewicz |
| 5,599,677 A | 2/1997 | Dowell et al. |
| 5,621,001 A | 4/1997 | Canetta et al. |
| 5,639,879 A | 6/1997 | Mease et al. |
| 5,660,827 A | 8/1997 | Thorpe et al. |
| 5,674,470 A | 10/1997 | Tweedle et al. |
| 5,697,902 A | 12/1997 | Goldenberg |
| 5,763,202 A | 6/1998 | Horoszewicz |
| 5,776,427 A | 7/1998 | Thorpe et al. |
| 5,804,602 A | 9/1998 | Slusher et al. |
| 5,846,519 A | 12/1998 | Tweedle et al. |
| 5,855,866 A | 1/1999 | Thorpe et al. |
| 5,863,538 A | 1/1999 | Thorpe et al. |
| 5,877,289 A | 3/1999 | Thorpe et al. |
| 5,935,818 A | 8/1999 | Israeli et al. |
| 5,958,474 A | 9/1999 | Lee et al. |
| 5,965,132 A | 10/1999 | Thorpe et al. |
| 6,004,554 A | 12/1999 | Thorpe et al. |
| 6,004,555 A | 12/1999 | Thorpe et al. |
| 6,022,524 A | 2/2000 | Maisano et al. |
| 6,036,955 A | 3/2000 | Thorpe et al. |

(Continued)

FOREIGN PATENT DOCUMENTS

AU    733544 B2    5/2001

(Continued)

OTHER PUBLICATIONS

Fundamental Immunology 242, William E. Paul, M.D. ed., 3d ed. 1993.*

(Continued)

*Primary Examiner*—Larry R. Helms
*Assistant Examiner*—David J. Blanchard
(74) *Attorney, Agent, or Firm*—Fish & Richardson P.C.

(57) ABSTRACT

Modified antibodies, or antigen-binding fragments thereof, to the extracellular domain of human prostate specific membrane antigen (PSMA) are provided. The modified anti-PSMA antibodies, or antigen-binding fragments thereof, have been rendered less immunogenic compared to their unmodified counterparts to a given species, e.g., a human. Pharmaceutical compositions including the aforesaid antibodies, nucleic acids, recombinant expression vectors and host cells for making such antibodies and fragments are also disclosed. Methods of using the antibodies of the invention to detect human PSMA, or to ablate or kill a PSMA-expressing cell, e.g., a PSMA-expressing cancer or prostatic cell, either in vitro or in vivo, are also provided.

142 Claims, 33 Drawing Sheets

U.S. PATENT DOCUMENTS

| | | | |
|---|---|---|---|
| 6,051,230 | A | 4/2000 | Thorpe et al. |
| 6,093,399 | A | 7/2000 | Thorpe et al. |
| 6,107,090 | A | 8/2000 | Bander |
| 6,136,311 | A | 10/2000 | Bander |
| 6,143,274 | A | 11/2000 | Tweedle et al. |
| 6,150,508 | A | 11/2000 | Murphy et al. |
| 6,200,765 | B1 | 3/2001 | Murphy et al. |
| 6,261,535 | B1 | 7/2001 | Thorpe et al. |
| 6,331,175 | B1 | 12/2001 | Goldenberg |
| 6,340,701 | B1* | 1/2002 | Chari et al. |
| 6,342,219 | B1* | 1/2002 | Thorpe et al. |
| 6,649,163 | B1 | 11/2003 | Bander |
| 6,770,450 | B1 | 8/2004 | Bander |
| 6,824,780 | B1 | 11/2004 | Devaux et al. |
| 2003/0003101 | A1 | 1/2003 | Bander |
| 2003/0031673 | A1 | 2/2003 | Bander |
| 2003/0161832 | A1 | 8/2003 | Bander |

FOREIGN PATENT DOCUMENTS

| | | |
|---|---|---|
| BR | 9710487 A | 8/1999 |
| CA | 2261018 A1 | 1/1998 |
| CA | 2452288 A1 | 3/2003 |
| CN | 1244921 A | 2/2000 |
| EA | 4634 B1 | 6/2004 |
| EP | 0 208 531 B1 | 1/1987 |
| EP | 0 232 751 B1 | 8/1987 |
| EP | 0 233 619 B1 | 8/1987 |
| EP | 0 279 397 B1 | 8/1988 |
| EP | 0 292 689 B1 | 11/1988 |
| EP | 0 299 795 A1 | 1/1989 |
| EP | 0 315 188 B1 | 5/1989 |
| EP | 0 382 583 B1 | 8/1990 |
| EP | 0 392 423 A2 | 10/1990 |
| EP | 0 466 200 AW | 1/1992 |
| EP | 0 495 878 B1 | 7/1992 |
| EP | 0 594 739 B1 | 5/1994 |
| EP | 0 882 454 AZ | 12/1998 |
| JP | 2002-513378 T | 5/2002 |
| NZ | 333683 A | 9/2001 |
| NZ | 524036 A | 12/2004 |
| WO | WO 86/06384 | 11/1986 |
| WO | WO 88/02635 | 4/1988 |
| WO | WO 89/00557 | 1/1989 |
| WO | WO 89/06979 | 8/1989 |
| WO | WO 91/15466 | 10/1991 |
| WO | WO 93/17715 | 9/1993 |
| WO | WO 93/19668 | 10/1993 |
| WO | WO 94/04702 | 3/1994 |
| WO | WO 94/09820 | 5/1994 |
| WO | WO 94/26297 | 11/1994 |
| WO | WO 95/26206 | 10/1995 |
| WO | WO 95/31444 | 11/1995 |
| WO | WO 96/26272 | 8/1996 |
| WO | WO 96/39185 | 12/1996 |
| WO | WO 96/40245 | 12/1996 |
| WO | WO 97/32862 | 9/1997 |
| WO | WO 97/35616 | 10/1997 |
| WO | WO 98/03873 | 1/1998 |
| WO | WO 98/52976 | 11/1998 |
| WO | WO 99/43710 | 9/1999 |
| WO | WO 00/34317 | 6/2000 |
| WO | WO 00/50457 | 8/2000 |
| WO | WO 00/52473 | 9/2000 |
| WO | WO 00/74729 | 12/2000 |
| WO | WO 02/098897 | 12/2002 |
| WO | WO 03/024388 | 3/2003 |

OTHER PUBLICATIONS

Rudikoff et al. Proc. Natl. Acad. Sci. USA 1982 vol. 79 pp. 1979-1983.*

Hinman et al. Cancer Research 53:3336-23342, 1993.*

Li et al. Bioconjugate Chemistry 5(2):101-104, 1994.*

Liu et al. Proc. Natl. Acad. Sci. USA 93:8618-8623, 1996.*

Ghosh et al. Journal of Cellular Biochemistry, 91(3):528-539, 2004.*

Richstone et al. Proceedings of the American Society of Clinical Oncology, vol. 19, abstract 1329, May 20, 2000.*

Barren et al. (1997), "Monoclonal Antibody 7E11.C5 Staining of Viable LNCaP Cells", Prostate 30(1):65-8.

Carter et al. (1996), "Prostate-specific Membrane Antigen is a Hydrolase with Substrate and Pharmacologic Characteristics of a Neuropeptidase", Proc. Natl. Acad. Sci. U.S.A. 93:749-751.

Chang et al. (1999), "Five Different Anti-Prostate-specific Membrane Antigen (PSMA) Antibodies Confirm PSMA Expression in Tumor-associated Neovasculature", Cancer Research, 59(13):3192-3198.

Diamond et al. (1997), "Monoclonal Antibody 225 Blockade of Prostate Specific Membrane Antigen (PSM) Expression: Potential Novel Therapy for Prostate Cancer", Journal of Urology 157(4 suppl):226 (Abstract 884).

Dillman et al. (1988), "Toxicities Associated with Monoclonal Antibody Infusions in Cancer Patients", Mol. Biother. 1(2):81-85.

Dillman et al. (1994), "Human Anti-Mouse Antibody Response in Cancer Patients Following Single Low-Dose Injections of Radiolabeled Murine Monoclonal Antibodies", Cancer Biotherapy 9(1):17-28.

Fair et al. (1997), "Prostate Specific Membrane Antigen", Prostate 32(2):140-8.

Goldsmith and Bander, "Monoclonal Antibody Therapy", Nuclear Oncology: Diagnosis and Therapy. Chapter 32: Prostate Carcinoma. pp. 433-439. Lippincott Williams and Wilkins, Philadelphia, 2001.

Hamilton et al. (1998), "A novel humanized antibody against Prostate Specific Membrane Antigen (PSMA) for in vivo targeting and therapy", Proc. Amer. Assoc. Cancer Res. 39:440, Abstract #2997.

Harlow and Lane (1988), "Antibodies: A laboratory manual", Cold Spring Harbor Laboratory, p. 139-243.

Heston (1997), "Characterization and Glutamyl Preferring Carboxypeptidase Function of Prostate Specific Membrane Antigen: A Novel Folate Hydrolase", Urology 49(3A):104-112.

Holmes (2001), "PSMA specific antibodies and their diagnostic and therapeutic use", Exp. Opin. Invest. Drugs 10(3):511-19.

Horoszewicz et al. (1987), "Monoclonal Antibodies to a New Antigenic Marker in Epithelial Prostatic Cells and Serum of Prostatic Cancer Patients", Anticancer Research 7(5B):927-936.

Israeli et al. (1993), "Molecular Cloning of a Complementary DNA Encoding a Prostate-Specific Membrane Antigen", Cancer Research 53(2):227-230.

Israeli et al. (1994), "Expression of the Prostate-Specific Membrane Antigen", Cancer Research 54(7):1807-1811.

Israeli et al. (1997), "Prostate Specific Membrane Antigen and Other Prostatic Tumor Markers on the Horizon", Urological Clinics of North America 24(2):439-50.

Jain, R.K. (1990), "Vacular and interstitial barriers to delivery of therapeutic agents in tumors", Cancer and Metastasis Reviews 9(3):253-266.

Leek et al. (1995), "Prostate-Specific Membrane Antigen: Evidence for the Existence of a Second Related Human Gene", British Journal of Cancer 72:583-588.

Leung et al. (1986), "Selection of a Monoclonal Antibody to a New Prostate Cancer Marker for In Vivo Clinical Trials", 6th International Congress of Immunology, p. 516 (Abstract 4.15.19).

Liu et al. (1997), "Monoclonal Antibodies to the Extracellular Domain of Prostate-specific Membrane Antigen also React with Tumor Vascular Endothelium", Cancer Research 57(18):3629-3634.

Liu, et al. (1998), "Constitutive and Antibody-Induced Internalization of Prostate-Specific Membrane Antigen", Cancer Research 58(18):4055-4060.

Liu et al. (1998), "mAbs to the Extracellular Domain of Prostate Specific Membrane Antigen (PSMA)", 11th International Conference on Monoclonal Antibodies for Cancer, Mar. 19-21, Abstract 2.

Murphy et al. (1995), "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement", The Prostate 26:164-168.

Murphy et al. (1995), "Comparison of Prostate Specific Membrane Antigen, and Prostate Specific Antigen Levels in Prostatic Cancer Patients", Anticancer Res. 15:1473-1480.

Murphy et al. (1996), "Measurement of Prostate-Specific Membrane Antigen in the Serum With a New Antibody", The Prostate 28(4):266-271.

Pinto et al. (1996), "Prostate-Specific Membrane Antigen: A Novel Folate Hydrolase in Human Prostatic Carcinoma Cells", Clincal Cancer Research 2(9):1445-51.

Rochon et al. (1994), "Western Blot Assay for Prostate-Specific Membrane Antigen in Serum of Prostate Cancer Patients", The Prostate 25(4):219-223.

Schlom (1991), "Monoclonal antibodies: They're more and less than you think", Molecular Foundations of Oncology, ed. Broder, Williams & Wilkins, p. 95-134.

Silver et al. (1997), "Prostate-specific Membrane Antigen Expression in Normal and Malignant Human Tissues", Clinical Cancer Research 3:81-85.

Smith (2001), "Technology evaluation: C242-DM1, ImmunoGen Inc.", Current Opin. In Mol Therapeutics 3(2):198-203.

Su et al. (1995), "Alternatively Spliced Variants of Prostate-specific Membrane Antigen RNA: Ratio of Expression as a Potential Measurement of Progression", Cancer Research 55:1441-1443.

Troyer et al. (1994), "Subcellular Localization of the 7E11-C5 Prostate Specific Antigen", Proc. Am. Assoc. Cancer Research 35:283 (Abstract 1688).

Troyer et al. (1995), "Biochemical Characterization and Mapping of the 7E11-C5.3 Epitope of the Prostate-Specific Membrane Antigen", Urol Oncol 1:29-37.

Troyer et al. (1995), "Detection and Characterization of the Prostate-Specific Membrane Antigen (PSMA) in Tissue Extracts and Body Fluids", International Journal of Cancer 62(5):552-558.

Troyer et al. (1997), "Location of prostate-specific membrane antigen in the LNCaP prostate carcinoma cell line", Prostate 30(4):232-242.

Uria et al. (1997), "Prostate Specific Membrane Antigen in Breast Carcinoma", The Lancet 349(9065):1601.

Wang et al. (1988), "Monoclonal Antibody Assays for Prostatic Tumor", Immunol Ser 39:195-219.

Wright (1990), "Characterization of a New Prostate Carcinoma-Associated Marker: 7E11-C5", Antibody Immunoconjugates and RadioPharmaceuticals 3:Abstract 193.

Wright et al. (1995), "Expression of Prostate-Specific Membrane Antigen in Normal, Benign, and Malignant Prostate Tissues", Urol Oncol, 1:18-28.

Yang et al. (1998), "Alpha particle emitter therapy of micrometastases: $^{213}$Bi-J5 (anti-PSMA) treatment of LNCaP spheroids", Proceedings of the American Association for Cancer Research 39:440 (Abstract #2996).

Bander, Oral Presentation: "mAb anti-PSMAext Therapy of Prostate Cancer", Oct. 1999.

Bander, CaPCURE Board Presentation: "Antibody Treatment of Prostate Cancer", Nov. 1999.

Bander, CaPCURE Board Presentation: "Monolconal Antibody Therapy of Prostate Cancer", 2001.

Bander, AACR Meeting Presentation: "mAb Therapy of Prostate Cancer Targeting PSMAext", Apr. 9, 2002.

Bander, ASCO Meeting Presentation: "Phase I Radioimmunotherapy Trials of mAb J591 to the Extracellular Domain of Prostate Specific Membrane Antigen (PSMAext) Radiolabeled with 90Y or 177Lu in Advanced Prostate Cancer", May 18-21, 2002.

Chang et al., "Prostate-Specific Membrane Antigen: Much More Than a Prostate Cancer Marker", Molecular Urology 3(3):313-321 (1999).

Chang et al., "The clinical role of prostate-specific membrane antigen (PSMA)", Urologic Oncology 7:7-12 (2002).

Chang et al., "Prostate-specific Membrane Antigen Is Produced in Tumor-associated Neovasculature", Clinical Cancer Research 674(5):2674-2681 (1999).

Chang et al., "Comparison of anti-prostate-specific membrane antigen antibodies and other immunomarkers in metastatic prostate carcinoma", Urology 57 (6):1179-1183 (2001).

Fracasso et al., "Anti-tumor Effects of Toxins Targeted to the Prostate Specific Membrane Antigen", The Prostate 53:9-23 (2002).

Gong et al., "Prostate-specific membrane antigen (PSMA)-specific monoclonal antibodies in the treatment of prostate and other cancers", Cancer and Metastasis Reviews 18:483-490 (1999).

Gong et al., "Overview of Evolving Strategies Incorporating Prostate-Specific Membrane Antigen as Target for Therapy", Molecular Urology 4(3):217-223 (2000).

Grauer et al., "Identification, Purification, and Subcellular Localization of Prostate-specific Membrane Antigen PSM' Protein in the LNCaP Prostatis Carcinoma Cell Line", Cancer Rearch 58:4787-4789 (1998).

Smith-Jones et al., "In Vitro Characterization of Radiolabeled Monoclonal Antibodies Specific for the Extracellular Domain of Prostrate-specific Membrane Antigen", Cancer Research 60:5237-5243 (2000).

Sokoloff et al., "A Dual-Monoclonal Sandwich Assay for Prostate-specific Membrane Antigen: Levels in Tissues, Seminal Fluid and Urine", The Prostate 43:150-157 (2000).

Wang et al., "Identification of Prostate Specific Membrane Antigen (PSMA) as the Target of Monoclonal Antibody 107-1A4 by Proteinchip®; Array, Surface-enhanced Laser Desorption/ionization (SELDI) Technology", Int. J. Cancer 92:871-876 (2001).

Consent Form for Clinical Investigation by the New York Hospital-Cornell Medical Center.

Bander et al., "Phase I clinical trial targeting a monoclonal antibody (mAb) to the extracellular domain of prostate specific membrane antigen (PSMAext) in hormone-independent patients", J. Urol. vol. 163, No. 4 Suppl., p. 160, 2000.

Goldsmith et al., "Evaluation of Anti-PSMA Antibody, . . ." J. of Nuclear Med. 41(5):80P, 2000 (Abstract).

Murphy et al., "Current Evaluation of the Tissue Localization and . . ."Cancer 83(11):2259-2269, 1998.

Smith-Jones et al., "Monoclonal Antibodies (MAB) Specific to Extracellular . . . " J. of Nuclear Med. 40(5):226P, 1999 (Abstract).

Smith-Jones et al., "Preclinical Studies with $^{131}$I and $^{111}$In labeled Monoclonal Antibodies . . . " J of Labeled Compounds and Radiopharm. 42(1):S701-S703, 1999.

Proceedings of American Society of Clinical Oncology vol. 20, May 12-15, 2001, San Francisco, CA.

US 6,290,956, 09/2001, Bander (withdrawn)

* cited by examiner

Amino Acid Sequence of Murine J591 Heavy Chain (CDRs are marked, numbering as Kabat)

```
EVQLQQSGPELKKPGTSVRISCKTS | GYTFTEYTIH | WVKQSHGKS
1         10        20            30            40
                                   CDR1

LEWIG | NINPNNGGTTYNQKFED | KATLTVDKSSSTAYMELRSLTS
        50          60          70          80
              CDR2

EDSAVYYCAA | GWNFDY | WGQGTTLTVSS
       90       100         110
              CDR3
```

FIG. 1A

Amino Acid Sequence of Murine J591 Light Chain (CDRs are marked, numbering as Kabat)

```
DIVMTQSHKFMSTSVGDRVSIIC | KASQDVGTAVD | WYQQKPGQSP
1         10        20            30            40
                                 CDR1

KLLIY | WASTRHT | GVPDRFTGSGSGTDFTLTITNVQSEDLADYFC
        50          60          70          80
           CDR2

| QQYNSYPLT | FGAGTMLDLK
   90              100
    CDR3
```

FIG. 1B

Amino Acid Sequence of DeImmunised J591 Heavy Chain (CDRs are marked, numbering as Kabat)

```
EVQLVQSGPEVKKPGATVKISCKTS | GYTFTEYTIH | WVKQAPGKG
1         10        20          30           40
                                CDR1

LEWIG | NINPNNGGTTYNQKFED | KATLTVDKSTDTAYMELSSLRS
    50              60          70          80
           CDR2

EDTAVYYCAA | GWNFDY | WGQGTLLTVSS
     90        100         110
            CDR3
```

FIG. 2A

Amino Acid Sequence of DeImmunised J591 Light Chain (CDRs are marked, numbering as Kabat)

```
DIQMTQSPSSLSTSVGDRVTLTC | KASQDVGTAVD | WYQQKPGPSP
1         10        20          30           40
                                CDR1

KLLIY | WASTRHT | GIPSRFSGSGSGTDFTLTISSLQPEDFADYYC
    50        60           70          80
        CDR2

| QQYNSYPLT | FGPGTKVDIK
   90            100
     CDR3              FIG. 2B
```

Location of T cell epitopes in J591 VH

```
        1                   10                   20
    1   E V Q L Q Q S G P E L V K P G T S V R I S C K T S    J591 MoVH
    1   E V Q L V Q S G P E V K K P G A T V K I S C K T S    J591 DIVH
                        30                   40                   50
   26   G Y T F T E Y T I H W V K Q S H G K S L E W I G N    J591 MoVH
   26   G Y T F T E Y T I H W V K Q A P G K G L E W I G N    J591 DIVH
                        60                   70
   51   I N P N N G G T T Y N Q K F E D K A T L T V D K S    J591 MoVH
   51   I N P N N G G T T Y N Q K F E D K A T L T V D K S    J591 DIVH
                        80                   90                  100
   76   S S T A Y M E L R S L T S E D S A V Y Y C A A G W    J591 MoVH
   76   T D T A Y M E L S S L R S E D T A V Y Y C A A G W    J591 DIVH
                       110
  101   N F D Y W G Q G T T L T V S S                        J591 MoVH
  101   N F D Y W G Q G T L L T V S S                        J591 DIVH
```

FIG. 3A

Location of T cell epitopes in J591 VK

```
1   D I V M T Q S H K F M S T S V G D R V S I I C K A    J591 MoVK
1   D I Q M T Q S P S S L S T S V G D R V T L T C K A    J591 DIVK
              10                  20

26  S Q D V G T A V D W Y Q Q K P G Q S P K L L I Y W    J591 MoVK
26  S Q D V G T A V D W Y Q Q K P G P S P K L L I Y W    J591 DIVK
          30                  40                  50

51  A S T R H T G V P D R E T G S G S G T D F T L T I    J591 MoVK
51  A S T R H T G I P S R F S G S G S G T D F T L T I    J591 DIVK
          60                  70

76  T N V Q S E D L A D Y F C Q Q Y N S Y P L T F G A    J591 MoVK
76  S S L Q P E D F A D Y Y C Q Q Y N S Y P L T F G P    J591 DIVK
          80                  90                  100

101 G T M L D L K                                         J591 MoVK
101 G T K V D I K                                         J591 DIVK
```

FIG. 3B

GCAGTGGATCTGGGACAGACTTCACTCTCACCATTTCTAGTCTTCAGCCTGAAGACTTTGCAGATTATTACTGTCAGCAATATAACAGCT
        |         |         |         |         |         |         |         |         | 540
CGTCACCTAGACCCTGTCTGAAGTGAGAGTGGTAAAGATCAGAAGTCGGACTTCTGAAACGTCTAATAATGACAGTCGTTATATTGTCGA

G  S  G  S  G  T  D  F  T  L  T  I  S  S  L  Q  P  E  D  F  A  D  Y  Y  C  Q  Q  Y  N  S
                                              └──VK                              └──CDR3

BamHI
ATCCTCCTTCAGGTTCGTTCCTGGACCAAGGTGGACATCAAACGTGAGTAGATTTAAACTTTGTCTCCTCAGTTGGATCC
        |         |         |         |         |         |         |         | 620
TAGGAGGAAGTCCAAGCAGGACCTGGTTCCACCTGTAGTTTGCACTCATCTAAATTTGAAACAGAGGAGTCAACCTAGG

Y  P  L  T  F  G  P  G  T  K  V  D  I  K
                └──VK
└──CDR3

FIG. 4B-3

|    | N | I | V | M | T | Q | F | P | K | S | M | S | A | S | A | G | E | R | M | T | L | T | C | K | A | S | E | Majority |
|----|---|---|---|---|---|---|---|---|---|---|---|---|---|---|---|---|---|---|---|---|---|---|---|---|---|---|---|----------|
| 1  | N | I | V | M | T | Q | F | P | K | S | M | S | I | S | V | G | E | R | V | T | L | T | C | K | A | S | E | J415VK   |
| 1  | N | I | V | M | T | Q | S | P | K | S | M | S | A | S | A | G | E | R | M | T | L | T | C | K | A | S | E | J415DIVK1 |
| 1  | N | I | V | M | T | Q | S | P | K | S | M | S | A | S | A | G | E | R | M | T | L | T | C | K | A | S | E | J415DIVK2 |
| 1  | N | I | V | M | T | Q | S | P | K | S | M | S | A | S | A | G | E | R | M | T | L | T | C | K | A | S | E | J415DIVK3 |
| 1  | N | I | V | M | T | Q | S | P | K | S | M | S | A | S | A | G | E | R | M | T | L | T | C | K | A | S | E | J415DIVK4 |
| 1  | N | I | V | M | T | Q | F | P | K | S | M | S | A | S | A | G | E | R | M | T | L | T | C | K | A | S | E | J415DIVK5 |
| 1  | N | I | V | M | T | Q | F | P | K | S | M | S | A | S | A | G | E | R | M | T | L | T | C | K | A | S | E | J415DIVK6 |
| 1  | N | I | V | M | T | Q | F | P | K | S | M | S | A | S | A | G | E | R | V | T | L | T | C | K | A | S | E | J415DIVK7 |
| 1  | N | I | V | M | T | Q | F | P | K | S | M | S | A | S | A | G | E | R | M | T | L | T | C | K | A | S | E | J415DIVK8 |

|    | N | V | G | T | Y | V | S | W | Y | Q | Q | K | P | T | Q | S | P | K | M | L | I | Y | G | A | S | N | R | Majority |
|----|---|---|---|---|---|---|---|---|---|---|---|---|---|---|---|---|---|---|---|---|---|---|---|---|---|---|---|----------|
| 28 | N | V | G | T | Y | V | S | W | Y | Q | Q | K | P | E | Q | S | P | K | M | L | I | Y | G | A | S | N | R | J415VK   |
| 28 | N | S | G | T | Y | V | S | W | Y | Q | Q | K | P | T | Q | S | P | K | M | L | I | Y | G | A | S | N | R | J415DIVK1 |
| 28 | N | V | G | T | Y | V | S | W | Y | Q | Q | K | P | T | Q | S | P | K | M | L | I | Y | G | A | S | N | R | J415DIVK2 |
| 28 | N | V | G | T | Y | V | S | W | Y | Q | Q | K | P | T | Q | S | P | K | M | L | I | Y | G | A | S | N | R | J415DIVK3 |
| 28 | N | V | G | T | Y | V | S | W | Y | Q | Q | K | P | T | Q | S | P | K | M | L | I | Y | G | A | S | N | R | J415DIVK4 |
| 28 | N | V | G | T | Y | V | S | W | Y | Q | Q | K | P | T | Q | S | P | K | M | L | I | Y | G | A | S | N | R | J415DIVK5 |
| 28 | N | V | G | T | Y | V | S | W | Y | Q | Q | K | P | E | Q | S | P | K | M | L | I | Y | G | A | S | N | R | J415DIVK6 |
| 28 | N | V | G | T | Y | V | S | W | Y | Q | Q | K | P | T | Q | S | P | K | M | L | I | Y | G | A | S | N | R | J415DIVK7 |
| 29 | N | S | G | T | Y | V | S | W | Y | Q | Q | K | P | E | Q | S | P | K | M | L | I | Y | G | A | S | N | R | J415DIVK8 |

|    | F | T | G | V | P | D | R | F | S | G | S | G | S | G | T | D | F | I | L | T | I | S | S | V | Q | A | E | Majority |
|----|---|---|---|---|---|---|---|---|---|---|---|---|---|---|---|---|---|---|---|---|---|---|---|---|---|---|---|----------|
| 55 | F | T | G | V | P | D | R | F | T | G | S | G | S | A | T | D | F | I | L | T | I | S | S | V | Q | T | E | J415VK   |
| 55 | F | T | G | V | P | D | R | F | S | G | S | G | S | G | T | D | F | I | L | T | A | S | S | V | Q | A | E | J415DIVK1 |
| 55 | F | T | G | V | P | D | R | F | S | G | S | G | S | G | T | D | F | I | L | T | A | S | S | V | Q | A | E | J415DIVK2 |
| 55 | F | T | G | V | P | D | R | F | S | G | S | G | S | G | T | D | F | I | L | T | A | S | S | V | Q | A | E | J415DIVK3 |
| 55 | F | T | G | V | P | D | R | F | S | G | S | G | S | G | T | D | F | I | L | T | I | S | S | V | Q | A | E | J415DIVK4 |
| 55 | F | T | G | V | P | D | R | F | S | G | S | G | S | G | T | D | F | I | L | T | I | S | S | V | Q | A | E | J415DIVK5 |
| 55 | F | T | G | V | P | D | R | F | S | G | S | G | S | G | T | D | F | I | L | T | I | S | S | V | Q | A | E | J415DIVK6 |
| 55 | F | T | G | V | P | D | R | F | S | G | S | G | S | G | T | D | F | I | L | T | I | S | S | V | Q | A | E | J415DIVK7 |
| 55 | F | T | G | V | P | D | R | F | S | G | S | G | S | G | T | D | F | I | L | T | I | S | S | V | Q | A | E | J415DIVK8 |

|    | D | L | V | D | Y | Y | C | G | Q | S | Y | T | F | P | Y | T | F | G | G | G | T | K | L | E | M | K | Majority |
|----|---|---|---|---|---|---|---|---|---|---|---|---|---|---|---|---|---|---|---|---|---|---|---|---|---|---|----------|
| 82 | D | L | V | D | Y | Y | C | G | Q | S | Y | T | F | P | Y | T | F | G | G | G | T | K | L | E | M | K | J415VK   |
| 82 | D | P | V | D | Y | Y | C | G | Q | S | Y | T | F | P | Y | T | F | G | G | G | T | K | L | E | M | K | J415DIVK1 |
| 82 | D | P | V | D | Y | Y | C | G | Q | S | Y | T | F | P | Y | T | F | G | G | G | T | K | L | E | M | K | J415DIVK2 |
| 82 | D | L | V | D | Y | Y | C | G | Q | S | Y | T | F | P | Y | T | F | G | G | G | T | K | L | E | M | K | J415DIVK3 |
| 82 | D | L | V | D | Y | Y | C | G | Q | S | Y | T | F | P | Y | T | F | G | G | G | T | K | L | E | M | K | J415DIVK4 |
| 82 | D | L | V | D | Y | Y | C | G | Q | S | Y | T | F | P | Y | T | F | G | G | G | T | K | L | E | M | K | J415DIVK5 |
| 82 | D | L | V | D | Y | Y | C | G | Q | S | Y | T | F | P | Y | T | F | G | G | G | T | K | L | E | M | K | J415DIVK6 |
| 82 | D | L | V | D | Y | Y | C | G | Q | S | Y | T | F | P | Y | T | F | G | G | G | T | K | L | E | M | K | J415DIVK7 |
| 82 | D | L | V | D | Y | Y | C | G | Q | S | Y | T | F | P | Y | T | F | G | G | G | T | K | L | E | M | K | J415DIVK8 |

```
                HindIII                                              BamHI
                   |                                                   |
GAAGTGAAGCTTGAGGAGTCTGGAGGAGGCTTGGTGCAACCTGGAGGATCCATGAAACTC      60
CTTCACTTCGAACTCCTCAGACCTCCTCCGAACCACGTTGGACCTCCTAGGTACTTTGAG E   V   K   L   E   E   S   G   G   G   L   V   Q   P   G   G   S   M   K   L
TCCTGTGTTGCCTCTGGATTCACTTTCAGTAATTACTGGATGAACTGGGTCCGCCAGTCT     120
AGGACACAACGGAGACCTAAGTGAAAGTCATTAATGACCTACTTGACCCAGGCGGTCAGA ┌─── CDR 1 ────▷
  S   C   V   A   S   G   F   T   F   S   N   Y   W   M   N   W   V   R   Q   S
CCAGAGAAGGGGCTTGAGTGGGTTGCTGAAATTAGATCGCAATCTAATAATTTTGCAACA     180
GGTCTCTTCCCCGAACTCACCCAACGACTTTAATCTAGCGTTAGATTATTAAAACGTTGT ┌──────── CDR 2 ────────
  P   E   K   G   L   E   W   V   A   E   I   R   S   Q   S   N   N   F   A   T
CATTATGCGGAGTCTGTGAAAGGGAGGGTCATCATCTCAAGAGATGATTCCAAGAGTAGT     240
GTAATACGCCTCAGACACTTTCCCTCCCAGTAGTAGAGTTCTCTACTAAGGTTCTCATCA ─────── CDR 2 ────▷
  H   Y   A   E   S   V   K   G   R   V   I   I   S   R   D   D   S   K   S   S
GTCTACCTGCAAATGAACAACTTGAGAGCTGAAGACACTGGCATTTATTACTGTACCAGG    300
CAGATGGACGTTTACTTGTTGAACTCTCGACTTCTGTGACCGTAAATAATGACATGGTCC V   Y   L   Q   M   N   N   L   R   A   E   D   T   G   I   Y   Y   C   T   R
CGATGGAATAATTTCTGGGGCCAAGGCACCACTCTCACAGTCTCCTCA                 348
GCTACCTTATTAAAGACCCCGGTTCCGTGGTGAGAGTGTCAGAGGAGT ┌─── CDR 3 ───▷
  R   W   N   N   F   W   G   Q   G   T   T   L   T   V   S   S
```

FIG. 7B

```
      E V K L E E S G G G L V Q P G G S M K L S C V A S G F T F S    Majority
      ├─────────┼───────────────────┼───────────────────┼──────┤
                10                  20                  30
  1   E V K L E E S G G G L V Q P G G S M K L S C V A S G F T F S    J415vh
  1   E V K L E E S G G G L V Q P G G S M K L S C V A S G F T F S    MUVHIIIO N Y W M N W V R Q S P E K G L E W V A E I R L Q S D N F A T    Majority
      ├─────────┼───────────────────┼───────────────────┼──────┤
                40                  50                  60
 31   N Y W M N W V R Q S P E K G L E W V A E I R S Q S N N F A T    J415vh
 31   N Y W M N W V R Q S P E K G L E W V A E I R L K S D N Y A T    MUVHIIIO H Y A E S V K G R V I I S R D D S K S S V Y L Q M N N L R A    Majority
      ├─────────┼───────────────────┼───────────────────┼──────┤
                70                  80                  90
 61   H Y A E S V K G R V I I S R D D S K S S V Y L Q M N N L R A    J415vh
 61   H Y A E S V K G R F T I S R D D S K S S V Y L Q M N N L R A    MUVHIIIO E D T G I Y Y C T T G G Y G G R R S W N A F W G Q G T L V T    Majority
      ├─────────┼───────────────────┼───────────────────┼──────┤
                100                 110                 120
 91   E D T G I Y Y C T - - - - - - - R R W N N F W G Q G T T L T    J415vh
 91   E D T G I Y Y C T T G G Y G G R R S W F A Y W G Q G T L V T    MUVHIIIO V S S                                                           Majority 114   V S S                                                           J415vh
121   V S S                                                           MUVHIIIO
```

```
                                                                BstEII
                                                                |
AACATTGTAATGACCCAATTTCCCAAATCCATGTCCATTTCAGTAGGAGAGAGGGTCACC
++++++++++++++++++++++++++++++++++++++++++++++++++++++++++++  60
TTGTAACATTACTGGGTTAAAGGGTTTAGGTACAGGTAAAGTCATCCTCTCTCCCAGTGG

N  I  V  M  T  Q  F  P  K  S  M  S  I  S  V  G  E  R  V  T
++++++++++++++++++++++++++++++++++++++++++++++++++++++++++++
TTGACCTGCAAGGCCAGTGAGAATGTGGGTACTTATGTGTCCTGGTATCAACAGAAACCA
++++++++++++++++++++++++++++++++++++++++++++++++++++++++++++  120
AACTGGACGTTCCGGTCACTCTTACACCCATGAATACACAGGACCATAGTTGTCTTTGGT

|――――― CDR 1 ―――――>
  L  T  C  K  A  S  E  N  V  G  T  Y  V  S  W  Y  Q  Q  K  P
++++++++++++++++++++++++++++++++++++++++++++++++++++++++++++
                                                              PvuI
                                                              |
GAACAGTCTCCTAAGATGTTGATATACGGGGCATCCAACCGGTTCACTGGGGTCCCCGAT
++++++++++++++++++++++++++++++++++++++++++++++++++++++++++++  180
CTTGTCAGAGGATTCTACAACTATATGCCCCGTAGGTTGGCCAAGTGACCCCAGGGGCTA

|――――― CDR 2 ―――>
  E  Q  S  P  K  M  L  I  Y  G  A  S  N  R  F  T  G  V  P  D
++++++++++++++++++++++++++++++++++++++++++++++++++++++++++++
CGCTTCACAGGCAGTGGATCTGCAACAGATTTCATTCTGACCATCAGCAGTGTGCAGACT
++++++++++++++++++++++++++++++++++++++++++++++++++++++++++++  240
GCGAAGTGTCCGTCACCTAGACGTTGTCTAAAGTAAGACTGGTAGTCGTCACACGTCTGA

R  F  T  G  S  G  S  A  T  D  F  I  L  T  I  S  S  V  Q  T
++++++++++++++++++++++++++++++++++++++++++++++++++++++++++++
GAAGACCTTGTAGATTATTACTGTGGACAGAGTTACACCTTTCCGTACACGTTCGGAGGG
++++++++++++++++++++++++++++++++++++++++++++++++++++++++++++  300
CTTCTGGAACATCTAATAATGACACCTGTCTCAATGTGGAAAGGCATGTGCAAGCCTCCC

|――――― CDR 3 ―――――>
  E  D  L  V  D  Y  Y  C  G  Q  S  Y  T  F  P  Y  T  F  G  G
++++++++++++++++++++++++++++++++++++++++++++++++++++++++++++
GGGACCAAGCTGGAAATGAAG
+++++++++++++++++++++  321
CCCTGGTTCGACCTTTACTTC

G  T  K  L  E  M  K                          FIG. 8B
++++++++++++++++++++++
```

```
               PvuII  PstI
                 |     |
       GAGGTCCAGCTGCAGCAGTCTGGACCTGAGCTGGTTAAGCCTGGGGCTTCAGTGAAGATG
       ++++++++++|++++++++++|++++++++++|++++++++++|++++++++++|++++++++++|   60
       CTCCAGGTCGACGTCGTCAGACCTGGACTCGACCAATTCGGACCCCGAAGTCACTTCTAC

E   V   Q   L   Q   Q   S   G   P   E   L   V   K   P   G   A   S   V   K   M

TCCTGCAAGGCTTCTGGATACACATTCACTGGCTATGTTATGCACTGGGTGAAGCAGAAG
       ++++++++++|++++++++++|++++++++++|++++++++++|++++++++++|++++++++++|  120
       AGGACGTTCCGAAGACCTATGTGTAAGTGACCGATACAATACGTGACCCACTTCGTCTTC
```

```
                                    ┌─────── CDR 1 ───────▶
         S   C   K   A   S   G   Y   T   F   T   G   Y   V   M   H   W   V   K   Q   K

CCTGGACAGGTCCTTGAGTGGATTGGATATATTAATCCTTACAATGATGTTACTAGGTAT
       ++++++++++|++++++++++|++++++++++|++++++++++|++++++++++|++++++++++|  180
       GGACCTGTCCAGGAACTCACCTAACCTATATAATTAGGAATGTTACTACAATGATCCATA
```

```
                                               ┌──────── CDR 2
         P   G   Q   V   L   E   W   I   G   Y   I   N   P   Y   N   D   V   T   R   Y

AATGGGAAGTTCAAAGGCAAGGCCACACTGACCTCAGACAAATATTCCAGCACAGCCTAC
       ++++++++++|++++++++++|++++++++++|++++++++++|++++++++++|++++++++++|  240
       TTACCCTTCAAGTTTCCGTTCCGGTGTGACTGGAGTCTGTTTATAAGGTCGTGTCGGATG
```

```
       ◀──── CDR 2 ────┐
         N   G   K   F   K   G   K   A   T   L   T   S   D   K   Y   S   S   T   A   Y

SacI
                |
       ATGGAGCTCAGCGGCCTGACCTCTGAGGACTCTGCGGTCTATTACTGTGCAAGAGGGGAG
       ++++++++++|++++++++++|++++++++++|++++++++++|++++++++++|++++++++++|  300
       TACCTCGAGTCGCCGGACTGGAGACTCCTGAGACGCCAGATAATGACACGTTCTCCCCTC
```

```
                                                              ┌─── CDR
         M   E   L   S   G   L   T   S   E   D   S   A   V   Y   Y   C   A   R   G   E

AACTGGTACTACTTTGACTCCTGGGGCCGAGGCGCCACTCTCACAGTCTCCTCA
       ++++++++++|++++++++++|++++++++++|++++++++++|++++++++++|+++++++    354
       TTGACCATGATGAAACTGAGGACCCCGGCTCCGCGGTGAGAGTGTCAGAGGAGT
```

```
       ┌──── CDR 3 ────▶
         N   W   Y   Y   F   D   S   W   G   R   G   A   T   L   T   V   S   S
                                                                              FIG. 9A
```

```
     EVQLQQSGPELVKPGASVKISCKASGYTFT      Majori
                     |                      |
                    10          20          30
     EVQLQQSGPELVKPGASVKMSCKASGYTFT      j533vh
  1  EVQLQQSGPELVKPGASVK I SCKASGYTFT    Muvhii
  1

GYVMNNWVKQSPGQVLEWIGDINPGNGGTS      Majori
                     |                      |
                    40          50          60
     GYVMH - WVKQKPGQVLEWIGYINPYNDVTR      j533vh
 31  DY Y M N N WVKQ  S PG K S LEWIG D INP G N GG T S   Muvhii
 31

YNGKFKGKATLTVDKSSSTAYMELSGLTSE      Majori
                     |                      |
                    70          80          90
     YNGKFKGKATLTSDKYSSTAYMELSGLTSE      j533vh
 60  YN Q KFKGKATLT V DKS S SSTAYM Q L S LTSE    Muvhii
 61

DSAVYYCARGENSSSYMAYYAFDSWGQGAT      Majori
                     |                      |
                   100         110         120
     DSAVYYCARGEN - - - W YYFDSWGRGAT      j533vh
 90  DSAVYYCARG Y YS S SYMA Y Y A  FD Y WG Q GTT    Muvhii
 91

VTVSS                              Majori

114  LTVSS                              j533vh
121   V TVSS                             Muvhii
```

FIG. 9B

```
 1 DIVLTQSPASLAVSLGQRATISCRASESVD  Majori
21 DIVLTQSPASLAVSLGQRATISCRASESID  j533vk
 1 DIVLTQSPASLAVSLGQRATISCRASES[V]D Muvk3

SYGNSFMHWYQQKPGQPPNLLIFAASSILES  Majori
51 SYDNTFMHWYQQKPGQPPNLLIFRASILES  j533vk
31 SY[G]N[S]FMHWYQQKPGQPP[K]LLI[YA]AS[N]LES Muvk3

GVPARFSGSGSGTDFTLTIHPVEADDAATY  Majori
81 GIPARFSGSGSGTDFTLTIYPVEADDVATY  j533vk
61 G[V]PARFSGSGSGTDFTL[N]I[H]PVE[DD][A]ATY Muvk3

YCQQSIEDPP-YTFGGGTKLEIK  Majori
111 YCHQSIEDPP-YTFGGGTKLEIK  j533vk
 91 YC[Q]QS[N]EDP[PW]TFGGGTKLEIK  Muvk3
```

FIG. 10B

```
CAGGTGCAGCTAAAGGAGTCAGGACCTGGCCTGGTGGCGTCCTCACAGAGCCTGTCCATC
                                                                    60
GTCCACGTCGATTTCCTCAGTCCTGGACCGGACCACCGCAGGAGTGTCTCGGACAGGTAG

Q  V  Q  L  K  E  S  G  P  G  L  V  A  S  S  Q  S  L  S  I

ACATGCACCGTCTCAGGATTCTCATTAACCGCCTATGGTATTAACTGGGTTCGCCAGCCT
                                                                    120
TGTACGTGGCAGAGTCCTAAGAGTAATTGGCGGATACCATAATTGACCCAAGCGGTCGGA

┌─── CDR 1 ───▶
 T  C  T  V  S  G  F  S  L  T  A  Y  G  I  N  W  V  R  Q  P

CCAGGAAAGGGTCTGGAGTGGCTGGGAGTGATATGGCCTGATGGAAACACAGACTATAAT
                                                                    180
GGTCCTTTCCCAGACCTCACCGACCCTCACTATACCGGACTACCTTTGTGTCTGATATTA

┌──── CDR 2 ────┐
 P  G  K  G  L  E  W  L  G  V  I  W  P  D  G  N  T  D  Y  N

TCAACTCTCAAATCCAGACTGAACATCTTCAAGGACAACTCCAAGAACCAAGTTTTCTTA
                                                                    240
AGTTGAGAGTTTAGGTCTGACTTGTAGAAGTTCCTGTTGAGGTTCTTGGTTCAAAAGAAT

┌─── CDR 2 ───▶
 S  T  L  K  S  R  L  N  I  F  K  D  N  S  K  N  Q  V  F  L

AAAATGAGCAGTTTCCAAACTGATGACACAGCCAGATACTTCTGTGCCAGAGATTCGTAT
                                                                    300
TTTTACTCGTCAAAGGTTTGACTACTGTGTCGGTCTATGAAGACACGGTCTCTAAGCATA

┌─── CDR 3 ───
 K  M  S  S  F  Q  T  D  D  T  A  R  Y  F  C  A  R  D  S  Y

GGTAACTTCAAGAGGGGTTGGTTTGACTTCTGGGGCCAGGGCACCACTCTCACAGTCTCC
                                                                    360
CCATTGAAGTTCTCCCCAACCAAACTGAAGACCCCGGTCCCGTGGTGAGAGTGTCAGAGG

───────────── CDR 3 ─────────────▶
 G  N  F  K  R  G  W  F  D  F  W  G  Q  G  T  T  L  T  V  S

TCA
─── 363
AGT
```

FIG. 11A

```
  QVQLKESGPGLVASSQSLSITCTVSGFSLT           Majori
                    |                  |
                   10                  20                  30
  1 QVQLKESGPGLVASSQSLSITCTVSGFSLT           E99vh
  1 QVQLKESGPGLVA[P]SQSLSITCTVSGFSLT          Muvhib

AYGVNVSWV

```
                                                                    BstEII
                                                                    |
AACATTGTGATGACCCAGTCTCAAAAATTCATGTCCACATCACCAGGAGACAGGGTCAGG
++++-+----+----+----+----+----+----+----+----+----+----+----+   60
TTGTAACACTACTGGGTCAGAGTTTTTAAGTACAGGTGTAGTGGTCCTCTGTCCCAGTCC

N   I   V   M   T   Q   S   Q   K   F   M   S   T   S   P   G   D   R   V   R
++++-+----+----+----+----+----+----+----+----+----+----+----+
GTCACCTGCAAGGCCAGTCAGAATGTGGGTTCTGATGTAGCCTGGTATCAAGCGAAACCA
++++-+----+----+----+----+----+----+----+----+----+----+----+   120
CAGTGGACGTTCCGGTCAGTCTTACACCCAAGACTACATCGGACCATAGTTCGCTTTGGT
```

┌──────────── CDR 1 ────────────▶
  V   T   C   K   A   S   Q   N   V   G   S   D   V   A   W   Y   Q   A   K   P

```
++++-+----+----+----+----+----+----+----+----+----+----+----+
GGACAATCTCCTAGAATACTGATTTACTCGACATCCTACCGTTACAGTGGGGTCCCTGAT
++++-+----+----+----+----+----+----+----+----+----+----+----+   180
CCTGTTAGAGGATCTTATGACTAAATGAGCTGTAGGATGGCAATGTCACCCCAGGGACTA
```

┌──────── CDR 2 ────────▶
  G   Q   S   P   R   I   L   I   Y   S   T   S   Y   R   Y   S   G   V   P   D

```
++++-+----+----+----+----+----+----+----+----+----+----+----+
CGCTTCACAGCCTATGGATCTGGGACAGATTTCACTCTCACCATTACCAATGTGCAGTCT
++++-+----+----+----+----+----+----+----+----+----+----+----+   240
GCGAAGTGTCGGATACCTAGACCCTGTCTAAAGTGAGAGTGGTAATGGTTACACGTCAGA
```

R   F   T   A   Y   G   S   G   T   D   F   T   L   T   I   T   N   V   Q   S
```
++++-+----+----+----+----+----+----+----+----+----+----+----+
GAAGACTTGACAGAGTATTTCTGTCAGCAATATAATAGCTATCCTCTCACGTTCGGTGCT
++++-+----+----+----+----+----+----+----+----+----+----+----+   300
CTTCTGAACTGTCTCATAAAGACAGTCGTTATATTATCGATAGGAGAGTGCAAGCCACGA
```

┌──────── CDR 3 ────────▶
  E   D   L   T   E   Y   F   C   Q   Q   Y   N   S   Y   P   L   T   F   G   A

```
GGGACCAAGCTGGAGCTGAAA
++++-+----+----+----+  321
CCCTGGTTCGACCTCGACTTT
```

```
         D I V M T Q S Q S S L A V S A G D K V T V S C K A S Q S L L   Majori
                         10                  20                  30
    1   N I V M T Q S Q K F M S T S P G D R V R V T C K A S Q - - -   e99VK
    1   D I V M T Q S Q P S S L A V S A G E K V T M S C K S S Q S L L Muvkl N V G S D K N Y V A W Y Q A K P G Q S P K L L I Y S A S T R   Majori
                         40                  50                  60
   28   N V G S D - - - V A W Y Q A K P G Q S P R I L I Y S T S Y R   e99VK
   31   N S G N Q K N Y L A W Y Q Q K P G Q S P K L L I Y W A S T R   Muvkl E S G V P D R F T G S G S G T D F T L T I S S V Q A E D L A   Majori
                         70                  80                  90
   55   Y S G V P D R F T A Y G S G T D F T L T I T N V Q S E D L T   e99VK
   61   E S G V P D R F T G S G S G T D F T L T I S S V Q A E D L A   Muvkl V Y F C Q N D N S Y P L T F G A G T K L E L K R A           Majori
                        100                 110
   85   E Y F C Q Q Y N S Y P L T F G A G T K L E L K               e99VK
   91   V Y Y C Q N D Y S Y P L T F G A G T K L E L K               Muvkl

FIG. 12B
```

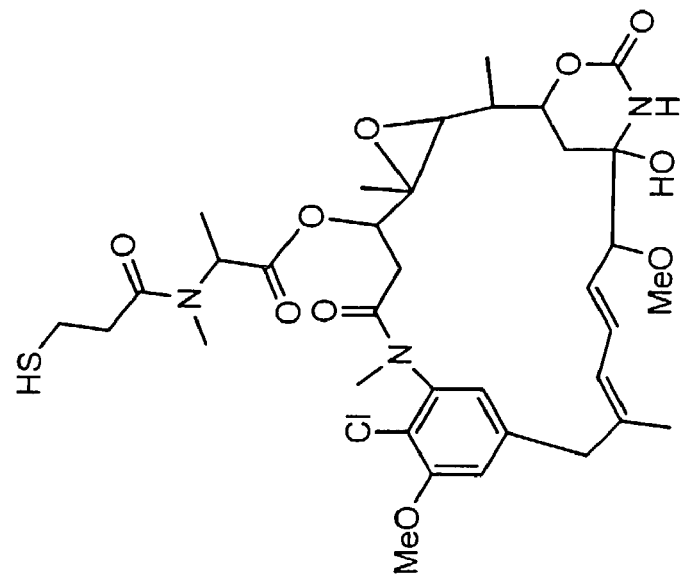
C$_{35}$H$_{48}$ClN$_3$O$_{10}$S
Exact Mass: 737.27
Mol. Wt.: 738.29
DM1
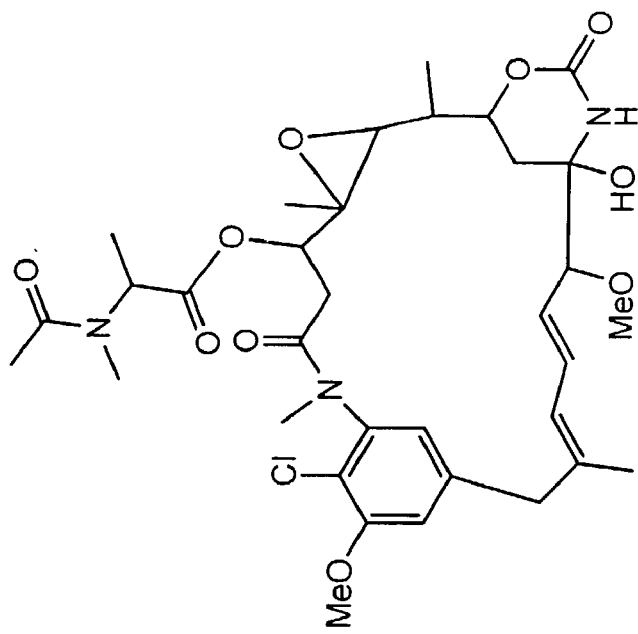
C$_{34}$H$_{46}$ClN$_3$O$_{10}$
Exact Mass: 691.29
Mol. Wt.: 692.20
Maytansine
FIG. 15

MODIFIED ANTIBODIES TO PROSTATE-SPECIFIC MEMBRANE ANTIGEN AND USES THEREOF

RELATED APPLICATIONS

This application claims priority to U.S. provisional application No. 60/295,214 filed on Jun. 1, 2001, 60/323,585 filed on Sep. 20, 2001, and 60/362,810 filed on Mar. 8, 2002, the contents of all of which are incorporated herein by reference.

This invention was made with government support under Department of Defense Grant number DAMD17-98-1-8594. The government has certain rights in the invention.

FIELD OF THE INVENTION

The present invention relates to antibodies, e.g., modified, e.g., deimmunized, antibodies, to the extracellular domain of human prostate specific membrane antigen (PSMA) and their uses in treating, preventing, and diagnosing prostatic disorders and cancers.

BACKGROUND OF THE INVENTION

Prostate cancer is one of the most common causes of cancer deaths in American males. In 1999, approximately 185,000 new cases were diagnosed and 37,500 died of this disease (NCI SEER data). It accounts for about 40% of all cancers diagnosed in men. A male born in the U.S. in 1990 has approximately a 1 in 8 likelihood of being diagnosed with clinically apparent prostate cancer in his lifetime. Even prior to the recent increase in incidence, prostate cancer was the most prevalent cancer in men (Feldman, A. R. et al. (1986) *NEJM* 315:1394–7).

There is currently very limited treatment for prostate cancer once it has metastasized (spread beyond the prostate). Currently, systemic therapy is limited to various forms of androgen (male hormone) deprivation. While most patients will demonstrate initial clinical improvement, virtually inevitably, androgen-independent cells develop. Endocrine therapy is thus palliative, not curative. In a study of 1387 patients with metastatic disease detectable by imaging (e.g., bone or CT scan), the median time to objective disease progression (excluding biochemical/PSA progression) after initiation of hormonal therapy (i.e., development of androgen-independence) was 16–48 months (Eisenberger M. A., et al. (1998) *NEJM* 339:1036–42). Median overall survival in these patients was 28–52 months from the onset of hormonal treatment (Eisenberger M. A., et al. (1998) supra.). Subsequent to developing androgen-independence, there is no effective standard therapy and the median duration of survival is 9–12 months (Vollmer, R. T., et al. (1999) *Clin Can Res* 5: 831–7; Hudes G., et al., (1997) *Proc Am Soc Clin Oncol* 16:316a (abstract); Pienta K. J., et al. (1994) *J Clin Oncol* 12(10):2005–12; Pienta K. J., et al. (1997) *Urology* 50:401–7; Tannock I. F., et al., (1996) *J Clin Oncol* 14:1756–65; Kantoff P. W., et al., (1996) *J. Clin. Oncol.* 15 (Suppl):25:110–25). Cytotoxic chemotherapy is poorly tolerated in this age group and generally considered ineffective and/or impractical. In addition, prostate cancer is relatively resistant to cytotoxic agents. Thus, chemotherapeutic regimen has not demonstrated a significant survival benefit in this patient group.

For men with a life expectancy of less than 10 years, watchful waiting is appropriate where low-grade, low-stage prostate cancer is discovered at the time of a partial prostatectomy for benign hyperplasia (W. J. Catalona, (1994) *New Engl. J. Med.*, 331(15):996–1004). Such cancers rarely progress during the first five years after detection. On the other hand, for younger men, curative treatment is often more appropriate.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. However, the use of prostate-specific antigen testing has permitted early detection of prostate cancer. As a result, surgery is less extensive with fewer complications. Patients with bulky, high-grade tumors are less likely to be successfully treated by radical prostatectomy.

After surgery, if there are detectable serum prostate-specific antigen concentrations, persistent cancer is indicated. In many cases, prostate-specific antigen concentrations can be reduced by radiation treatment. However, this concentration often increases again within two years.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When either LHRH agonists, such as leuprolide, buserelin, or goserelin, or gonadotropin-releasing hormone antagonists, such as Abarelix, are administered testosterone concentrations are ultimately reduced. Flutamide and other nonsteroidal, anti-androgen agents block binding of testosterone to its intracellular receptors. As a result, it blocks the effect of testosterone, increasing serum testosterone concentrations and allows patients to remain potent a significant problem after radical prostatectomy and radiation treatments.

In view of the shortcoming of existing therapies, there exists a need for improved modalities for preventing and treating cancers, such as prostate cancer.

SUMMARY OF THE INVENTION

This invention provides, inter alia, antibodies and particularly, modified antibodies, or antigen-binding fragments thereof, that bind to the extracellular domain of human prostate specific membrane antigen (PSMA). The modified anti-PSMA antibodies, or antigen-binding fragments thereof, have been rendered less immunogenic compared to their unmodified counterparts to a given species, e.g., a human. The modified anti-PSMA antibodies, or fragments thereof, bind to human PSMA with high affinity and specificity, and thus can be used as diagnostic, prophylactic, or therapeutic agents in vivo and in vitro. Accordingly, the invention provides antibodies and particularly modified anti-PSMA antibodies, antibody fragments, and pharmaceutical compositions thereof, as well as nucleic acids, recombinant expression vectors and host cells for making such antibodies and fragments. Methods of using the antibodies of the invention to detect PSMA, or to ablate or kill a PSMA-expressing cell, e.g., a PSMA-expressing cancer, a prostatic, or a vascular cell, either in vitro or in vivo, are also encompassed by the invention. Preferably, the modified antibodies are those having one or more complementarity determining regions (CDRs) from a J591, J415, J533 or E99 antibody. As discussed herein, the modified antibodies can be CDR-grafted, humanized, deimmunized, or, more generally, antibodies having the CDRs from a non-human antibody, e.g., murine J591, J415, J533 or E99 antibody, and a framework that is selected as less immunogenic in humans, e.g., less antigenic than the murine frameworks in which a murine CDR naturally occurs.

The antibodies, e.g., modified antibodies of the invention interact with, e.g., bind to, PSMA, preferably human PSMA, with high affinity and specificity. For example, the antibody binds to human PSMA with an affinity constant of at least $10^7$ $M^{-1}$, preferably between $10^8$ $M^{-1}$ and $10^{10}$ $M^{-1}$, or about $10^9$ $M^{-1}$. Preferably, the antibody interacts with, e.g., binds to, the extracellular domain of PSMA, and most preferably, the extracellular domain of human PSMA (e.g., amino acids 44–750 of human PSMA).

In some embodiments, the anti-PSMA antibody binds all or part of an epitope bound by an antibody described herein, e.g., a J591, E99, J415, and J533 antibody. The anti-PSMA antibody can inhibit, e.g., competitively inhibit, the binding of an antibody described herein, e.g., a J591, E99, J415, and J533 antibody, to human PSMA. An anti-PSMA antibody may bind to an epitope, e.g., a conformational or a linear epitope, which epitope when bound prevents binding of an antibody described herein, e.g., a J591, E99, J415, and J533 antibody. The epitope can be in close proximity spatially or functionally-associated, e.g., an overlapping or adjacent epitope in linear sequence or conformational space, to the one recognized by the J591, E99, J415, or J533 antibody.

In some embodiments, the anti-PSMA antibody binds to an epitope located wholly or partially within the region of about amino acids 120 to 500, preferably 130 to 450, more preferably, 134 to 437, or 153 to 347, of human PSMA. Preferably, the epitope includes at least one glycosylation site, e.g., at least one N-linked glycosylation site (e.g., the asparagine residue located at about amino acids 190–200, preferably at about amino acid 195, of human PSMA).

Human PSMA is expressed on the surface of normal, benign hyperplastic, and cancerous prostate epithelial cells, as well as vascular endothelial cells proximate to cancerous cells, e.g., renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct), melanoma (e.g., malignant melanoma), or soft tissue sarcoma cancerous cells. The expression of human PSMA is substantially lower on non-malignant prostate cells where PSM', a splice variant that lacks a portion of the N-terminal domain that includes the transmembrane domain, is more abundant. Due to the absence of the N-terminal region containing the transmembrane domain, PSM' is primarily cytoplasmic and is not located on the cell membrane. The antibodies, e.g., the modified antibodies, of the invention bind to the cell surface of cells that express PSMA. PSMA is normally recycled from the cell membrane into the cell. Thus, the antibodies of the invention are internalized with PSMA through the process of PSMA recirculation, thereby permitting delivery of an agent conjugated to the antibody, e.g., a labeling agent, a cytotoxic agent, or a viral particle (e.g., a vital particle containing genes that encode cytotoxic agents, e.g., apoptosis-promoting factors). Accordingly, antibodies, e.g., modified antibodies, described herein, can be used to target living normal, benign hyperplastic, and cancerous prostate epithelial cells as well as vascular endothelial cells proximate to cancerous cells.

An antibody, e.g., a modified antibody, is preferably monospecific, e.g., a monoclonal antibody, or an antigen-binding fragment thereof. The antibodies, e.g., the modified antibodies, can be full-length (e.g., an IgG (e.g., an IgG1, IgG2, IgG3, IgG4), IgM, IgA (e.g., IgA1, IgA2), IgD, and IgE, but preferably an IgG) or can include only an antigen-binding fragment (e.g., a Fab, F(ab')$_2$ or scFv fragment, or one or more CDRs). An antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. A preferred anti-PSMA antibody includes a heavy and light chain constant region substantially from a human antibody, e.g., a human IgG1 constant region, a portion thereof, or a consensus sequence.

In a preferred embodiment, the antibodies (or fragments thereof) are recombinant or modified anti-PSMA antibodies chosen from, e.g., a chimeric, a humanized, a deimmunized, or an in vitro generated antibody. In other embodiments, the anti-PSMA antibodies are human antibodies. In one embodiment, a modified antibody of the invention is a deimmunized anti-PSMA antibody, e.g., a deimmunized form of E99, J415, J533 or J591 (e.g., a deimmunized form of an antibody produced by a hybridoma cell line having an ATCC Accession Number HB-12101, HB-12109, HB-12127, and HB-12126, respectively). Preferably, a modified antibody is a deimmunized form of J591 or J415 (referred to herein as "deJ591" or "deJ415", respectively). Most preferably, the antibody is a deimmunized form of J591.

Any combination of anti-PSMA antibodies is within the scope of the invention, e.g., two or more antibodies that bind to different regions of PSMA, e.g., antibodies that bind to two different epitopes on the extracellular domain of PSMA.

In some embodiments, the anti-PSMA antibody, e.g., the modified anti-PSMA antibody or antigen-binding fragment thereof, includes at least one light or heavy chain immunoglobulin (or preferably, at least one light chain immunoglobulin and at least one heavy chain immunoglobulin). Preferably, each immunoglobulin includes a light or a heavy chain variable region having at least one, two and, preferably, three CDRs substantially identical to a CDR from a non-human anti-PSMA light or heavy chain variable region, respectively. For example, the antibody or antigen-binding fragment thereof can have at least one, two and preferably three CDRs from: the heavy chain variable region of murine J591 (see SEQ ID NO:1, 2, and 3, depicted in FIG. 1A); the light chain variable region of murine J591 (see SEQ ID NO:4, 5, and 6, depicted in FIG. 1B); the heavy chain variable region of murine J415 (see SEQ ID NO:29, 30, and 31, depicted in FIG. 5); the light chain variable region of murine J415 (see SEQ ID NO:32, 33, and 34, depicted in FIG. 6); the heavy chain variable region of murine J533 (see SEQ ID NO:93, 94, and 95, depicted in FIG. 9A); the light chain variable region of murine J533 (see SEQ ID NO:96, 97, and 98, depicted in FIG. 10A); the heavy chain variable region of murine E99 (see SEQ ID NO:99, 100, and 101, depicted in FIG. 11A); or the light chain variable region of murine E99 (see SEQ ID NO:102, 103, and 104, depicted in FIG. 12A). In other embodiments, the modified antibody or antigen-binding fragment thereof can have at least one, two, and preferably three CDRs from the light or heavy chain variable region of the antibody produced by the cell line having ATCC Accession Number HB-12126 or the deimmunized J591 antibody produced by the cell line having ATCC Accession Number PTA-3709. In other embodiments, the modified antibody or antigen-binding fragment thereof can have at least one, two and preferably three CDRs from the light or heavy chain variable region of the antibody produced by the cell line having ATCC Accession Number HB-12109 or the deimmunized J415 antibody produced by a cell line having ATCC Accession Number PTA-4174. In still other embodiments, the modified antibody or antigen-binding fragment thereof can have at least one, two and preferably three CDRs from the light or heavy chain variable region of the antibody produced by the cell line having ATCC Accession Number HB-12127 or the antibody produced by a cell line having ATCC Accession Number HB-12101.

In one preferred embodiment, the modified antibody or antigen-binding fragment thereof includes all six CDRs from the same non-human anti-PSMA antibody, e.g., a murine J591, J415, J533 or E99 antibody. In some embodiments, the CDRs have the amino acid sequences of SEQ ID NO:1, 2, 3, 4, 5 and 6 (corresponding to murine J591 heavy and light chain CDRs), the amino acid sequences of the CDRs of the antibody produced by the cell line having ATCC Accesion number HB-12126, or the deimmunized J591 antibody produced by the cell line having ATCC Accession Number PTA-3709, or sequences substantially identical thereto. In other embodiments, the CDRs have the amino acid sequences of SEQ ID NO:29, 30, 31, 32, 33, and 34 (corresponding to murine J415 heavy and light chain CDRs), the amino acid sequences of the CDRs of the antibody produced by the cell line having ATCC Accession Number HB-12109, or the deimmunized J415 antibody produced by the cell line having ATCC Accession Number PTA-4174, or sequences substantially identical thereto. In other embodiments, the CDRs have the amino acid sequences of SEQ ID NO:93, 94, 95, 96, 97, and 98 (corresponding to murine J533 heavy and light chain CDRs), the amino acid sequences of the CDRs of the antibody produced by the cell line having ATCC Accession Number HB-12127, or sequences substantially identical thereto. In still other embodiments, the CDRs have the amino acid sequences of SEQ ID NO:99, 100, 101, 102, 103, and 104 (corresponding to murine E99 heavy and light chain CDRs), the amino acid sequences of the CDRs of the antibody produced by the cell line having ATCC Accession Number HB-12101, or sequences substantially identical thereto.

The amino acid sequence of the CDRs for antibodies J591, J415, J533 and E99 are provided below in Table 1.

TABLE 1

CDR Sequences

| NAME | Organism | FIG. | SEQ ID NO: | SEQUENCE |
|---|---|---|---|---|
| $V_H$CDR1 J591 | Mus musculus | FIG. 1A | 1 | GYTFTEYTIH |
| $V_H$CDR2 J591 | Mus musculus | FIG. 1A | 2 | NINPNNGGTTYNQKFED |
| $V_H$CDR3 J591 | Mus musculus | FIG. 1A | 3 | GWNFDY |
| $V_L$CDR1 J591 | Mus musculus | FIG. 1B | 4 | KASQDVGTAVD |
| $V_L$CDR2 J591 | Mus musculus | FIG. 1B | 5 | WASTRHT |
| $V_L$CDR3 J591 | Mus musculus | FIG. 1B | 6 | QQYNSYPLT |
| $V_H$CDR1 J415 | Mus musculus | FIG. 5 | 29 | GFTFSNYWMN |
| $V_H$CDR2 J415 | Mus musculus | FIG. 5 | 30 | EIRSQSNNFATHYAESVKG |
| $V_H$CDR3 J415 | Mus musculus | FIG. 5 | 31 | RWNNF |
| $V_L$CDR1 J415 | Mus musculus | FIG. 6 | 32 | KASENVGTYVS |
| $V_L$CDR2 J415 | Mus musculus | FIG. 6 | 33 | GASNRFT |
| $V_L$CDR3 J415 | Mus musculus | FIG. 6 | 34 | GQSYTFPYT |
| $V_H$CDR1 J533 | Mus musculus | FIG. 9A | 93 | GYTFTGYVMH |
| $V_H$CDR2 J533 | Mus musculus | FIG. 9A | 94 | YINPYNDVTRYNGKFKG |
| $V_H$CDR3 J533 | Mus musculus | FIG. 9A | 95 | GENWYYFDS |
| $V_L$CDR1 J533 | Mus musculus | FIG. 10A | 96 | RASESIDSYDNTFMH |
| $V_L$CDR2 J533 | Mus musculus | FIG. 10A | 97 | RASILES |
| $V_L$CDR3 J533 | Mus musculus | FIG. 10A | 98 | HQSIEDPYT |
| $V_H$CDR1 E99 | Mus musculus | FIG. 11A | 99 | GFSLTAYGIN |

TABLE 1-continued

CDR Sequences

| NAME | Organism | FIG. | SEQ ID NO: | SEQUENCE |
|---|---|---|---|---|
| V<sub>H</sub>CDR2 E99 | Mus musculus | FIG. 11A | 100 | VIWPDGNTDYNSTLKS |
| V<sub>H</sub>CDR3 E99 | Mus musculus | FIG. 11A | 101 | DSYGNFKRGWFDF |
| V<sub>L</sub>CDR1 E99 | Mus musculus | FIG. 12A | 102 | KASQNVGSDVA |
| V<sub>L</sub>CDR2 E99 | Mus musculus | FIG. 12A | 103 | STSYRYS |
| V<sub>L</sub>CDR3 E99 | Mus musculus | FIG. 12A | 104 | QQYNSYPLT |

The light or heavy chain immunoglobulin of the modified anti-PSMA antibody or antigen-binding fragment thereof can further include a light chain or a heavy chain variable framework sequence from a light chain or heavy chain variable framework present in a human or a non-human, e.g., rodent, antibody (e.g., the murine J591, J415, J533 or E99 antibody heavy chain or light chain variable framework). In some embodiments, the light chain or the heavy chain variable framework can be chosen from:

i a light or heavy chain variable framework including at least 5, 10, 20, 30, 40, 50, 60, 70, or 80 amino acid residues from a human light or heavy chain variable framework, e.g., a light or heavy chain variable framework residue from a mature human antibody, a human germline antibody sequence, or a human consensus antibody sequence;

ii a light or heavy chain variable framework including at least 5, but less than 30, amino acid residues from a human light chain or heavy chain variable framework, e.g., a light chain or heavy chain variable framework residue from a mature human antibody, a human germline antibody sequence, or a human consensus antibody sequence;

iii a light or heavy chain variable framework including at least 5, 10, 20, 30, 40, 50, 60, 75 or more amino acid residues from a light or heavy variable framework from a non-human antibody, e.g., a murine antibody (e.g., an anti-PSMA antibody having the framework amino acid sequence shown in SEQ ID NO:7 or 8 (from the heavy and light chain, respectively, of murine J591; see FIGS. 1A and 1B), SEQ ID NO:35 or 36 (from the heavy and light chain, respectively, of murine J415; see FIGS. 5 and 6), SEQ ID NO:109 or 114 (from the heavy and light chain, respectively, of murine J533; see FIGS. 9A and 10A), or SEQ ID NO:119 or 124 (from the heavy and light chain, respectively, of murine E99; see FIGS. 11A and 12A), or the framework of a murine antibody described herein (e.g., a murine J591, J415, J533, or E99 antibody produced by a hybridoma cell line having an ATCC Accession Number HB-12126, HB-12109, HB-12127 or HB-12101);

iv a light or heavy chain variable framework, which has at least 60%, 65%, 70%, 72%, 75%, 80%, 85%, 90%, 95%, 96%, 97%, 98%, 99% or more identity with, or which has an amino acid sequence which differs by at least 1, 2, 5, or more residues, but less than 10, 20, 30 or 40 residues from, the sequence of the framework of a light or heavy chain variable region of a non-human antibody, e.g., a murine antibody (e.g., an anti-PSMA antibody having the framework amino acid sequence shown in SEQ ID NO:7 or 8 (from the heavy and light chain, respectively, of murine J591; see FIGS. 1A and 1B), SEQ ID NO:35 or 36 (from the heavy and light chain, respectively, of murine J415; see FIGS. 5 and 6), SEQ ID NO:109 or 114 (from the heavy and light chain, respectively, of murine J533; see FIGS. 9A and 10A), or SEQ ID NO:119 or 124 (from the heavy and light chain, respectively, of murine E99; see FIGS. 11A and 12A)), or the framework of a murine antibody described herein (e.g., a murine antibody produced by a hybridoma cell line having an ATCC Accession Number HB-12126, HB-12109, HB-12127 or HB-12101); or v a non-human, e.g., a murine, e.g., a J591 or J415, light or heavy chain variable region framework which has at least 5 amino acid replacements.

In some embodiments, the light chain variable region of the non-human anti-PSMA antibody or antigen-binding fragment thereof has at least one, two, three and preferably four amino acid sequences chosen from SEQ ID NO:13, 14, 15, and 16 (corresponding to deimmunized J591 light chain FR's 1–4; see FIG. 2B) or SEQ ID NO:41, 42, 43, and 44 (corresponding to deimmunized J415 light chain (J415DIVK5) FR's 1–4; see FIG. 6), or at least one, two, three and preferably four light chain framework regions from the antibody produced by the cell line having ATCC Accession Number PTA-3709 or PTA-4174. In other embodiments, the heavy chain variable region of the non-human anti-PSMA antibody or antigen binding portion thereof has at least one, two, three, and preferably four amino acid sequences chosen from SEQ ID NO:9, 10, 11, and 12 (corresponding to deimmunized J591 heavy chain FR's 1–4; see FIG. 2A) or SEQ ID NO:37, 38, 39, and 40 (corresponding to deimmunized J415 heavy chain (J415DIVH4) FR's 1–4; see FIG. 5), or at least one, two, three and preferably four heavy chain framework regions of the antibody produced by the cell line having ATCC Accession Number PTA-3709 or PTA-4174. In other embodiments, the heavy or light chain framework has an amino acid sequence which has at least 80%, 85%, 90%, 95%, 97%, 98%, 99% or more identity with SEQ ID NO:17 or SEQ ID NO:18, respectively (corresponding to deimmunized J591 framework sequence; see FIGS. 2A–2B), SEQ ID NO:45 or SEQ ID NO:46, respectively (corresponding to deimmunized J415 framework sequences J415DIVH4 and J415DIVK5; see FIG. 5 or 6), or with the heavy or light chain framework sequence of an antibody produced by the cell line having ATCC Accession Number PTA-3709 or PTA-4174. In still other embodiments, the heavy or light chain framework has an amino acid sequence which differs by at least 1, 2, 5, or more residues, but less than 10, 20, 30, or 40 residues, from the amino acid sequence of SEQ ID NO:17 or SEQ ID NO:18, respectively, SEQ ID NO:45 or SEQ ID NO:46, respectively, or the heavy or light chain framework sequence of the antibody produced by the cell line having ATCC Accession Number PTA-3709 or PTA-4174. Preferably, the heavy or light chain framework region includes the amino acid sequence shown in SEQ ID NO:17 or SEQ ID NO:18, respectively, SEQ ID NO:45 or SEQ ID NO:46, respectively, or the heavy or light chain framework sequence of the antibody produced by the cell line having ATCC Accession Number PTA-3709 or PTA-4174.

In other embodiments, the heavy or light chain variable region of the modified anti-PSMA antibody has an amino acid sequence which has at least 80%, 85%, 90%, 95%, 97%, 98%, 99% or more identity with SEQ ID NO:21 or SEQ ID NO:22, respectively (corresponding to the heavy and light chain variable regions of deimmunized J591; see FIGS. 2A–2B), SEQ ID NO:49 or SEQ ID NO:50, respectively (corresponding to the heavy and light chain variable regions of deimmunized J415, J415DIVH4 and J415DIVK5; see FIG. 5 or 6), or the heavy or light chain variable region sequence of the antibody produced by the cell line having ATCC Accession Number PTA-3709 or PTA-4174. In other embodiments, the heavy or light chain variable region of the modified anti-PSMA antibody has an amino acid sequence that differs by at least 1, 2, 5, or more residues, but less than 10, 20, 30, or 40 residues, from the amino acid sequence of SEQ ID NO:21 or SEQ ID NO:22, respectively, SEQ ID NO:49 or SEQ ID NO:50, respectively, or the heavy or light chain variable region sequence of the antibody produced by the cell line having ATCC Accession Number PTA-3709 or PTA-4174. Preferably, the light or heavy chain variable region includes the amino acid sequence shown in SEQ ID NO:21 or SEQ ID NO:22, respectively, SEQ ID NO:49 or SEQ ID NO:50, respectively, or the heavy or light chain variable region sequence of the antibody produced by the cell line having ATCC Accession Number PTA-3709 or PTA-4174.

Preferred modified anti-PSMA antibodies include at least one, preferably two, light chain variable regions and at least one, preferably two, heavy chain variable regions having the amino acid sequence shown in SEQ ID NO:21 and SEQ ID NO:22, respectively (corresponding to the heavy and light chain variable regions of deimmunized J591; see FIGS. 2A–2B), SEQ ID NO:49 and SEQ ID NO:50, respectively (corresponding to the heavy and light chain variable regions of deimmunized J415, J415DIVH4 and J415DIVK5; see FIGS. 5 and 6), or at least one, preferably two, modified light chain variable region sequences and at least one, preferably two, heavy chain variable region sequences of the antibody produced by the cell line having ATCC Accession Number PTA-3709 or PTA-4174.

In other embodiments, the light or heavy chain variable framework of the anti-PSMA antibody, or antigen-binding fragment thereof, includes at least one, two, three, four, five, six, seven, eight, nine, ten, fifteen, sixteen, or seventeen amino acid residues from a human light or heavy chain variable framework, e.g., a light or heavy chain variable framework residue from a mature human antibody, a human germline antibody sequence, or a consensus antibody sequence.

In some embodiments, the amino acid residue from the human light chain variable framework is the same as the residue found at the same position in a human germline antibody sequence. Preferably, the amino acid residue from the human light chain variable framework is the most common residue at the same position in the human germline antibody sequence. Preferably, the light chain variable framework of the modified anti-PSMA antibody, or antigen-binding fragment thereof, has at least one, two, three, five, seven, ten amino acid residues which differ from the framework of the non-human anti-PSMA light chain variable region (e.g., the murine J591 light chain variable region), or which is from a human light chain variable framework (e.g., a human germline, mature, or consensus framework sequence), at a position selected from the group consisting of: residue 8, 9, 10, 11, 20, 22, 60, 63, 76, 77, 78, 80, 83, 87, 103, 104 and 106 (Kabat numbering as shown in Table 2). Preferably, the light chain variable framework of the modified anti-PSMA antibody, or antigen-binding fragment thereof, has at least one, two, three, five, seven, or ten amino acid residues from the human light chain variable framework selected from the group consisting of: residue 8 (proline), 9 (serine), 10 (serine), 11 (leucine), 20 (threonine), 22 (threonine), 60 (serine), 63 (serine), 76 (serine), 77 (serine), 78 (leucine), 80 (proline), 83 (phenylalanine), 87 (tyrosine), 103 (lysine), 104 (valine) and 106 (isoleucine) (Kabat numbering as shown in Table 2).

The amino acid replacements in the deimmunized J591 light chain variable region are provided below in Table 2. The left panel indicates the amino acid number according to Kabat, E. A., et al. (1991) supra; the middle panel indicates the replacements of the residue in the mouse sequence and the corresponding mouse residues; and the right panel indicates the most common residue in the corresponding position in the human germline.

TABLE 2

| Position Kabat No | Substitution of mouse sequence | Most common in human germline |
|---|---|---|
| 3 | V→Q | V |
| 8 | H→P | P |
| 9 | K→S | S |
| 10 | F→S | S |
| 11 | M→L | L |
| 20 | S→T | T |
| 21 | I→L | I |
| 22 | I→T | T |
| 42 | Q→P | K |
| 58 | V→I | V |
| 60 | D→S | S |
| 63 | T→S | S |
| 76 | T→S | S |
| 77 | T→S | S |
| 78 | V→L | L |
| 80 | S→P | P |
| 83 | L→F | F |
| 87 | F→Y | Y |
| 100 | A→P | Q |
| 103 | M→K | K |
| 104 | L→V | V |
| 106 | L→I | I |

In other embodiments, the light chain variable framework of the anti-PSMA antibody, or antigen-binding fragment thereof, has at least one, two, three, five, or seven amino acid residues which differ from the framework of a non-human anti-PSMA light chain variable region (e.g., the murine J415 light chain variable region), or which is from a human light chain variable framework (e.g., a human germline, mature, or consensus framework), at a position selected from the group consisting of: residue 13, 15, 19, 41, 63, 68, and 80 (linear numbering as show in FIG. 6). Preferably, the light chain variable framework of the modified antibody, or antigen-binding fragment thereof, has at least one, two, three, five, or seven amino acid residues from the human consensus light chain variable framework selected from the group consisting of: residue 13 (alanine), 15 (alanine), 19 (methionine), 41 (threonine), 63 (serine), 68 (glycine), and 80 (alanine) (linear numbering as shown in FIG. 6).

The amino acid replacements in the deimmunized J415 light chain variable region are provided below in Table 3.

The left panel indicates the amino acid number using linear numbering; the middle panel indicates the replacements of the residue in the mouse sequence and the corresponding mouse residues, and the right panel indicates the most common residue in the corresponding position in the human germline.

TABLE 3

| Position Linear No | Substitution of mouse sequence | Most common in human germline |
|---|---|---|
| 13 | I→A | A |
| 15 | V→A | A |
| 19 | V→M | M |
| 41 | E→T | T |
| 63 | T→S | S |
| 68 | A→G | G |
| 80 | T→A | A |

In other embodiments, the light chain variable framework of the anti-PSMA antibody, or antigen-binding fragment thereof, includes at least 5, but no more than 80, amino acid residues from the light chain-variable framework shown in SEQ ID NO:8 (from murine J591; see FIG. 1B), SEQ ID NO:36 (from murine J415; see FIG. 6), SEQ ID NO:114 (from murine J533; see FIG. 10A), or SEQ ID NO:124 (from murine E99; see FIG. 12A), or the light chain variable framework of an antibody produced by the hybridoma cell line having an ATCC Accession Number HB-12126, HB-12109, MB-12127 or HB-12101. Preferably, the light chain variable framework has at least 60%, 65%, 70%, 72%, 75%, 80%, 85%, 90%, or 94% identity with, or differs by at least 5, 7, 10, 20, or 30 but less than 10, 20, 30, or 40 amino acid residues from, the non-human light chain variable framework, e.g., the murine J591 or J415 light chain variable framework shown in SEQ ID NO:8 or SEQ ID NO:36, respectively, or the light chain variable framework of the antibody produced by the hybridoma cell line having an ATCC Accession Number HB-12126 or HB-12109. In other embodiments, the light chain variable framework is from murine J591 antibody (SEQ ID NO:8; see FIG. 1B), from murine J415 antibody (SEQ ID NO:36; see FIG. 6), from murine J533 antibody (SEQ ID NO:114; see FIG. 10A), or from murine E99 antibody (SEQ ID NO:124; see FIG. 12A), or the light chain variable framework of the antibody produced by the hybridoma cell line having an ATCC Accession Number HB-12126, HB-12109, HB-12127 or HB-12101.

In yet other embodiments, the light chain variable framework of the modified anti-PSMA antibody, or antigen-binding fragment thereof, includes a non-human (e.g., a murine) light chain variable framework (e.g., a murine J591 light chain variable framework as shown in SEQ ID NO:8 or the light chain variable framework of the antibody produced by the hybridoma cell line having an ATCC Accession Number HB-12126) which has at least 5, 10, 15, 16, 17, 18, 19, 20, 21, 22, or 23 amino acid replacements. In one embodiment, the non-human light chain variable framework includes one or more of:

a framework region 1 having at least 5, 6, 7, or 8 replacements;

a framework region 2 having at least one replacement;

a framework region 3 having at least 5, 6, 7, 8, or 9 replacements; or a framework region 4 having at least 2, 3 or 4 replacements.

In yet other embodiments, the light chain variable framework of the modified anti-PSMA antibody, or antigen-binding fragment thereof, includes a non-human (e.g., a murine) light chain variable framework (e.g., a murine J415 light chain variable framework as shown in SEQ ID NO:36 or the light chain variable framework of the antibody-produced by the hybridoma cell line having an ATCC Accession Number HB-12109) which has at least 1, 2, 3, 4, 5, 6, 7, 8, or 10 amino acid replacements. In some embodiments, the non-human light chain variable framework includes one or more of:

a framework region 1 having at least 1, 2 or 3 replacements;

a framework region 2 having at least one replacement; or a framework region 3 having at least 1, 2 or 3 replacements.

The replacement can be selected from: a conservative substitution of a non-human residue, or a residue found in a human germline, mature or consensus framework sequence at the same position, e.g. the most common residue in the human germline sequence at the same position. In some embodiments, the light chain variable framework has at least 3, 4 and preferably 5 conservative substitutions. In other embodiments, the light chain variable framework has at least 5, 7, 10, 15, 16, or 17 amino acid replacements wherein the replacement amino acid residue is the most common residue in the human germline framework sequence at the same position.

In some embodiments, the non-human light chain variable framework has at least one, two, three, five, seven, ten, eleven, fifteen, sixteen, seventeen, nineteen, twenty, twenty-one or twenty-two amino acid replacements at a position selected from the group consisting of: residue 3, 8, 9, 10, 11, 20, 21, 22, 42, 58, 60, 63, 76, 77, 78, 80, 83, 87, 100, 103, 104 and 106 (Kabat numbering as shown in Table 2). The replacement can be chosen from one or more of: residue 3 (glutamine), 8 (proline), 9 (serine), 10 (serine), 11 (leucine), 20 (threonine), 21 (leucine), 22 (threonine), 42 (proline), 58 (isoleucine), 60 (serine), 63 (serine), 76 (serine), 77 (serine), 78 (leucine), 80 (proline), 83 (phenylalanine), 87 (tyrosine), 100 (proline), 103 (lysine), 104 (valine) and 106 (isoleucine) (Kabat numbering as shown in Table 2).

In other embodiments, the non-human light chain variable framework has at least one, two, three, five, or seven amino acid replacements at a position selected from the group consisting of: residue 13, 15, 19, 41, 63, 68 and 80 (linear numbering as shown in Table 3). Preferably the light chain variable framework of the modified antibody, or antigen-binding fragment thereof, has at least one, two, three, five, seven amino acid residues from the human consensus light chain variable framework selected from the group consisting of: residue 13 (alanine), 15 (alanine), 19 (methionine), 41 (threonine), 63 (serine), 68 (glycine) and 80 (alanine) (linear numbering as shown in Table 3).

Preferably, the heavy chain variable framework of the modified anti-PSMA antibody, or antigen-binding fragment thereof, has at least one, two, three, five, seven, or eight amino acid residues, which differ from the framework of the non-human anti-PSMA heavy chain variable region (e.g., the murine J591 heavy chain variable region), or which is from a human heavy chain variable framework (e.g., a human germline framework), at a position selected from the group consisting of: residue 5, 40, 41, 44, 82a, 83, 87, and 108 (Kabat numbering as shown in Table 4). Preferably, the heavy chain variable framework of the recombinant antibody, or antigen-binding fragment thereof, has at least one amino acid residue from the human heavy chain variable framework selected from the group consisting of: residue 5 (valine), 40 (alanine), 41 (proline), 44 (glycine), 82a (serine), 83 (arginine), 87 (threonine), or 108 (leucine) (Kabat numbering as shown in Table 4).

The amino acid replacements in the deimmunized J591 heavy chain variable region are provided below in Table 4. The left panel indicates the amino acid number according to Kabat, E. A., et al. (1991) supra; the middle panel indicates the replacements of the residue in the mouse sequence and the corresponding mouse residues; and the right panel indicates the most common residue in the corresponding position in the human germline.

TABLE 4

| Position Kabat No. | Substitution of mouse sequence | Most common in human germline |
|---|---|---|
| 5 | Q→V | V |
| 11 | L→V | L |
| 12 | V→K | V |
| 16 | T→A | G |
| 17 | S→T | S |
| 19 | R→K | R |
| 40 | S→A | A |
| 41 | H→P | P |
| 44 | S→G | G |
| 75 | S→T | K |
| 76 | S→D | N |
| 82a | R→S | S |
| 83 | T→R | R |
| 87 | S→T | T |
| 108 | T→L | L |

In other embodiments, the heavy chain variable framework of the modified anti-PSMA antibody, or antigen-binding fragment thereof, has at least one, two, three, four, five amino acid residues, which differ from the framework of a non-human anti-PSMA heavy chain variable region (e.g., the murine J415 heavy chain variable region), or which is from a human heavy chain variable framework (e.g., a human mature, consensus, or germline framework), at a position selected from the group consisting of: residue 20, 87, 94, 95, and 112 (linear numbering as shown in Table 5). Preferably, the heavy chain variable framework of the recombinant antibody, or antigen-binding fragment thereof, has at least one, two, three, four, five amino acid residues from the human heavy chain variable framework selected from the group consisting of: residue 20 (isoleucine), 87 (serine), 94 (alanine), 95 (valine), and 112 (valine) (linear numbering as shown in Table 5).

The amino acid replacements in the deimmunized J415 heavy chain variable region are provided below in Table 5. The left panel indicates the linear amino acid number; the middle panel indicates the replacements of the residue in the mouse sequence and the corresponding mouse residues; and the right panel indicates the most common residue in the corresponding position in the human germline.

TABLE 5

| Position Kabat No | Substitution of mouse sequence | Most common in human germline |
|---|---|---|
| 20 | L→I | I |
| 87 | N→S | S |
| 94 | G→A | A |
| 95 | I→V | V |
| 112 | L→V | V |

In other embodiments, the heavy chain variable framework of the modified anti-PSMA antibody, or antigen-binding fragment thereof, includes at least 5 but no more than 75 or 82 amino acid residues from the heavy chain variable framework shown in SEQ ID NO:7 (from murine J591; see FIG. 1A), SEQ ID NO:35 (from murine J415; see FIG. 5), SEQ ID NO:109 (from murine J533; see FIG. 9A), or SEQ ID NO:119 (from murine E99; see FIG. 11A), or the heavy chain variable framework of the antibody produced by the hybridoma cell line having an ATCC Accession Number HB-12126, HB-12109, HB-12127 or HB-12101. Preferably, the heavy chain variable framework has at least 60%, 65%, 70%, 80%, 82%, 85%, 90%, or 94% identity with, or differs by at least 5, 10, 20, or 30 but less than 10, 20, 30, or 40 residues from, a non-human heavy chain variable framework, e.g., the murine J591 or J415 or heavy chain variable framework shown in SEQ ID NO:7 or SEQ ID NO:35, respectively, or a heavy chain variable framework of the antibody produced by the hybridoma cell line having an ATCC Accession Number HB-12126 or 12109. In other embodiments, the non-human heavy chain variable framework is from murine J591 antibody (SEQ ID NO:7; see FIG. 1A), from murine J415 antibody (SEQ ID NO:35; see FIG. 5), from murine J533 antibody (SEQ ID NO:109; see FIG. 9A), or from murine E99 antibody (SEQ ID NO:119; see FIG. 1A), or the heavy chain variable framework of the antibody produced by the hybridoma cell line having an ATCC Accession Number HB-12126, HB-12109, HB-12127 or HB-12101.

In yet other embodiments, the heavy chain variable framework of the modified anti-PSMA antibody, or antigen-binding fragment thereof, includes a non-human (e.g., a marine) heavy chain variable frame work (e.g., a murine J591 heavy chain variable framework (SEQ ID NO:7, as shown FIG. 1A, or the heavy chain variable framework of the antibody produced by the hybridoma cell line having an ATCC Accession Number HB-12126) which has at least 3, 5, 10, 15, 16, 17, 18, or 19 amino acid replacements. In one embodiment, the non-human heavy chain variable framework of the modified anti-PSMA antibody includes one or more of:

a framework region 1 having at least 4, 5, or 6 replacements;

a framework region 2 having at least 1, 2, or 3 replacements;

a framework region 3 having at least 3, 4, or 5 replacements; or a framework region 4 having at least one replacement.

In yet other embodiments, the heavy chain variable framework of the modified anti-PSMA antibody, or antigen-binding fragment thereof, includes a non-human (e.g., a murine) heavy chain variable framework (e.g., a murine J415 heavy chain variable framework (SEQ ID NO:35, as shown in FIG. 5, or the heavy chain variable framework of the antibody produced by the hybridoma cell line having an ATCC Accession Number HB-12109) which has at least 1, 2, 3, 4, or 5 amino acid replacements. In one embodiment, the non-human heavy chain-variable framework of the modified anti-PSMA antibody includes one or more of:

a framework region 1 having at least one replacement;

a framework region 3 having at least 1, 2, or 3 replacements; or a framework region 4 having at least one replacement.

The replacement can be chosen from: a conservative substitution of a non-human residue, or a residue found in a human germline, mature or consensus sequence at the same position, e.g. the most common residue in the human germline at the same position. In one embodiment, the heavy chain variable framework has at least 3, 4, 5, 6 and preferably 7 conservative substitutions. Preferably, the heavy chain variable framework has at least 5, 6, 7 and preferably 8 replacements by the most common residue in the human germline at the same position.

In some embodiments, the non-human heavy chain variable framework has at least one amino acid replacement at a position selected from the group consisting of: residue 5, 11, 12, 16, 17, 19, 40, 41, 44, 75, 76, 82a, 83, 87, and 108 (Kabat numbering as shown in Table 3). The replacement can be chosen from one or more of: 5 (valine), 11 (valine), 12 (lysine), 16 (alanine), 17 (threonine), 19 (lysine), 40 (alanine), 41 (proline), 44 (glycine), 75 (threonine), 76 (aspartate), 82a (serine), 83 (arginine), 87 (threonine), and 108 (leucine) (Kabat numbering as shown in Table 4).

In other embodiments, the non-human heavy chain variable framework has at least one amino acid replacement at a position selected from the group consisting of: residue 20, 87, 94, 95 and 112 (linear numbering as shown in Table 5). The replacement can be chosen from one or more of: residue 20 (isoleucine), 87 (serine), 94 (alanine), 95 (valine), and 112 (valine) (linear numbering as shown in Table 5).

The amino acid sequence of the framework regions of the light and heavy chains regions of antibodies J591, J415, J533 and E99 are provided in Table 6, below.

TABLE 6

Framework Sequences

| NAME | Organism | FIG. | SEQ ID NO: | SEQUENCE |
|---|---|---|---|---|
| V_HFR1–FR4 J591 | Mus musculus | FIG. 1A | 7 | EVQLQQSGPELKKPGTSVRISCK TSWVKQSHGKSLEWIGKATLTV DKSSSTAYMELRSLTSEDSAVY YCAAWGQGTTLTVSS |
| V_LFR1–FR4 J591 | Mus musculus | FIG. 1B | 8 | DIVMTQSHKFMSTSVGDRVSIIC WYQQKPGQSPKLLIYGVPDRFT GSGSGTDFTLTTTNVQSEDLADY FCFGAGTMLDLK |
| V_HFR1 (Deimm) J591 | Artificial - deimmunized heavy chain J591 | FIG. 2A | 9 | EVQLVQSGPEVKKPGATVKISC KTS |
| V_HFR2 (Deimm) J591 | Artificial - deimmunized heavy chain J591 | FIG. 2A | 10 | WVKQAPGKGLEWIG |
| V_HFR3 (Deimm) J591 | Artificial- deimmunized heavy chain J591 | FIG. 2A | 11 | KATLTVDKSTDTAYMELSSLRS EDTAVYYCAA |
| V_HFR4 (Deimm) J591 | Artificial - deimmunized heavy chain J591 | FIG. 2A | 12 | WGQGTLLTVSS |
| V_LFR1 (Deimm) J591 | Artificial - deimmunized light chain J591 | FIG. 2B | 13 | DIQMTQSPSSLSTSVGDRVTLTC |

TABLE 6-continued

Framework Sequences

| NAME | Organism | FIG. | SEQ ID NO: | SEQUENCE |
|---|---|---|---|---|
| $V_L$FR2 (Deimm) J591 | Artificial - deimmunized light chain J591 | FIG. 2B | 14 | WYQQKPGPSPKLLIY |
| $V_L$FR3 (Deimm) J591 | Artificial - deimmunized light chain J591 | FIG. 2B | 15 | GIPSRFSGSGSGTDFTLTISSLQPE DFADYYC |
| $V_L$FR4 (Deimm) J591 | Artificial - deimmunized light chain J591 | FIG. 2B | 16 | FGPGTKVDIK |
| $V_H$FR1–FR4 (Deimm) J591 | Artificial - deimmunized heavy chain J591 | FIG. 2A | 17 | EVQLVQSGPEVKKPGATVKISC KTSWVKQAPGKGLEWIGKATLT VDKSTDTAYMELSSLRSEDTAV YYCAAWGQGTLLTVSS |
| $V_L$FR1–FR4 (Deimm) J591 | Artificial - deimmunized light chain J591 | FIG. 2B | 18 | DIQMTQSPSSLSTSVGDRVTLTC WYQQKPGPSPKLLIYGIPSRFSGS GSGTDFTLTISSLQPEDFADYYC FGPGTKVDIK |
| $V_H$FR1–FR4 J415 | *Mus musculus* | FIG. 5 | 35 | EVKLEESGGGLVQPGGSMKLSC VASWVRQSPEKGLEWVARVIIS RDDSKSSVYLQMNNLRAEDTGI YYCTRWGQGTTLTVSS |
| $V_L$FR1–FR4 J415 | *Mus musculus* | FIG. 6 | 36 | NIVMTQFPKSMSISVGERVTLTC WYQQKPEQSPKMLIYGVPDRFT GSGSATDFILTISSVQTEDLVDY YCFGGGTKLEMK |
| $V_H$FR1 (Deimm) J415-4 | Artificial - deimmunized heavy chain J415-4 | FIG. 5 | 37 | EVKLEESGGGLVQPGGSMKISC VAS |
| $V_H$FR2 (Deimm) J415-4 | Artificial - deimmunized heavy chain J415-4 | FIG. 5 | 38 | WVRQSPEKGLEWVA |

TABLE 6-continued

Framework Sequences

| NAME | Organism | FIG. | SEQ ID NO: | SEQUENCE |
|---|---|---|---|---|
| $V_H$FR3 (Deimm) J415-4 | Artificial-deimmunized heavy chain J415-4 | FIG. 5 | 39 | RVIISRDDSKSSVYLQMNSLRAEDTAVYYCTR |
| $V_H$FR4 (Deimm) J415-4 | Artificial - deimmunized heavy chain J415-4 | FIG. 5 | 40 | WGQGTTVTVSS |
| $V_L$FR1 (Deimm) J415-5 | Artificial - deimmunized light chain J415-5 | FIG. 6 | 41 | NIVMTQFPKSMSASAGERMTLTC |
| $V_L$FR1 (Deimm) J415-5 | Artificial - deimmunized light chain J415-5 | FIG. 6 | 42 | WYQQKPTQSPKMLIY |
| $V_L$FR3 (Deimm) J415-5 | Artificial - deimmunized light chain J415-5 | FIG. 6 | 43 | GVPDRFSGSGSGTDFILTISSVQAEDLVDYYC |
| $V_L$FR4 (Deimm) J415-5 | Artificial - deimmunized light chain J415-5 | FIG. 6 | 44 | FGGGTKLEMK |
| $V_H$FR1–FR4 (Deimm) J415-4 | Artificial - deimmunized heavy chain J415-4 | FIG. 5 | 45 | EVKLEESGGGLVQPGGSMKISCVASWVRQSPEKGLEWVARVIISRDDSKSSVYLQMNSLRAEDTAVYYCTRWGQGTTVTVSS |
| $V_L$FR1–FR4 (Deimm) J415-5 | Artificial - deimmunized light chain J415-5 | FIG. 6 | 46 | NIVMTQFPKSMSASAGERMTLTCWYQQKPTQSPKMLIYGVPDRFSGSGSGTDFILTISSVQAEDLVDYYCFGGGTKLEMK |
| $V_H$FR1 J533 | Mus musculus | FIG. 9A | 105 | EVQLQQSGPELVKPGASVKMSCKAS |
| $V_H$FR2 J533 | Mus musculus | FIG. 9A | 106 | WVKQKPGQVLEWIG |

TABLE 6-continued

Framework Sequences

| NAME | Organism | FIG. | SEQ ID NO: | SEQUENCE |
|---|---|---|---|---|
| V$_H$FR3 J533 | Mus musculus | FIG. 9A | 107 | KATLTSDKYSSTAYMELSGLTSE DSAVYYCAR |
| V$_H$FR4 J533 | Mus musculus | FIG. 9A | 108 | WGRGATLTVSS |
| V$_H$FR1–FR4 J533 | Mus musculus | FIG. 9A | 109 | EVQLQQSGPELVKPGASVKMSC KASWVKQKPGQVLEWIGKATLT SDKYSSTAYMELSGLTSEDSAV YYCARWGRGATLTVSS |
| V$_L$FR1 J533 | Mus musculus | FIG. 10A | 110 | DIVLTQSPASLAVSLGQRATISC |
| V$_L$FR2 J533 | Mus musculus | FIG. 10A | 111 | WYQQKPGQPPNLLIF |
| V$_L$FR3 J533 | Mus musculus | FIG. 10A | 112 | GIPARFSGSGSGTDFTLTIYPVEA DDVATYYC |
| V$_L$FR4 J533 | Mus musculus | FIG. 10A | 113 | FGGGTKLEIK |
| V$_L$FR1–FR4 J533 | Mus musculus | FIG. 10A | 114 | DIVLTQSPASLAVSLGQRATISC WYQQKPGQPPNLLIFGIPARFSG SGSGTDFTLTIYPVEADDVATYY CFGGGTKLEIK |
| V$_H$FR1 E99 | Mus musculus | FIG. 11A | 115 | QVQLKESGPGLVASSQSLSITCT VS |
| V$_H$FR2 E99 | Mus musculus | FIG. 11A | 116 | WVRQPPGKGLEWLG |
| V$_H$FR3 E99 | Mus musculus | FIG. 11A | 117 | RLNIFKDNSKNQVFLKMSSFQTD DTARYFCAR |
| V$_H$FR4 E99 | Mus musculus | FIG. 11A | 118 | WGQGTTLTVSS |
| V$_H$FR1–FR4 E99 | Mus musculus | FIG. 11A | 119 | QVQLKESGPGLVASSQSLSITCT VSWVRQPPGKGLEWLGRLNIFK DNSKNQVFLKMSSFQTDDTARY FCARWGQGTTLTVSS |
| V$_L$FR1 E99 | Mus musculus | FIG. 12A | 120 | NIVMTQSQKFMSTSPGDRVRVT C |
| V$_L$FR2 E99 | Mus musculus | FIG: 12A | 121 | WYQAKPGQSPRILIY |

TABLE 6-continued

Framework Sequences

| NAME | Organism | FIG. | SEQ ID NO: | SEQUENCE |
|---|---|---|---|---|
| V<sub>L</sub>FR3 E99 | Mus musculus | FIG. 12A | 122 | GVPDRFTAYGSGTDFTLTITNVQ SEDLTEYFC |
| V<sub>L</sub>FR4 E99 | Mus musculus | FIG. 12A | 123 | FGAGTKLELK |
| V<sub>L</sub>FR1–FR4 E99 | Mus musculus | FIG. 12A | 124 | NIVMTQSQKFMSTSPGDRVRVT CWYQAKPGQSPRILIYGVPDRFT AYGSGTDFTLTTTNVQSEDLTEY FCFGAGTKLELK |

In other embodiments, the anti-PSMA antibody, or antigen-binding fragment thereof, includes at least one light chain or heavy chain immuglobulin or, preferably, at least one light chain immuglobulin and at least one heavy chain immuglobulin. Preferably, the light chain immunoglobulin includes a non-human light chain variable region comprising three CDRs from a non-human, e.g., murine, anti-PSMA light chain variable region (e.g., the murine J591 or J415 light chain variable region shown in SEQ ID NO:20 (see FIG. 1B) or SEQ ID NO:48 (see FIG. 6), respectively, or the light chain variable region of the antibody produced by the hybridoma cell line having an ATCC Accession Number HB-12126 or 12109) and a light chain framework which differs from the framework of the non-human, e.g., murine, anti-PSMA light chain framework (e.g., the murine J591 of J415 light chain framework shown in SEQ ID NO:8 (see FIG. 1B) or SEQ ID NO:36 (see FIG. 6), respectively, or the light chain variable framework of the antibody produced by the hybridoma cell line having an ATCC Accession Number HB-12126 or 12109) at one, two, three, four, five, six, seven or more positions selected from the group consisting of: residue 3, 8, 9, 10, 11, 20, 21, 22, 42, 58, 60, 63, 76, 77, 78, 80, 83, 87, 100, 103, 104 and 106 (Kabat numbering as in Table 2), or residues 13, 15, 19, 41, 63, 68, and 80 (linear numbering as in Table 3).

In other preferred embodiments, the heavy chain immunoglobulin includes a non-human heavy chain variable region comprising three complementarity determining regions (CDRs) from a non-human, e.g., murine, anti-PSMA heavy chain variable region (e.g., the murine J591 or J415 heavy chain variable region shown in SEQ ID NO:19 (see FIG. 1A) or SEQ ID NO:47 (see FIG. 5), respectively, or the heavy chain variable region of the antibody produced by the hybridoma cell line having an ATCC Accession Number HB-12126 or HB-12109) and a modified heavy chain framework which differs from the framework of the non-human, e.g., murine, anti-PSMA heavy chain framework (e.g., the murine J591 or J415 heavy chain framework shown in SEQ ID NO:7 (see FIG. 1A) or SEQ ID NO:35 (see FIG. 5), respectively, or the heavy chain variable framework of the antibody produced by the hybridoma cell line having an ATCC Accession Number HB-12126 or HB-12109) at one, two, three, four, five or more positions selected from the group consisting of: residue 5, 11, 12, 16, 17, 19, 40, 41, 44, 75, 76, 82a, 83, 87, and 108 (Kabat numbering as in Table 4), or residue 20, 87, 94, 95 and 112 (linear numbering as in Table 5).

In yet other embodiments, the modified anti-PSMA antibody, or antigen-binding fragment thereof, includes at least one light or heavy chain immuglobulin or, more preferably, at least one light chain immuglobulin and at least one heavy chain immuglobulin. Preferably, the light chain immunoglobulin includes a modified non-human light chain variable region comprising three CDRs from a non-human, e.g., murine, anti-PSMA light chain variable region (e.g., the murine J591 light chain variable region shown in SEQ ID NO:20 (see FIG. 1B), or the light chain variable region of the antibody produced by the hybridoma cell line having an ATCC Accession Number HB-12126) and a modified light chain framework which differs from the framework of the non-human anti-PSMA light chain variable region, e.g., the murine J591 light chain variable region (SEQ ID NO:20 or the light chain variable region of the antibody produced by the hybridoma cell line having an ATCC Accession Number HB-12126), by at least one, two, three, four, five, six, seven, eight, nine, ten positions selected from the group consisting of:

a position within or adjacent to one or more of residues 1, 2, 3, 4, 5, 6, 7, 8, 9, 10, 11, 12 or 13, or a T cell epitope which includes one or more of residues 1–13 (numbering as in FIG. 3B);

a position within or adjacent to one or more of residues 8, 9, 10, 11, 12, 13, 14, 15, 16, 17, 18, 19 or 20, or a T cell epitope which includes one or more of residues 8–20 (numbering as in FIG. 3B);

a position within or adjacent to one or more of residues 17, 18, 19, 20, 21, 22, 23, 24, 25, 26, 27, 28 or 29, or a T cell epitope which includes one or more of residues 17–29 (numbering as in FIG. 3B);

a position within or adjacent to one or more of residues 27, 28, 29, 30, 31, 32, 33, 34, 35, 36, 37, 38 or 39, or a T cell epitope which includes one or more of residues 27–39 (numbering as in FIG. 3B);

a position within or adjacent to one or more of residues 30, 31, 32, 33, 34, 35, 36, 37, 38, 39, 40, 41, 42 or 43, or a T cell epitope which includes one or more of residues 30–43 (numbering as in FIG. 3B);

a position within or adjacent to one or more of residues 45, 46, 47, 48, 49, 50, 51, 52, 53, 54, 55, 56, or 57, or a T cell epitope which includes one or more of residues 45–57 (numbering as in FIG. 3B);

a position within or adjacent to one or more of residues 56, 57, 58, 59, 60, 61, 62, 63, 64, 65, 66, 67, or 68, or a T cell epitope which includes one or more of residues 56–68 (numbering as in FIG. 3B);

a position within or adjacent to one or more of residues 71, 72, 73, 74, 75, 76, 77, 78, 79, 80, 81, 82, or 83, or a T cell epitope which includes one or more of residues 71–83 (numbering as in FIG. 3B);

a position within or adjacent to one or more of residues 73, 74, 75, 76, 77, 78, 79, 80, 81, 82, 83, 84 or 85, or a T cell epitope which includes one or more of residues 73–85 (numbering as in FIG. 3B); and a position within or adjacent to one or more of residues 94, 95, 96, 97, 98, 99, 100, 101, 102, 103, 104, 105, or 106, or a T cell epitope which includes one or more of residues 94–106 (numbering as in FIG. 3B).

In yet other embodiments, the anti-PSMA antibody, or antigen-binding fragment thereof, includes at least one light or heavy chain immuglobulin or, more preferably, at least one light chain immuglobulin and at least one modified heavy chain immuglobulin. Preferably, the light chain immunoglobulin includes a modified non-human light chain variable region comprising three CDRs from a non-human, e.g., murine, anti-PSMA light chain variable region (e.g., the murine J415 light chain variable region shown in SEQ ID NO:48 (FIG. 37), or the light chain variable region of the antibody produced by the hybridoma cell line having an ATCC Accession Number HB-12109) and a light chain framework which differs from the framework of the non-human anti-PSMA light chain variable region, e.g., the murine J415 light chain variable region (SEQ ID NO:48 or the light chain variable region of the antibody produced by the hybridoma cell line having an ATCC Accession Number HB-12109), by at least one, two, three, four, five, six, seven positions selected from the group consisting of:

a position within or adjacent to one or more of residues 5, 6, 7, 8, 9, 10, 11, 12, 13, 14, 15, 16, 17 or 18, or a T cell epitope which includes one or more of residues 5–18 (linear numbering as in FIG. 6);

a position within or adjacent to one or more of residues 11, 12, 13, 14, 15, 16, 17, 18, 19, 20, 21, 22, 23, or 24, or a T cell epitope which includes one or more of residues 11–24 (linear numbering as in FIG. 6);

a position within or adjacent to one or more of residues 13, 14, 15, 16, 17, 18, 19, 20, 21, 22, 23, 24, 25, or 26, or a T cell epitope which includes one or more of residues 13–26 (linear numbering as in FIG. 6);

a position within or adjacent to one or more of residues 17, 18, 19, 20, 21, 22, 23, 24, 25, 26, 27, 28, 29, or 30, or a T cell epitope which includes one or more of residues 17–30 (linear numbering as in FIG. 6);

a position within or adjacent to one or more of residues 27, 28, 29, 30, 31, 32, 33, 34, 35, 36, 37, 38, 39, or 40, or a T cell epitope which includes one or more of residues 27–40 (linear numbering as in FIG. 6);

a position within or adjacent to one or more of residues 31, 32, 33, 34, 35, 36, 37, 38, 39, 40, 41, 42, 43, or 44, or a T cell epitope which includes one or more of residues 31–44 (linear numbering as in FIG. 6);

a position within or adjacent to one or more of residues 56, 57, 58, 59, 60, 61, 62, 63, 64, 65, 66, 67, 68, or 69, or a T cell epitope which includes one or more of residues 56–69 (linear numbering as in FIG. 6);

a position within or adjacent to one or more of residues 60, 61, 62, 63, 64, 65, 66, 67, 68, 69, 70, 71, 72, or 73, or a T cell epitope which includes one or more of residues 60–73 (linear numbering as in FIG. 6);

a position within or adjacent to one or more of residues 70, 71, 72, 73, 74, 75, 76, 77, 78, 79, 80, 81, 82, or 83, or a T cell epitope which includes one or more of residues 70–83 (linear numbering as in FIG. 6);

a position within or adjacent to one or more of residues 71, 72, 73, 74, 75, 76, 77, 78, 79, 80, 81, 82, 83 or 84, or a T cell epitope which includes one or more of residues 71–84 (linear numbering as in FIG. 6);

a position within or adjacent to one or more of residues 73, 74, 75, 76, 77, 78, 79, 80, 81, 82, 83, 84, 85 or 86, or a T cell epitope which includes one or more of residues 73–86 (linear numbering as in FIG. 6);

a position within or adjacent to one or more of residues 76, 77, 78, 79, 80, 81, 82, 83, 84, 85, 86, 87, 88, 89, 90, 91, or 92, or a T cell epitope which includes one or more of residues 76–92 (linear numbering as in FIG. 6); and a position within or adjacent to one or more of residues 81, 82, 83, 84, 85, 86, 87, 88, 89, 90, 91, 92, 93, or 94, or a T cell epitope which includes one or more of residues 81–94 (linear numbering as in FIG. 6).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J591 heavy chain variable region shown in SEQ ID NO:19 (see FIG. 1A), or the heavy chain variable region of the antibody produced by the hybridoma cell line having an ATCC Accession Number HB-12126) and a heavy chain framework which differs from the framework of the non-human anti-PSMA heavy chain variable region (e.g., the murine J591 heavy chain variable region of SEQ ID NO:19 or the heavy chain variable framework of the antibody produced by the hybridoma cell line having an ATCC Accession Number HB-12126), by at least one, two, three, five, seven, ten positions selected from the group consisting of:

a position within or adjacent to one or more of residues 2, 3, 4, 5, 6, 7, 8, 9, 10, 11, 12, 13, or 14, or a T cell epitope-which includes one or more of residues 2–14 (numbering as in FIG. 3A);

a position within or adjacent to one or more of residues 10, 11, 12, 13, 14, 15, 16, 17, 18, 19, 20, 21, or 22, or a T cell epitope which includes one or more of residues 10–22 (numbering as in FIG. 3A);

a position within or adjacent to one or more of residues 16, 17, 18, 19, 20, 21, 22, 23, 24, 25, 26, 27, or 28, or a T cell epitope which includes one or more of residues 16–28 (numbering as in FIG. 3A);

a position within or adjacent to one or more of residues 30, 31, 32, 33, 34, 35, 36, 37, 38, 39, 40, 41, or 42, or a T cell epitope which includes one or more of residues 30–42 (numbering as in FIG. 3A);

a position within or adjacent to one or more of residues 32, 33, 34, 35, 36, 37, 38, 39, 40, 41, 42, 43, or 44, or a T cell epitope which includes one or more of residues 32–44 (numbering as in FIG. 3A);

a position within or adjacent to one or more of residues 43, 44, 45, 46, 47, 48, 49, 50, 51, 52, 53, 54, or 55, or a T cell epitope which includes one or more of residues 43–55 (numbering as in FIG. 3A);

a position within or adjacent to one or more of residues 46, 47, 48, 49, 50, 51, 52, 53, 54, 55, 56, 57, or 58, or a T cell epitope which includes one or more of residues 46–58 (numbering as in FIG. 3A);

a position within or adjacent to one or more of residues 58, 59, 60, 61, 62, 63, 64, 65, 66, 67, 68, 69, or 70, or a T cell epitope which includes one or more of residues 58–70 (numbering as in FIG. 3A);

a position within or adjacent to one or more of residues 62, 63, 64, 65, 66, 67, 68, 69, 70, 71, 72, 73 or 74, or a T cell epitope which includes one or more of residues 62–74 (numbering as in FIG. 3A);

a position within or adjacent to one or more of residues 70, 71, 72, 73, 74, 75, 76, 77, 78, 79, 80 or 81 or a T cell epitope which includes one or more of residues 70–81 (numbering as in FIG. 3A);

a position within or adjacent to one or more of residues 81, 82, 83, 84, 85, 86, 87, 88, 89, 90, 91, 92, or 93, or a T cell epitope which includes one or more of residues 81–93 (numbering as in FIG. 3A);

a position within or adjacent to one or more of residues 84, 85, 86, 87, 88, 89, 90, 91, 92, 93, 95, or 96, or a T cell epitope which includes one or more of residues 84–96 (numbering as in FIG. 3A);

a position within or adjacent to one or more of residues 91, 92, 93, 95, 96, 97, 98, 99, 100, 101, 102, or 103, or a T cell epitope which includes one or more of residues 91–103 (numbering as in FIG. 3A); and a position within or adjacent to one or more of residues 100, 101, 102, 103, 104, 105, 106, 107, 108, 109, 110, 111, or 112, or a T cell epitope which includes one or more of residues 100–112 (numbering as in FIG. 3A).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J415 heavy chain variable region shown in SEQ ID NO:47 (see FIG. 5), or the heavy chain variable region of the antibody produced by the hybridoma cell line having an ATCC Accession Number HB-12109) and a heavy chain framework which differs from the framework of the non-human anti-PSMA heavy chain variable region, e.g., the murine J591 heavy chain variable region of SEQ ID NO:47 or the heavy chain variable framework of the antibody produced by the hybridoma cell line having an ATCC Accession Number HB-12109), by at least one, two, three, four, five positions selected from the group consisting of:

a position within or adjacent to one or more of residues 10, 11, 12, 13, 14, 15, 16, 17, 18, 19, 20, 21, 22 or 23, or a T cell epitope which includes one or more of residues 10–23 (numbering as in FIG. 5);

a position within or adjacent to one or more of residues 16, 17, 18, 19, 20, 21, 22, 23, 24, 25, 26, 27, 28, or 29, or a T cell epitope which includes one or more of residues 16–29 (numbering as in FIG. 5);

a position within or adjacent to one or more of residues 21, 22, 23, 24, 25, 26, 27, 28, 29, 30, 31, 32, 33, or 34, or a T cell epitope which includes one or more of residues 21–34 (numbering as in FIG. 5);

a position within or adjacent to one or more of residues 30, 31, 32, 33, 34, 35, 36, 37, 38, 39, 40, 41, 42, or 43, or a T cell epitope which includes one or more of residues 30–43 (numbering as in FIG. 5);

a position within or adjacent to one or more of residues 35, 36, 37, 38, 39, 40, 41, 42, 43, 44, 45, 46, 47, 48, or a T cell epitope which includes one or more of residues 35–48 (numbering as in FIG. 5);

a position within or adjacent to one or more of residues 43, 44, 45, 46, 47, 48, 49, 50, 51, 52, 53, 54, 55, or 56, or a T cell epitope which includes one or more of residues 43–56 (numbering as in FIG. 5);

a position within or adjacent to one or more of residues 46, 47, 48, 49, 50, 51, 52, 53, 54, 55, 56, 57, 58 or 59, or a T cell epitope which includes one or more of residues 46–59 (numbering as in FIG. 5);

a position within or adjacent to one or more of residues 49, 50, 51, 52, 53, 54, 55, 56, 57, 58, 59, 60, 61, or 62, or a T cell epitope which includes one or more of residues 49–62 (numbering as in FIG. 5);

a position within or adjacent to one or more of residues 64, 65, 66, 67, 68, 69, 70, 71, 72, 73, 74, 75, 76, or 77, or a T cell epitope which includes one or more of residues 64–77 (numbering as in FIG. 5);

a position within or adjacent to one or more of residues 80, 81, 82, 83, 84, 85, 86, 87, 88, 89, 90, 91, 92, or 93, or a T cell epitope which includes one or more of residues 80–93 (numbering as in FIG. 5);

a position within or adjacent to one or more of residues 86, 87, 88, 89, 90, 91, 92, 93, 94, 95, 96, 97, 98, or 99, or a T cell epitope which includes one or more of residues 86–99 (numbering as in FIG. 5); and a position within or adjacent to one or more of residues 104, 105, 106, 107, 108, 109, 110, 111, 112, 113, 114, 115, 116, or 117; or a T cell epitope which includes one or more of residues 104–117 (numbering as in FIG. 5).

In yet other embodiments, the anti-PSMA antibody, or antigen-binding fragment thereof, includes at least one light or heavy chain immuglobulin or, more preferably, at least one light chain immunoglobulin and at least one heavy chain immuglobulin. Preferably, the light chain immunoglobulin includes a non-human light chain variable region comprising three CDRs from a non-human, e.g., murine, anti-PSMA light chain variable region (e.g., the murine J591 light chain variable region shown in SEQ ID NO:20 (FIG. 1B), or the light chain variable region of the antibody produced by the hybridoma cell line having an ATCC Accession Number HB-12126) and a light chain framework which differs from the framework of the non-human anti-PSMA light chain variable region, e.g., murine J591 light chain variable region, by at least one position while having a residue from the non-human anti-PSMA light chain variable region at at least one, two, three, five, seven, ten, fifteen, or twenty residues selected from the group consisting of 1, 2, 4–7, 12–19, 23, 31–41, 43–49, 57, 59, 61, 62, 64–75, 79, 82, 83, 85–87, 89, 98, 99, 101, 102, 105, and 106 (numbering as in FIG. 3B). The light chain framework can differ at positions chosen from one, two, three, four, five, six, seven, eight, nine, ten, eleven, twelve, thirteen, fourteen, fifteen, sixteen, nineteen, twenty or more residues selected from the group consisting of 3, 8, 9, 10, 11, 20, 21, 22, 42, 58, 60, 63, 76, 77, 78, 80, 83, 87, 100, 103, and 104 (numbering as in FIG. 3B).

In yet other embodiments, the anti-PSMA antibody, or antigen-binding fragment thereof, includes at least one light or heavy chain immuglobulin or, more preferably, at least one light chain immunoglobulin and at least one heavy chain immuglobulin. Preferably, the modified light chain immunoglobulin includes a non-human light chain variable region comprising three CDRs from a non-human, e.g., murine, anti-PSMA light chain variable region (e.g., the murine J415 light chain-variable region shown in SEQ ID NO:48 (FIG. 6), or the light chain variable region of the antibody produced by the hybridoma cell line having an ATCC Accession Number HB-12109) and a light chain framework which differs from the framework of the non-human anti-PSMA light chain variable region, e.g., murine J415 light chain variable region, by at least one position while having a residue from the non-human anti-PSMA light chain variable region at at least one, two, three, five, seven, ten, fifteen, or twenty residues selected from the group consisting of 1–12, 14, 16–18, 20–40, 42–62, 64–67, 69–79, and 81–107 (linear numbering as in FIG. 6). The modified light chain framework can differ at at least one, two, three, four, five, six, or seven positions selected from the group consisting of 13, 15, 19, 41, 63, 68 and 80 (linear numbering as in FIG. 6).

In other embodiments, the heavy chain immunoglobulin of the modified anti-PSMA antibody, or antigen-binding fragment thereof, includes a non-human heavy chain variable region comprising three CDRs from a non-human, e.g., murine, anti-PSMA heavy chain variable region (e.g., the murine J591 heavy chain variable region shown in SEQ ID NO:19 (FIG. 1A), or the heavy chain variable region of the antibody produced by the hybridoma cell line having an ATCC Accession Number HB-12126) and a modified heavy chain framework which differs from the framework of the non-human anti-PSMA heavy chain variable region by at least one position while having a residue from the non-human anti-PSMA heavy chain variable region at at least one, two, three, four, five, six, seven, eight, nine, ten, eleven, twelve, thirteen, or fourteen residues selected from the group consisting of 1–4, 6–10, 13–15, 18, 20–25, 36–39, 42, 43, 45–49, 67–75, 78–83, 85, 86, 88–90, 92–98, 105–109, and 111–115 (numbering as in FIG. 3A). The modified heavy chain framework can differ at at least one, two, three, four, five, six, seven, eight, nine, ten, eleven, twelve, thirteen, or fourteen positions selected from the group consisting of 5, 11–12, 16–17, 19, 26–35, 40–41, 44, 50–66, 76–77, 84, 87, 91, 99–104, and 110 (numbering as in FIG. 3A).

In other embodiments, the heavy chain immunoglobulin of the anti-PSMA antibody, or antigen-binding fragment thereof, includes a non-human heavy chain variable region comprising three CDRs from a non-human, e.g., murine, anti-PSMA heavy chain variable region (e.g., the murine J415 heavy chain variable region shown in SEQ ID NO:47 (FIG. 5), or the heavy chain variable region of the antibody produced by the hybridoma cell line having an ATCC Accession Number HB-12109) and a heavy chain framework which differs from the framework of the non-human anti-PSMA heavy chain variable region by at least one position while having a residue from the non-human anti-PSMA heavy chain variable region at at least one, two, three, four, or five residues selected from the group consisting of 1–19, 21–86, 88–93, 96–111, and 113–116 (numbering as in FIG. 5). The heavy chain framework can differ at a positions selected from the group consisting of 20, 87, 94, 95 and 112 (numbering as in FIG. 5).

In yet another aspect, the heavy chain immunoglobulin of the anti-PSMA antibody, or antigen-binding fragment thereof, includes a heavy chain variable region comprising at least one, two, three, four, five, six, seven, eight, nine, ten, twenty, twenty-five, thirty, thirty-five, forty, forty-five, or fifty amino acid residues chosen from one or more of the following residues and located at a position chosen from one or more of residue 1 (glutamate), 2 (valine), 4 (leucine), 7 (serine), 8 (glycine), 11 (leucine), 14 (proline), 15 (glycine), 19 (lysine), 20 (isoleucine), 21 (serine), 22 (cysteine), 25 (serine), 26 (glycine), 28 (threonine), 29 (phenylalanine), 32 (tyrosine), 36 (tryptophan), 37 (valine), 38 (arginine/lysine), 39 (glutamine), 41 (proline), 43 (lysine), 44 (glycine), 45 (leucine), 46 (glutamate), 47 (tryptophan), 51 (isoleucine), 67 (arginine/lysine), 73 (aspartate), 75 (serine), 80 (tyrosine), 85 (serine), 86 (leucine), 87 (arginine), 89 (glutamate), 90 (aspartate), 91 (threonine), 92 (alanine), 93 (valine), 94 (tyrosine), 95 (tyrosine), 96 (cysteine), 100 (tryptophan), 101 (asparagine), 105 (tryptophan), 106 (glycine), 107 (glutamine), 108 (glycine), 109 (threonine), 112 (threonine), 113 (valine), 114 (serine), or 115 (serine) (linear numbering as shown in FIG. 3A).

In one embodiment, the heavy chain immunoglobulin of the anti-PSMA antibody, or antigen-binding fragment thereof, includes one or more of:

a framework region 1 having at least one, two, three, four, five, six, seven, eight, nine, ten, eleven, twelve, thirteen amino acids selected from the group consisting of residue 1 (glutamate), 2 (valine), 4 (leucine), 7 (serine), 8 (glycine), 11 (leucine), 14 (proline), 15 (glycine), 19 (lysine), 20 (isoleucine), 21 (serine), 22 (cysteine), and 25 (serine) (linear numbering as shown in FIG. 3A);

a CDR1 having at least one, two, three, four amino acids selected from the group consisting of residue 26 (glycine), 28 (threonine), 29 (phenylalanine), and 32 (tyrosine) (linear numbering as shown in FIG. 3A);

a framework region 2 having at least one, two, three, four, five, six, seven, eight, nine, ten amino acids selected from the group consisting of residue 36 (tryptophan), 37 (valine), 38 (arginine/lysine), 39 (glutamine), 41 (proline), 43 (lysine), 44 (glycine), 45 (leucine), 46 (glutamate), and 47 (tryptophan) (linear numbering as shown in FIG. 3A);

a CDR2 having at least one isoleucine at position 51 (linear numbering as shown in FIG. 3A);

a framework region 3 having at least one, two, three, four, five, six, seven, eight, nine, ten, eleven, twelve, thirteen, fourteen amino acids selected from the group consisting of residue 67 (arginine/lysine), 73 (aspartate), 75 (serine), 80 (tyrosine), 85 (serine), 86 (leucine), 87 (arginine), 89 (glutamate), 90 (aspartate), 91 (threonine), 92 (alanine), 93 (valine), 94 (tyrosine), 95 (tyrosine), and 96 (cysteine) (linear numbering as shown in FIG. 3A);

a CDR3 having at least one, two amino acids selected from the group consisting of residue 100 (tryptophan) and 101 (asparagine) (linear numbering as shown in FIG. 3A); or a framework region 4 having at least one, two, three, four, five, six, seven, eight, nine amino acids selected from the group consisting of residue 105 (tryptophan), 106 (glycine), 107 (glutamine), 108 (glycine), 109 (threonine), 112 (threonine), 113 (valine), 114 (serine), and 115 (serine) (linear numbering as shown in FIG. 3A).

In yet another embodiment, the light chain immunoglobulin of the modified anti-PSMA antibody, or antigen-binding fragment thereof, includes a light chain variable region comprising at least one, two, three, four, five, six, seven, eight, nine, ten, eleven, twelve, thirteen, fourteen, twenty, thirty, forty, fifty, sixty, or seventy amino acids chosen from one or more of the following residues and located at a position chosen from one or more of: residue 2 (isoleucine), 4 (methionine), 5 (threonine), 6 (glutamine), 8 (proline), 10 (serine), 12 (serine), 14 (serine), 16 (glycine), 17 (glutamate/aspartate), 18 (arginine), 20 (threonine), 21 (leucine), 22 (threonine), 23 (cysteine), 24 (lysine), 25 (alanine), 26 (serine), 29 (valine), 30 (glycine), 31 (threonine), 33 (valine), 35 (tryptophan), 36 (tryosine), 37 (glutamine), 38 (glutamine), 39 (lysine), 40 (proline), 43 (serine), 44 (proline), 45 (lysine), 47 (leucine), 48 (isoleucine), 49. (tyrosine), 51 (alanine), 52 (serine), 54 (arginine), 56 (threonine), 57 (glycine), 59 (proline), 61 (arginine), 62 (phenylalanine), 63 (serine), 64 (glycine), 65 (serine), 66

(glycine), 67 (serine), 68 (glycine), 69 (threonine), 70 (aspartate), 71 (phenylalanine), 73 (leucine), 74 (threonine), 75 (threonine), 76 (serine), 77 (serine), 79 (glutamine), 81 (glutamate), 82 (aspartate), 85 (aspartate), 86 (tyrosine), 87 (tyrosine), 88 (cysteine), 90 (glutamine), 95 (proline), 97 (threonine), 98 (phenylalanine), 99 (glycine), 101 (glycine), 102 (threonine), 103 (lysine), 105 (glutamate/aspartate), or 107 (lysine) (linear numbering as in FIG. 3B).

In one embodiment, the light chain immunoglobulin of the anti-PSMA antibody, or antigen-binding fragment thereof, includes one or more of:

a framework region 1 having at least one, two, three, four, five, six, seven, eight, nine, ten, eleven, twelve, fourteen, fifteen amino acids selected from the group consisting of residue 2 (isoleucine), 4 (methionine), 5 (threonine), 6 (glutamine), 8 (proline), 10 (serine), 12 (serine), 14 (serine), 16 (glycine), 17 (glutamate/aspartate), 18 (arginine), 20 (threonine), 21 (leucine), 22 (threonine), and 23 (cysteine) (linear numbering as shown in FIG. 3B);

a CDR1 having at least one, two, three, four, five, six, seven amino acids selected from the group consisting of residue 24 (lysine), 25 (alanine), 26 (serine), 29 (valine), 30 (glycine), 31 (threonine), and 33 (valine) (linear numbering as shown in FIG. 3B);

a framework region 2 having at least one, two, three, four, five, six, seven, eight, nine, ten, eleven, twelve amino acids selected from the group consisting of residue 35 (tryptophan), 36 (tryrosine), 37 (glutamine), 38 (glutamine), 39 (lysine), 40 (proline), 43 (serine), 44 proline), 45 (lysine), 47 (leucine), 48 (isoleucine), and 49 (tyrosine) (linear numbering as shown in FIG. 3B);

a CDR2 having at least one, two, three, four amino acids selected from the group consisting of residue 51 (alanine), 52 (serine), 54 (arginine), and 56 (threonine) (linear numbering as shown in FIG. 3B);

a framework region 3 having at least one, two, three, four, five, six, seven, eight, nine, ten, eleven, twelve, thirteen, fourteen, fifteen, twenty, twenty-one, twenty-two, twenty-three, twenty-four amino acids selected from the group consisting of residue 59 (proline), 61 (arginine), 62 (phenylalanine), 63 (serine), 64 (glycine), 65 (serine), 66 (glycine), 67 (serine), 68 (glycine), 69 (threonine), 70 (aspartate), 71 (phenylalanine), 73 (leucine), 74 (threonine), 75 (threonine), 76 (serine), 77 (serine), 79 (glutamine), 81 (glutamate), 82 (aspartate), 85 (aspartate), 86 (tyrosine), 87 (tyrosine), and 88 (cysteine) (linear numbering as shown in FIG. 3B);

a CDR3 having at least one, two, three, four amino acids selected from the group consisting of residue 90 (glutamine), 95 (proline), 97 (threonine), and 98 (phenylalanine) (linear numbering as shown in FIG. 3B); or a framework region 4 having at least one, two, three, four, five, six amino acid selected from the group consisting of residue 99 (glycine), 101 (glycine), 102 (threonine), 103 (lysine), 105 (glutamate/aspartate), and 107 (lysine) (linear numbering as shown in FIG. 3B).

An anti-PSMA antibody, e.g., a modified anti-PSMA antibody, or antigen-binding fragment thereof, described herein can be used alone, e.g., can be administered to a subject, or used in vitro, in non-derivatized or unconjugated forms. In other embodiments, the anti-PSMA antibody, or antigen-binding fragment thereof, can be derivatized or linked to another molecular entity, typically a label or a therapeutic (e.g., a cytotoxic or cytostatic) agent. The molecular entity can be, e.g., another peptide, protein (including, e.g., a viral coat protein of e.g., a recombinant viral particle), a non-peptide chemical compound, isotope, etc.

The anti-PSMA antibody, or antigen-binding fragment thereof, can be functionally linked, e.g., by chemical coupling, genetic fusion, non-covalent association or otherwise, to one or more other molecular entities. For example, the anti-PSMA antibody, or antigen-binding fragment thereof, can be coupled to a label, such as a fluorescent label, a biologically active enzyme label, a radioisotope (e.g., a radioactive ion), a nuclear magnetic resonance active label, a luminescent label, or a chromophore. In other embodiments, the anti-PSMA antibody, or antigen-binding fragment thereof, can be coupled to a therapeutic agent, e.g., a cytotoxic moiety, e.g., a therapeutic drug, a radioisotope, molecules of plant, fungal, or bacterial origin, or biological proteins (e.g., protein toxins) or particles (e.g., recombinant viral particles, e.g., via a viral coat protein), or mixtures thereof. The therapeutic agent can be an intracellularly active drug or other agent, such as short-range radiation emitters, including, for example, short-rage, high-energy α-emitters, as described herein. In some preferred embodiments, the anti-PSMA antibody, or antigen binding fragment thereof, can be coupled to a molecule of plant or bacterial origin (or derivative thereof), e.g., a maytansinoid (e.g., maytansinol or the DM1 maytansinoid, see FIG. 15), a taxane, or a calicheamicin. A radioisotope can be an α-, β-, or γ-emitter, or an β- and γ-emitter. Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99m}$Tc), phosphorus ($^{32}$P), carbon ($^{14}$C), and tritium ($^3$H), or one of the therapeutic isotopes listed above. The anti-PSMA antibody, or antigen-binding fragment thereof can also be linked to another antibody to form, e.g., a bispecific or a multispecific antibody.

In another aspect, the invention features, an anti-PSMA antibody, e.g., an antibody described herein, coupled, e.g., by covalent linkage, to a proteosome inhibitor or a topoisomerase inhibitor. [(1R)-3-methyl-1-[[(2S)-1-oxo-3-phenyl-2-[(3-mercaptoacetyl) amino]propyl]amino]butyl] Boronic acid is a suitable proteosome inhibitor. N,N'-bis[2-(9-methylphenazine-1-carboxamido)ethyl]-1,2-ethanediamine is a suitable topoisomerase inhibitor.

In another aspect, the invention provides, compositions, e.g., pharmaceutical compositions, which include a pharmaceutically acceptable carrier, excipient or stabilizer, and at least one of the anti-PSMA antibodies, e.g., the modified anti-PSMA antibodies (or fragments thereof) described herein. In a preferred embodiment the antibody is conjugated to a label or a therapeutic agent. In one embodiment, the compositions, e.g., the pharmaceutical compositions, comprise a combination of two or more of the aforesaid anti-PSMA antibodies. For example, a composition, e.g., pharmaceutical composition, which comprises a deimmunized J591 antibody, in combination with another anti-PSMA antibody, or an antibody to another tumor cell-associated antigen, e.g., EGF receptor, Her-2/neu, etc. Combinations of the anti-PSMA antibody and a drug, e.g., a therapeutic agent (e.g., a cytototoxic or cytostatic drug, e.g., DM1, calicheamicin, or taxanes, topoisomerase inhibitors, or an immunomodulatory agent, e.g., IL-1, 2, 4, 6, or 12, interferon alpha or gamma, or immune cell growth factors such as GM-CSF) are also within the scope of the invention.

The invention also features nucleic acid sequences that encode a heavy and light chain immunoglobulin described herein. For example, the invention features, a first and second nucleic acid encoding a modified heavy and light chain variable region, respectively, of a modified anti-PSMA antibody molecule as described herein. In another aspect, the invention features host cells and vectors containing the nucleic acids of the invention.

In another aspect, the invention features a method of producing an anti-PSMA antibody, e.g., a modified anti-PSMA antibody, or antigen-binding fragment thereof. The method includes:

providing a first nucleic acid encoding a heavy chain variable region, e.g., a modified heavy chain variable region as described herein;

providing a second nucleic acid encoding a light chain variable region, e.g., a modified light chain variable region as described herein; and introducing said first and second nucleic acids into a host cell under conditions that allow expression and assembly of said light and heavy chain variable regions.

The first and second nucleic acids can be linked or unlinked, e.g., expressed on the same or different vector, respectively.

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NS0), Chinese hamster ovary cells (CHO), COS cells, oocyte cells, and cells from a transgenic animal, e.g., mammary epithelial cell. For example, nucleic acids encoding the modified antibody described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent.

The invention also features a method of ablating or killing, a cell, e.g., a prostatic cell (e.g., a cancerous or non-cancerous prostatic cell, e.g., a normal, benign or hyperplastic prostatic epithelial cell), or a malignant, non-prostatic cell, e.g., cell found in a non-prostatic solid tumor that, e.g., has vasculature which expresses PSMA, a soft tissue tumor, or a metastatic lesion (e.g., a cell found in renal, urothelial (e.g. bladder), colonic, rectal, pulmonary, breast or hepatic cancers and/or metastases thereof). Methods of the invention include contacting the cell, or a nearby cell, e.g., a vascular endothelial cell proximate to the cell, with an anti-PSMA antibody as described herein, e.g., a modified anti-PSMA antibody, in an amount sufficient to ablate or kill, the cell. Alternatively, an anti-PSMA antibody as described herein, e.g., a modified anti-PSMA antibody, preferably a fragment of a modified anti-PSMA antibody, can be conjugated to a viral particle, e.g., to a coat protein of a viral particle. The anti-PSMA/viral particle conjugate can be used to target prostate cells, e.g., cancerous prostate cells, with genetically engineered viral particles that infect the cells and express, e.g., pro apoptotic genes, to thereby kill the cells or inhibit cell growth.

The methods can be used on cells in culture, e.g. in vitro or ex vivo. For example, prostatic cells (e.g., malignant or normal, benign or hyperplastic prostate epithelial cells) or non-prostatic cancerous or metastatic cells (e.g., renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct), melanoma (e.g., malignant melanoma), or soft tissue sarcoma cancerous cells) can be cultured in vitro in culture medium and the contacting step can be effected by adding the modified anti-PSMA antibody or fragment thereof, to the culture medium. The method can be performed on cells (e.g., prostatic cells, or non-prostatic cancerous or metastatic cells) present in a subject, as part of an in vivo (e.g., therapeutic or prophylactic) protocol.

Methods of the invention can be used, for example, to treat or prevent a disorder, e.g., a prostatic disorder (e.g., a cancerous or non-cancerous prostatic disorder, e.g., a benign or hyperplastic prostatic disorder), or a non-prostatic disorder (e.g., cancer, e.g., malignant cancer), by administering to a subject an antibody described herein, preferably a modified PSMA antibody, or antigen-binding fragment thereof, in an amount effective to treat or prevent such disorder. Particularly preferred antibodies include modified antibodies having CDRs from any of a J591, J415, J533 or E99, and in particular deimmunized versions of these antibodies, particularly deJ591 or deJ415. Examples of prostatic disorders that can be treated or prevented include, but are not limited to, genitourinary inflammation (e.g., inflammation of smooth muscle cells) as in prostatitis; benign enlargement, for example, nodular hyperplasia (benign prostatic hypertrophy or hyperplasia); and cancer, e.g., adenocarcinoma or carcinoma, of the prostate and/or testicular tumors. Methods and compositions disclosed herein are particularly useful for treating metastatic lesions associated with prostate cancer. In some embodiments, the patient will have undergone one or more of prostatectomy, chemotherapy, or other anti-tumor therapy and the primary or sole target will be metastatic lesions, e.g., metastases in the bone marrow or lymph nodes. Examples of non-prostatic cancerous disorders include, but are not limited to, solid tumors, soft tissue tumors, and particularly metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), genitals and genitourinary tract (e.g., renal, urothelial, bladder cells), pharynx, CNS (e.g., neural or glial cells), skin (e.g., melanoma), and pancreas, as well as adenocarcinomas which include malignancies such as most colon cancers, rectal cancer, renal-cell carcinoma, liver cancer, non-small cell carcinoma of the lung, cancer of the small intestine and cancer of the esophagus. Methods and compositions disclosed herein are particularly useful for treating metastatic lesions associated with the aforementioned cancers. In some embodiments, the patient will have undergone one or more of surgical removal of a tissue, chemotherapy, or other anti-cancer therapy and the primary or sole target will be metastatic lesions, e.g., metastases in the bone marrow or lymph nodes.

In a preferred embodiment the subject is treated to prevent a disorder, e.g., a prostatic disorder. The subject can be one at risk for the disorder, e.g., a subject having a relative afflicted with the disorder, e.g., a subject with one or more of a grandparent, parent, uncle or aunt, sibling, or child who has or had the disorder, or a subject having a genetic trait associated with risk for the disorder. In a preferred embodiment the disorder is a prostatic disorder (e.g., a cancerous or non-cancerous prostatic disorder, e.g., a benign or hyperplastic prostatic disorder), or a non-prostatic disorder (e.g., cancer, e.g., malignant cancer) and the subject has one or more of a grandfather, father, uncle, brother, or son who has or had the disorder, or a subject having a genetic trait associated with risk for the disorder.

The subject can be a mammal, e.g., a primate, preferably a higher primate, e.g., a human (e.g., a patient having, or at risk of, a disorder described herein, e.g., a prostatic or a cancer disorder). In one embodiment, the subject is a patient having prostate cancer (e.g., a patient suffering from recurrent or metastatic prostate cancer).

The modified anti-PSMA antibody or fragment thereof, e.g., a modified anti-PSMA antibody or fragment thereof as described herein, can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The methods of the invention, e.g., methods of treatment or preventing, can further include the step of monitoring the subject, e.g., for a change (e.g., an increase or decrease) in one or more of: tumor size; levels of a cancer marker, e.g., levels of PSA, alkaline phosphatase, or serum hemoglobin for a patient with prostate cancer; the rate of appearance of new lesions, e.g., in a bone scan; the appearance of new disease-related symptoms; the size of soft tissue mass, e.g., a decreased or stabilization; quality of life, e.g., amount of disease associated pain, e.g., bone pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same modified anti-PSMA antibody or fragment thereof or for additional treatment with additional agents. Generally, a decrease in one or more of the parameters described above is indicative of the improved condition of the subject, although with serum hemoglobin levels, an increase can be associated with the improved condition of the subject.

The methods of the invention can further include the step of analyzing a nucleic acid or protein from the subject, e.g., analyzing the genotype of the subject. In one embodiment, a nucleic acid encoding human PSMA and/or an upstream or downstream component(s) of human PSMA signalling, e.g., an extracellular or intracellular activator or inhibitor of human PSMA, is analyzed. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the modified anti-PSMA antibody or fragment thereof to thereby determine appropriate dosage(s) and treatment regimen(s) of the modified anti-PSMA antibody or fragment thereof (e.g., amount per treatment or frequency of treatments) for prophylactic or therapeutic treatment of the subject.

The modified anti-PSMA antibody or fragment thereof can be used alone in unconjugated form to thereby ablate or kill the PSMA-expressing prostatic or cancerous cells by, e.g., antibody-dependent cell killing mechanisms such as complement-mediated cell lysis and/or effector cell-mediated cell killing. In other embodiments, the modified anti-PSMA antibody or fragment thereof can be bound to a substance, e.g., a cytotoxic agent or moiety, e.g., a therapeutic drug, a compound emitting radiation, molecules of plant, fungal, or bacterial origin, or a biological protein (e.g., a protein toxin) or particle (e.g., a recombinant viral particle, e.g., via a viral coat protein). For example, the modified anti-PSMA antibody, or antigen-binding fragment thereof, can be coupled to a radioactive isotope such as an $\alpha$-, $\beta$-, or $\gamma$-emitter, or a $\beta$- and $\gamma$-emitter. Examples of radioactive isotopes include iodine ($^{131}$I or $^{125}$I), yttrium ($^{90}$Y), lutetium ($^{177}$Lu), actinium ($^{225}$Ac), praseodymium, or bismuth ($^{212}$Bi or $^{213}$Bi). Alternatively, the anti-PSMA antibody, or antigen-binding fragment thereof, can be coupled to a biological protein, a molecule of plant or bacterial origin (or derivative thereof), e.g., a maytansinoid (e.g., maytansinol or DM1), as well as a taxane (e.g., taxol or taxotere), or calicheamicin. The maytansinoid can be, for example, maytansinol or a maytansinol analogue. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogues are described, for example, in U.S. Pat. No. 6,333,410, the contents of which is incorporated herein by reference. The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include $\alpha_1$-BR, $\alpha_2$-BR, $\alpha_3$-BR, $\alpha_4$-BR, $\beta_1$-BR, $\beta_2$-BR and $\gamma_1$-BR. Iodo-complex calicheamicins include $\alpha_1$-I, $\alpha_2$-I, $\alpha_3$-I, $\beta_1$-I, $\beta_2$-I, $\delta_1$-I and $\gamma_1$-BR. Calicheamicin and mutants, analogs and mimics thereof are described, for example, in U.S. Pat. No. 4,970,198, issued Nov. 13, 1990, U.S. Pat. No. 5,264,586, issued Nov. 23, 1993, U.S. Pat. No. 5,550,246, issued Aug. 27, 1996, U.S. Pat. No. 5,712,374, issued Jan. 27, 1998, and U.S. Pat. No. 5,714,586, issued Feb. 3, 1998, the contents of which are incorporated herein by reference. Maytansinol can be coupled to antibodies using, e.g., an N-succinimidyl 3-(2-pyridyldithio)proprionate (also known as N-succinimidyl 4-(2-pyridyldithio)pentanoate or SPP), 4-succinimidyl-oxycarbonyl-a-(2-pyridyldithio)-toluene (SMPT), N-succinimidyl-3-(2-pyridyldithio)butyrate (SDPB), 2-iminothiolane, or S-acetylsuccinic anhydride.

The methods and compositions of the invention can be used in combination with other therapeutic modalities. In one embodiment, the methods of the invention include administering to the subject a modified anti-PSMA antibody or fragment thereof, e.g., a modified anti-PSMA antibody or fragment thereof as described herein, in combination with a cytotoxic agent, in an amount effective to treat or prevent said disorder. The antibody and the cytotoxic agent can be administered simultaneously or sequentially. In other embodiments, the methods and compositions of the invention are used in combination with surgical and/or radiation procedures. In yet other embodiments, the methods can be used in combination with immunodulatory agents, e.g., IL-1, 2, 4, 6, or 12, or interferon alpha or gamma, or immune cell growth factors such as GM-CSF.

Exemplary cytotoxic agents that can be administered in combination with the anti-PSMA antibodies include antimicrotubule agents, topoisomerase inhibitors, antimetabolites, mitotic inhibitors, alkylating agents, intercalating agents, agents capable of interfering with a signal transduction pathway, agents that promote apoptosis and radiation.

In therapies of prostatic disorders, e.g., prostate cancer, the anti-PSMA antibodies can be used in combination with existing therapeutic modalities, e.g., prostatectomy (partial or radical), radiation therapy, hormonal therapy, androgen ablation therapy, and cytotoxic chemotherapy. Typically, hormonal therapy works to reduce the levels of androgens in a patient, and can involve administering a leuteinizing hormone-releasing hormone (LHRH) analog or agonist (e.g., Lupron, Zoladex, leuprolide, buserelin, or goserelin), as well as antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), surgical castration, PROSCAR™, secondary or tertiary hormonal manipulations (e.g., involving corticosteroids (e.g., hydrocortisone, prednisone, or dexamnethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

Any combination and sequence of modified anti-PSMA and other therapeutic modalities can be used. The modified anti-PSMA and other therapeutic modalities can be administered during periods of active disorder, or during a period of remission or less active disease. The modified anti-PSMA and other therapeutic modalities can be administered before treatment, concurrently with treatment, post treatment, or during remission of the disorder.

In another aspect, the invention features methods for detecting the presence of a PSMA protein in a sample in vitro (e.g., a biological sample, e.g., serum, semen or urine, or a tissue biopsy, e.g., from a prostatic or cancerous lesion). The subject method can be used to evaluate, e.g., diagnose or stage a disorder described herein, e.g., a prostatic or cancerous disorder. The method includes: (i) contacting the sample (and optionally, a reference, e.g., a control sample) with a modified anti-PSMA antibody, or fragment thereof, as described herein, under conditions that allow interaction of the anti-PSMA antibody and the PSMA protein to occur, and (ii) detecting formation of a complex between the anti-PSMA antibody, and the sample (and optionally, the reference, e.g., control, sample). Formation of the complex is indicative of the presence of PSMA protein, and can indicate the suitability or need for a treatment described herein. For example, a statistically significant change in the formation of the complex in the sample relative to the reference sample, e.g., the control sample, is indicative of the presence of PSMA in the sample. In some embodiments, the methods can include the use of more than one anti-PSMA antibody, e.g., two anti-PSMA antibodies that bind to different epitopes on PSMA. For example, the method can involve an ELISA assay, e.g., as described in Example 19.

In yet another aspect, the invention provides a method for detecting the presence of PSMA in vivo (e.g., in vivo imaging in a subject). The method can be used to evaluate, e.g., diagnose or stage a disorder described herein, e.g., a prostatic or a cancerous disorder, in a subject, e.g., a mammal, e.g., a primate, e.g., a human. The method includes: (i) administering to a subject a modified anti-PSMA antibody (or antigen binding fragment thereof), under conditions that allow interaction of the modified anti-PSMA antibody (or fragment thereof) and the PSMA protein to occur; and (ii) detecting formation of a complex between the antibody or fragment and PSMA. A statistically significant change in the formation of the complex in the subject relative to the reference, e.g., the control subject or subject's baseline, is indicative of the presence of the PSMA.

In other embodiments, a method of diagnosing or staging a disorder as described herein (e.g., a prostatic or cancerous disorder) is provided. The method includes: (i) identifying a subject having, or at risk of having, the disorder; (ii) obtaining a sample of a tissue or cell affected with the disorder; (iii) contacting said sample or a control sample with an anti-PSMA antibody as described herein, e.g., a modified anti-PSMA antibody or fragment, under conditions that allow interaction of the binding agent and the PSMA protein to occur, and (iv) detecting formation of a complex. A statistically significant increase in the formation of the complex between the antibody (or fragment thereof) with respect to a reference sample, e.g., a control sample, is indicative of the disorder or the stage of the disorder.

Preferably, the modified anti-PSMA antibody or fragment thereof, used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials. In some embodiments, the modified anti-PSMA antibody or fragment thereof is coupled to a radioactive ion, e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99}$mTc), praseodymium, or phosphorous ($^{32}$P).

In another aspect, the invention provides a method for determining the dose, e.g., radiation dose, that different tissues are exposed to when a subject, e.g., a human subject, is administered an anti-PSMA antibody that is conjugated to a radioactive isotope. The method includes: (i) administering an anti-PSMA antibody as described herein, e.g., a modified anti-PSMA antibody, that is labeled with a radioactive isotope, e.g., $^{111}$In, to a subject; (ii) measuring the amount of radioactive isotope located in different tissues, e.g., prostate, liver, kidney, or blood, at various time points until most, e.g., 50%, 80%, 90%, 95%, or more, of the radioactive isotope has been eliminated from the body of the subject; and (iii) calculating the total dose of radiation received by each tissue analyzed. In some embodiments, the measurements are taken at scheduled time points, e.g., day 1, 2, 3, 5, 7, and 12, following administration (at day 0) of the radioactively labeled anti-PSMA antibody to the subject. In some embodiments, the radiation dose that a tissue receives for one radioactive isotope, e.g., a gamma-emitter, e.g., $^{111}$In, can be used to calculate the expected dose that the same tissue would receive from a different radioactive isotope, e.g., a beta-emitter, e.g., $^{90}$Y.

In another aspect, the invention features methods of treating pain, e.g., reducing pain, experienced by a subject having or diagnosed with prostate disease, e.g., benign prostatic hyperplasia or prostate cancer, or non-prostate cancer, e.g., a cancer having vasculature which expresses PSMA (e.g., renal, urothelial (e.g., bladder), testicular, colon, rectal, lung (e.g., non-small cell lung carcinoma), breast, liver, neural (e.g., neuroendocrine), glial (e.g., glioblastoma), or pancreatic (e.g., pancreatic duct) cancer, melanoma (e.g., malignant melanoma), or soft tissue sarcoma). The methods include administering an anti-PSMA antibody as described herein, e.g., a modified anti-PSMA antibody, to a subject in an amount sufficient to treat, e.g., reduce, the pain associated with prostate disease or non-prostate cancer. In some embodiments, the subject may have no signs of prostate disease or non-prostate cancer other than, e.g., elevated levels of serum PSA and the sensation of pain. The pain can be bone pain, as well as, pain associated with obstructive voiding symptoms due to enlarged prostate, e.g., urinary hesitancy or diminished urinary stream, frequency or nocturia. The treatment of pain using the modified anti- PSMA antibodies of the invention can lead to a decreased or dramatically lowered need, or even eliminate the need, for analgesics, e.g., narcotics. In addition, by reducing pain, the methods of treatment can restore the mobility of e.g., limbs, that have become dysfunctional as a result of pain associated with movement.

In some embodiments, the modified anti-PSMA antibody is administered in an unconjugated form in an amount sufficient to treat, e.g., reduce, pain associated with prostate disease or non-prostate cancer. In other embodiments, the modified anti-PSMA antibody, or antigen-binding fragment thereof, is administered in a derivatized form, e.g., linked to another functional molecule, as described herein.

Other features and advantages of the instant invention will become more apparent from the following detailed description and claims.

BRIEF DESCRIPTION OF THE DRAWINGS

FIGS. 1A–1B depict the amino acid sequence of murine J591 heavy and light chain variable region, respectively. The location of the CDRs is indicated in the Figures; the amino acid numbering is according the Kabat numbering (see, Kabat, E. A., et al. (1991) *Sequences of Proteins of Immunological Interest, Fifth Edition*, U.S. Department of Health and Human Services, NIH Publication No. 91-3242). Note that the CDRs are considered to encompass the Chothia loops and the Kabat hypervariable regions together and the sequences have been annotated accordingly. Heavy Chain: CDR1 is depicted in SEQ ID NO:1; CDR2 is depicted in SEQ ID NO:2; CDR3 is depicted in SEQ ID NO:3; the framework excluding CDR regions is depicted in SEQ ID NO:7; and the framework including CDR regions is depicted in SEQ ID NO:19. Light Chain: CDR1 is depicted in SEQ ID NO:4; CDR2 is depicted in SEQ ID NO:5; CDR3 is depicted in SEQ ID NO:6; the framework excluding CDR regions is depicted in SEQ ID NO:8; and the framework including CDR regions is depicted in SEQ ID NO:20.

FIGS. 2A–2B depict the amino acid sequence of the deimmunized J591 heavy and light chain variable region, respectively. The location of the CDRs is indicated in the Figures; the amino acid numbering is according the Kabat numbering (see, Kabat, E. A., et al. (1991) supra). Note that the CDRs are considered to encompass the Chothia loops and the Kabat hypervariable regions together and the sequences have been annotated accordingly. Heavy Chain: CDR1 is depicted in SEQ ID NO:1; CDR2 is depicted in SEQ ID NO:2; CDR3 is depicted in SEQ ID NO:3; framework 1 is depicted in SEQ ID NO:9; framework 2 is depicted in SEQ ID NO:10; framework 3 is depicted in SEQ ID NO:11; framework 4 is depicted in SEQ ID NO:12; the framework excluding CDR regions is depicted in SEQ ID NO:17; and the framework including CDR regions is depicted in SEQ ID NO:21. Light Chain: CDR1 is depicted in SEQ ID NO:4; CDR2 is depicted in SEQ ID NO:5; CDR3 is depicted in SEQ ID NO:6; framework 1 is depicted in SEQ ID NO:13; framework 2 is depicted in SEQ ID NO:14; framework 3 is depicted in SEQ ID NO:15; framework 4 is depicted in SEQ ID NO:16; the framework excluding CDR regions is depicted in SEQ ID NO:18; and the framework including CDR regions is depicted in SEQ ID NO:22.

FIGS. 3A–3B depict an alignment of the murine J591 and deimmunized heavy chain variable regions (3A; SEQ ID NO:19 and 21, respectively) and light chain variable regions (3B; SEQ ID NO:20 and 22, respectively). Potential T cell epitopes (identified using a peptide threading program) in murine J591 VH and VK are shown in FIGS. 3A–3B, respectively. The 13-mer peptides predicted to bind to MHC class II are indicated by the underline; the CDRs are located at residues 26 to 35, 50 to 66, and 99–104 of FIG. 3A and residues 24 to 34, 50 to 56, and 89 to 97 of FIG. 3B; and residues altered in the deimmunized heavy and light chain variable regions are boxed. Where possible, amino acid substitutions are those commonly used in human germline VH regions. The amino acid numbering is linear, not according to Kabat.

FIG. 4A shows an alignment of the coding and noncoding nucleotide strands of deimmunized J591 heavy chain variable region (SEQ ID NOs:23 and 24, respectively) with the corresponding amino acid sequence (SEQ ID NO:27). FIG. 4B shows an alignment of the coding and noncoding nucleotide strands of deimmunized J591 light chain variable region (SEQ ID NOs:25 and 26, respectively) with the corresponding amino acid sequence (SEQ ID NO:28). The location of the signal peptide and CDRs 1–3 is indicated in each alignment.

FIG. 6 depicts an alignment of the amino acid sequences for the murine and several deimmunized light chain variable regions of the J415 antibody. The murine amino acid sequence is shown as J415VK (SEQ ID NO:48); the deimmunized sequences are depicted as J415DIVK1 (amino acid residues 18 to 124 of SEQ ID NO:57), J415DIVK2 (SEQ ID NO:62), J415DIVK3 (SEQ ID NO:63), J415DIVK4 (SEQ ID NO:64), J415DIVK5 (SEQ ID NO:50), J415DIVK6 (SEQ ID NO:65), J415DIVK7 (SEQ ID NO:66), and J415DIVK8 (SEQ ID NO:67). The preferred sequence is J415DIVK5 (SEQ ID NO:50). The amino acid replacements are indicated by the boxed residues. A consensus sequence is labeled "majority" (SEQ ID NO:68).

FIG. 7B depicts the nucleic acid coding sequence, the amino acid sequence, and the nucleic acid reverse complement sequence of the murine J415 heavy chain variable region (SEQ ID NO:125, 47, and 126, respectively). The relative locations of the CDRs and some restriction sites are indicated.

FIG. 7C depicts an alignment of the amino acid sequence of the murine J415 heavy chain variable region (SEQ ID NO:47) and a consensus sequence for Kabat subgroup murine VHIIIC (MUVHIII, SEQ ID NO:69). A consensus majority sequence based on the alignment is also shown (SEQ ID NO:70).

FIG. 8A depicts the nucleic acid coding sequence, the amino acid sequence, and the nucleic acid reverse complement sequence of the deimmunized J415 light chain variable region (J415DIVK1) (SEQ ID NO:56–58, respectively). The relative location of the signal sequence, intron and J415DIVK1 amino acid sequence is indicated, as well as some restriction sites.

FIG. 8B depicts the nucleic acid coding sequence, the amino acid sequence, and the nucleic acid reverse complement sequence of the murine J415 light chain variable region (SEQ ID NOs:127, 48, and 128, respectively). The relative locations of the CDRs and some restriction sites are also indicated.

FIG. 9A depicts the nucleic acid coding sequence, the amino acid sequence, and the nucleic acid reverse complement sequence of the murine J533 heavy chain variable region (SEQ ID NO:73–75, respectively). The relative locations of the CDRs and restriction sites are indicated.

FIG. 9B depicts an alignment of the amino acid sequence of the murine J533 heavy chain variable region (SEQ ID NO:74) and a consensus sequence for Kabat subgroup murine variable heavy chain (MuVHIIA, SEQ ID NO:79). A consensus majority sequence based upon the alignment is also shown (SEQ ID NO:80).

FIG. 10B depicts an alignment of the amino acid sequence of the murine J533 light chain variable region (SEQ ID NO:77) and a consensus sequence for Kabat subgroup murine MuVKIII, SEQ ID NO:81). A consensus majority sequence based upon the alignment is also shown (SEQ ID NO:82).

FIG. 11A depicts the nucleic acid coding sequence, the amino acid sequence, and the nucleic acid reverse complement sequence of the murine E99 heavy chain variable region (SEQ ID NO:83–85, respectively). The relative locations of the CDRs and some restriction sites are indicated.

FIG. 11B depicts an alignment of the amino acid sequence of the murine E99 heavy chain variable region (SEQ ID NO:84) and a consensus sequence for Kabat subgroup murine variable heavy chain (MuVHIB, SEQ ID NO:89). A consensus majority sequence based upon the alignment is also shown (SEQ ID NO:90).

FIG. 12A depicts the nucleic acid coding sequence, the amino acid sequence, and the nucleic acid reverse complement sequence of the murine E99 light chain variable region (SEQ ID NO:86–88, respectively). The relative locations of the CDRs and some restriction sites are indicated.

FIG. 12B depicts an alignment of the amino acid sequence of the murine E99 light chain variable region (SEQ ID NO:87) and a consensus sequence for Kabat subgroup murine variable light chain (MuVKI, SEQ ID NO:91). A consensus majority sequence based upon the alignment is also shown (SEQ ID NO:92).

FIG. 15 depicts the chemical structures of DM1 and maytansine, a related molecule that lacks the thiol reactive group of DM1 used to conjugate DM1 to antibodies.

DETAILED DESCRIPTION OF THE INVENTION

Figures 1, 4A:
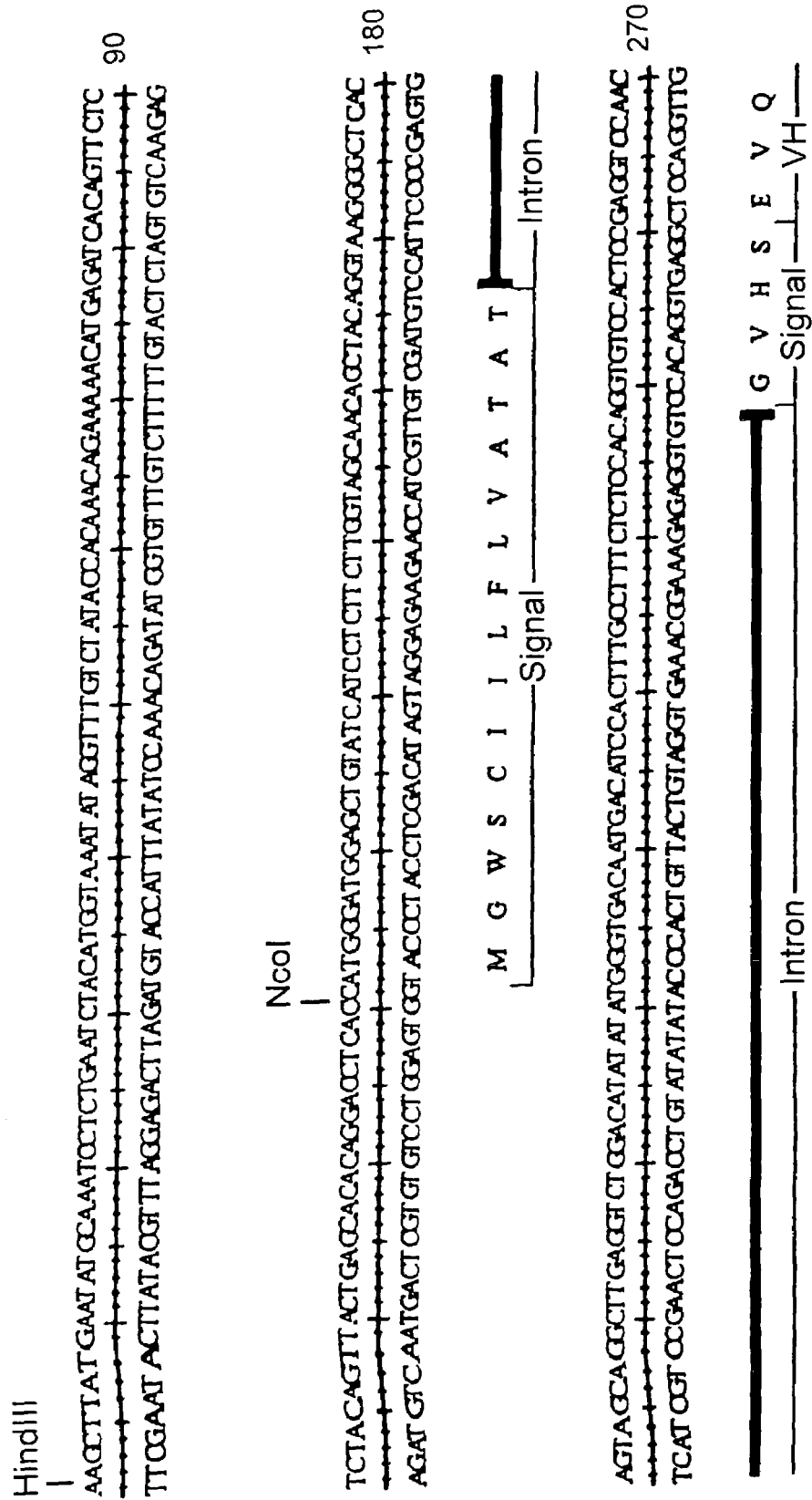
FIGS. 4A–4B depict the nucleotide sequences of the deimmunized J591 heavy and light chain variable region, respectively.

This invention provides, inter alia, antibodies, e.g., modified antibodies, or antigen-binding fragments thereof, to the extracellular domain of human prostate specific membrane antigen (PSMA). The modified anti-PSMA antibodies, or antigen-binding fragments thereof, have been rendered less immunogenic compared to their unmodified counterparts to a given species, e.g., a human. Human PSMA is expressed on the surface of normal, benign hyperplastic epithelial cells (e.g., benign prostate secretory-acinar epithelium), and cancerous prostate epithelial cells (e.g., prostatic intraepithelial neoplasia and prostatic adenocarcinoma), as well as vascular endothelial cells, proximate to cancerous cells, e.g., renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct), melanoma (e.g., malignant melanoma), or soft tissue sarcoma cancerous cells. The antibodies, e.g., the modified antibodies, of the invention bind to the cell surface of cells that express PSMA. PSMA is normally recycled from the cell membrane into the cell. Thus, the antibodies of the invention are internalized with PSMA through the process of PSMA recirculation, thereby permitting delivery of an agent conjugated to the antibody, e.g., a labeling agent, a cytotoxic agent, or a viral particle (e.g., a viral particle containing genes that encode cytotoxic agents, e.g., apoptosis-promoting factors).

In order that the present invention may be more readily understood, certain terms are first defined. Additional definitions are set forth throughout the detailed description.

As used herein, "PSMA" or "prostate-specific membrane antigen" protein refers to mammalian PSMA, preferably human PSMA protein. Human PSMA includes the two protein products, PSMA and PSM', encoded by the two alternatively spliced mRNA variants (containing about 2,653 and 2,387 nucleotides, respectively) of the PSMA cDNA disclosed in Israeli et al. (1993) *Cancer Res.* 53:227–230; Su et al. (1995) *Cancer Res.* 55:1441–1443; U.S. Pat. No. 5,538,866, U.S. Pat. No. 5,935,818, and WO 97/35616, the contents of which are hereby incorporated by reference. The long transcript of PSMA encodes a protein product of about 100–120 kDa molecular weight characterized as a type II trasmembrane receptor having sequence homology with the transferrin receptor and having NAALA-Dase activity (Carter et al. (1996) *Proc. Natl. Acad. Sci. USA* 93:749–753). Accordingly, the term "human PSMA" refers to at least two protein products, human PSMA and PSM', which have or are homologous to (e.g., at least about 85%, 90%, 95% identical to) an amino acid sequence as shown in Israeli et al. (1993) *Cancer Res.* 53:227–230; Su et al. (1995) *Cancer Res.* 55:1441–1443; U.S. Pat. No. 5,538,866, U.S. Pat. No. 5,935,818, and WO 97/35616; or which is encoded by (a) a naturally occurring human PSMA nucleic acid sequence (e.g., Israeli et al. (1993) *Cancer Res.* 53:227–230 or U.S. Pat. No. 5,538,866); (b) a nucleic acid sequence degenerate to a naturally occurring human PSMA sequence; (c) a nucleic acid sequence homologous to (e.g., at least about 85%, 90%, 95% identical to) the naturally occurring human PSMA nucleic acid sequence; or (d) a nucleic acid sequence that hybridizes to one of the foregoing nucleic acid sequences under stringent conditions, e.g., highly stringent conditions.

An "anti-PSMA antibody" is an antibody that interacts with (e.g., binds to) PSMA, preferably human PSMA protein. Preferably, the anti-PSMA antibody interacts with, e.g., binds to, the extracellular domain of PSMA, e.g., the extracellular domain of human PSMA located at about amino acids 44–750 of human PSMA (amino acid residues correspond to the human PSMA sequence disclosed in U.S. Pat. No. 5,538,866). In one embodiment, the anti-PSMA antibody binds all or part of the epitope of an antibody described herein, e.g., J591, E99, J415, and J533. The anti-PSMA antibody can inhibit, e.g., competitively inhibit, the binding of an antibody described herein, e.g., J591, E99, J415, and J533, to human PSMA. An anti-PSMA antibody may bind to an epitope, e.g., a conformational or a linear epitope, which epitope when bound prevents binding of an antibody described herein, J591, E99, J415, and J533. The epitope can be in close proximity spatially or functionally-associated, e.g., an overlapping or adjacent epitope in linear sequence or conformationally to the one recognized by the J591, E99, J415, or J533 antibody. In one embodiment, the anti-PSMA antibody binds to an epitope located wholly or partially within the region of about amino acids 120 to 500, preferably 130 to 450, more preferably, 134 to 437, or 153 to 347, of human PSMA (amino acid residues correspond to the human PSMA sequence disclosed in U.S. Pat. No. 5,538,866). Preferably, the epitope includes at least one glycosylation site, e.g., at least one N-linked glycosylation site (e.g., an asparagine residue located at about amino acids 190–200, preferably at about amino acid 195, of human PSMA; amino acid residues correspond to the human PSMA sequence disclosed in U.S. Pat. No. 5,538,866).

Cell lines that produce anti-PSMA antibodies, e.g., murine and modified anti-PSMA antibodies, described herein have been deposited with the ATCC. The ATCC designations of the cell lines that produce each of the anti-PSMA antibodies are listed in Table 7.

TABLE 7

| Anti-PSMA Antibody | ATCC Designation |
|---|---|
| E99 | HB-12101 |
| J415 | HB-12109 |
| J533 | HB-12127 |
| J591 | HB-12126 |
| deJ591 | PTA-3709 |
| deJ415 | PTA-4174 |

In a preferred embodiment, the interaction, e.g., binding, occurs with high affinity (e.g., affinity constant of at least $10^7$ $M^{-1}$, preferably, between $10^8$ $M^{-1}$ and $10^{10}$, or about $10^9$ $M^{-1}$) and specificity. Preferably, the anti-PSMA antibody treats, e.g., ablates or kills, a cell, e.g., a PSMA-expressing cell (e.g., a prostatic or cancerous cell). The mechanism by which the anti-PSMA antibody treats, e.g., ablates or kills, the cell is not critical to the practice of the invention. In one embodiment, the anti-PSMA antibody may bind to and be internalized with the PSMA expressed in the cells and/or vascular endothelial cells proximate to the cells. In those embodiments, the anti-PSMA antibody can be used to target a second moiety, e.g., a labeling agent, a labeling agent, or a viral agent, to the cell. In other embodiments, the anti-PSMA antibody may mediate host-mediated-killing, e.g., complement- or ADCC-mediated killing, of the cell and/or the vascular cell proximate thereto, upon binding to the extracellular domain of PSMA. The cell can be killed directly by the anti-PSMA antibody by binding directly to the cell or the vascular endothelial cells proximate thereto. Alternatively, the anti-PSMA antibody can treat, e.g., kill or ablate, or otherwise change the properties of the vascular endothelial cells to which it binds so that blood flow to the cells proximate thereto is reduced, thereby causing the cells to be killed or ablated. Examples of anti-PSMA antibodies include, e.g., monospecific, monoclonal (e.g., human), recombinant or modified, e.g., chimeric, CDR-grafted, humanized, deimmunized, and in vitro generated anti-PSMA antibodies.

As used herein, the term "treat" or "treatment" is defined as the application or administration of an anti-PSMA antibody or antigen binding fragment thereof to a subject, e.g., a patient, or application or administration to an isolated tissue or cell from a subject, e.g., a patient, which is returned to the patient. The anti-PSMA antibody or antigen binding fragment thereof, can be administered alone or in combination with, a second agent. The subject can be a patient having a disorder (e.g., a disorder as described herein), a symptom of a disorder or a predisposition toward a disorder. The treatment can be to cure, heal, alleviate, relieve, alter, remedy, ameliorate, palliate, improve or affect the disorder, the symptoms of the disorder or the predisposition toward the disorder. While not wishing to be bound by theory treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a cancer or prostatic disorder).

As used herein, an amount of an anti-PSMA antibody effective to treat a disorder, or a "therapeutically effective amount" refers to an amount of the antibody which is effective, upon single or multiple dose administration to a subject, in treating a cell, e.g., a prostatic or cancer cell (e.g., a PSMA-expressing prostatic or cancer cell, or a vascular cell proximate thereto), or in prolonging curing, alleviating, relieving or improving a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, an amount of an anti-PSMA antibody effective to prevent a disorder, or a "a prophylactically effective amount" of the antibody refers to an amount of an anti-PSMA antibody, e.g., an anti-PSMA antibody as described herein, which is effective, upon single- or multiple-dose administration to the subject, in preventing or delaying the occurrence of the onset or recurrence of a disorder, e.g., a cancer or prostatic disorder as described herein, or treating a symptom thereof.

The terms "induce", "inhibit", "potentiate", "elevate", "increase", "decrease" or the like, e.g., which denote quantitative differences between two states, refer to a difference, e.g., a statistically or clinically significant difference, between the two states. For example, "an amount effective to inhibit the proliferation of the PSMA-expressing hyperproliferative cells" means that the rate of growth of the cells will be different, e.g., statistically different, from the untreated cells.

As used herein, "specific binding" refers to the property of the antibody to: (1) to bind to PSMA, e.g., human PSMA protein, with an affinity of at least $1 \times 10^7$ $M^{-1}$, and (2) preferentially bind to PSMA, e.g., human PSMA protein, with an affinity that is at least two-fold, 50-fold, 100-fold, 1000-fold, or more greater than its affinity for binding to a non-specific antigen (e.g., BSA, casein) other than PSMA.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901–917, which are incorporated herein by reference). Preferably, each VH and VL is composed of three CDRs and four FRs, arranged from amino-terminus to carboxy-terminus in the following order FR1, CDR1, FR2, CDR2, FR3, CDR3, FR4.

The VH or VL chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a non-human source, e.g., from a non-human antibody, e.g., from a mouse immunoglobulin or another non-human immunoglobulin, from a consensus sequence, or from a sequence generated by phage display, or any other method of generating diversity; and having a framework that is less antigenic in a human than a non-human framework, e.g., in the case of CDRs from a non-human immunoglobulin, less antigenic than the non-human framework from which the non-human CDRs were taken. The framework of the immunoglobulin can be human, humanized non-human, e.g., a mouse, framework modified to decrease antigenicity in humans, or a synthetic framework, e.g., a consensus sequence. These are sometimes referred to herein as modified immunoglobulins. A modified antibody, or antigen binding fragment thereof, includes at least one, two, three or four modified immunoglobulin chains, e.g., at least one or two modified immunoglobulin light and/or at least one or two modified heavy chains. In one embodiment, the modified antibody is a tetramer of two modified heavy immunoglobulin chains and two modified light immunoglobulin chains.

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to a portion of an antibody which specifically binds to PSMA (e.g., human PSMA), e.g., a molecule in which one or more immunoglobulin chains is not full length but which specifically binds to PSMA (e.g., human PSMA protein). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding fragment" of an antibody. These antibody fragments are obtained-using conventional techniques known to those with skill in the art, and the fragments are screened for utility in the same manner as are intact antibodies.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

The term "recombinant" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated (e.g., by phage display) antibodies, and may optionally include constant regions derived from human germline immunoglobulin sequences.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences cab be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444–453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation of the invention) are a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the antibodies and antigen binding fragment thereof of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, J U et al. (1990) *Science* 247:1306–1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Anti-PSMA Antibodies

Many types of anti-PSMA antibodies, or antigen-binding fragments thereof, are useful in the methods of this invention. The antibodies can be of the various isotypes, including: IgG (e.g., IgG1, IgG2, IgG3, IgG4), IgM, IgA1, IgA2, IgD, or IgE. Preferably, the antibody is an IgG isotype, e.g., IgG1. The antibody molecules can be full-length (e.g., an IgG1 or IgG4 antibody) or can include only an antigen-binding fragment (e.g., a Fab, F(ab')$_2$, Fv or a single chain Fv fragment). These include monoclonal antibodies, recombinant antibodies, chimeric antibodies, humanized antibodies, deimmunized antibodies, and human antibodies, as well as antigen-binding fragments of the foregoing.

Monoclonal anti-PSMA antibodies can be used in the methods of the invention. Preferably, the monoclonal antibodies bind to the extracellular domain of PSMA (i.e., an epitope of PSMA located outside of a cell). Examples of preferred murine monoclonal antibodies to human PSMA include, but are not limited to, E99, J415, J533 and J591, which are produced by hybridoma cell lines having an ATCC Accession Number HB-12101, HB-12109, HB-12127, and HB-12126, respectively, all of which are disclosed in U.S. Pat. No. 6,107,090 and U.S. Pat. No. 6,136,311, the contents of which are expressly incorporated by reference. Most preferably, the murine monoclonal antibody is J591, produced by HB-12126.

Additional monoclonal antibodies to PSMA can be generated using techniques known in the art. Monoclonal antibodies can be produced by a variety of techniques, including conventional monoclonal antibody methodology e.g., the standard somatic cell hybridization technique of Kohler and Milstein, *Nature* 256: 495 (1975). See generally, Harlow, E. and Lane, D. (1988) *Antibodies: A Laboratory Manual*, Cold Spring Harbor Laboratory Press, Cold Spring Harbor, N.Y.

Useful immunogens for the purpose of this invention include PSMA (e.g., human PSMA)-bearing cells (e.g., a prostate tumor cell line, e.g., LNCap cells, or fresh or frozen prostate tumor cells); membrane fractions of PSMA-expressing cells (e.g., a prostate tumor cell line, e.g., LNCap cells, or fresh or frozen prostate tumor cells); isolated or purified PSMA, e.g., human PSMA protein (e.g., biochemically isolated PSMA, or a portion thereof, e.g., the extracellular domain of PSMA). Techniques for generating antibodies to PSMA are described in U.S. Pat. No. 6,107,090, U.S. Pat. No. 6,136,311, the contents of all of which are expressly incorporated by reference.

Human monoclonal antibodies (mAbs) directed against human proteins can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

Anti-PSMA antibodies or fragments thereof useful in the present invention may also be recombinant antibodies produced by host cells transformed with DNA encoding immunoglobulin light and heavy chains of a desired antibody. Recombinant antibodies may be produced by known genetic engineering techniques. For example, recombinant antibodies may be produced by cloning a nucleotide sequence, e.g., a cDNA or genomic DNA, encoding the immunoglobulin light and heavy chains of the desired antibody. The nucleotide sequence encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding", *Ann. Rev. Biochem.* 51, pp. 459–89 (1982)). It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for PSMA binding, e.g., the constant region may be modified by, for example, deleting specific amino acids. The molecules expressed from such truncated DNA molecules are useful in the methods of this invention. In addition, bifunctional antibodies may be produced in which one heavy and one light chain are anti-PSMA antibody and the other heavy and light chain are specific for an antigen other than PSMA, or another epitope of PSMA.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J. Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

An antibody or an immunoglobulin chain can be humanized by methods known in the art Once the murine antibodies are obtained, the variable regions can be sequenced. The location of the CDRs and framework residues can be determined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901–917, which are incorporated herein by reference). The light and heavy chain variable regions can, optionally, be ligated to corresponding constant regions.

Murine anti-PSMA antibodies can be sequenced using art-recognized techniques. As an example, hybridomas expressing murine hybridomas J533, J415 and E99 were propagated in culture in RPMI 1640 medium supplemented with 10% fetal calf serum. The isotype of the antibodies secreted was confirmed as IgG1κ, IgG1κ, and IgG3κ respectively. These monoclonal antibodies, like J591, bind to the external domain of prostate specific membrane antigen. J591, J533 and E99 recognize the same epitope, while J415 recognizes an independent epitope. Total RNA for each monoclonal was prepared from $10^7$ hybridoma cells. $V_H$ and $V_K$ cDNA was prepared using reverse transcriptase and mouse κ constant region and mouse IgG constant region primers. The first strand cDNAs were amplified by PCR using a variety of mouse signal sequence primers (6 for $V_H$ and 7 for $V_K$). The amplified DNAs were gel-purified and cloned into the vector pT7Blue. The $V_H$ and $V_K$ clones obtained were screened for correct inserts by PCR and the DNA sequence of selected clones determined by the dideoxy chain termination method (see Table 7).

The DNA and amino acid sequences for the heavy and light chain variable regions from J415 were obtained and are shown in FIGS. 7B ($V_H$) and 8B ($V_K$) (also, see Table 5). The location of the CDRs is shown. J415 $V_H$ can be assigned to Mouse Heavy Chains Subgroup IIIC (Kabat E A et al; ibid). The sequence of J415 $V_H$ compared to the consensus sequence for this subgroup is shown in FIG. 7C. J415 $V_K$ can be assigned to Mouse Kappa Chains Subgroup I (Kabat E A et al; ibid). The sequence of J415 $V_K$ compared to the consensus sequence for this subgroup is shown in FIG. 8C.

The DNA and amino acid sequences encoding the heavy and light chain variable regions J533 were obtained and are shown in FIGS. 9A ($V_H$) and 10A ($V_K$) (see also Table 5). The location of the CDRs is shown in each figure. J533 $V_H$ can be assigned to Mouse Heavy Chains Subgroup IIA (Kabat E A et al; Sequences of proteins of Immunological Interest, US Department of Health and Human Services, 1991). The sequence of J533 $V_H$ compared to the consensus sequence for this subgroup is shown in FIG. 9B. J533 $V_K$ can be assigned to Mouse Kappa Chains Subgroup III (Kabat E A et al; ibid). The sequence of J533 $V_K$ compared to the consensus sequence for this subgroup is shown in FIG. 10B.

The DNA and amino acid sequences of the heavy and light chain variable regions of E99 were obtained and are shown in FIGS. 11A ($V_H$) and 12A ($V_K$) (see also Table 5). The location of the CDRs is shown. E99 $V_H$ can be assigned to Mouse Heavy Chains Subgroup IB (Kabat E A et al; ibid). The sequence of E99 $V_H$ compared to the consensus sequence for this subgroup is shown in FIG. 11B. E99 $V_K$ can be assigned Mouse Kappa Chains Subgroup I (Kabat E A et al; ibid). The sequence of E99 $V_K$ compared to the consensus sequence for this subgroup is shown in FIG. 12B.

The amino acid sequence and nucleotide sequences encoding the variable region of antibodies J415, deJ415, J591, deJ591, J533 and E99 are provided below in Table 8.

TABLE 8

Antibody variable chain sequences

| NAME | Organism | FIG. | SEQ ID NO: | SEQUENCE |
|---|---|---|---|---|
| $V_H$J415 | *Mus musculas* | FIG. 7B | 125 | gaagtgaagcttgaggagtctggaggaggcttggtgcaacctgg aggatccatgaaactctcctgtgttgcctctggattcactttcagtaat tactggatgaactgggtccgccagtctccagagaaggggcttgag tgggttgctgaaattagatcgcaatctaataattttgcaacacattatg cggagtctgtgaaagggagggtcatcatctcaagagatgattcca agagtagtgtctacctgcaaatgaacaacttgagagctgaagaca ctggcatttattactgtaccaggcgatggaataatttctggggccaa ggcaccactctcacagtctcctca |
| $V_H$Variable Region J591 | *Mus musculus* | FIG. 1A | 19 | EVQLQQSGPELKKPGTSVRISCKTSGYTFT EYTIHWVKQSHGKSLEWIGNINPNNGGTT YNQKFEDKATLTVDKSSSTAYMELRSLTS EDSAVYYCAAGWNFDYWGQGTTLTVSS |
| $V_H$J415 (complementary strand of SEQ ID NO: 125) | *Mus musculus* | FIG. 7B | 126 | tgaggagactgtgagagtggtgccttggccccagaaattattccat cgcctggtacagtaataaatgccagtgtcttcagctctcaagttgttc atttgcaggtagacactactcttggaatcatctcttgagatgatgacc ctcccttcacagactccgcataatgtgttgcaaaattattagattgc gatctaatttcagcaacccactcaagcccttctctggagactggc ggacccagttcatccagtaattactgaaagtgaatccagaggcaa cacaggagagtttcatggatcctccaggttgcaccaagcctcctcc agactcctcaagcttcacttc |
| $V_L$J415 | *Mus musculus* | FIG. 8B | 127 | aacattgtaatgacccaatttcccaaatccatgtccatttcagtagga gagagggtcaccttgacctgcaaggccagtgagaatgtgggtact tatgtgtcctggtatcaacagaaaccagaacagtctcctaagatgtt gatatacgggcatccaaccggttcactggggtccccgatcgctt cacaggcagtggatctgcaacagatttcattctgaccatcagcagt gtgcagactgaagaccttgtagattattactgtggacagagttacac ctttccgtacacgttcggagggggggaccaagctggaaatgaag |

TABLE 8-continued

Antibody variable chain sequences

Figures 2, 4A:
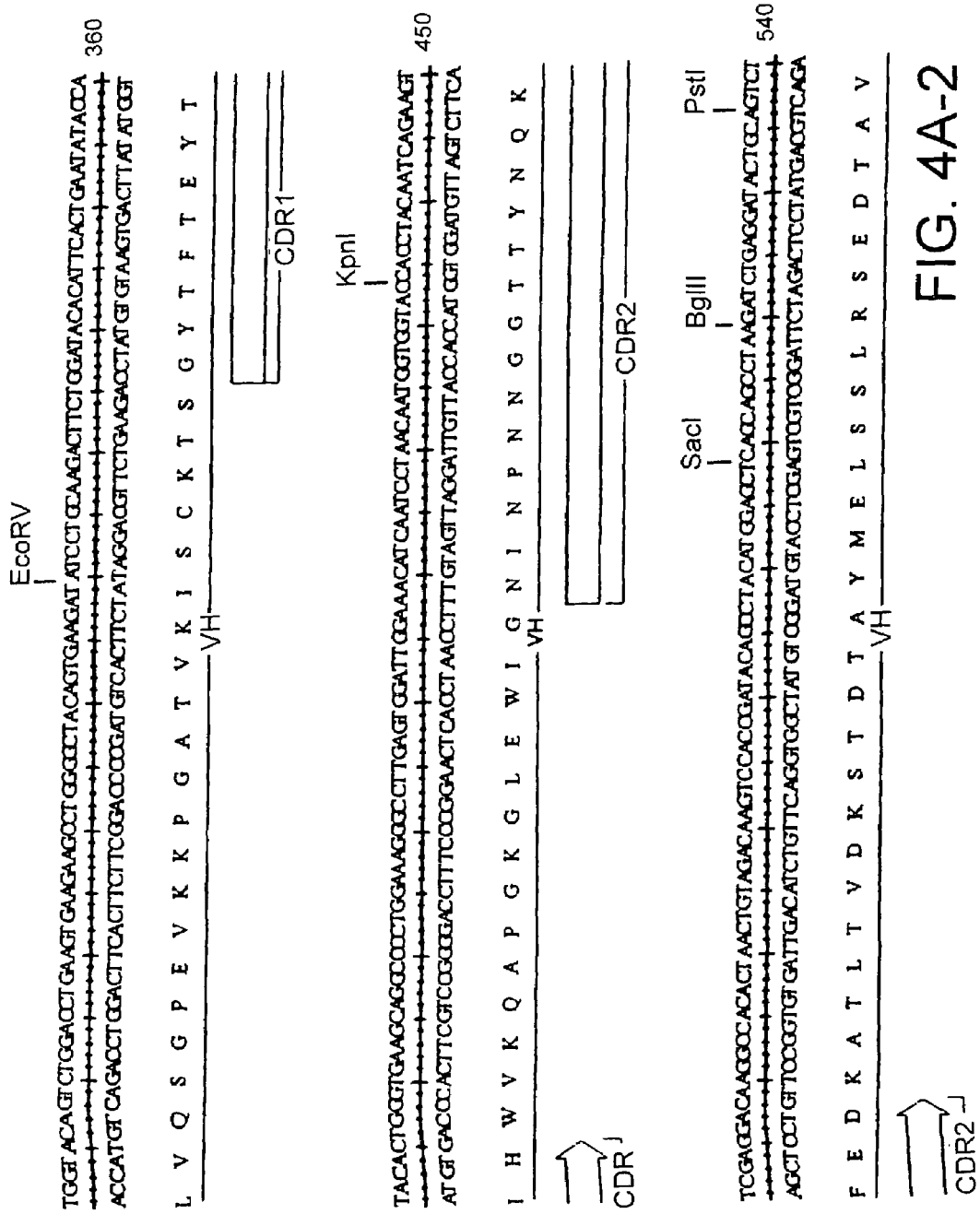

| NAME | Organism | FIG. | SEQ ID NO: | SEQUENCE |
|---|---|---|---|---|
| V_L Variable Region J591 | Mus musculus | FIG. 1B | 20 | DIVMTQSHKFMSTSVGDRVSIICKASQDV GTAVDWYQQKPGQSPKLLIYWASTRHTG VPDRFTGSGSGTDFTLTTTNVQSEDLADYF CQQYNSYPLTFGAGTMLDLK |
| V_L J415 (complementary strand of SEQ ID NO: 127) | Mus musculus | FIG. 8B | 128 | cttcatttccagcttggtccccctccgaacgtgtacggaaaggtgt aactctgtccacagtaataatctacaaggtcttcagtctgcacactg ctgatggtcagaatgaaatctgttgcagatccactgcctgtgaagc gatcggggaccccagtgaaccggttggatgccccgtatatcaaca tcttaggagactgttctggtttctgttgataccaggacataagtac ccacattctcactggccttgcaggtcaaggtgaccctctctcctact gaaatggacatggatttgggaaattgggtcattacaatgtt |
| V_H Variable Region (Deimm) J591 | Artificial - deimmunized heavy chain J591 | FIG. 2A | 21 | EVQLVQSGPEVKKPGATVKISCKTSGYTFT EYTIHWVKQAPGKGLEWIGNINPNNGGTT YNQKFEDKATLTVDKSTDTAYMELSSLRS EDTAVYYCAAGWNFDYWGQGTLLTVSS |
| V_L Variable Region (Deimm) J591 | Artificial - deimmunized light chain J591 | FIG. 2B | 22 | DIQMTQSPSSLSTSVGDRVTLTCKASQDV GTAVDWYQQKPGPSPKLLIYWASTRHTGI PSRFSGSGSGTDFTLTISSLQPEDFADYYCQ QYNSYPLTFGPGTKVDIK |
| V_H Deimmunized J591 CDS (122– 166) & CDS (249– 605) | Artificial - deimmunized heavy chain J591 | FIG. 4A | 23 | aagcttatgaatatgcaaatcctctgaatctacatggtaaatataggt ttgtctataccacaaacagaaaaacatgagatcacagttctctctac agttactgagcacacaggacctcaccatgggatggagctgtatcat cctcttcttggtagcaacagctacaggtaaggggctcacagtagca ggcttgaggtctggacatatatatgggtgacaatgacatccactttg cctttctctccacaggtgtccactccgaggtccaactggtacagtct ggacctgaagtgaagaagcctggggctacagtgaagatatcctg caagacttctggatacacattcactgaatataccatacactgggtga agcaggcccctggaaagggccttgagtggattggaaacatcaatc ctaacaatggtggtaccacctacaatcagaagttcgaggacaagg ccacactaactgtagacaagtccaccgatacagcctacatggagc tcagcagcctaagatctgaggatactgcagtctattattgtgcagct ggttggaactttgactactggggccaagggaccctgctcaccgtct cctcaggtgagtccttacaacctctctcttctattcagcttaaatagat tttactgcatttgttgggggggaaatgtgtgtatctgaatttcaggtca tgaaggactagggacaccttgggagtcagaaagggtcattggga gcccgggctgatgcagacagacatcctcagctcccagacttcatg gccagagatttataggatcc |

TABLE 8-continued

Antibody variable chain sequences

Figures 3, 4A:
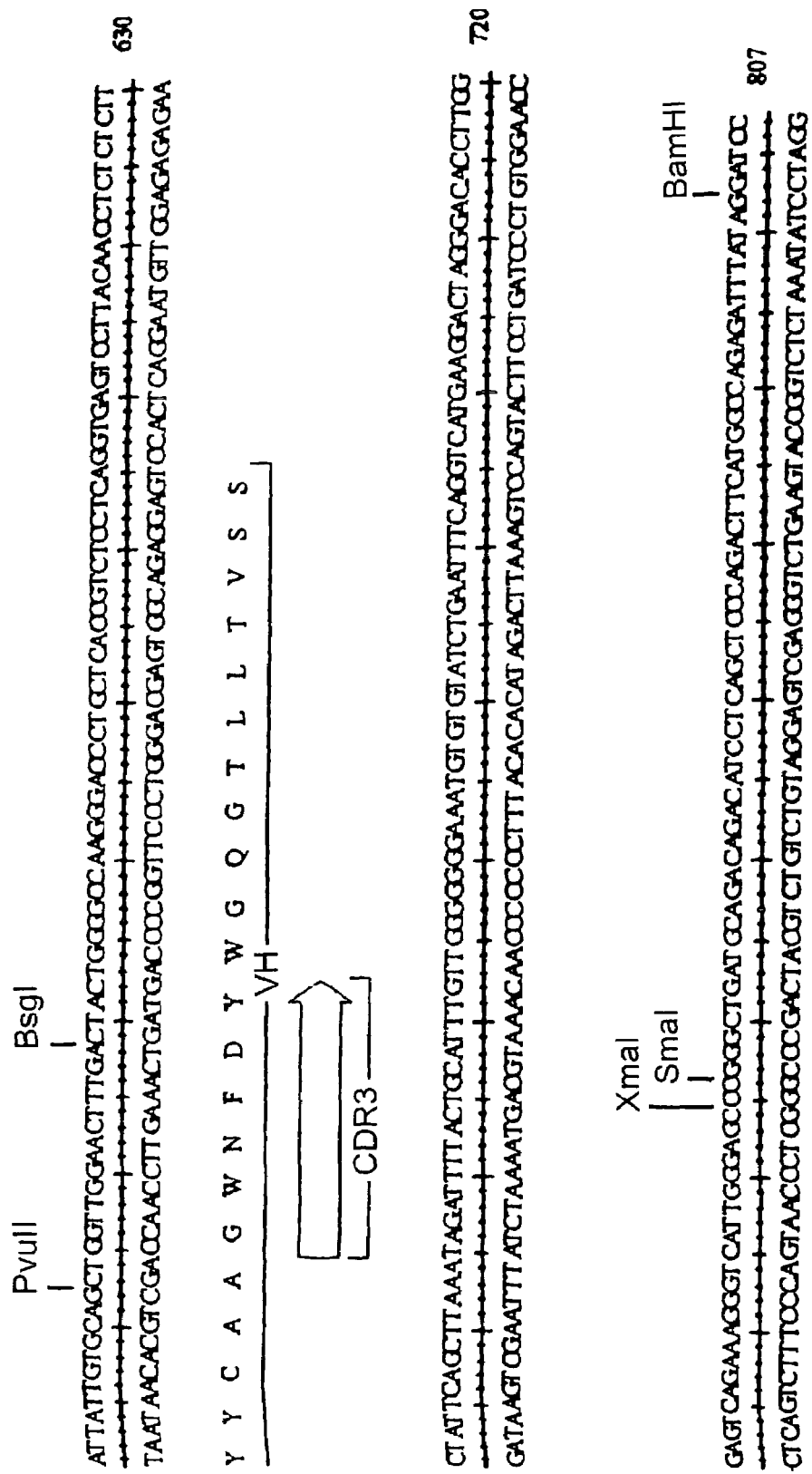
Figures 1, 4B:
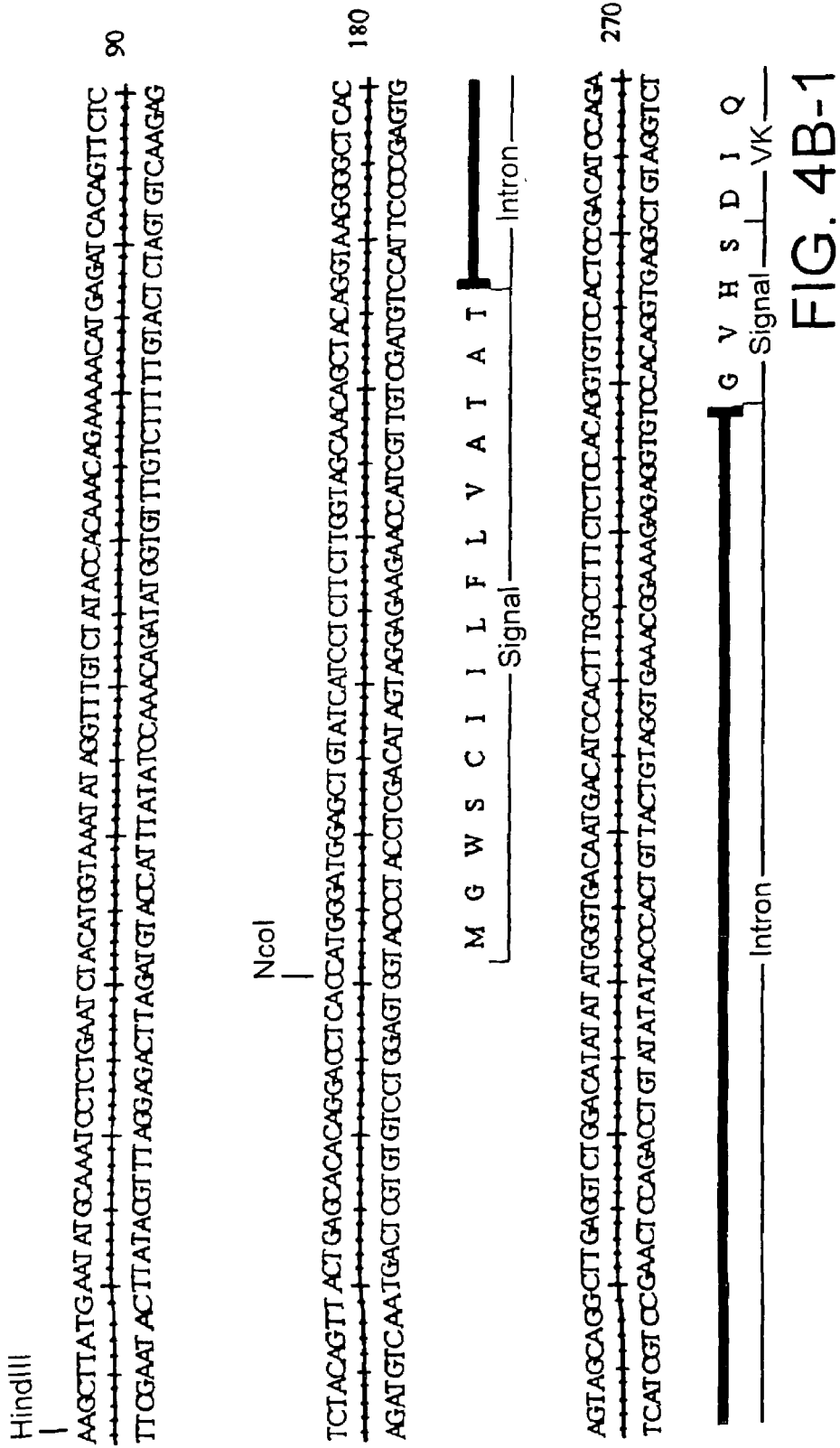
Figures 2, 4B:
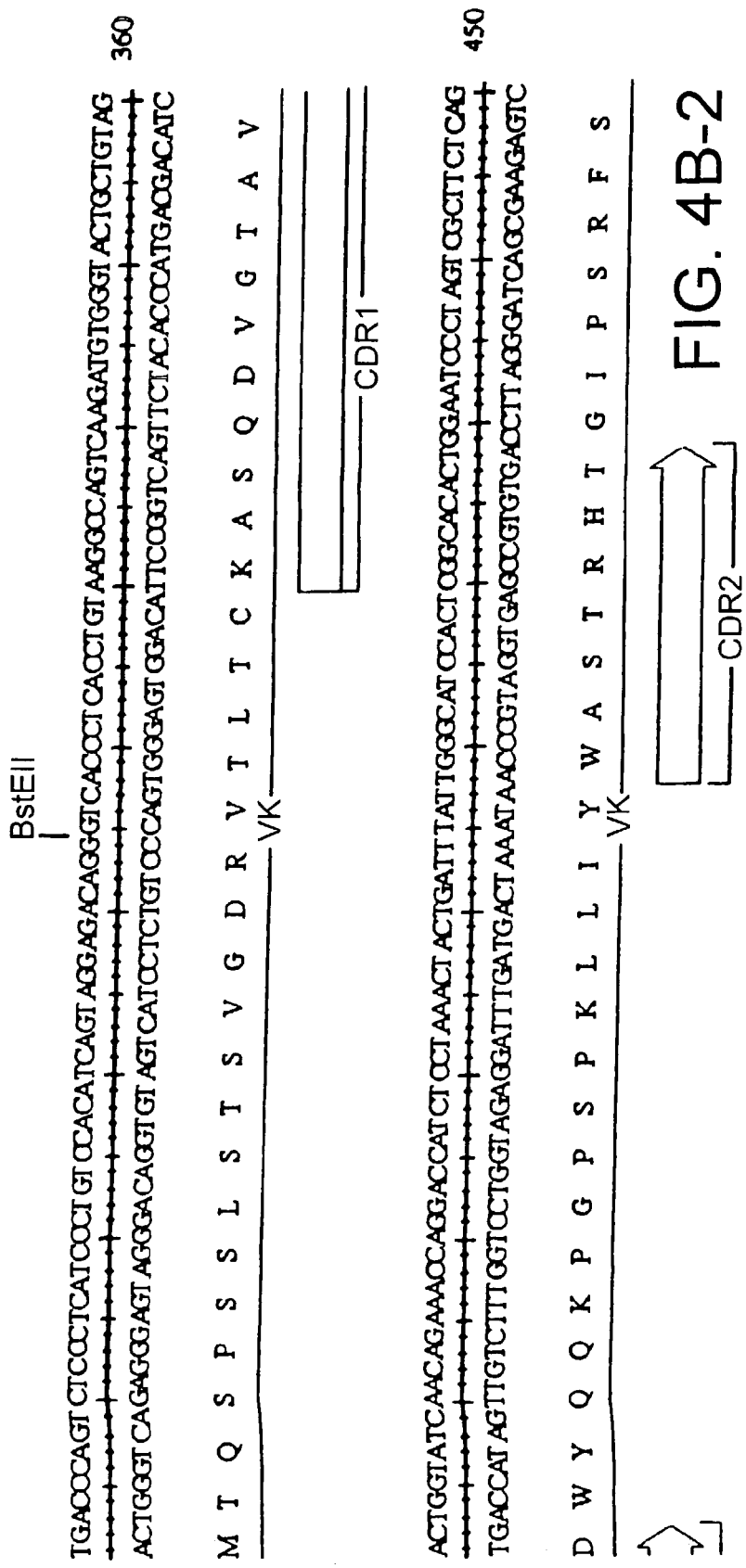

| NAME | Organism | FIG. | SEQ ID NO: | SEQUENCE |
|---|---|---|---|---|
| V_H Deimmunized (complimentary strand of SEQ ID NO: 23) J591 | Artificial - deimmunized heavy chain J591 | FIG. 4A | 24 | ggatcctataaatctctggccatgaagtctgggagctgaggatgtc tgtctgcatcagcccgggctcccaatgacccttctgactcccaag gtgtccctagccttcatgacctgaaattcagatacacacatttcccc cccaacaaatgcagtaaaatctatttaagctgaatagaagagagag gttgtaaggactcacctgaggagacggtgagcagggtcccttggc cccagtagtcaaagttccaaccagctgcacaataatagactgcagt atcctcagatcttaggctgctgagctccatgtaggctgtatcggtgg acttgtctacagttagtgtggccttgtcctcgaacttctgattgtaggt ggtaccaccattgttaggattgatgtttccaatccactcaaggcccttt tccaggggcctgcttcacccagtgtatggtatattcagtgaatgtgt atccagaagtcttgcaggatatcttcactgtagccccaggcttcttc acttcaggtccagactgtaccagttggacctcggagtggacacct gtggagagaaaggcaagtggatgtcattgtcacccatatatatgt ccagacctcaagcctgctactgtgagccccttacctgtagctgttgc taccaagaagaggatgatacagctccatcccatggtgaggtcctgt gtgctcagtaactgtagagagaactgtgatctcatgtttttctgtttgt ggtatagacaaacctatatttaccatgtagattcagaggatttgcata ttcataagctt |
| V_L Deimmunized J591 CDS (122– 166) & CDS (249– 581) | Artificial - deimmunized light chain J591 | FIG. 4B | 25 | aagcttatgaatatgcaaatcctctgaatctacatggtaaatataggt ttgtctataccacaaacagaaaaacatgagatcacagttctctctac agttactgagcacacaggacctcaccatgggatggagctgtatcat cctcttcttggtagcaacagctacaggtaaggggctcacagtagca ggcttgaggtctggacatatatatgggtgacaatgacatccactttg cctttctctccacaggtgtccactccgacatccagatgacccagtct ccctcatccctgtccacatcagtaggagacagggtcaccctcacct gtaaggccagtcaagatgtgggtactgctgtagactggtatcaaca gaaaccaggaccatctcctaaactactgatttattgggcatccactc ggcacactggaatccctagtcgcttctcaggcagtggatctggga cagacttcactctcaccatttctagtcttcagcctgaagactttgcag attattactgtcagcaatataacagctatcctctcacgttcggtcctg ggaccaaggtggacatcaaacgtgagtagaatttaaactttgcttc ctcagttggatcc |
| V_L Deimmunized (complimentary strand of J591 | Artificial - deimmunized light chain J591 | FIG. 4B | 26 | ggatccaactgaggaagcaaagtttaaattctactcacgtttgatgt ccaccttggtcccaggaccgaacgtgagaggatagctgttatattg ctgacagtaataatctgcaaagtcttcaggctgaagactagaaatg gtgagagtgaagtctgtcccagatccactgcctgagaagcgacta |

TABLE 8-continued

Antibody variable chain sequences

Figure 5:
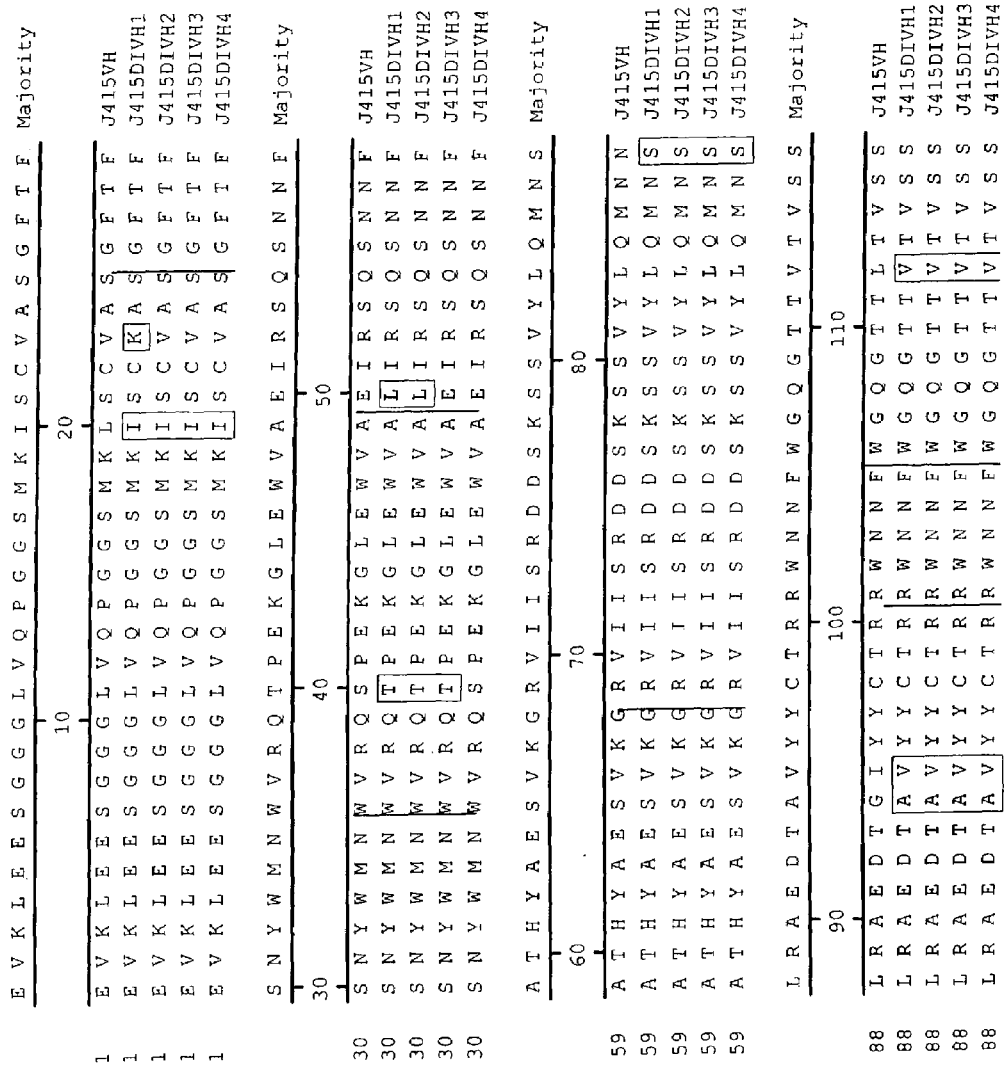
FIG. 5 depicts an alignment of the amino acid sequences for the murine and several deimmunized heavy chain variable regions of the J415 antibody. The murine amino acid sequence is shown as J415VH (SEQ ID NO:47); the deimmunized sequences are depicted as J415DIVH1 (amino acid residues 18 to 133 of SEQ ID NO:54), J415DIVH2 (SEQ ID NO:59), J415DIVH3 (SEQ ID NO:60), and J415DIVH4 (SEQ ID NO:49). The preferred sequence is J415DIVH4 (SEQ ID NO:49). The amino acid replacements are indicated by the boxed residues. A consensus sequence is labeled "majority" (SEQ ID NO:61).

| NAME | Organism | FIG. | SEQ ID NO: | SEQUENCE |
|---|---|---|---|---|
| SEQ ID NO: 25) J591 | | | | gggattccagtgtgccgagtggatgcccaataaatcagtagtttag gagatggtcctggtttctgttgataccagtctacagcagtacccaca tcttgactggccttacaggtgagggtgaccctgtctcctactgatgt ggacagggatgagggagactgggtcatctggatgtcggagtgga cacctgtggagagaaaggcaaagtggatgtcattgtcacccatata tatgtccagacctcaagcctgctactgtgagccccttacctgtagct gttgctaccaagaagaggatgatacagctccatcccatggtgagg tcctgtgtgctcagtaactgtagagagaactgtgatctcatgtttttct gtttgtggtatagacaaacctatatttaccatgtagattcagaggattt gcatattcataagctt |
| $V_H$ Deimmunized (predicted a.a. of SEQ ID NO: 23) J591 | Artificial - deimmunized heavy chain J591 | FIG. 4A | 27 | MGWSCIILFLVATATGVHSEVQLVQSGPE VKKPGATVKISCKTSGYTFTEYTIHWVKQ APGKGLEWIGNINPNNGGTTYNQKFEDKA TLTVDKSTDTAYMELSSLRSEDTAVYYCA AGWNFDYWGQGTLLTVSS |
| $V_L$ Deimmunized (predicted a.a. of SEQ ID NO: 25) J591 | Artificial - deimmunized light chain J591 | FIG. 4B | 28 | MGWSCIILFLVATATGVHSDIQMTQSPSSL STSVGDRVTLTCKASQDVGTAVDWYQQK PGPSPKLLIYCASTRHTGIPSRFSGSGSGTD FTLTISSLQPEDFADYYCQQYNSYPLTFGP GTKVDIK |
| $V_H$ Variable Region J415 | Mus musculus | FIG. 5 | 47 | EVKLEESGGGLVQPGGSMKLSCVASGFTF SNYWMNWVRQSPEKGLEWVAEIRSQSNN FATHYAESVKGRVIISRDDSKSSVYLQMN NLRAEDTGIYYCTRRWNNFWGQGTTLTV SS |
| $V_L$ Variable Region J415 | Mus musculus | FIG. 6 | 48 | NIVMTQFPKSMSISVGERVTLTCKASENVG TYVSWYQQKPEQSPKMLIYGASNRFTGVP DRFTGSGSATDFILTISSVQTEDLVDYYCG QSYTFPYTFGGGTKLEMK |
| $V_H$ Variable Region (Deimm) J415-4 | Artificial - deimmunized heavy chain J415-4 | FIG. 5 | 49 | EVKLEESGGGLVQPGGSMKISCVASGFTFS NYWMNWVRQSPEKGLEWVAEIRSQSNNF ATHYAESVKGRVIISRDDSKSSVYLQMLNS LRAEDTAVYYCTRRWNNFWGQGTTVTVS S |

TABLE 8-continued

Antibody variable chain sequences

Figures 1, 7A:
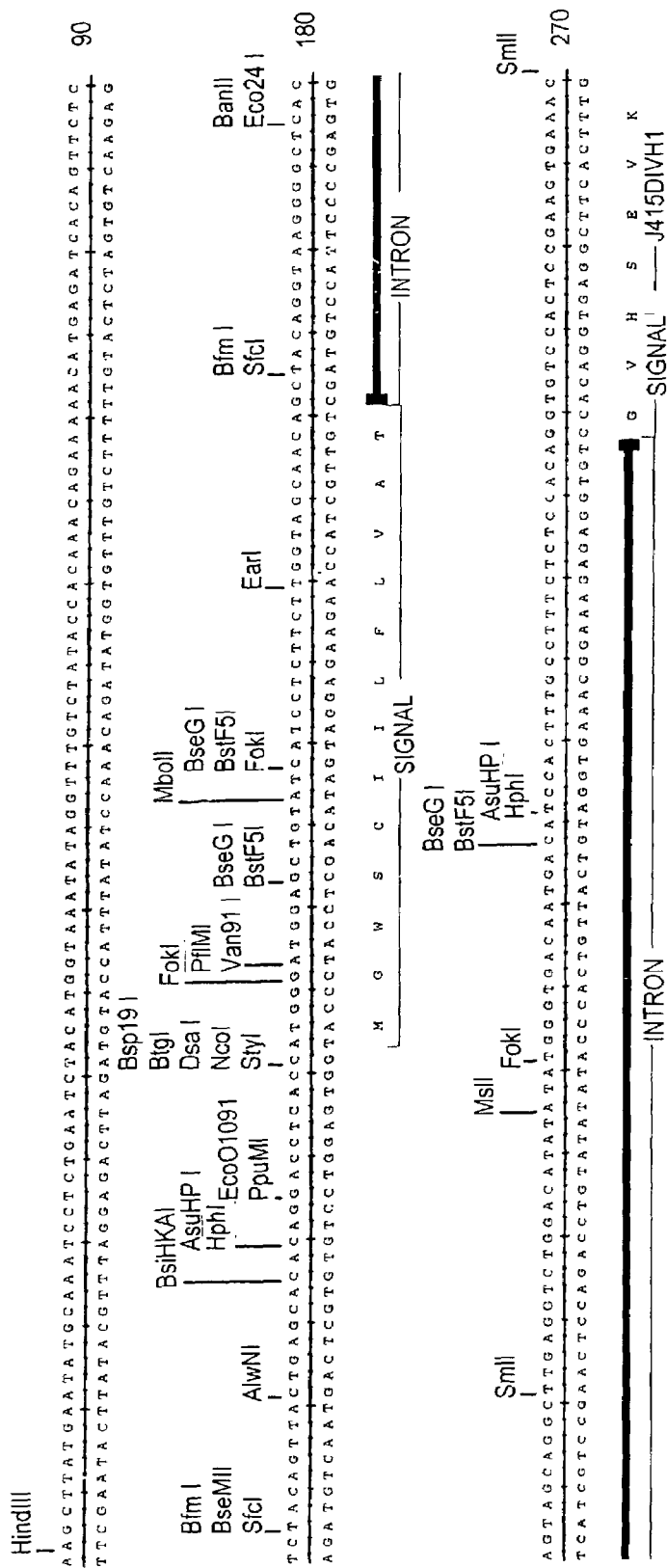
FIG. 7A depicts the nucleic acid coding sequence, the amino acid sequence, and the nucleic acid reverse complement sequence of the deimmunized J415 heavy chain variable region (J415DIVH1) (SEQ ID NO:53–55, respectively). The relative location of the signal sequence, intron and J415DIVH1 amino acid sequence is indicated, as well as some restriction sites.
Figures 2, 7A:
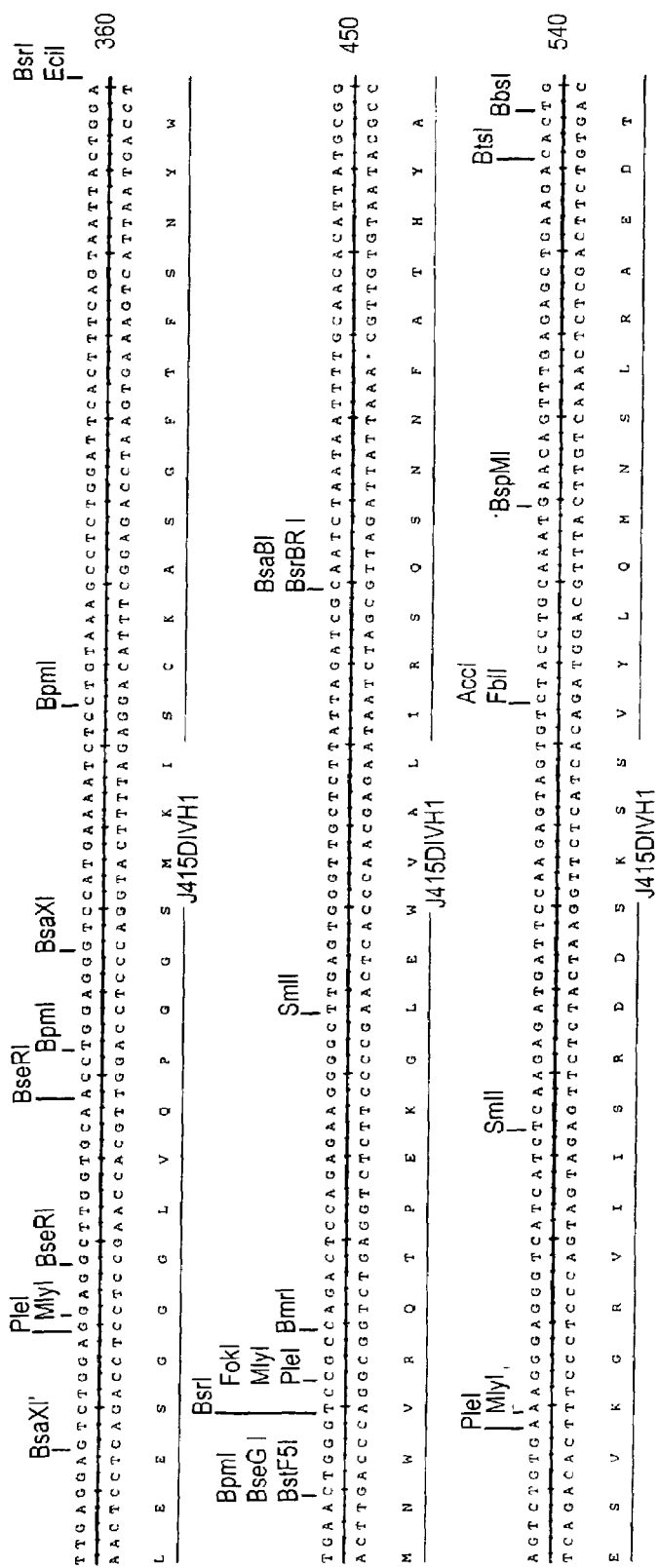
Figure 8C:
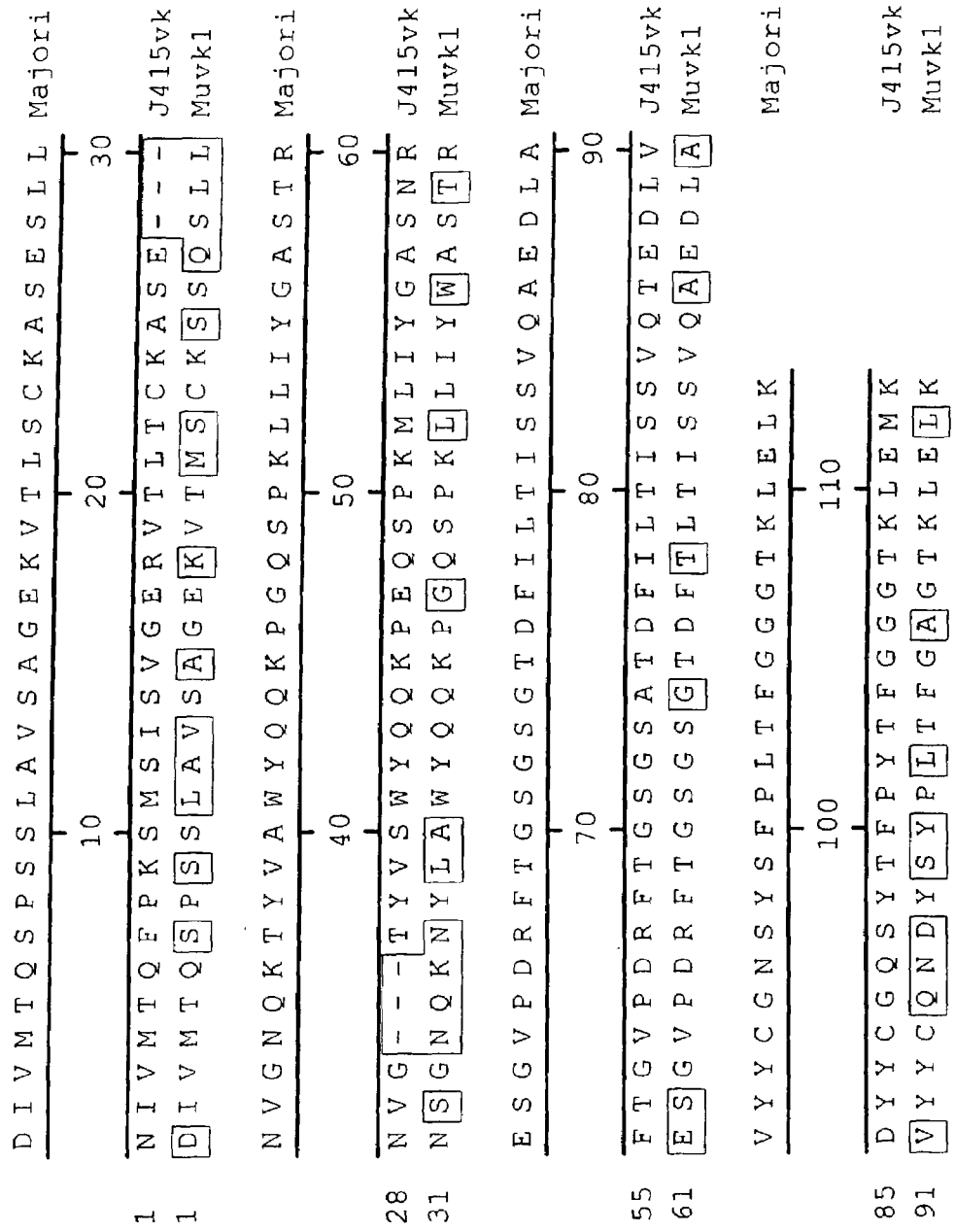
FIG. 8C depicts an alignment of the amino acid sequence of the murine J415 light chain variable region (SEQ ID NO:48) and a consensus sequence for Kabat subgroup murine variable light chain (MuVKI, SEQ ID NO:71). A consensus majority sequence based on the alignment is also shown (SEQ ID NO:72).

| NAME | Organism | FIG. | SEQ ID NO: | SEQUENCE |
|---|---|---|---|---|
| V$_L$ Variable Region (Deimm) J415-5 | Artificial - deimmunized light chain J415-5 | FIG. 6 | 50 | NIVMTQFPKSMSASAGERMTLTCKASENV GTYVSWYQQKPTQSPKMLIYGASNRFTGV PDRFSGSGSGTDFILTISSVQAEDLVDYYC GQSYTFPYTFGGGTKLEMK |
| V$_H$ Deimmunized J415-4 | Artificial - deimmunized heavy chain J415-4 | | 51 | gaagtgaaacttgaggagtctggaggaggcttggtgcaacctgg agggtccatgaaaatctcctgtgttgcctctggattcactttcagtaa ttactggatgaactgggtccgccagtctccagagaaggggcttga gtgggttgctgaaattagatcgcaatctaataattttgcaacacattat gcggagtctgtgaaagggagggtcatcatctcaagagatgattcc aagagtagtgtctacctgcaaatgaacagtttttgagagctgaagaca ctgccgtttattactgtaccaggcgatggaataatttctggggccaa ggcaccactgtcacagctcctca |
| V$_L$ Deimmunized J415-5 | Artificial - deimmunized light chain J415-5 | | 52 | aacattgtaatgacccaatttcccaaatccatgtccgcctcagcagg agagaggatgaccttgacctgcaaggccagtgagaatgtgggta cttatgtgcctggtatcaacagaaaccaacacagtctcctaagatg ttgatatacggggcatccaaccggttcactggggtcccagatcgct tctccggcagtggatctggaacagatttcattctgaccatcagcagt gtgcaggcagaagaccttgtagattattactgtggacagagttaca cctttccgtacacgttcggaggggggaccaagctggaaatgaag |
| V$_H$ Deimmunized J415-1 CDS (122– 160) & CDS (249– 608) Mature (18– 133) | Artificial - deimmunized heavy chain J415-1 | FIG. 7A | 53 | aagcttatgaatatgcaaatcctctgaatctacatggtaaatataggt ttgtctataccacaaacagaaaaacatgagatcacagttctctctac agttactgagcacacaggacctcaccatgggatggagctgtatca tcctcttcttggtagcaacagctacaggtaaggggctcacagtagc aggcttgaggtctggacatatatatgggtgacaatgacatccacttt gcctttctctccacaggtgtccactccgaagtgaaacttgaggagt ctggaggaggcttggtgcaacctggagggtccatgaaaatctcct gtaaagcctctggattcactttcagtaattactggatgaactgggtcc gccagactccagagaaggggcttgagtgggttgctcttattagatc gcaatctaataattttgcaacacattatgcggagtctgtgaaaggga gggtcatcatctcaagagatgattccaagagtagtgtctacctgca aatgaacagtttgagagctgaagacactgccgtttattactgtacca ggcgatggaataatttctggggccaaggcaccactgtcacagtct cctcaggtgagtccttacaacctctctcttctattcagcttaaatagat tttactgcatttgttggggggggaaatgtgtgtatctgaatttcaggtca tgaaggactagggacaccttgggagtcagaaagggtcattggga |

TABLE 8-continued

Antibody variable chain sequences

| NAME | Organism | FIG. | SEQ ID NO: | SEQUENCE |
|---|---|---|---|---|
| | | | | gcccgggctgatgcagacagacatcctcagctcccagacttcatg |
| | | | | gccagagatttataggatcc |
| V_H Deimmunized (predicted a.a. of SEQ ID NO: 53) J415-1 | Artificial - deimmunized heavy chain J415-1 | FIG. 7A | 54 | MGWSCIILFLVATGVHSEVKLEESGGGLV QPGGSMKISCKASGFTFSNYWMNWVRQT PEKGLEWVALIRSQSNNFATHYAESVKGR VIISRDDSKSSVYLQMNSLRAEDTAVYYC TRRWNNFWGQGTTVTVSS |
| V_H Deimmunized (complimentary strand of SEQ ID NO: 53) J415-1 | Artificial - deimmunized heavy chain J415-1 | FIG. 7A | 55 | ggatcctataaatctctggccatgaagtctgggagctgaggatgtc tgtctgcatcagcccgggctcccaatgacccttctgactcccaag gtgtccctagtccttcatgacctgaaattcagatacacacatttcccc cccaacaaatgcagtaaaatctatttaagctgaatagaagagag gttgtaaggactcacctgaggagactgtgacagtggtgccttggc cccagaaattattccatcgcctggtacagtaataaacggcagtgtct tcagctctcaaactgttcatttgcaggtagacactactcttggaatca tctcttgagatgatgaccctccctttcacagactccgcataatgtgtt gcaaaattattagattgcgatctaataagagcaacccactcaagcc ccttctctggagtctggcggacccagttcatccagtaattactgaaa gtgaatccagaggctttacaggagattttcatggaccctccaggttg caccaagcctcctccagactcctcaagtttcacttcggagtggaca cctgtggagagaaaggcaaagtggatgtcattgtcacccatatata tgtccagacctcaagcctgctactgtgagccccttacctgtagctgt tgctaccaagaagaggatgatacagctccatcccatggtgaggtc ctgtgtgctcagtaactgtagagagaactgtgatctcatgtttttctgt ttgtggtatagacaaacctatatttaccatgtagattcagaggatttg catattcataagctt |
| V_L Deimmunized J415-1 CDS (122– 160) & CDS (249– 581) | Artificial - deimmunized light chain J415-1 | FIG. 8A | 56 | aagcttatgaatatgcaaatcctctgaatctacatggtaaatataggt ttgtctataccacaaacagaaaaacatgagatcacagttctctctac agttactgagcacacaggacctcaccatgggatggagctgtatca tcctcttcttggtagcaacagctacaggtaaggggctcacagtagc aggcttgaggtctggacatatatatgggtgacaatgacatccacttt gcctttctctccacaggtgtccactccaacattgtaatgacccaatc ccccaaatccatgtccgcctcagcaggagagaggatgaccttgac ctgcaaggccagtgagaattccggtacttatgtgtcctggtatcaac agaaaccaacacagtctcctaagatgttgatatacggggcatccaa ccggttcactggggtcccagatcgcttctccggcagtggatctgga |

TABLE 8-continued

Antibody variable chain sequences

| NAME | Organism | FIG. | SEQ ID NO: | SEQUENCE |
|---|---|---|---|---|
| | | | | acagatttcattctgaccgccagcagtgtgcaggcagaagaccct |
| | | | | gtagattattactgtggacagagttacacctttccgtacacgttcgga |
| | | | | gggggaccaagctggaaatgaagcgtgagtagaatttaaacttt |
| | | | | gcttcctcagttggatcc |
| V_L Deimmunized (predicted a.a. of SEQ ID NO: 56) J415-1 | Artificial - deimmunized light chain J415-1 | FIG. 8A | 57 | MGWSCIILFLVATGVHSNIVMTQSPKSMS ASAGERMTLTCKASENSGTYVSWYQQKP TQSPKMLIYGASNRFTGVPDRFSGSGSGTD FILTASSVQAEDPVDYYCGQSYTFPYTFGG GTKLEMK |
| V_L Deimmunized (complimentary strand of SEQ ID NO: 56) J415-1 | Artificial - deimmunized light chain J415-1 | FIG. 8A | 58 | ggatccaactgaggaagcaaagtttaaattctactcacgcttcatttc cagcttggtccccctccgaacgtgtacggaaaggtgtaactctgt ccacagtaataatctacagggtcttctgcctgcacactgctggcgg tcagaatgaaatctgttccagatccactgccggagaagcgatctgg gaccccagtgaaccggttggatgccccgtatatcaacatcttagga gactgtgttggtttctgttgataccaggacacataagtaccggaatt ctcactggccttgcaggtcaaggtcatcctctctcctgctgaggcg gacatggatttgggggattgggtcattacaatgttggagtggacac ctgtggagagaaaggcaaagtggatgtcattgtcacccatatatat gtccagacctcaagcctgctactgtgagccccttacctgtagctgtt gctaccaagaagaggatgatacagctccatcccatggtgaggtcc tgtgtgctcagtaactgtagagagaactgtgatctcatgtttttctgttt gtggtatagacaaacctatatttaccatgtagattcagaggatttgca tattcataagctt |
| V_H Deimmunized J415-2 | Artificial - deimmunized heavy chain J415-2 | FIG. 5 | 59 | EVKLEESGGGLVQPGGSMKISCVASGFTFS NYWMNWVRQTPEKGLEWVALIRSQSNNF ATHYAESVKGRVIISRDDSKSSVYLQMNS LRAEDTAVYYCTRRWNNFWGQGTTVTVS S |
| V_H Deimmunized J415-3 | Artificial - deimmunized heavy chain J415-3 | FIG. 5 | 60 | EVKLEESGGGLVQPGGSMKISCVASGFTFS NYWMNWVRQTPEKGLEWVAEIRSQSNNF ATHYAESVKGRVIISRDDSKSSVYLQMNS LRAEDTAVYYCTRRWNNFWGQGTTVTVS S |
| J415 V_H(DI) majority | Artificial - majority | FIG. 5 | 61 | EVKLEESGGGLVQPGGSMKISCVASGFTFS NYWMNWVRQTPEKGLEWVAEIRSQSNNF |

TABLE 8-continued

Antibody variable chain sequences

| NAME | Organism | FIG. | SEQ ID NO: | SEQUENCE |
|---|---|---|---|---|
| sequence | sequence | | | ATHYAESVKGRVIISRDDSKSSVYLQMNSLRAEDTAVYYCTRRWNNFWGQGTTVTVSS |
| V$_L$ Deimmunized J415-2 | Artificial - deimmunized light chain | FIG. 6 | 62 | NIVMTQSPKSMSASAGERMTLTCKASENVGTYVSWYQQKPTQSPKMLIYGASNRFTGVPDRFSGSGSGTDFILTASSVQAEDPVDYYCGQSYTFPYTFGGGTKLEMK J415-2 |
| V$_L$ Deimmunized J415-3 | Artificial - deimmunized light chain | FIG. 6 | 63 | NIVMTQSPKSMSASAGERMTLTCKASENVGTYVSWYQQKPTQSPKMLIYGASNRFTGVPDRFSGSGSGTDFILTASSVQAEDLVDYYCGQSYTFPYTFGGGTKLEMK J415-3 |
| V$_L$ Deimmimized J415-4 | Artificial - deimmimized light chain | FIG. 6 | 64 | NIVMTQSPKSMSASAGERMTLTCKASENVGTYVSWYQQKPTQSPKMLIYGASNRFTGVPDRFSGSGSGTDFILTISSVQAEDLVDYYCGQSYTFPYTFGGGTKLEMK J415-4 |
| V$_L$ Deimmunized J415-6 | Artificial - deimmunized light chain | FIG. 6 | 65 | NIVMTQFPKSMSASAGERMTLTCKASENVGTYVSWYQQKPEQSPKMLIYGASNRFTGVPDRFSGSGSGTDFILTISSVQAEDLVDYYCGQSYTFPYTFGGGTKLEMK J415-6 |
| V$_L$ Deimmunized J415-7 | Artificial - deimmunized light chain | FIG. 6 | 66 | NIVMTQFPKSMSASAGERVTLTCKASENVGTYVSWYQQKPTQSPKMLIYGASNRFTGVPDRFSGSGSGTDFILTISSVQAEDLVDYYCGQSYTFPYTFGGGTKLEMK J415-7 |
| V$_L$ Deimmunized J415-8 | Artificial - deimmunized light chain | FIG. 6 | 67 | NIVMTQFPKSMSASAGERMTLTCKASENSGTYVSWYQQKPEQSPKMLIYGASNRFTGVPDRFSGSGSGTDFILTISSVQAEDLVDYYCGQSYTFPYTFGGGTKLEMK J415-8 |
| J415 V$_L$(DI) majority sequence | Artificial - majority sequence | FIG. 6 | 68 | NIVMTQFPKSMSASAGERMTLTCKASENVGTYVSWYQQKPTQSPKMLIYGASNRFTGVPDRFSGSGSGTDFILTISSVQAEDLVDYYCGQSYTFPYTFGGGTKLEMK |
| MuV$_H$IIIC | Mus musculus | FIG. 7C | 69 | EVKLEESGGGLVQPGGSMKLSCVASGFTFSNYWMNWVRQSPEKGLEWVAEIRLKSDNYATHYAESVKGRFTISRDDSKSSVYLQMNNLRAEDTGIYYCTTGGYGGRRSWFAYWGQGTLVTVSS |

TABLE 8-continued

Antibody variable chain sequences

Figure 10A:
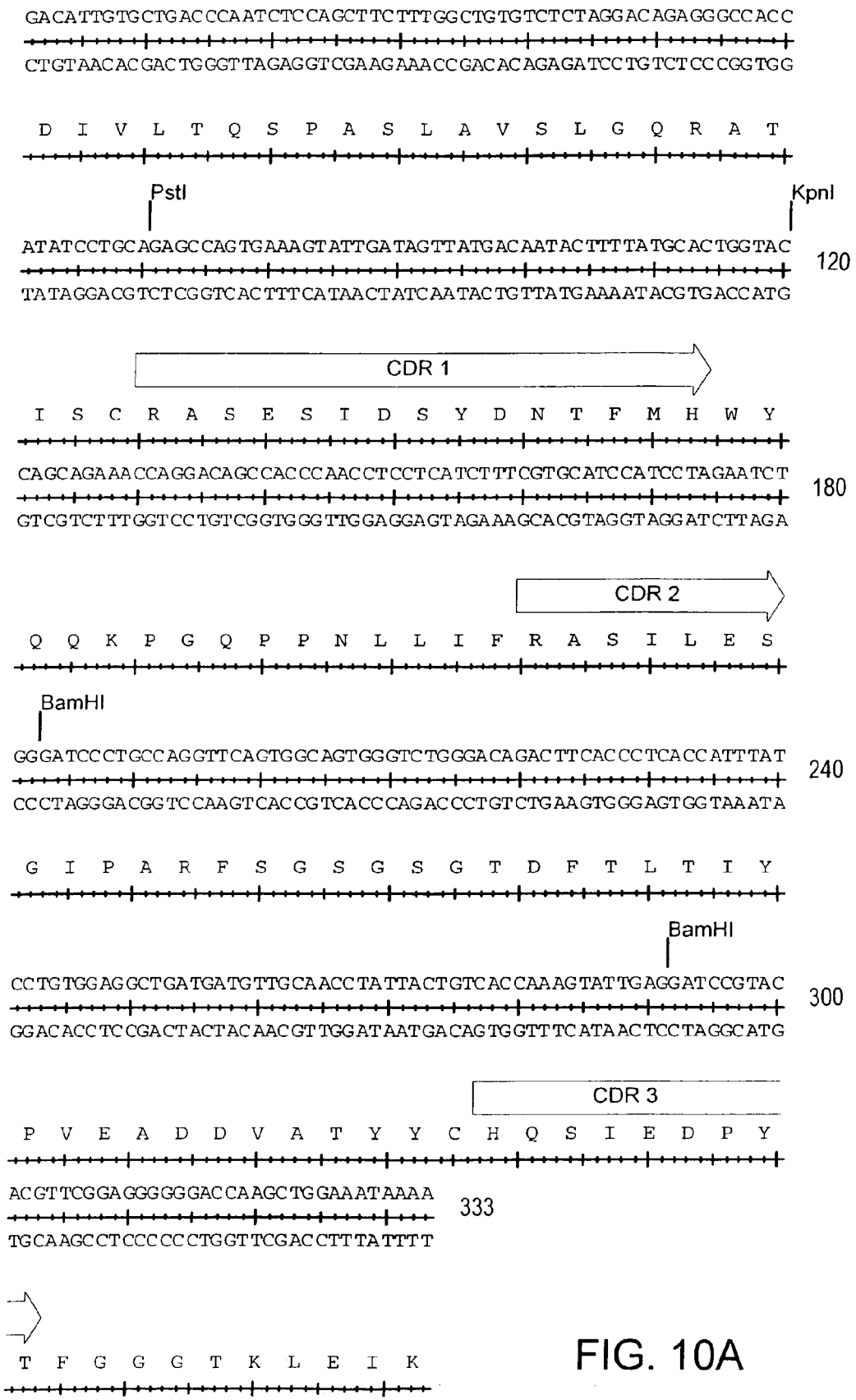
FIG. 10A depicts the nucleic acid coding sequence, the amino acid sequence, and the nucleic acid reverse complement sequence of the murine J533 light chain variable region (SEQ ID NO:76–78, respectively). The relative locations of the CDRs and some restriction sites are indicated.

| NAME | Organism | FIG. | SEQ ID NO: | SEQUENCE |
|---|---|---|---|---|
| J415V$_H$/MuV$_H$IIIC majority sequence | Artificial - majority sequence | FIG. 7C | 70 | EVKLEESGGGLVQPGGSMKLSCVASGFTF SNYWMNWVRQSPEKGLEWVAEIRLQSDN FATHYAESVKGRVIISRDDSKSSVYLQMN NLRAEDTGIYYCTTGGYGGRRSWNAFWG QGTLVTVSS |
| MuV$_L$1 | Mus musculus | FIG. 8C | 71 | DIVMTQSPSSLAVSAGEKVTMSCKSSQSLL NSGNQKNYLAWYQQKPGQSPKLLIYWAS TRESGVPDRFTGSGSGTDFTLTISSVQAED LAVYYCQNDYSYPLTFGAGTKLELK |
| J415V$_L$/MuV$_L$1 majority sequence | Artificial - majority sequence | FIG. 8C | 72 | DIVMTQSPSSLAVSAGEKVTLSCKASESLL NVGNQKTYVAWYQQKPGQSPKLLIYGAS TRESGVPDRFTGSGSGTDFILTISSVQAEDL AVYYCGNSYSFPLTFGGGTKLELK |
| J533 V$_H$ CDS (1–354) | Mus musculus | FIG. 9A | 73 | gaggtccagctgcagcagtctggacctgagctggttaagcctggg gcttcagtgaagatgtcctgcaaggcttctggatacacattcactgg ctatgttatgcactgggtgaagcagaagcctggacaggtccttgag tggattggatatattaatccttacaatgatgttactaggtataatggga agttcaaaggcaaggccacactgacctcagacaaatattccagca cagcctacatggagctcagcggcctgacctctgaggactctgcgg tctattactgtgcaagaggggagaactggtactactttgactcctgg ggccgaggcgccactctcacagtctcctca |
| J533 V$_H$ (predicted amino acid of SEQ ID NO: 73) | Mus musculus | FIG. 9A | 74 | EVQLQQSGPELVKPGASVKMSCKASGYTF TGYVMHWVKQKPGQVLEWIGYINPYNDV TRYNGKFKGKATLTSDKYSSTAYMELSGL TSEDSAVYYCARGENWYYFDSWGRGATL TVSS |
| J533 V$_H$ (complementary strand of SEQ ID NO: 73) | Mus musculus | FIG. 9A | 75 | tgaggagactgtgagagtggcgcctcggcccaggagtcaaagt agtaccagttctcccctcttgcacagtaatagaccgcagagtcctc agaggtcaggccgctgagctccatgtaggctgtgctggaatatttg tctgaggtcagtgtggccttgcctttgaacttcccattatacctagta acatcattgtaaggattaatatatccaatccactcaaggacctgtcc aggcttctgcttcacccagtgcataacatagccagtgaatgtgtatc cagaagccttgcaggacatcttcactgaagccccaggcttaacca gctcaggtccagactgctgcagctggacctc |
| J533 V$_L$ CDS (1–333) | Mus musculus | FIG. 10A | 76 | gacattgtgctgacccaatctccagcttctttggctgtgtctctagga cagagggccaccatatcctgcagagccagtgaaagtattgatagtt atgacaatacttttatgcactggtaccagcagaaaccaggacagcc |

TABLE 8-continued

Antibody variable chain sequences

| NAME | Organism | FIG. | SEQ ID NO: | SEQUENCE |
|---|---|---|---|---|
| | | | | acccaacctcctcatctttcgtgcatccatcctagaatctgggatcc |
| | | | | ctgccaggtcagtggcagtgggtctgggacagacttcaccctca |
| | | | | ccatttatcctgtggaggctgatgatgttgcaacctattactgtcacc |
| | | | | aaagtattgaggatccgtacacgttcggagggggaccaagctg |
| | | | | gaaataaaa |
| J533 V<sub>L</sub> (predicted amino acid of SEQ ID NO: 76) | Mus musculus | FIG. 10A | 77 | DIVLTQSPASLAVSLGQRATISCRASESIDS YDNTFMHWYQQKPGQPPNLLIFRASILES GIPARFSGSGSGTDFTLTIYPVEADDVATY YCHQSIEDPYTFGGGTKLEIK |
| J533 V<sub>L</sub> (complementary strand of SEQ ID NO: 76) | Mus musculus | FIG. 10A | 78 | ttttatttccagcttggtccccctccgaacgtgtacggatcctcaat actttggtgacagtaataggttgcaacatcatcagcctccacaggat aaatggtgagggtgaagtctgtcccagacccactgccactgaacc tgcagggatcccagattctaggatggatgcacgaaagatgagg aggttgggtggctgtcctggtttctgctggtaccagtgcataaagt attcataactatcaatactttcactggctctgcaggatatggtggc cctctgtcctagagacacagccaaagaagctggagattgggtcag cacaatgtc |
| MuV<sub>H</sub>II | Mus musculus | FIG. 9B | 79 | EVQLQQSGPELVKPGASVKISCKASGYTFT DYYMNNWVKQSPGKSLEWIGDINPGNGG TSYNQKFKGKATLTVDKSSSTAYMQLSSL TSEDSAVYYCARGYYSSSYMAYYAFDYW GQGTTVTVSS |
| J533V<sub>H</sub>/MuV<sub>H</sub>II majority sequence | Artificial - majority sequence | FIG. 9B | 80 | EVQLQQSGPELVKPGASVKISCKASGYTFT GYVMNNWVKQSPGQVLEWIGDINPGNGG TSYNGKFKGKATLTVDKSSSTAYMELSGL TSEDSAVYYCARGENSSSYMAYYAFDSW GQGATVTVSS |
| MuV<sub>L</sub>-3 | Mus musculus | FIG. 10B | 81 | DIVLTQSPASLAVSLGQRATISCRASESVDS YGNSFMHWYQQKPGQPPKLLIYAASNLES GVPARFSGSGSGTDFTLNIHPVEEDDAATY YCQQSNEDPPWTFGGGTKLEIK |
| J533V<sub>L</sub>/ MuV<sub>L</sub>-3 majority sequence | Artificial - majority sequence | FIG. 10B | 82 | DIVLTQSPASLAVSLGQRATISCRASESVDS YGNSFMHWYQQKPGQPPNLLIFAASILES GVPARFSGSGSGTDFTLTIHPVEADDAATY YCQQSIEDPPYTFGGGTKLEIK |

TABLE 8-continued

Antibody variable chain sequences

| NAME | Organism | FIG. | SEQ ID NO: | SEQUENCE |
|---|---|---|---|---|
| E99 V$_H$ CDS (1–363) | Mus musculus | FIG. 11A | 83 | caggtgcagctaaaggagtcaggacctggcctggtggcgtcctc acagagcctgtccatcacatgcaccgtctcaggattctcattaacc gcctatggtattaactgggttcgccagcctccaggaaagggtctgg agtggctgggagtgatatggcctgatggaaacacagactataattc aactctcaaatccagactgaacatcttcaaggacaactccaagaac caagttttcttaaaaatgagcagtttccaaactgatgacacagccag atacttctgtgccagagattcgtatggtaacttcaagaggggttggtt tgacttctggggccagggcaccactctcacagtctcctca |
| E99 V$_H$ (predicted amino acid of SEQ ID NO: 83) | Mus musculus | FIG. 11A | 84 | QVQLKESGPGLVASSQSLSITCTVSGFSLT AYGINWVRQPPGKGLEWLGVIWPDGNTD YNSTLKSRLNIFKDNSKNQVFLKMSSFQT DDTARYFCARDSYGNFKRGWFDFWGQGT TLTVSS |
| E99 V$_H$ (complementary strand of SEQ ID NO: 83) | Mus musculus | FIG. 11A | 85 | tgaggagactgtgagagtggtgccctggccccagaagtcaaacc aacccctcttgaagttaccatacgaatctctggcacagaagtatctg gctgtgtcatcagtttggaaactgctcattttttaagaaaacttggttctt ggagttgtccttgaagatgttcagtctggatttgagagttgaattata gtctgtgtttccatcaggccatatcactcccagccactccagaccct ttcctggaggctggcgaacccagttaataccataggcggttaatga gaatcctgagacggtgcatgtgatggacaggctctgtgaggacgc caccaggccaggtcctgactcctttagctgcacctg |
| E99 V$_L$ CDS (1–321) | Mus musculus | FIG. 12A | 86 | aacattgtgatgacccagtctcaaaaattcatgtccacatcaccagg agacagggtcagggtcacctgcaaggccagtcagaatgtgggtt ctgatgtagcctggtatcaagcgaaaccaggacaatctcctagaat actgattactcgacatcctaccgttacagtggggtccctgatcgctt cacagcctatggatctgggacagatttcactctcaccattaccaatg tgcagtctgaagacttgacagagtatttctgtcagcaatataatagct atcctctcacgttcggtgctgggaccaagctggagctgaaa |
| E99 V$_L$ (predicted amino acid of SEQ ID NO: 86) | Mus musculus | FIG. 12A | 87 | NIVMTQSQKFMSTSPGDRVRVTCKASQNV GSDVAWYQAKPGQSPRILIYSTSYRYSGVP DRFTAYGSGTDFTLTTTNVQSEDLTEYFCQ QYNSYPLTFGAGTKLELK |
| E99 V$_L$ (comlementary strand of SEQ ID | Mus musculus | FIG. 12A | 88 | tttcagctccagcttggtcccagcaccgaacgtgagaggatagcta ttatattgctgacagaactctgtcaagtcttcagactgcacattg gtaatggtgagagtgaaatctgtcccagatccataggctgtgaagc gatcagggaccccactgtaacggtaggatgtcgagtaaatcagta |

TABLE 8-continued

Antibody variable chain sequences

| NAME | Organism | FIG. | SEQ ID NO: | SEQUENCE |
|---|---|---|---|---|
| NO: 86) | | | | ttctaggagattgtcctggtttcgcttgataccaggctacatcagaac |
| | | | | ccacattctgactggccttgcaggtgaccctgaccctgtctcctggt |
| | | | | gatgtggacatgaattttttgagactgggtcatcacaatgtt |
| MuV$_H$IB | Mus musculus | FIG. 11B | 89 | QVQLKESGPGLVASSQSLSITCTVSGFSLT |
| | | | | AYGINWVRQPPGKGLEWLGVIWPDGNTD |
| | | | | YNSTLKSRLNIFKDNSKNQVFLKMSSFQT |
| | | | | DDTARYFCARDSYGNFKRGWFDFWGQGT |
| | | | | TLTVSS |
| E99V$_H$/MuV$_H$ IB majority sequence | Artificial - majority sequence | FIG. 11B | 90 | QVQLKESGPGLVASSQSLSITCTVSGFSLT |
| | | | | AYGINWVRQPPGKGLEWLGVIWPDGNTD |
| | | | | YNSTLKSRLNIFKDNSKNQVFLKMSSFQT |
| | | | | DDTARYFCARDSYGNFKRGWFDFWGQGT |
| | | | | TLTVSS |
| MuV$_L$-1 | Mus musculus | FIG. 12B | 91 | DIVMTQSPSSLAVSAGEKVTMSCKSSQSLL |
| | | | | NSGNQKNYLAWYQQKPGQSPKLLIYWAS |
| | | | | TRESGVPDRFTGSGSGTDFTLTISSVQAED |
| | | | | LAVYYCQNDYSYPLTFGAGTKLELK |
| E99V$_L$/MuV$_L$-1 majority sequence | Artificial - majority sequence | FIG. 12B | 92 | DIVMTQSQSSLAVSAGDKVTVSCKASQSL |
| | | | | LNVGSDKNYVAWYQAKPGQSPKLLIYSAS |
| | | | | TRESGVPDRFTGSGSGTDFTLTISSVQAED |
| | | | | LAVYFCQNDNSYPLTFGAGTKLELKRA |

Humanized or CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference.

Winter describes a CDR-grafting method that may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

Also within the scope of the invention are humanized antibodies in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the contents of which are hereby incorporated by reference. The acceptor framework can be a mature human antibody framework sequence or a consensus sequence.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

Other techniques for humanizing antibodies are described in Padlan et al. EP 519596 A1, published on Dec. 23, 1992.

The anti-PSMA antibody, or antigen fragment thereof, may also be modified by specific deletion of human T cell epitopes or "deimmunization" by the methods disclosed in WO 98/52976 and WO 00/34317, the contents of which are specifically incorporated by reference herein. Briefly, the murine heavy and light chain variable regions of an anti-PSMA antibody can be analyzed for peptides that bind to MHC Class II; these peptides represent potential T-cell epitopes (as defined in WO 98/52976 and WO 00/34317). For detection of potential T-cell epitopes, a computer modelling approach termed "peptide threading" can be applied, and in addition a database of human MHC class II binding peptides can be searched for motifs present in the murine $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al. (1992) *J. Mol. Biol.* 227:776–798; Cook, G. P. et al. (1995) *Immunol. Today* Vol. 16 (5): 237–242; Chothia, D. et al. (1992) *J. Mol. Bio.* 227:799–817. The V BASE directory provides a comprehensive directory of human immunoglobulin variable region sequences (compiled by Tomlinson, I. A. et al. MRC Centre for Protein Engineering, Cambridge, UK). After the deimmunized $V_H$ and $V_L$ of an anti-PSMA antibody are constructed by mutagenesis of the murine $V_H$ and $V_L$ genes. The mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region.

The recombinant deimmunized antibody can be transfected into a suitable host cell for expression, for example, NS0 or CHO cells, to produce complete recombinant antibodies.

In one embodiment, deimmunized $V_H$ and $V_L$ of murine J591 regions were constructed by mutagenesis of the murine $V_H$ and $V_L$ genes. The murine J591 variable region sequences are shown in FIGS. 1A–1B. Potential epitopes (identified using a peptide threading program) in murine J591 heavy chain and light chain variable regions are shown in FIGS. 3A and 3B, respectively. The 13-mer peptides predicted to bind to MHC class II are indicated by the underline, the CDRs are located at residues 26 to 35, 50 to 66, and 99 to 104 of FIG. 3A and residues 24 to 34, 50 to 56, and 89 to 97 of FIG. 3B, and residues altered in the deimmunized heavy and light chain variable regions are boxed. Where possible, amino acid substitutions are those commonly used in human germline heavy and light chain variable regions. In addition to the in silico analysis using the peptide threading software, a database of human MHC class II binding peptides was searched for motifs present in the murine J591 sequence.

The following 13-mers (labelled by first linear residue number of the 13-mer) of the murine J591 heavy chain variable region were predicted to bind to MHC Class II were 2, 10, 16, 30, 32, 35, 43, 46, 58, 62, 70, 81, 84, 91, and 100 (FIG. 3A). An explanation of the rationale behind changes made to the residues in the murine J591 heavy chain variable region is set forth below (note residues altered are identified under the Kabat numbering system):

5Q→V removes the potential epitope at residue 2;

11,12LV→VK remove the potential epitope at residue 10;

12V→K is also changed to remove a motif from the database of human MHC class II binding peptides;

16,17TS→AT, and 19R→K remove the potential epitope at residue 16;

the epitope at residue 30 spans CDR1 and is therefore unaltered;

40,41SH→AP removes potential epitopes at residues 32 and 35;

44S→G reduces binding score for epitope at 43, this 13 mer spans CDR2;

the epitopes at residues 46, 58 and 62 span CDR2, and are thus unaltered;

75,76SS→TD remove the potential epitope at residue 70;

82aR→S, 83T→R remove potential epitopes at residues 81 and 84;

87S→T this change made to remove a motif from the database of human MHC class II binding peptides;

the epitope at residue 91 spans CDR3 and is therefore unaltered; and

108T→L removes the potential epitope at residue 100.

The following 13-mers (labelled by first linear residue number of the 13-mer) of the murine J591 light chain variable region that were predicted to bind to MHC Class II molecules were 1, 8, 17, 27, 30, 31, 35, 45, 47, 56, 60, 71, 73, 81, 94 (FIG. 3B). An explanation of the rationale behind changes made to the residues in the murine J591 light chain variable region is set forth below (note residues altered are identified under the Kabat numbering system):

3V→Q removes potential epitope at residue 1;

8–11HKFM→PSSL removes potential epitope at residue 8(13);

20–22SII→TLT removes potential epitopes at residues 17 and 20;

21I→L is also changed to remove a motif from the database of human MHC class II binding peptides;

the epitope at residue 27 spans CDR1 and is therefore unaltered;

42Q→P reduces the binding score for the epitope at residue 31;

the epitopes at residues 44 and 47 span CDR2 and are thus unaltered;

58V→I is changed to remove a motif from the database of human MHC class II binding peptides;

60D→S, 62T→S removes the epitopes at residues 56 and 60;

76–78TNV→SSL, 80S→P, 83L→F removes the epitopes at residues 71, 73, 76, and 81;

87F→Y I is changed to remove a motif from the database of human MHC class II binding peptides;

100 A→P and 103 M→K remove the epitope at residue 94; and

104 L→V and 106 L→I are changed to remove a motif from the database of human MHC class II binding peptides.

The amino acid and nucleotide sequences for the deimmunized J591 heavy and light chain variable regions are shown in FIGS. 2A–2B and 4A–4B, respectively (see also Table 8).

Human IgG1 or κ constant regions were added and the composite genes transfected into NS0 cells to produce complete recombinant anti-PSMA antibodies. These antibodies bound to PSMA (on LNCap cells) as efficiently as the original murine antibody, and have reduced or no immunogenicity in man.

The design of deimmunized J415 was similar to the making of the deimmunized J591 antibody. The heavy and light chain sequences were cloned from the hybridoma designated HB-12109. These sequences were cloned, sequenced and expressed as a chimaeric antibody for use as a control antibody. The murine V region sequences were subjected to peptide threading to identify potential T cell epitopes, through analysis of binding to 18 different human MHC class II allotypes. The results of the peptide threading analysis for the murine sequences are shown in Table 9.

TABLE 9

Potential T cell epitopes in murine J415 sequences

| Sequence | Number of potential T cell | Location of potential epitopes[+] (no. of potential MHC binders from 18 groups tested) |
|---|---|---|
| Murine J415 V$_H$ | 12 | 10(17), 16(13), 21(9), 30(6), 35(16), 43(8), 46(6), 49(8), 64(6), 80(15), 86(15), 104(6) |

TABLE 9-continued

Potential T cell epitopes in murine J415 sequences

| Sequence | Number of potential T cell | Location of potential epitopes[+] (no. of potential MHC binders from 18 groups tested) |
|---|---|---|
| Murine J415 V$_K$ | 13 | 5(5), 11(18), 13(11), 17(5), 27(8), 31(7), 56(15), 60(12), 70(5), 71(11), 73(17), 76(7), 81(17) |

[+]first amino acid of potential epitope, numbering E or N amino acid number 1 to S or K amino acid number 107 and 116 for V$_H$ and V$_K$ respectively.

Primary deimmunized V$_H$ and V$_L$ sequences were defined (J415D1VH1, J415D1VK1). As generation of the primary deimmunized sequences requires a small number of amino acid substitutions that might affect the binding of the final deimmunized molecule, three other variant V$_H$S and seven other V$_L$S were designed (see FIGS. 5 and 6). The nucleotide sequences for the primary deimmunized V$_H$ and V$_L$ regions are shown in FIGS. 7A and 8A, respectively. Comparisons of the amino acid sequences of the murine and deimmunized V regions of J415 are shown in FIG. 5 for V$_H$ and FIG. 6 for V$_L$.

An explanation of the rational behind some of the changes made to the residues in the murine J415 heavy chain variable region is set forth below (note residues altered are identified according to the linear numbering shown in FIG. 5):

20L→I removes the potential epitope at residues 10 and 16;

87N→S removes the potential epitopes at residues 80 and 86;

94,95GI→AV remove the potential epitope at residue 86; and

112L→V removes the potential epitope at residue 104.

An explanation of the rational behind some of the changes made to the residues in the murine J415 light chain variable region is set forth below (note residues altered are identified according to the linear numbering shown in FIG. 6):

13I A removes the potential epitopes at residues 5, 11 and 13;

15V A removes the potential epitopes at residues 5, 11, and 13;

19V-M removes the potential epitopes at residues 11, 13, and 17;

41E-T removes the potential epitope at residue 31

63T-S removes the potential epitopes at residues 56 and 60;

68A-G removes the potential epitopes at residues 56 and 60; and

80T-A removes the potential epitopes at residues 70, 71, 73, and 76;

The deimmunized variable regions for J415 were constructed by the method of overlapping PCR recombination. The cloned murine V$_H$ and V$_K$ genes were used as templates for mutagenesis of the framework regions to the required deimmunized sequences. Sets of mutagenic primer pairs were synthesized encompassing the regions to be altered. The vectors VH-PCR1 and VK-PCR1 (Riechmann et al. (1988) Nature 332:323–7) were used as templates to introduce 5' flanking sequence including the leader signal peptide, leader intron and the murine immunoglobulin promoter, and 3' flanking sequence including the splice site, and intron sequences. The deimmunized V regions produced were cloned into pUC19 and the entire DNA sequence was confirmed to be correct for each deimmunized V$_H$ and V$_L$.

The deimmunized heavy and light chain V-region genes were excised from pUC19 as HindIII to BamHI fragments, which include the murine heavy chain immunoglobulin promoter, the leader signal peptide, leader intron, the $V_H$ or $V_L$ sequence and the splice site. These were transferred to the expression vectors pSVgpt and pSVhyg, which include human IgG1 or κ constant regions respectively and markers for selection in mammalian cells. The DNA sequence was confirmed to be correct for the deimmunized $V_H$ and $V_L$ in the expression vectors.

For the transfection of expression vectors pSVgptJ415VHHuIgG1 and pSVhygJ415VKHuCK into NS0 (a non-immunoglobulin producing mouse myeloma, obtained from the European Collection of Animal Cell Cultures, Porton UK (ECACC No. 85110503)) cells, 3 and 6 ug of plasmid DNA respectively was prepared and then linearized with PvuI to improve transfection efficiency. The ethanol precipitated DNA was then mixed with a semi-confluent flask of NS0 cells that had been harvested by centrifugation and resuspended in 0.5 ml of non-selective Dulbecco's Modified Eagle's Medium (DMEM)(Life Technologies Inc.) in a 0.4 cm gene pulser cuvette. The cells and DNA were chilled on ice for 5 minutes before a pulse of 170V, 960 μF was applied. The cuvette was returned to ice for a further 20 minutes before being transferred to a 75 cm² flask containing 20 mls non-selective DMEM to recover for 24 hours. The cells were then harvested and resuspended in selective DMEM and plated over 4×96 well plates, 200 μl/well. A similar protocol was followed for the transfection of expression vectors encoding the deJ591 antibody heavy chain and light chain subunits into NS0 cells.

To culture, select, and expand NS0 cell lines, the cells are grown at 37° C., 5% $CO_2$ and 10% FBS. To prepare non-selective medium for routine culture of NS0 cells, the culture medium is Dulbecco's Modification of Eagle's Medium (DMEM)(Life Technologies, Catalogue No: 31965-023) supplemented with 10% fetal bovine serum of USA origin (Life Technologies, Fetal Bovine Serum Cat No: 16000), Antibiotic/Antimycotic solution (Life Technologies, Cat No: 15240), Gentamycin (Life Technologies, catalogue No: 15710), Sodium pyruvate (Life Technologies, Catalogue No: 11360-039). When growing NS0 cells up to saturation for antibody production do not add the xanthine and mycophenolic acid and the FBS is reduced to 5%.

To prepare selective medium for culture of NS0 transfectomas, the culture medium is Dulbecco's Modification of Eagle's Medium (DMEM)(Life Technologies, Catalogue No: 31965-023) supplemented with 10% foetal bovine serum of USA origin (Life Technologies, Fetal Bovine Serum Cat No: 16000), Antibiotic/Antimycotic solution (Life Technologies, Cat No: 15240), Gentamycin (Life Technologies, catalogue No: 15710), Sodium pyruvate (Life Technologies, Catalogue No: 11360-039), 250 μg/ml xanthine (Sigma Catalogue No: X-3627, stock made up at 25 mg/ml in 0.5M NaOH), and 0.8 μg/ml mycophenolic acid (Sigma Catalogue No: M-3536, stock made up at 2.5 mg/ml in 100% ethanol).

After approximately 10 days the cell colonies expressing the gpt gene were visible to the naked eye. The plates were then screened for antibody production using the following protocol for human IgG1/κ Screening ELISA. 6 single colonies were picked from wells with high ODs greater than 0.7 into a 24 well cell culture plate. Within 5–6 days the cells were expanded into a 25 cm² flask. The antibody productivity of the selected clones was assayed using the following protocol for human IgG1/κ ELISA from saturated cultures in the 24 well and 25 cm² flasks.

The details of the protocol are as follows. ELISA plates (Dynatech Immulon 2) are coated with 100 μL per well with sheep α human κ antibody (The Binding Site Cat No: AU015) diluted 1:1000 in carbonate/bicarbonate coating buffer pH9.6 (Sigma Cat: C-3041). The coated plate is incubated at 4° C. overnight or 1 hr at 37° C. The plate is then washed 3 times with PBST (PBS with 0.05% Tween 20). The samples are added, 100 μL per well from 24 well plates, 25 μL+75 μL PBST for 96 well plates. Blank wells are treated with PBST only. The reaction mixture is incubated at room temperature for 1 hr. Then, the plate is wash 3 times with PBST (PBS with 0.05% Tween 20). The secondary antibody, peroxidase conjugated sheep α human IgG γ chain specific is added (The Binding Site Cat No: APO04) at a ratio of 1:1000 in PBST, 100 μL per well. The mixture is incubated at room temperature for 1 hour. The mixture is then washed 3 times with PBST (PBS with 0.05% Tween 20).

To make up the substrate, one tablet (20 mg) of OPD (o-PHENYLENE DIAMINE) (Sigma Cat No: P-7288) is dissolved in 45 ml of $H_2O$ plus 5 ml 10× peroxidase buffer (make 10× peroxidase buffer with Sigma phosphate citrate buffer tablets pH 5.0, P-4809), add 10 μL 30% (w/w) hydrogen peroxide (Sigma Cat No: H1109) just before use. The substrate is then added at 100 μL per well and incubate RT for 5 min or as required. When the color develops, the reaction can be stopped by adding 25 μL 12.5% $H_2SO_4$. The results are read at 492 nm.

Expression and Expansion of J591 and J415 Deimmunized Antibodies

The clones with the highest productivity were expanded into a 75 cm² flask and then into 2×175 cm² flasks. The cells from one of the 175 cm² flask was used to inoculate 4× triple layer flasks (500 cm², Nalge Nunc International) containing non selective DMEM containing 5%0 FBS, cells from the other were frozen as detailed in the protocol for freezing NS0 cells detailed below.

To cryoprotect mammalian cells and resurrect cells from liquid nitrogen, the following materials are needed: Fetal Bovine serum (Life Technologies Cat No: 16000), DMSO (Sigma, Cat No: D4540), 2 ml cryotubes (Nunc or Greiner), and polystyrene box with walls 1–2 cm thick. Briefly, actively growing cells are harvested by centrifugation (1000 rpm, 5 min) and resuspended at about $10^7$ cells/ml in 10% DMSO/90% FBS. As a rough guide, cells grown to a semi-confluency should be resuspended in 1 ml for a 75 cm² flask or 2.5 ml for a 175 cm² flask. A required number of tubes are cooled and labeled in ice. 1 ml portions are aliquoted to labeled cryotubes. The cryotubes are placed in polystyrene box at −70° C. for at least 4 h, or overnight. The vials are transferred to canes and place in liquid nitrogen. A record of the storage should be made both in the canister index and the central cell line indexing system.

To thaw the cells from liquid nitrogen, the vial is removed from liquid nitrogen and contents are thawed quickly by incubation at 37° C., while swirling in a waterbath. The outside of the vial is cleaned with 70% methylated spirits. The suspension is transferred to a universal container. 10 ml of the medium to be used to propagate the cell line is added dropwise, swirling to mix. The cells are harvested by centrifugation (1000 rpm, 5 min). The supernatant is discarded. The cells are resuspended in 20 ml growth medium and transfer to a 75 cm² flask. If low viability is suspected, extra serum can be added to the growth medium to 20%, use only 5 ml, and transfer to a 25 cm² flask.

After 10–14 days the 500 ml to 1 liter static saturated cultures were harvested. Antibody was purified, by ProSepA (Millipore Ltd.) affinity chromatography using the following protocol for antibody purification. The purified antibody preparation was sterilized by filtration and stored at 4° C.

The antibody purification protocol is as follows: NS0 transfectoma cell line producing antibody is grown in DMEM 5% FCS in Nunc Triple layer flasks, 250 ml per flask (total volume 1 L) for 10–14 days until nearing saturation. Conditioned medium collected and spun at 3000 rpm for 5 min in bench centrifuge 5 mins to remove cells. $\frac{1}{10}^{th}$ volume 1M Tris-HCl pH 8 (Sigma Cat: T3038) is then added to cell supernatant to make this 0.1 M Tris-HCl pH8. 0.5 to 1 ml Prosep A (Millipore Cat: 113 111824) is added and stirred overnight at room temperature. Prosep A collected by spinning at 3000 rpm for 5 mins then packed into a Biorad Poly-Prep column (Cat: 73 1-1550). The column is washed with 10 ml PBS, then eluted in 1 ml fractions with 0.1M Glycine pH 3.0. Each fraction is collected into a tube containing 100 microL 1M Tris-HCl pH 8 (Sigma, as above). Absorbance of each fraction is measured at 280 nm. Fractions containing the antibody are pooled and dialyzed against PBS overnight at room temperature. The preparation is sterilized by filtration through a 0.2 micron syringe filter and the absorbance of each fraction is measured at 280 nm. The antibody concentration is determined by ELISA for human IgG.

The purified antibody can be quantified using the protocol for Human IgG1/κ ELISA described above.

Testing of J415 Deimmunized Antibodies

The J415 deimmunized antibodies (including various combinations of the deimmunized light chain and heavy chain subunits) were tested in an ELISA for binding to LNCap membrane preparation following the protocol as detailed above. ELISA plates were coated with LNCap membrane preparation and blocked with 5% BSA in phosphate buffered saline. Doubling dilutions of the J415 chimeric antibody (murine variable heavy and light chain regions fused to human constant heavy and light chain regions, respectively) and the deimmunized antibodies were applied. Detection was with horseradish peroxidase conjugated goat anti-human IgG and donkey anti-mouse for chimeric and mouse antibodies respectively. Color was developed with o-phenylene diamine substrate.

The antibody composed of deimmunized J415 heavy chain version 4 combined with deimmunized J415 light chain version 5 shows equivalent binding to LNCap cells as compared to the chimeric antibody. Also, when DIVK5 is combined with heavy chain versions 1 and 2, binding to LNCap cells is equivalent to that of the chimeric antibody when tissue culture supernatant is analyzed. These data can be confirmed with purified antibody. When light chains 1, 2, 3 were combined with any of the J415 heavy chain versions 1, 2, 3, and 4 no antibody was produced. Deimmunized J415 light chain versions 1, 2, and 3 may be defective on structural grounds. The best chain combination for higher affinity and decreased immunogenicity is D1VH4/DIVK5.

The antibody composed of deimmunized heavy chain version 4 combined with deimmunized light chain version 5 showed equivalent binding to LNCap compared to the chimeric antibody. Also, when DIVK5 is combined with heavy chain versions 1 and 2, binding to LNCap cells is two-fold less than that of the chimeric when purified antibody is analyzed.

Monoclonal anti-PSMA antibodies can also be generated by other methods known to those skilled in the art of recombinant DNA technology.

Anti-PSMA antibodies that are not intact antibodies are also useful in this invention. Such antibodies may be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci USA* 85:5879–5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes.

Monoclonal, chimeric, humanized, deimmunized antibodies, which have been modified by, e.g., deleting; adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others.

In one embodiment, the constant region of the antibody can be replaced by another constant region from, e.g., a different species. This replacement can be carried out using molecular biology techniques. For example, the nucleic acid encoding the VL or VH region of a antibody can be converted to a full-length light or heavy chain gene, respectively, by operatively linking the VH or VL-encoding nucleic acid to another nucleic acid encoding the light or heavy chain constant regions. The sequences of human light and heavy chain constant region genes are known in the art. Preferably, the constant region is human, but constant species from other species, e.g., rodent (e.g., mouse or rat), primate, camel, rabbit can also be used. Constant regions from these species are known in the art (see e.g., Kabat, E.

A., et al. (1991) *Sequences of Proteins of Immunological Interest, Fifth Edition*, U.S. Department of Health and Human Services, NIH Publication No. 91-3242).

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

An anti-PSMA antibody, or antigen-binding fragment thereof, can be derivatized or linked to another functional molecule (e.g., another peptide or protein). Accordingly, the antibodies and antibody portions of the invention are intended to include derivatized and otherwise modified forms of the antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibodies can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An anti-PSMA antibody or antigen-binding fragment thereof may be conjugated to a another molecular entity, typically a label or a therapeutic (e.g., a cytotoxic or cytostatic) agent or moiety.

Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The invention provides radiolabeled anti-PSMA antibodies and methods of labeling the same. In one embodiment, a method of labeling an anti-PSMA antibody is disclosed. The method includes contacting an anti-PSMA antibody, e.g. an anti-PSMA antibody described herein, with a chelating agent, e.g., 1,4,7,10-tetraazacyclododecane-N,N',N'',N'''-tetraacetic acid (DOTA), to thereby produced a conjugated antibody. The conjugated antibody is radiolabeled with a radioisotope, e.g., $^{111}$Indium, $^{90}$Yttrium and $^{177}$Lutetium, to thereby produce a labeled anti-PSMA antibody. Detailed procedures for radiolabeling an anti-PSMA antibody are described in more detail in the sections below and the appended examples. For example, the anti-PSMA antibodies can be radiolabeled with $^{111}$Indium, $^{90}$Yttrium, or $^{177}$Lutetium by coupling with 1,4,7,10-tetraazacyclododecane-N,N',N'',N'''-tetraacetic acid (DOTA) as described in U.S. Ser. No. 60/295,214, filed on Jun. 1, 2001, the contents of which are incorporated by reference in its entirety. Detailed experimental protocols for chelating anti-PSMA antibodies are described in Example 16 of U.S. Ser. No. 60/295,214, which is specifically incorporated by reference in the present application and is reproduced below as Example 1.

As is discussed above the antibody can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

The conjugates of the invention can be used for modifying a given biological response. The therapuetic agent is not to be construed as limited to classical chemical therapeutic agents. For example, the therapeutic agent may be a protein or polypeptide possessing a desired biological activity. Such proteins may include, for example, a toxin such as abrin, ricin A, pseudomonas exotoxin, diphtheria toxin, or a component thereof (e.g., a component of pseudomonas exotoxin is PE38); a protein such as tumor necrosis factor, interferon, nerve growth factor, platelet derived growth factor, tissue plasminogen activator, or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Similarly, the therapeutic agent can be a viral particle, e.g., a recombinant viral particle, that is conjugated (e.g., via a chemical linker) or fused (e.g., via a viral coat protein) to an anti-PSMA antibody of the invention. Introduction of the viral nucleic acid molecules, e.g., recombinant viral nucleic acid molecules, into cells, e.g., prostate cancer cells or vascular endothelial cells associated with tumors, that express PSMA can occur following binding and endocytosis of the anti-PSMA antibody/viral particle conjugate or fusion.

Nucleic Acids, Vectors and Host Cells

Another aspect of the invention pertains to isolated nucleic acid, vector and host cell compositions that can be used for recombinant expression of the modified antibodies and antigen-binding fragment of the invention. In one embodiment, a first and second isolated nucleic acid comprising a nucleotide sequence encoding heavy and light chain variable regions, respectively of an anti-PSMA antibody, e.g., a modified anti-PSMA antibody (e.g., a deimmunized J591 or J415 anti-PSMA antibody), or an antigen fragment thereof, are provided.

The nucleotide and amino acid sequence of the modified (deimmunized) anti-PSMA J591 immunoglobulin light chain variable region is shown in FIG. 4B. (SEQ ID NO:25 and 22, respectively). The non-coding complementary nucleotide sequence is also shown in FIG. 4B (SEQ ID NO:26). The J591 deimmunized anti-PSMA antibody light chain variable region contains the following regions: an FR1 domain corresponding to about amino acid residues 1–23 of SEQ ID NO:22 (linear numbering; see also SEQ ID NO:13), which is encoded by about nucleotides 261–329 of SEQ ID NO:25; a CDR1 domain corresponding to about amino acid residues 24–34 of SEQ ID NO:22 (linear numbering; see also SEQ ID NO:4), which is encoded by about nucleotides 330–362 of SEQ ID NO:25; an FR2 domain corresponding to about amino acid residues 35–49 of SEQ ID NO:22 (linear numbering; see also SEQ ID NO:14), which is encoded by about nucleotides 363–407 of SEQ ID NO:25; a CDR2 domain corresponding to about amino acid residues 50–56 of SEQ ID NO:22 (linear numbering; see SEQ ID NO:5), which is encoded by about nucleotides 408–428 of SEQ ID NO:25; an FR3 domain corresponding to about amino acid residues 57–88 of SEQ ID NO:22 (linear numbering; see also SEQ ID NO:15), which is encoded by about nucleotides 429–524 of SEQ ID NO:25; a CDR3 domain corresponding to about amino acid residues 89–97 of SEQ ID NO:22 (linear numbering; see also SEQ ID NO:6), which is encoded by about nucleotides 525–551 of SEQ ID NO:25; and an FR4 domain corresponding to about amino acid residues 98–107 of SEQ ID NO:22 (linear numbering; see also SEQ ID NO:16), which is encoded by about nucleotides 552–581 of SEQ ID NO:25.

The nucleotide and amino acid sequence of the modified (deimmunized) anti-PSMA J591 immunoglobulin heavy chain variable region is shown in FIG. 4A (SEQ ID NO:23 and 21, respectively). The non-coding complementary sequence is also shown in FIG. 4A (SEQ ID NO:24). The J591 deimmunized anti-PSMA antibody heavy chain variable region contains the following regions: an FR1 domain corresponding to about amino acid residues 1–25 of SEQ ID NO:21 (linear numbering; see also SEQ ID NO:9), which is encoded by about nucleotides 261–335 of SEQ ID NO:23; a CDR1 domain corresponding to about amino acid residues 26–35 of SEQ ID NO:21 (linear numbering; see also SEQ ID NO:1), which is encoded by about nucleotides 336–365 of SEQ ID NO:23; an FR2 domain corresponding to about amino acid residues 36–49 of SEQ ID NO:21 (linear numbering; see also SEQ ID NO:10), which is encoded by about nucleotides 366–407 of SEQ ID NO:23; a CDR2 domain of corresponding to about amino acid residues 50–66 of SEQ ID NO:21 (linear numbering; see also SEQ ID NO:2), which is encoded by about nucleotides 408–458 of SEQ ID NO:23; an FR3 domain corresponding to about amino acid residues 67–98 of SEQ ID NO:21 (linear numbering; see also SEQ ID NO:11), which is encoded by about nucleotides 459–554 of SEQ ID NO:23; a CDR3 domain corresponding to about amino acid residues 99–104 of SEQ ID NO:21 (linear numbering; see also SEQ ID NO:3), which is encoded by about nucleotides 555–572 of SEQ ID NO:23; and an FR4 domain corresponding to about amino acid-residues 105–115 of SEQ ID NO:21 (linear numbering; see also SEQ ID NO:9), which is encoded by about nucleotides 573–605 of SEQ ID NO:23.

The nucleotide and amino acid sequence of the modified (deimmunized) anti-PSMA J415 immunoglobulin light chain variable region (J415DIVK1) is shown in FIG. 8A (SEQ ID NO:56 and 57, respectively). The non-coding complementary nucleotide sequence of J415DIVK1 is also shown in FIG. 8A (SEQ ID NO:58). The J415 deimmunized anti-PSMA antibody light chain variable region contains the following regions: an FR1 domain corresponding to about amino acid residues 1–23 of SEQ ID NO:57 (linear numbering; see also SEQ ID NO:41), which is encoded by about nucleotides 261–329 of SEQ ID NO:56; a CDR1 domain corresponding to about amino acid residues 24–34 of SEQ ID NO:57 (linear numbering; see also SEQ ID NO:32), which is encoded by about nucleotides 330–362 of SEQ ID NO:56; an FR2 domain corresponding to about amino acid residues 35–49 of SEQ ID NO:57 (linear numbering, see also SEQ ID NO:42), which is encoded by about nucleotides 363–407 of SEQ ID NO:56; a CDR2 domain corresponding to about amino acid residues 50–56 of SEQ ID NO:57

(linear numbering; see also SEQ ID NO:33), which is encoded by nucleotides 408–428 of SEQ ID NO:56; an FR3 domain corresponding to about amino acid residues 57–88 of SEQ ID NO:57 (linear numbering; see also SEQ ID NO:43), which is encoded by about nucleotides 429–524 of SEQ ID NO:56; a CDR3 domain corresponding to about amino acid residues 89–97 of SEQ ID NO:57 (linear numbering; see also SEQ ID NO:34), which is encoded by about nucleotides 525–551 of SEQ ID NO:56; and an FR4 domain corresponding to about amino acid residues 98–107 of SEQ ID NO:57 (linear numbering; see also SEQ ID NO:44), which is encoded by about nucleotides 552–581 of SEQ ID NO:56. The nucleotide and amino acid sequences of the preferred modified (deimmunized) anti-PSMA J415 immunoglobulin light chain variable region (J415DIVK5) are shown in SEQ ID NO:50 and 52, respectively; J415DIVK5 can be broken down into its component sequences in a manner identical to that shown above for J415DIVK1.

The nucleotide and amino acid sequence of the modified (deimmunized) anti-PSMA J415 immunoglobulin heavy chain variable region is shown in FIG. 7A (SEQ ID NO:53 and 54, respectively). The non-coding complementary sequence is also shown in FIG. 7A (SEQ ID NO:55). The J415 deimmunized anti-PSMA antibody heavy chain variable region contains the following regions: an FR1 domain corresponding to about amino acid residues 1–25 of SEQ ID NO:54 (linear numbering; see also SEQ ID NO:37), which is encoded by about nucleotides 261–335 of SEQ ID NO:53; a CDR1 domain corresponding to about amino acid residues 26–35 of SEQ ID NO:54 (linear numbering; see also SEQ ID NO:29), which is encoded by about nucleotides 336–365 of SEQ ID NO:53; an FR2 domain corresponding to about amino acid residues 36–49 of SEQ ID NO:54 (linear numbering; see also SEQ ID NO:38), which is encoded by about nucleotides 366–407 of SEQ ID NO:53; a CDR2 domain corresponding to about amino acid residues 50–68 of SEQ ID NO:54 (linear numbering; see also SEQ ID NO:30), which is encoded by about nucleotides 408–464 of SEQ ID NO:53; an FR3 domain corresponding to about amino acid residues 69–100 of SEQ ID NO:54 (linear numbering; see also SEQ ID NO:39), which is encoded by about nucleotides 465–560 of SEQ ID NO:53; a CDR3 domain corresponding to about amino acid residues 101–105 of SEQ ID NO:54 (linear numbering; see also SEQ ID NO:31), which is encoded by about nucleotides 561–575 of SEQ ID NO:53; and an FR4 domain corresponding to about amino acid residues 106–116 of SEQ ID NO:54 (linear numbering; see also SEQ ID NO:40), which is encoded by about nucleotides 576–608 of SEQ ID NO:53. The nucleotide and amino acid sequences of the preferred modified (deimmunized) anti-PSMA J415 immunoglobulin heavy chain variable region (J415DIVH4) are shown in SEQ ID NO:51 and 49, respectively, J415DIVH4 can be broken down into its component sequences in a manner identical to that shown above for J415DIVH1.

It will be appreciated by the skilled artisan that nucleotide sequences encoding anti-PSMA modified antibodies (e.g., FR domains, e.g., FR1–4), can be derived from the nucleotide and amino acid sequences described in the present application using the genetic code and standard molecular biology techniques.

In one embodiment, the isolated nucleic acid comprises an anti-PSMA modified antibody heavy chain variable region nucleotide sequence having a nucleotide sequence as shown in FIG. 4A (SEQ ID NO:23), FIG. 7A (SEQ ID NO:53), or SEQ ID NO:51 (for J415DIVH4) or a complement thereof (e.g., SEQ ID NO:24 or SEQ ID NO:55), the nucleotide sequence of the heavy chain variable region of the antibody produced by the NS0 cell line having ATCC Accession Number PTA-3709 or PTA-4174 or a complement thereof; a sequence at least 85%, 90%, 95%, 99% or more identity thereto; or a sequence capable of hybridizing under stringent conditions described herein (e.g., highly stringent conditions) to a nucleotide sequence shown in FIG. 4A (SEQ ID NO:23), FIG. 7A (SEQ ID NO:53), SEQ ID NO:51, or a complement thereof (e.g., SEQ ID NO:24 or SEQ ID NO:55), or the nucleotide sequence of the heavy chain variable region of the antibody produced by the NS0 cell line having ATCC Accession Number PTA-3709 or PTA-4174, or a complement thereof.

In another embodiment, the isolated nucleic acid encodes an anti-PSMA modified antibody heavy chain variable region amino acid sequence having an amino acid sequence as shown in FIG. 2A (SEQ ID NO:21) or FIG. 5 (e.g., SEQ ID NO:49), or the amino acid sequence of the heavy chain variable region of the antibody produced by the NS0 cell line having ATCC Accession Number PTA-3709 or PTA-4174; a sequence at least 85%, 90%, 95%, 99% or more identical thereto; or a sequence capable of hybridizing under stringent conditions described herein (e.g., highly stringent conditions) to a nucleotide sequence encoding the amino acid sequence as shown in FIG. 2A (SEQ ID NO:21), FIG. 5 (e.g., SEQ ID NO:49), or the amino acid sequence of the heavy chain variable region of the antibody produced by the NS0 cell line having ATCC Accession Number PTA-3709 or PTA-4174.

In another embodiment, the isolated nucleic acid comprises a nucleotide sequence encoding at least one, preferably two, and most preferably three, CDRs of the heavy chain variable region of the anti-PSMA antibody chosen from the amino acid sequences of SEQ ID NO:1, 2, and 3, or 29, 30 and 31, or 93, 94, and 95, or 99, 100 and 101, or a CDR sequence which differs by one or two amino acids from the sequences described herein. In yet another embodiment, the isolated nucleic acid comprises a nucleotide sequence encoding CDRs 1, 2, or 3 shown in FIG. 4A (SEQ ID NO:23), in SEQ ID NO:51, in FIG. 7B (SEQ ID NO:125), in FIG. 9A (SEQ ID NO:73) or in FIG. 11A (SEQ ID NO:83), or a complement thereof, or a sequence encoding a CDR that differs by one or two amino acids from the sequences described herein.

In another embodiment, the isolated nucleic acid comprises a nucleotide sequence encoding at least one, preferably two, three and most preferably four amino acid sequences from the heavy chain variable framework region of the anti-PSMA modified antibody chosen from SEQ ID NO:9, 10, 11 and 12, or 37, 38, 39 and 40, or a sequence at least 85%, 90%, 95%, 99% or more identical thereto.

In yet another embodiment, the isolated nucleic acid comprises an anti-PSMA modified antibody light chain variable region nucleotide sequence having a sequence as shown in FIG. 4B (SEQ ID NO:25), FIG. 8A (SEQ ID NO:56), or SEQ ID NO:52, or a complement thereof (e.g., SEQ ID NO:26 or 58), or the nucleotide sequence of the light chain variable region of the antibody produced by the NS0 cell line having ATCC Accession Number PTA-3709 or PTA-4174; a sequence at least 85%, 90%, 95%, 99% or more identical thereto; or a sequence capable of hybridizing under stringent conditions described herein (e.g., highly stringent conditions) to the nucleotide sequence as shown in FIG. 4B (SEQ ID NO:25), FIG. 8A (SEQ ID NO:56), SEQ ID NO:52, or a complement thereof (e.g., SEQ ID NO:26 or 58), or the nucleotide sequence of the light chain variable region of the antibody produced by the NS0 cell line having ATCC Accession Number PTA-3709 or PTA-4174, or a complement thereof. In another embodiment, the isolated nucleic acid encodes an anti-PSMA modified antibody light chain variable region amino acid sequence having a sequence as shown in FIG. 2B (SEQ ID NO:22) or in FIG. 6 (e.g., SEQ ID NO:50), the amino acid sequence of the light chain variable region of the antibody produced by the NS0 cell line having ATCC Accession Number PTA-3709 or PTA-4174; a sequence at least 85%, 90%, 95%, 99% or more identity thereto; or a sequence capable of hybridizing under stringent conditions described herein (e.g., highly stringent conditions) to a nucleotide sequence encoding the amino acid sequence as shown in FIG. 2B (SEQ ID NO:22) or in FIG. 6 (SEQ ID NO:50), or the amino acid sequence of the light chain variable region of the antibody produced by the NS0 cell line having ATCC Accession Number PTA-3709 or PTA-4174.

In another embodiment, the isolated nucleic acid comprises a nucleotide sequence encoding at least one, preferably two, and most preferably three, CDRs of the light chain variable region of the anti-PSMA antibody chosen from the amino acid sequences of SEQ ID NO:4, 5, and 6, or 32, 33, and 34, or 96, 97, and 98, or 102, 103, and 104, or a sequence encoding a CDR which differs by one or two amino acids from the sequences described herein.

In yet another embodiment, the isolated nucleic acid comprises a nucleotide sequence selected encoding CDRs 1–3 of the light chain variable nucleotide sequence shown in SEQ ID NO:25, or a sequence encoding a CDR which differs by one or two amino acids from the sequences described herein. In another embodiment, the isolated nucleic acid comprises a nucleotide sequence encoding at least one, preferably two, three and most preferably four amino acid sequences from the light chain variable framework region of the anti-PSMA modified antibody chosen from SEQ ID NO:13, 14, 15, and 16, or 41, 42, 43, and 44, or a sequence at least 85%, 90%, 95%, 99% or more identical thereto.

In a preferred embodiment, there is an isolated first and second nucleic acid which have nucleotide sequences encoding a light chain and the heavy chain variable regions of an anti-PSMA antibody, respectively, wherein each isolated nucleic acid has at least one, two, three, four, five and preferably all CDRs chosen from the amino acid sequences of SEQ ID NO:1, 2, 3, 4, 5, and 6, or 29, 30, 31, 32, 33 and 34, or 93, 94, 95, 96, 97, and 98, or 99, 100, 101, 102, 103, and 104, or sequence encoding a CDR which differs by one or two amino acids from the sequences described herein.

The nucleic acid can encode only the light chain or the heavy chain variable region, or can also encode an antibody light or heavy chain constant region, operatively linked to the corresponding variable region. In one embodiment, the light chain variable region is linked to a constant region chosen from a kappa or a lambda constant region. Preferably, the light chain constant region is from a lambda type (e.g., a human type lambda). In another embodiment, the heavy chain variable region is linked to a heavy chain constant region of an antibody isotype selected from the group consisting of IgG (e.g., IgG1, IgG2, IgG3, IgG4), IgM, IgA1, IgA2, IgD, and IgE. Preferably, the heavy chain constant region is from an IgG (e.g., an IgG1) isotype, e.g., a human IgG1.

Nucleic acids of the invention can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, NS0, or CHO cells.

In a preferred embodiment, the nucleic acid differs (e.g., differs by substitution, insertion, or deletion) from that of the sequences provided, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences. The differences are, preferably, differences or changes at nucleotides encoding a non-essential residue(s) or a conservative substitution(s).

In one embodiment, the first and second nucleic acids are linked, e.g., contained in the same vector. In other embodiments, the first and second nucleic acids are unlinked, e.g., contained in different vectors.

In another aspect, the invention features host cells and vectors (e.g., recombinant expression vectors) containing the nucleic acids, e.g., the first and second nucleic acids, of the invention.

Prokaryotic or eukaryotic host cells may be used. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic, e.g., bacterial cells such as E. coli, or eukaryotic, e.g., insect cells, yeast, or preferably mammalian cells (e.g., cultured cell or a cell line). Other suitable host cells are known to those skilled in the art.

Preferred mammalian host cells for expressing the anti-PSMA antibodies, or antigen-binding fragments thereof, include Chinese Hamster Ovary (CHO cells) (including dhfr-CHO cells, described in Urlaub and Chasin, (1980) Proc. Natl. Acad. Sci. USA 77:4216–4220, used with a DHFR selectable marker, e.g., as described in R. J. Kaufman and P. A. Sharp (1982) Mol. Biol. 159:601–621), lymphocytic cell lines, e.g., NS0 myeloma cells and SP2 cells, COS cells, and a cell from a transgenic animal, e.g., e.g., mammary epithelial cell.

In another aspect, the invention features a vector, e.g., a recombinant expression vector. The recombinant expression vectors of the invention can be designed for expression of the modified antibodies, or an antigen-binding fragment thereof, in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to an antibody encoded therein, usually to the constant region of the recombinant antibody.

In addition to the antibody chain genes, the recombinant expression vectors of the invention carry regulatory sequences that are operatively linked and control the expression of the antibody chain genes in a host cell.

In an exemplary system for recombinant expression of a modified antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Pharmaceutical Compositions

In another aspect, the present invention provides compositions, e.g., pharmaceutically acceptable compositions, which include a modified antibody molecule described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The modified antibodies and antibody-fragments of the present invention can be administered by a variety of methods known in the art, although for many therapeutic applications, the preferred route/mode of administration is intravenous injection or infusion. As described in the Examples below, the anti-PSMA antibody can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Therapeutic compositions can be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1–20 mg/kg, more preferably 1–10 mg/kg. As described in Examples 10 and 12, the anti-PSMA antibody can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits comprising an anti-PSMA antibody, preferably a modified antibody, or antigen-binding fragment thereof. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the anti-PSMA antibodies (or antigen-binding fragment thereof) to detect PSMA, in vitro, e.g., in a sample, e.g., a biopsy or cells from a patient having a cancer or prostatic disorder, or in vivo. The instructions can include instructions for therapeutic application including suggested dosages and/or modes of administration, e.g., in a patient with a cancer or prostatic disorder. Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. The kit can include a reagent useful for chelating or otherwise coupling a label or therapeutic agent to the antibody, e.g., a reagent discussed herein. For example, a macrocyclic chelating agent, preferably 1,4,7, 10-tetraazacyclododecane-N,N',N'',N'''-tetraacetic acid (DOTA), can be included. The DOTA can be supplied as a separate component or the DOTA (or other chelator or conjugating agent) can be supplied already coupled to the antibody. Additional coupling agents, e.g., an agent such as N-hydroxysuccinimide (NHS), can be supplied for coupling the chelator, e.g., DOTA, to the antibody. In some applications the antibody will be reacted with other components; e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-PSMA antibodies (or fragments thereof), formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody.

The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers (phenol, sulfites, glutathione, cysteine, gentisic acid, nicotinic acid, ascorbyl palmitate, HOP(:O)H$_2$I glycerol, sodium formaldehyde sulfoxylate, Na$_2$S$_2$O., Na$_2$S$_2$O$_3$, and SO$_2$, etc.).

A preferred kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient with or without further purification. The chelator-conjugated antibody may be supplied in lyophilized form.

Uses of the Invention

The modified antibodies have in vitro and in vivo diagnostic, therapeutic and prophylactic utilities. For example, these antibodies can be administered to cells in culture, e.g. in vitro or ex vivo, or in a subject, e.g., in vivo, to treat, prevent, and/or diagnose a variety of disorders, such as cancers (prostatic and non-prostatic cancers), as well as non-cancerous prostatic conditions (e.g., benign hyperplastic prostatic disorders).

As used herein, the term "subject" is intended to include human and non-human animals. Preferred human animals include a human patient having a disorder characterized by abnormal functioning of a PSMA-expressing cell, e.g., a cancer cell or a prostatic cell. The term "non-human animals" of the invention includes all vertebrates, e.g., mammals and non-mammals, such as non-human primates, sheep, dog, cow, chickens, amphibians, reptiles, etc.

In one embodiment, the subject is a human subject. Alternatively, the subject can be a mammal expressing a PSMA-like antigen with which a modified antibody of the invention cross-reacts. A modified antibody molecule of the invention can be administered to a human subject for therapeutic purposes (discussed further below). Moreover, a modified anti-PSMA antibody (or fragment thereof) can be administered to a non-human mammal expressing the PSMA-like antigen with which the modified antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

Therapeutic Uses

In one embodiment, the invention provides a method of treating, e.g., ablating or killing, a cell, e.g., a prostatic cell (e.g., a cancerous or non-cancerous prostatic cell, e.g., a normal, benign or hyperplastic prostatic epithelial cell), or a malignant, non-prostatic cell, e.g., cell found in a non-prostatic solid tumor, a soft tissue tumor, or a metastatic lesion (e.g., a cell found in renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct) cancer and/or metastasis, melanoma (e.g., malignant melanoma), or soft tissue sarcoma). Methods of the invention include the steps of contacting the cell, or a nearby cell, e.g., a vascular endothelial cell proximate to the cell, with a modified anti-PSMA antibody, e.g., a modified anti-PSMA antibody as described herein, in an amount sufficient to treat, e.g., ablate or kill, the cell.

The subject method can be used on cells in culture, e.g. in vitro or ex vivo. For example, prostatic cells (e.g., malignant or normal, benign or hyperplastic prostate epithelial cells) or non-prostatic cancerous or metastatic cells (e.g., renal, an urothelial, colon, rectal, lung, breast or liver, cancerous or metastatic cells) can be cultured in vitro in culture medium and the contacting step can be effected by adding the modified anti-PSMA antibody or fragment thereof, to the culture medium. The method can be performed on cells (e.g., prostatic cells, or non-prostatic cancerous or metastatic cells) present in a subject, as part of an in vivo (e.g., therapeutic or prophylactic) protocol. For in vivo embodiments, the contacting step is effected in a subject and includes administering the modified anti-PSMA antibody or fragment thereof to the subject under conditions effective to permit both binding of the antibody or fragment to the cell, or the vascular endothelial cell proximate to the cell, and the treating, e.g., the killing or ablating of the cell.

Examples of prostatic disorders that can be treated or prevented include, but are not limited to, genitourinary inflammation (e.g., inflammation of smooth muscle cells) as in prostatitis; benign enlargement, for example, nodular hyperplasia (benign prostatic hypertrophy or hyperplasia); and cancer, e.g., adenocarcinoma or carcinoma, of the prostate and/or testicular tumors.

As used herein, the term "cancer" is meant to include all types of cancerous growths or oncogenic processes, metastatic tissues or malignantly transformed cells, tissues, or organs, irrespective of histopathologic type or stage of invasiveness.

Examples of non-prostatic cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), bladder, genitourinary tract (e.g., prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In other embodiments, the antibodies of the invention can be used for the diagnosis and treatment of a subject experiencing pain or suffering from a pain-associated disorder. Preferably, the subject is a human, e.g., a patient with pain or a pain-associated disorder disclosed herein. For example, the subject could have a disease of the prostate, e.g., benign prostatic hyperplasia or prostate cancer, or non-prostate cancer, e.g., a cancer having vasculature which expresses PSMA (e.g., renal, urothelial (e.g., bladder), testicular, colon, rectal, lung (e.g., non-small cell lung carcinoma), breast, liver, neural (e.g., neuroendocrine), glial (e.g., glioblastoma), or pancreatic (e.g., pancreatic duct) cancer, melanoma (e.g., malignant melanoma), or soft tissue sarcoma). The pain can be associated with bones, as well as with obstructive voiding symptoms due to enlarged prostate, e.g., urinary hesitancy or diminished urinary stream, frequency or nocturia. The treatment of pain using the modified anti-PSMA antibodies of the invention can lead to a decreased or dramatically lowered need, or even eliminate the need, for analgesics, e.g., narcotics. In addition, by reducing pain, the methods of treatment can restore the mobility of, e.g., limbs, that have become dysfunctional as a result of pain associated with movement.

Methods of administering modified antibody molecules are described above. Suitable dosages of the molecules used will depend on the age and weight of the subject and the particular drug used. The modified antibody molecules can be used as competitive agents for ligand binding to inhibit, reduce an undesirable interaction.

In one embodiment, the anti-PSMA antibodies, e.g., the modified anti-PSMA antibodies, or antigen-binding fragments thereof, can be used to kill or ablate cancerous cells and normal, benign hyperplastic, and cancerous prostate epithelial cells in vivo. For example, the anti-PSMA antibodies can be used to treat or prevent a disorder described herein. The antibodies, e.g., the modified antibodies, (or fragments thereof) can be used by themselves or conjugated to a second agent, e.g., a cytotoxic drug, radioisotope, or a protein, e.g., a protein toxin or a viral protein. This method includes: administering the modified antibody, alone or conjugated to a cytotoxic drug, to a subject requiring such treatment.

Since the anti-PSMA antibodies (or fragments thereof) recognize normal, benign hyperplastic, and cancerous prostate epithelial cells, any such cells to which the modified antibodies bind are destroyed. Although such administration may destroy normal prostate epithelial cells, this is not problematic, because the prostate is not required for life or survival. Although the prostate may indirectly contribute to fertility, this is not likely to be a practical consideration in patients receiving the treatment of the present invention. In the case of cancerous tissues, since the modified antibodies recognize vascular endothelial cells that are proximate to cancerous cells, binding of the modified antibody/cytotoxic drug complex to these vascular endothelial cells destroys them, thereby cutting off the blood flow to the proximate cancerous cells and, thus, killing or ablating these cancerous cells. Alternatively, the modified antibodies, by virtue of their binding to vascular endothelial cells that are proximate to cancerous cells, are localized proximate to the cancerous cells. Thus, by use of suitable modified antibodies (including those containing substances effective to kill cells nondiscriminatingly but only over a short range), cells in cancerous tissue (including cancerous cells) can be selectively killed or ablated.

The antibodies of the present invention may be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g., via a viral coat protein), or mixtures thereof. The therapeutic agent can be an intracellularly active drug or other agent, such as short-range radiation emitters, including, for example, short-range, high-energy α-emitters, as described herein. In some preferred embodiments, the anti-PSMA antibody, or antigen binding fragment thereof, can be coupled to a molecule of plant or bacterial origin (or derivative thereof), e.g., a maytansinoid (e.g., maytansinol or the DM1 maytansinoid, see FIG. 15). DM1 is a sulfhydryl-containing derivative of maytansine that can be linked to antibodies via a disulfide linker that releases DM1 when inside target cells. The disulfide linkers display greater stability in storage and in serum than other linkers. Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. Alternatively, the anti-PSMA antibody, or antigen binding fragment thereof, can be coupled to a taxane, a calicheamicin, a proteosome inhibitor, or a topoisomerase inhibitor. [(1R)-3-methyl-1-[[(2S)-1-oxo-3-phenyl-2-[(3-mercaptoacetyl) amino]propyl]amino]butyl] Boronic acid is a suitable proteosome inhibitor. N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudonmonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In a preferred embodiment, the anti-PSMA antibody is conjugated to maytansinoids, e.g., maytansinol (see U.S. Pat. No. 5,208,020), CC-1065 (see U.S. Pat. Nos. 5,475,092, 5,585, 499, 5,846,545). Procedures for preparing enzymatically active polypeptides of the immunotoxins are described in WO84/03508 and WO85/03508, which are hereby incorporated by reference, and in the appended Examples below. Examples of cytotoxic moieties that can be conjugated to the antibodies include adriamycin, chlorambucil, daunomycin, methotrexate, neocarzinostatin, and platinum.

To kill or ablate normal, benign hyperplastic, and cancerous prostate epithelial cells, a first antibody, e.g., a modified antibody, can be conjugated with a prodrug which is activated only when in close proximity with a prodrug activator. The prodrug activator is conjugated with a second antibody, e.g., a second modified antibody according to the present invention, preferably one that binds to a non-competing site on the prostate specific membrane antigen molecule. Whether two modified antibodies bind to competing or non-competing binding sites can be determined by conventional competitive binding assays. For example, monoclonal antibodies J591, J533, and E99 bind to competing binding sites on the prostate specific membrane antigen molecule. Monoclonal antibody J415, on the other hand, binds to a binding site that is non-competing with the site to which J591, J533, and E99 bind. Thus, for example, the first modified antibody can be one of J591, J533, and E99, and the second modified antibody can be J415. Alternatively, the first modified antibody can be J415, and the second modified antibody can be one of J591, J533, and E99. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," (1996) *Cancer Research*, 56:3287–3292, which is hereby incorporated by reference.

Alternatively, the antibody, e.g., the modified antibody, can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303–316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y. Radiotherapy is expected to be particularly effective, because prostate epithelial cells and vascular endothelial cells within cancers are relatively radiosensitive. Moreover, $Lu^{117}$ may also be used as both an imaging and cytotoxic agent.

Radioimmunotherapy (RIT) using antibodies labeled with $^{131}$I, $^{90}$Y, and $^{117}$Lu is under intense clinical investigation.

There are significant differences in the physical characteristics of these three nuclides and as a result, the choice of radionuclide can be important in order to deliver maximum radiation dose to the tumor. The higher beta energy particles of $^{90}$Y may be good for bulky tumors, but it may not be necessary for small tumors and especially bone metastases, (e.g. those common to prostate cancer). The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2–0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., (1995) *Clin Cancer Res.* 1: 1447–1454; Meredith R F, et al. (1996) *J Nucl Med* 37:1491–1496; Alvarez R D, et al. (1997) *Gynecologic Oncology* 65: 94–101).

The antibodies of the invention can also be conjugated or fused to viral surface proteins present on viral particles. For example, a single-chain anti-PSMA antibody of the present invention could be fused (e.g., to form a fusion protein) to a viral surface protein. Alternatively, a whole anti-PSMA antibody of the present invention, or a fragment thereof, could be chemically conjugated (e.g., via a chemical linker) to a viral surface protein. Preferably, the virus is one that fuses with endocytic membranes, e.g., an influenza virus, such that the virus is internalized along with the anti-PSMA antibody and thereby infects PSMA-expressing cells. The virus can be genetically engineered as a cellular toxin. For example, the virus could express or induce the expression of genes that are toxic to cells, e.g., cell death promoting genes. Preferably, such viruses would be incapable of viral replication.

The antibodies, e.g., the modified antibodies of the invention, can be used directly in vivo to eliminate antigen-expressing cells via natural complement or antibody-dependent cellular cytotoxicity (ADCC). Modified antibody molecules of the invention, which have complement binding sites, such as portions from IgG1, -2, or -3 or IgM which bind complement can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with modified antibodies or fragments thereof of the invention can be improved by binding of complement proteins. In another embodiment target cells coated with the modified antibodies or fragments thereof can also be lysed by complement.

The antibodies, e.g., the modified antibodies, of the present invention can be used and sold together with equipment, as a kit, to detect the particular label.

Also encompassed by the present invention is a method of killing or ablating cells which involves using the antibodies described herein, e.g., the modified antibodies for preventing a PSMA-related disorder. For example, these materials can be used to prevent or delay development or progression of prostate or other cancers.

Use of the therapeutic methods of the present invention to treat prostate and other cancers has a number of benefits.

Since the modified antibodies according to the present invention only target cancerous cells (such as cells of cancerous tissues containing vascular endothelial cells) and prostate epithelial cells, other tissue is spared. As a result, treatment with such modified antibodies is safer, particularly for elderly patients. Treatment according to the present invention is expected to be particularly effective, because it directs high levels of modified antibodies, such as antibodies or binding portions thereof, probes, or ligands, to the bone marrow and lymph nodes where prostate cancer metastases and metastases of many other cancers predominate. Moreover, the methods of the present invention are particularly well-suited for treating prostate cancer, because tumor sites for prostate cancer tend to be small in size and, therefore, easily destroyed by cytotoxic agents. Treatment in accordance with the present invention can be effectively monitored with clinical parameters, such as, in the case of prostate cancer, serum prostate specific antigen and/or pathological features of a patient's cancer, including stage, Gleason score, extracapsular, seminal, vesicle or perineural invasion, positive margins, involved lymph nodes, disease related pain, e.g., bone pain, etc. Alternatively, these parameters can be used to indicate when such treatment should be employed.

The invention also features methods of treating pain, e.g., reducing pain, experienced by a subject having or diagnosed with prostate disease, e.g., benign prostatic hyperplasia or prostate cancer, or non-prostate cancer, e.g., a cancer having vasculature which expresses PSMA (e.g., renal, urothelial (e.g., bladder), testicular, colon, rectal, lung (e.g., non-small cell lung carcinoma), breast, liver, neural (e.g., neuroendocrine), glial (e.g., glioblastoma), or pancreatic (e.g., pancreatic duct) cancer, melanoma (e.g., malignant melanoma), or soft tissue sarcoma). The methods include administering an anti-PSMA antibody as described herein, e.g., a modified anti-PSMA antibody, to a subject in an amount sufficient to treat, e.g., reduce, the pain associated with prostate disease or non-prostate cancer. The subject may have no signs of prostate disease or non-prostate cancer other than, e.g., elevated levels of serum PSA and the sensation of pain. Patients that have prostate cancer often experience bone pain, as well as, pain associated with obstructive voiding symptoms due to enlarged prostate, e.g., urinary hesitancy or diminished urinary stream, frequency or nocturia. The treatment of pain using the modified anti-PSMA antibodies of the invention can lead to a decreased or dramatically lowered need, or even eliminate the need, for analgesics, e.g., narcotics. By reducing pain, the methods of treatment can restore the mobility of, e.g., limbs, that have become dysfunctional as a result of pain associated with movement.

Because the antibodies, e.g., the modified antibodies, of the present invention bind to living prostate cells, therapeutic methods for treating prostate cancer using these modified antibodies are not dependent on the presence of lysed prostate cells. For the same reasons, diagnostic and imaging methods which determine the location of living normal, benign hyperplastic, or cancerous prostate epithelial cells (as well as vascular endothelial cells within cancers) are much improved by employing the modified antibodies of the present invention. In addition, the ability to differentiate between living and dead prostate cells can be advantageous, especially to monitor the effectiveness of a particular treatment regimen.

The antibodies, e.g., the modified antibodies, or antigen-binding portions thereof, of the present invention bind to extracellular domains of prostate specific membrane antigens or portions thereof in normal, benign hyperplastic, and cancerous prostate epithelial cells as well as vascular endothelial cells proximate to cancerous cells. As a result, when practicing the methods of the present invention to kill, ablate, or detect normal, benign hyperplastic, and cancerous prostate epithelial cells as well as vascular endothelial cells proximate to cancerous cells, the antibodies, e.g., the modified antibodies, bind to all such cells, not only to cells which are fixed or cells whose intracellular antigenic domains are otherwise exposed to the extracellular environment. Consequently, binding of the antibodies, e.g., the modified antibodies, is concentrated in areas where there are prostate epithelial cells, irrespective of whether these cells are fixed or unfixed, viable or necrotic. Additionally or alternatively, these antibodies, e.g., these modified antibodies, or binding portions thereof, bind to and are internalized with prostate specific membrane antigens or portions thereof in normal, benign hyperplastic, and cancerous prostate epithelial cells.

Combination Therapy

The anti-PSMA antibodies described herein, e.g., the modified anti-PSMA antibodies, or antigen-binding fragments thereof, may be used in combination with other therapies. For example, the combination therapy can include a composition of the present invention coformulated with, and/or coadministered with, one or more additional therapeutic agents, e.g., one or more anti-cancer agents, cytotoxic or cytostatic agents, hormone treatment, vaccines, and/or other immunotherapies. In other embodiments, the anti-PSMA antibodies are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Anti-PSMA antibodies of the invention can be administered in combination with one or more of the existing modalities for treating prostate cancers, including, but not limited to: surgery (e.g., radical prostatectomy); radiation therapy (e.g., external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy); hormonal therapy, which can be administered before or following radical prostatectomy or radiation (e.g., treatments which reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Nonsteroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In other embodiments, the anti-PSMA antibodies, e.g., the modified anti-PSMA antibodies, are administered in combination with an immunomodulatory agent, e.g., IL-1, 24, 6, or 12, or interferon alpha or gamma. As described in Example 14 below, the combination of antibodies having a human constant regions and IL-2 potentially is expected to enhance the efficacy of the monoclonal antibody. IL-2 will function to augment the reticuloendothelial system to recognize antigen-antibody complexes by its effects on NK cells and macrophages. Thus, by stimulating NK cells to release IFN, GM-CSF, and TNF, these cytokines will increase the cell surface density of Fc receptors, as well as the phagocytic capacities of these cells. Therefore, the effector arm of both the humoral and cellular arms will be artificially enhanced. The net effect will be to improve the efficiency of monoclonal antibody therapy, so that a maximal response may be obtained. A small number of clinical trials have combined IL-2 with a monoclonal antibody (Albertini et al. (1997) *Clin Cancer Res* 3: 1277–1288; Frost et al. (1997) *Cancer* 80:317–333; Kossman et al. (1999) *Clin Cancer Res* 5:2748–2755). IL-2 can be administered by either bolus or continuous infusion. Accordingly, the antibodies of the invention can be administered in combination with IL-2 to maximize their therapeutic potential.

Diagnostic Uses

In one aspect, the present invention provides a diagnostic method for detecting the presence of a PSMA protein in vitro (e.g., in a biological sample, such as a tissue biopsy, e.g., from a cancerous or prostatic tissue) or in vivo (e.g., in vivo imaging in a subject). The method includes: (i) contacting the sample with a modified anti-PSMA antibody or fragment thereof, or administering to the subject, the modified anti-PSMA antibody; (optionally) (ii) contacting a reference sample, e.g., a control sample (e.g., a control biological sample, such as plasma, tissue, biopsy) or a control subject)); and (iii) detecting formation of a complex between the anti-PSMA antibody, and the sample or subject, or the control sample or subject, wherein a change, e.g., a statistically significant change, in the formation of the complex in the sample or subject relative to the control sample or subject is indicative of the presence of PSMA in the sample.

Preferably, the anti-PSMA antibody (or fragment thereof) is directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

Complex formation between the anti-PSMA antibody and PSMA can be detected by measuring or visualizing either the antibody (or antibody fragment) bound to the PSMA antigen or unbound antibody (or antibody fragment). Conventional detection assays can be used, e.g., an enzyme-linked immunosorbent assays (ELISA), an radioimmunoassay (RIA) or tissue immunohistochemistry. Alternative to labeling the anti-PSMA antibody, the presence of PSMA can be assayed in a sample by a competition immunoassay utilizing standards labeled with a detectable substance and an unlabeled anti-PSMA antibody. In this assay, the biological sample, the labeled standards and the PSMA binding agent are combined and the amount of labeled standard bound to the unlabeled antibody is determined. The amount of PSMA in the sample is inversely proportional to the amount of labeled standard bound to the PSMA binding agent.

In still another embodiment, the invention provides a method for detecting the presence of PSMA-expressing cancerous tissues (particularly the vascular endothelial cells therein) and normal, benign hyperplastic, and cancerous prostate epithelial cells in vivo. The method includes (i) administering to a subject (e.g., a patient having a cancer or prostatic disorder) an anti-PSMA antibody, preferably a modified antibody, conjugated to a detectable marker; (ii) exposing the subject to a means for detecting said detectable marker to the PSMA-expressing tissues or cells. Particularly preferred antibodies include modified antibodies having CDRs from any of a J591, J415, J533 or E99, and in particular deimmunized versions of these antibodies, particularly deJ591 or deJ415.

Examples of labels useful for diagnostic imaging in accordance with the present invention are radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The modified antibody can be labeled with such reagents using techniques known in the art. For example, see Wensel and Meares (1983) *Radioimmunoimaging and Radioimmunotherapy*, Elsevier, New York, which is hereby incorporated by reference, for techniques relating to the radiolabeling of antibodies. See also, D. Colcher et al. (1986) *Meth. Enzymol.* 121: 802–816, which is hereby incorporated by reference.

In the case of a radiolabeled modified antibody, the modified antibody is administered to the patient, is localized to the tumor bearing the antigen with which the modified antibody reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65–85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled modified antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer (1968) *Science*, 162:526 and Brand, L. et al. (1972) *Annual Review of Biochemistry*, 41:843–868, which are hereby incorporated by reference. The modified antibodies can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

In cases where it is important to distinguish between regions containing live and dead prostate epithelial cells or to distinguish between live and dead prostate epithelial cells, the antibodies of the present invention (or other modified antibodies of the present invention), labeled as described above, can be coadministered along with an antibody or other modified antibody which recognizes only living or only dead prostate epithelial cells labeled with a label which can be distinguished from the label used to label the subject antibody. By monitoring the concentration of the two labels at various locations or times, spatial and temporal concentration variations of living and dead normal, benign hyperplastic, and cancerous prostate epithelial cells can be ascertained. In particular, this method can be carried out using the labeled antibodies of the present invention, which recognize both living and dead epithelial prostate cells, and labeled 7E11 antibodies (Horoszewicz et al. (1987) *Anticancer Research* 7:927–936), which recognize only dead epithelial prostate cells.

In other embodiments, the invention provide methods for determining the dose, e.g., radiation dose, that different tissues are exposed to when a subject, e.g., a human subject, is administered an anti-PSMA antibody that is conjugated to a radioactive isotope. The method includes: (i) administering an anti-PSMA antibody as described herein, e.g., a modified anti-PSMA antibody, that is labeled with a radioactive isotope to a subject; (ii) measuring the amount of radioactive isotope located in different tissues, e.g., prostate, liver, kidney, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled anti-PSMA antibody to the subject. The concentration of radioisotope present in a given tissue, integrated over time, and multiplied by the specific activity of the radioisotope can be used to calculate the dose that a given tissue receives. Pharmacological information generated using anti-PSMA antibodies labeled with one radioactive isotope, e.g., a gamma-emitter, e.g., $^{111}$In, can be used to calculate the expected dose that the same tissue would receive from a different radioactive isotope which cannot be easily measured, e.g., a beta-emitter, e.g., $^{90}$Y.

Pharmacogenomics

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. See, for example, Eichelbaum, M. et al. (1996) Clin. Exp. Pharmacol. Physiol. 23:983–985 and Linder, M. W. et al. (1997) Clin. Chem. 43:254–266. Differences in metabolism of therapeutics can lead to severe toxicity or therapeutic failure by altering the relation between dose and blood concentration of the pharmacologically active drug. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. More specifically, the term refers the study of how a patient's genes determine his or her response to a drug (e.g., a patient's "drug response phenotype," or "drug response genotype.") Thus, another aspect of the invention provides methods for tailoring an individual's prophylactic or therapeutic treatment according to that individual's drug response genotype.

Information generated from pharmacogenomic research can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a composition consisting of one or more anti-PSMA antibodies, or derivatized form(s) thereof, to a patient, as a means of treating a disorder, e.g., a cancer or prostatic disorder as described herein.

In one embodiment, a physician or clinician may consider applying knowledge obtained in relevant pharmacogenomics studies when determining whether to administer a pharmaceutical composition, e.g., a composition consisting of one or more anti-PSMA antibodies, derivatized form(s) thereof, and optionally a second agent, to a subject. In another embodiment, a physician or clinician may consider applying such knowledge when determining the dosage, e.g., amount per treatment or frequency of treatments, of a pharmaceutical composition, e.g., a pharmaceutical composition as described herein, administered to a patient.

In yet another embodiment, a physician or clinician may determine the genotypes, at one or more genetic loci, of a group of subjects participating in a clinical trial, wherein the subjects display a disorder, e.g., a cancer or prostatic disorder as described herein, and the clinical trial is designed to test the efficacy of a pharmaceutical composition, e.g., a composition consisting of one or more anti-PSMA antibodies, and optionally a second agent, and wherein the physician or clinician attempts to correlate the genotypes of the subjects with their response to the pharmaceutical composition.

Deposits

Hybridomas E99, J415, J533, and J591 have been deposited pursuant to, and in satisfaction of, the requirements of the Budapest Treaty on the International Recognition of the Deposit of Microorganisms for the Purposes of Patent Procedure with the American Type Culture Collection ("A.T.C.C.") at 10801 University Boulevard, Manassas, Va. 20110-2209. Hybridoma E99 was deposited on May 2, 1996, and received A.T.C.C. Designation Number HB-12101. Hybridoma J415 was deposited on May 30, 1996, and received A.T.C.C. Designation Number HB-12109. Hybridomas J533 and J591 were deposited on Jun. 6, 1996, and received A.T.C.C. Designation Numbers HB-12127 and HB-12126, respectively.

An NS0 cell line producing deimmunized J591 was deposited with American Type Culture Collection (ATCC), 10801 University Boulevard, Manassas, Va. 20110-2209, on Sep. 18, 2001 and assigned Accession Number PTA-3709. An NS0 cell line producing deimmunized J415 was deposited with American Type Culture Collection (ATCC), 10801 University Boulevard, Manassas, Va. 20110-2209, on Mar. 21, 2002 and assigned Accession Number PTA-4174. These deposits will be maintained under the terms of the Budapest Treaty on the International Recognition of the Deposit of Microorganisms for the Purposes of Patent Procedure. This deposit was made merely as at convenience for those of skill in the art and is not an admission that a deposit is required under 35 U.S.C. §112.

The following invention is further illustrated by the following examples, which should not be construed as further limiting. The contents of all references, pending patent applications and published patents, cited throughout this application are hereby expressly incorporated by reference.

EXAMPLES

Example 1

Chelation of Anti-PSMA Antibodies to $^{111}$Indium, $^{90}$Yttrium, and $^{177}$Lutetium The modified anti-PSMA monoclonal antibodies can be radiolabeled with $^{111}$Indium, $^{90}$Yttrium, or $^{177}$Lutetium by directly coupling one of the four carboxylic acid groups of the chelator 1,4,7,10-tetraazacyclododecane-N,N',N'',N'''-tetraacetic acid (DOTA) to primary amines present on the surface of the antibodies. The DOTA conjugated antibody is then purified, sterile filtered, and vialed. Prior to use, the purified antibodies can be mixed with the desired radiolabel which binds to DOTA.

Chelation Process

Monoclonal antibody deJ591 was conjugated with 1,4,7,10-tetraazacyclododecane-N,N',N'',N'''-tetraacetic acid (DOTA) and subsequently radiolabeled with $^{111}$In, $^{90}$Y and $^{177}$Lu. Radiolabeling and quality control tests were performed on three separate vials of clinical grade mAb deJ591.

All reagents used in the conjugation and purification of deJ591 were made from pyrogen-free water. In the specific case of $NH_4OAC$ buffer and sodium phosphate buffer, the solutions were purified with Chelex 100 (Bio-Rad, CA) to remove any metal ions.

Conjugation of Antibody with 1,4,7,10-Tetraazacyclododecane-N,N',N'',N'''-tetraacetic acid (DOTA)

The monoclonal antibody deJ591 was modified with 1,4,7,10-tetraazcyclododecane-N,N',N'',N'''-tetraacetic acid (DOTA) as follows. Briefly, 25 mg of deJ591 was concentrated in a 30 kDa microsep centrifugal concentrator (Pall Filtron, MA) and washed with 5×4 mL of 1% DTPA (pH 5.0), over a period of 24 hours. The antibody buffer was then changed to 0.1 M phosphate (pH 7.0) using the same centrifugal technique. An active ester of DOTA was created by dissolving 146 mg DOTA (0.361 mmoles) and 36 mg N-hydroxysuccinimide (0.313 mmoles) in 2 ml of water and adjusting the pH to 7.3 with NaOH, prior to the addition of 10 mg of 1-ethyl-3-(3-dimethylaminopropyl)carbodiimide (see below).

ratio between $^{111}$In and DOTA-deJ591 and the observed ratio of $^{111}$In and $^{111}$In-DOTA-J591 detected. Typically, 5.1 molecules of DOTA are conjugated to deJ591. Table 10 shows the results from two conjugations of deJ591.

TABLE 10

Calculation of the Mean Number of DOTA Molecules Conjugated to deJ591

| Test number | Known $^{111}$In/DOTA-J591 Reaction ratio | Observed $^{111}$In/DOTA-J591 TLC ratio | Mean number of DOTA mols per mAb |
|---|---|---|---|
| A | 11.76 | 1.338 | 5.03 |
| B | 17.64 | 2.469 | 5.09 |

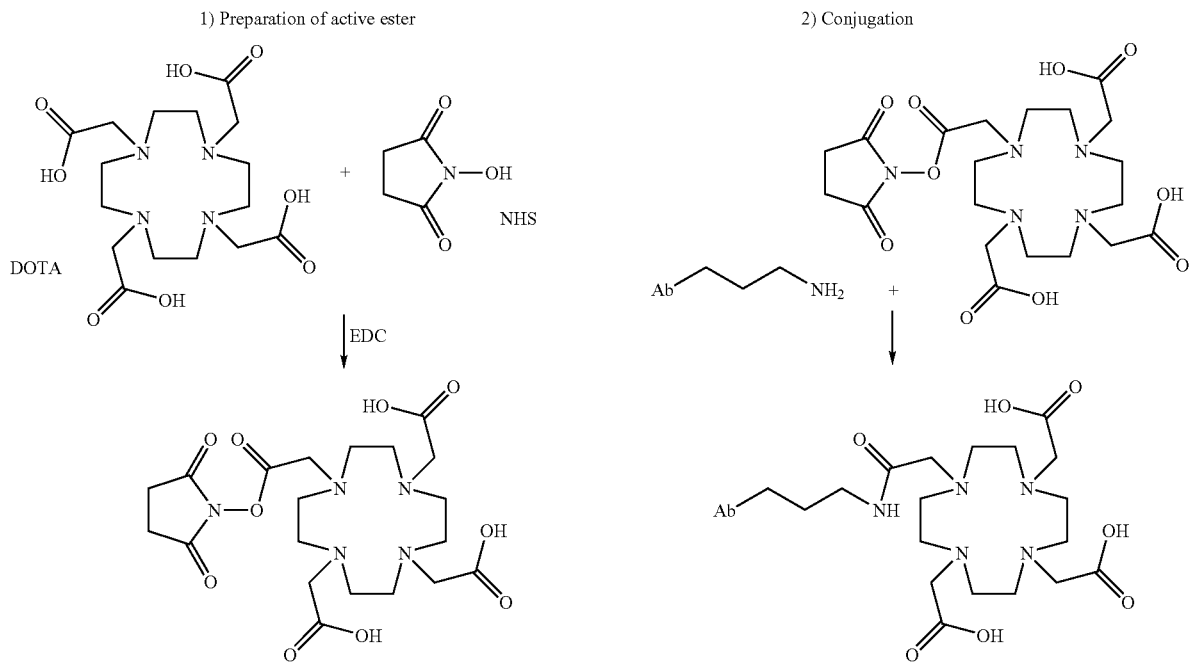

This reaction mixture was cooled on ice for 1 hour before being added to the deJ591 solution. The resultant DOTA-deJ591 was separated from the excess DOTA and other reactants by repeated washing with 0.3 M NH$_4$OAc (20×4 mL) and centrifugal concentration. The purified conjugate was then sterilized by filtration through a 0.22 μm filter and stored in a sterile polypropylene vial at 4° C.

The concentration of the DOTA-deJ591 conjugate was assayed by determining the UV absorption at 280 nm and two 50 μL aliquots mixed with either 20 or 30 μL of a 1.30 mM solution of InCl$_3$ (0.01 M HCl) spiked with a tracer amount of $^{111}$In. The mixture is incubated at 37° C. for 16 hours and then analyzed by ITLC, using silica gel impregnated glass fiber 10 cm strip (ITLC-SG, Gelman, prod. # 61885) and an eluant of 1% DTPA (pH 6.0). The antibody bound activity remains at the origin and free $^{111}$In moves with the solvent front as an $^{111}$In-DTPA complex. The relative amounts of $^{111}$In and $^{111}$In-DOTA-J591 is determined by cutting the ITLC strip at a Rf of 0.5 and counting the two halves with a Na(Tl)I detector. The number of binding sites is calculated by considering the molar reaction Radiolabeling The following radiolabeling procedure is described for $^{111}$In, but may be used with other radiolabels such as $^{90}$Y or $^{177}$Lu. Radiolabeling was achieved by adding the $^{111}$In (in dilute HCl) to the ammonium acetate buffered DOTA-deJ591. To avoid the effects of autoradiolysis on the antibody, the reaction time was minimized and the reaction mixture purified with a size exclusion column prior to administration. Briefly, a mixture composed of 20 μL of $_{111}$InCl$_3$ (8 mCi, 0.01 M HCl, 400 μL DOTA-deJ591 (4 mg/ml, 0.3 M NH$_4$OAc, pH 7) was allowed to react at 37° C. for 20 minutes. The reaction mixture was then separated on a 16 mL Biogel-P6DG column (Bio-Rad, CA) equilibrated with 4×10 mL of sterile 1% HSA in PBS (HSA meets specification for US licensed albumin; manufactured by Central Laboratory Blood Transfusion Service Swiss Red Cross, Bern, Switzerland, License No. 647). Once the reaction mixture was loaded onto the column, it was washed with a further 2 mL of 1% HSA PBS, before the main $^{111}$In-DOTA-deJ591 fraction was eluted with 5 mL of 1% HSA PBS. The purified $^{111}$In-DOTA-deJ591 was then sterile filtered into a sterile evacuated vial. Using this method, specific activity of 7.6 mCi $^{111}$In/mg DOTA-deJ591 was achieved.

Alternative Radiolabeling Procedure for $^{111}$In

The following radiolabeling procedure can be used for the routine preparation of $^{111}$In-DOTA-J591 for clinical studies and stability studies. Radiolableing is achieved by the addition of $^{111}$In chloride and Ammonium acetate buffer (1 M) to DOTA-J591 solution (8 mg/ml, 0.3 M Ammonium acetate, pH 7). To avoid the effects of autoradiolysis on the antibody, the reaction time has been minimized. The labeled $^{111}$In-DOTA-J591 is purified using a size exclusion column and sterile filtered using a 0.2 m millipore membrane filter prior to administration to patients.

Briefly, ammonium acetate, (10 μL for each mCi of $^{111}$In) is added to a reaction vial containing $^{111}$In-chloride solution. Subsequently, the DOTA-J591 solution (30 mL or 0.24 mg for each mCi of $^{111}$In) is added to the reaction vial and the mixture is gently mixed and incubated at 37° C. for 20–30 min. An aliquot of the mixture is tested to determine labeling efficiency using ITLC (SG and 5 mM DTPA, pH 5). If the binding is optimal (>70%), the reaction is stopped by the addition of 10–40 mL of 5 mM DTPA.

In order to separate or purify $^{111}$In-DOTA-J591 from free $^{111}$In, the reaction mixture is applied on a Biogel-P6DG column (Bio-Rad, CA), prewashed with 4×10 ml of PBS containing 1% Human Serum Albumin (meets specification for US licensed albumin; manufactured by Central Laboratory Blood Transfusion Service Swiss Red Cross, Bern, Switzerland, License No. 647). The $^{111}$In-DOTA-J591 is eluted from the column using PBS with 1% HSA and the fractions containing the labeled antibody (typically 5–8 ml) are collected into a sterile container. Following determination of radiochemical purity using ITLC (as before), and if the labeling efficiency is >95%, the labeled complex is filtered into a sterile vial using 0.2 m Filter. The final specific activity is typically 3–5 mCi/mg of antibody.

Radiolabeling with $^{90}$Y

The procedure is identical to the procedure described above for $^{111}$In, except the incubation time is 10–15 min. Radiochemical purity of 90Y-DOTA-J591 must be >97%.

Radiolabeling with $^{177}$Lu

The procedure is similar to the procedure described above except for two changes. The amount of Ammonium acetate added is reduced (3–5 mL for each mCi of $^{177}$Lu) and the incubation time is only 5 min. Radiochemical purity of $^{177}$Lu-DOTA-J591 should be >97%.

Radiochemical Purity

The amount of free $^{111}$In in radiolabeled DOTA-deJ591 preparations was evaluated using the instant thin layer chromatography method with a silica gel impregnated glass fiber support and a mobile phase of 1% DTPA (pH 5.5). Briefly, a portion of the radiolabeled DOTA-deJ591 was spotted on a 10 cm ITLC-SG strip (Gelman, prod. # 61885) and developed in 1% DTPA (pH 5.5). Once the solvent front had reached the end of the strip, it was removed from the solvent and cut at a $R_f$ of 0.5. The two portions were assayed for radioactivity and the radiochemical purity determined using the following equation:

Radiochemical purity=(Activity in between $R_f$0 and 0.5)/(Total activity in strip)

Immunoreactivity

The immunoreactivity of the $^{111}$In-DOTA-deJ591 preparations was assessed according to the method of Lindmo (Lindmo T. et al. (1994) *J. Immunol. Methods*, 72:77–89, 1994) that extrapolates the binding of the radiolabeled antibody at an infinite excess of antigen. Briefly, five test solutions were prepared (in duplicate) containing 10,000 cpm of $^{111}$In-DOTA-deJ591 and various amounts of LNCaP cells, in a total test volume of 250 μL of 0.2% BSA 10 mM HEPES. The solutions were incubated at 4° C. for 60 minutes prior to being isolated (by centrifugation) and washed with ice cold PBS. The membranes were then counted in a gamma counter with standards representing the total radioactivity added. The data was plotted using the Lindmo method as the reciprocal of the substrate concentration (x-axis) against the reciprocal of the fraction bound (y-axis). The data was then fitted according to a least squares linear regression method (Sigma Plot) and the y intercept taken as the reciprocal of the immunoreactivity. A similar method using membranes derived from LNCaP cells, and subsequent centrifugation isolation of the membranes, gave similar results. The results gave an average immunoreactivity of 72% (see Table 11).

Immunohistochemistry immunohistochemistry was performed on the DOTA conjugated, partially purified, bulk intermediate deJ591. The results showed that the preparation was specific to prostate tissue and the reactivity was equivalent to the naked deJ591 antibody.

Sterility

The sterility of $^{111}$In-DOTA-deJ591 preparations was determined using thioglycollate medium according to the method of USP 24/NF 19. Briefly, quadruplicate 0.1 mL samples of the $^{111}$In-DOTA-deJ591 preparations were transferred to 15 mL of fluid thioglycollate medium and the mixture incubated at 35° C. for 14 days. The media were visually inspected on the 4th, 7th and 14 days of any signs of growth. All three preparations showed no growth (See Table 11).

Endotoxin

The endotoxin of $^{111}$In-DOTA-deJ591 preparations was determined using the Limulus amebocyte lysate assay according to the USP 24/NF 19. Briefly, a Limulus amebocyte lysate kit (Bio Whittaker lot # 7L3790, sensitivity 0.125 EU/mL) was reconstituted with 0.25 mL of test sample. The quadruplicate test samples, artificially positive test samples, negative controls and positive controls were incubated at 37° C. for 60 minutes. Positive results were typified by the formation of a viscous gel that was unaffected by 180° inversion. The single preparation gave a value of less than 5 EU/mL. This assay can (and will) be repeated on the patient dose immediately prior to administration.

TABLE 11

Analytical Results of Radiolabeled $^{111}$In-DOTA-deJ591

| Test | Result |
| --- | --- |
| Radiolabeling yield | 85% |
| Radiochemical Purity | >99% |
| Immunoreactivity | 72% |
| Endotoxin | <5 Eu/mL |
| Sterility | Sterile |

Lot # of deJ591: BIOV983.2-2

Large-Scale Manufacture/Process

The large-scale manufacture of the DOTA conjugated deJ591 antibody is described in the following paragraphs. The major differences from the above methodology were the use of a stirred cell, instead of a microsep centrifugal concentrator to concentrate and diafilter the antibody and the use of a Sephadex G-25 column to remove the unreacted DOTA and other reagents from the DOTA conjugated antibody. These changes were necessitated by the increase in scale. The ratios of the starting materials are given in Table 12 for a nominal 1000 milligram scale. The process may be scaled up using equivalent ratios of starting materials.

TABLE 12

Unit Ratios of Starting Materials

| Starting Material | Unit Ratio |
| --- | --- |
| deJ591 antibody | X mgs |
| 1,4,7,10-tetraazacyclododecane-N,N',N'',N'''-tetraacetic acid (DOTA) | 1.25 X mgs |
| N-hydroxysuccinimide (NHS) | 0.275 X mgs |
| 1-Ethyl-3-(3-dimethylaminopropyl) carbodiimide (EDC) | 0.3 X mgs |

Aseptic practices were observed in order to minimize contamination and environmental monitoring was conducted at periodic intervals during the manufacture. All solutions, buffers and reagents used in the conjugation and purification of DOTA-deJ591 antibody were made with Water For Injection (WFI). Throughout the process, metal free components were used in the manufacture in order to avoid the chelation of any free metal residues by the DOTA moiety. In the specific case of ammonium acetate buffer and sodium phosphate buffer, the solutions were purified with Chelex 100 to remove any metal ions. Sterile, pyrogen free and metal free containers were used to mix reactants. The final bulk sterile filtration was conducted in an area that meets Class 100 specifications.

The deJ591 was prepared by buffer exchanging the antibody into metal free, 0.1 M Sodium Phosphate, pH 7.1, over a Chelex 100 (BioRad or equivalent) column. The antibody was then concentrated to approximately 10 mg/mL using a Stirred Cell Unit (Millipore or equivalent) equipped with a 30 kD cut-off membrane. The concentrated antibody was then sterile-filtered through a 0.22 μm filter.

To conjugate one gram of antibody, the active ester of DOTA was prepared by adding 6.3 mL of 0.49 M DOTA in metal free, Sodium Phosphate Buffer, pH 7.1, to 2.7 mL of 0.87 M N-hydroxysuccinimide in metal free, Sodium Phosphate Buffer, pH 7.1. To this mixture, 0.1 N Sodium Hydroxide was added until the DOTA was completely dissolved (approximately a 1:1 ratio of 0.1 M Sodium Hydroxide to DOTA/NHS solution). The pH was between 6.9 and 7.2. The solution was cooled for not less than 30 minutes at 2–8° C. To the DOTA/NHS solution, 1.5 mL of 1.0 M of EDC in Sodium Phosphate Buffer, pH 7.1, was added and allowed to cool at 2–8° C. for not less than 1 hour.

The active DOTA ester was added to 1 gram of antibody and incubated overnight (12–14 hrs) at 2–8° C. The DOTA conjugated antibody was purified over a Sephadex G-25 column (Pharmacia or equivalent) in metal free, 0.3 M Ammonium Acetate Buffer, pH 7.2. The eluate fraction containing the DOTA conjugated antibody was concentrated using a Stirred Cell equipped with a 30 kD cut-off membrane to approximately 10 mg/mL. The DOTA conjugated deJ591 Antibody was then diafiltered in 0.3 M Ammonium Acetate, pH 7.2 to remove any excess reagents and diluted to a final concentration of 8.0 mg/mL prior to sterile filtering through a 0.22 μm filter.

DOTA conjugated deJ591 was tested for concentration, immunoreactivity, conjugation, endotoxin, and sterility. The endotoxin limit is based on the low clinical dose of the radiolabeled DOTA conjugated deJ591 antibody required, which ranges from 1 to 5 mg. Bioburden testing was performed on the bulk purified DOTA conjugated antibody instead of sterility because of the small batch sizes. Sterility (21 CFR 610) will be performed on the final vialed drug product. The target for immunoreactivity and number of DOTA moles per antibody was based on previous clinical experience. DOTA conjugated antibody with immunoreactivity values of as low as 72% have been successfully used in the clinic. The number of DOTA moles per antibody is based on the results from previous clinical lots.

Protein Concentration

A sample of DOTA-deJ591 was analyzed by optical density in a spectrophotometer at a wavelength of 280 nm. The extinction coefficient used for these calculations was $A_{280}$, $E_{1\ cm}^{0.1\%}=1.4$. The test sample was suitably diluted to give an absorbance reading in the working range of the assay (0.2 OD units to 1.2 OD units, linear, CV less than 2%). The acceptable limit for protein concentration is 8.0 mg/mL±0.5 mg/mL.

Endotoxin

Samples of DOTA-deJ591 were tested for pyrogens using a validated Limulus Amebocyte Lysate test (LAL) Gel Clot Assay (BioWhittaker or equivalent). A 0.06 EU/mL sensitivity Lysate was utilized and samples were diluted either 1:10 or 1:25 in Endotoxin free water for analysis in order to overcome the inhibition level of certain chemicals to the gel clot assay. Duplicate determinations were made for each buffer or intermediate sample during processing and the sample values needed to be equal to or less than the value obtained at the dilution level set for that buffer. A positive and negative control, as well as an inhibition control, was run with every sample. The proposed acceptable limits were not more than 5 EU per mg of DOTA-deJ591.

Bioburden

Aliquots of DOTA-deJ591 were directly inoculated in fluid thioglycollate and soybean-casein broth. The media were examined after fourteen days of incubation. As necessary, both media showed no growth after fourteen days.

Immunoreactivity

The immunoreactivity of the DOTA-deJ591 preparations was assessed according to the method of Lindmo (Lindmo T. et al. (1994) *J. Immunol. Methods* 72:77–89) which extrapolates the binding of the radiolabeled antibody at an infinite amount of excess antigen. Briefly five test solutions were prepared (in duplicate) containing 10,000 cpm of [111]Indium labeled-DOTA-deJ591 and various amounts of LNCaP cells or cell membranes, in a total test volume of 250 μL of 0.2% BSA 10 mM HEPES. The solutions were incubated at 4° C. for 60 minutes prior to being isolated (by centrifugation) and washed with ice cold PBS. The membranes were then counted in a gamma counter with standards representing the total radioactivity added. The data was plotted using the Lindmo method as the reciprocal of the substrate concentration (x-axis) against the reciprocal of the fraction bound (y-axis). The data was then fitted according to a least squares linear regression method (Sigma Plot) and the y intercept used as the reciprocal of the immunoreactivity. The target for immunoreactivity was not less than 75%.

Number of DOTA Moles per Antibody

The number of DOTA bound per antibody was determined using a saturation binding method with natural occurring isotope of Indium and $^{111}$Indium. Multiple aliquots (minimum two) of DOTA-deJ591 were mixed with various amounts, ranging from 10 to 30 µL, of a 3.0 mM solution of InCl$_3$ (0.01 M HCl) spiked with a tracer amount of $^{111}$In. The mixture was incubated at 37° C. for 16 hours and then analyzed by ITLC, using silica gel impregnated glass fiber 10 cm strip (ITLC-SG, Gelman, or equivalent) and an eluant of 1% DTPA (pH 6.0). The antibody bound activity remains at the origin and free $^{111}$In moves with the solvent front as an $^{111}$In-DTPA complex. The relative amounts of $^{111}$In and $^{111}$In-DOTA-J591 was determined by cutting the ITLC strip at a $R_f$ of 0.5 and counting the two halves with a Na(Tl)I detector. The number of binding sites was calculated by considering the molar reaction ratio between $^{111}$In and DOTA-deJ591 and the observed ratio of $^{111}$In and $^{111}$In-DOTA-J591 detected. The target number of DOTA molecules per antibody was between 4 and 6.

The analytical results for a sample lot of DOTA conjugated deJ591 antibody are shown below in Table 13.

TABLE 13

| Test | Proposed Acceptable Limits | Results |
| --- | --- | --- |
| Appearance | Clear Colorless Solution | Clear Colorless Solution |
| Concentration | 8.0 mg/mL ± 0.5 mg/mL | 8.4 mg/mL |
| Endotoxin | NMT 5 EU per mg | <1.2 EU/mg |
| Bioburden | No growth | No growth |
| Immunoreactivity | For Information Only (Target NLT 75%) | 95% |
| Number of DOTA moles per Antibody | For Information Only (Target 4–6 DOTA per Antibody) | 6 |

The DOTA conjugation numbers for a previous lot of DOTA conjugated antibody (Biov983.2-2) and current Lot 243101 are shown in Table 14. The average number of DOTA moles per antibody for Lot Biov983.2-2 was 5.06 and for Lot 243101 was 5.96. Although the number of moles of DOTA conjugated per antibody was slightly higher for Lot 243101, the immunoreactivity was not affected as shown in Table 15. In fact, the immunoreactivity for Lot 243101 was higher than that for the comparison lot, which is beneficial. It should be noted that other small-scale clinical lots have had immunoreactivity values of greater than 90% (data not shown).

TABLE 14

Comparison of the Mean Number of DOTA Molecules Conjugated to deJ591 antibody

| Lot number | Known $^{111}$In/DOTA-deJ591 Reaction ratio | Observed $^{111}$In/DOTA-deJ591 TLC ratio | Mean number of DOTA mols per mAb |
| --- | --- | --- | --- |
| BIOV983.2-2 | | | |
| A | 11.76 | 1.338 | 5.03 |
| B | 17.64 | 2.469 | 5.09 |
| Ave | | | 5.06 |
| Lot 243101 | | | |
| A | 10.98 | 0.8608 | 5.90 |
| B | 16.46 | 1.7301 | 6.03 |
| C | 21.95 | 2.8226 | 5.74 |
| D | 32.93 | 4.3498 | 6.15 |
| Ave | | | 5.96 |

A = 10 µL of In-natural/$^{111}$In solution,
B = 15 µL of In-natural/$^{111}$In solution,
C = 20 µL of In-natural/$^{111}$In solution,
D = 30 µL of In-natural/$^{111}$In solution

TABLE 15

Comparison of Immunoreactivity of DOTA-deJ591

| Test | Lot BIOV983.2-2 | Lot 243101 |
| --- | --- | --- |
| Immunoreactivity | 72% | 95% |

Alternatives

An alternative synthesis of the DOTA-J591 immunoconjugate is as follows: 956.5 mg of deJ591 was diafiltered six times. The antibody was concentrated in a 30 kDa microsep centrifugal concentrator (Pall Filtron, MA) to approximately 15 mg/mL and diluted 12.5 fold with metal free 0.1 M Sodium phosphate at pH 7.1. This procedure was performed six times. An active ester of DOTA was created by mixing 598 mg of DOTA (1.48 mmoles) in 5.95 mL 0.1 M metal free phosphate buffer and 132 mg N-hydroxysuccinimide (1.15 mmoles) in 2.7 ml of 0.1 M metal free phosphate buffer. The pH was adjusted to 6.9–7.2 with NaOH, prior to the addition of 144 mg (0.75 mmoles) of 1-ethyl-3-(3-dimethylaminopropyl)carbodiimide in 1.45 mL 0.1 M metal free phosphate buffer. This reaction mixture was filtered through a 0.2 micron sterile filter and cooled on ice for 1 hour before being added to the deJ591 solution and incubated overnight at 2–8° C. for 14–18 hours. The resultant DOTA-deJ591 was separated from the excess DOTA and other reactants by purifying it through a G-25 column equilibrated in 0.3 M metal free ammonium acetate. The purified conjugate was concentrated to 10 mg/mL in a stirred cell unit and washed with 0.3 M ammonium acetate, then sterilized by filtration through a 0.22 um filter and stored in a sterile polypropylene vial at 2–8° C.

Yet another alternative is to use a conjugation process that involves pure DOTA-NHS mono-active ester (commercially available from Macrocyclics) so as to achieve better control over the amount and purity of the DOTA-NHS mono-active ester used in the conjugation process, as well as to limit unanticipated chemical side-reactions produced when DOTA is activated in-situ. Problems associated with the use of in-situ acitivated DOTA (i.e., DOTA activated without any purification prior to being added to the antibody) include: fluctuation of DOTA/antibody incorporation ratio due to the variable generation of DOTA-NHS; the use of a large excess of DOTA which needs to be purified away from the conjugated antibody and can compete for binding to radioactive isotopes; unreacted EDAC can result in the cross-linking of lysine and glutamic or aspartic acid residues on proteins and consequently the formation of undersired protein aggregates; and there is the possibility that two or more active esters are formed on a significant fraction of the activated DOTA molecules which enables proteins to become crosslinked and uses additional carboxylate groups that are needed for metal coordination.

To minimize the loss of antibody binding activity resulting from its conjugation to DOTA, it is desirable to incorporate about 2–10, preferably about 5–7 DOTA molecules per antibody molecule. Using DOTA-NHS monoactivated ester, a 3–30 fold excess of DOTA-NHS relative to antibody produces this desired level of DOTA incorporation. Studies are currently being conducted using input ratios of DOTA-NHS to antibody of 7:1, 9:1, 11:1, 15:1, 20:1, and 30:1.

The protocol is as follows. Starting materials: J591 antibody, 10.5 mg/ml is sodium phosphate buffer (0.1M, pH 7.1), treated with Chelex 100 resin (1 ml resin per 10 mg of antibody); 0.3 M ammonium acetate buffer (pH 7.0), treated with Chelex 100 resin (20 ml resin per one liter buffer); DOTA-NHS.PF6 (FW 646.4), Macrocyclics, Dallas, Tex. Experimental procedures: Three polypropylene vials were separately charged with 2.0 ml of J591 antibody (10.5 mg/ml, 143 nmol) and chilled on ice over a period of 30 minutes. 3.3 mg of DOTA-NHS were dissolved in 0.356 ml of metal-free water (treated with Chelex 100 resin and pre-chilled on ice for 30 minutes) to give a concentration of 14.3 nmol per microliter. To the three antibody solutions were separately added 70, 90, and 110 microliters of this freshly prepared DOTA-NHS solution. The reaction mixtures were slowly stirred with magnetic stirring bars at room temperature over a period of 4 hours, and then diluted with 0.3 M ammonium acetate buffer (pH 7.0, Chelex 100 treated) to 15 ml in CentriCon-30 for buffer exchange. The concentrates (about 1.5 ml) were then diluted again to 1.5 ml and concentrated down to 1.5 ml. These concentrates were then filtered through 0.2 micron filters. The CentriCon tube and filters were washed with a small amount of ammonium acetate buffer and filtered into final products (total of 2.0 ml each).

Antibodies conjugated to DOTA using the 7:1, 9:1, and 11:1 input ration of DOTA-NHS to antibody have been analyzed for $^{90}$Y binding stability and the formation of protein aggregates. All three conjugates displayed a high percentage of stability after 2–3 days of labeling with $^{111}$In or $^{90}$Y, in the presence of PBS, DTPA chelate challenger, serum and transferrin. In addition, all three conjugates displayed little or no process-related aggregate formation. The remaining three conjugates, produced using the higher DOTA-NHS to antibody input ratios, are currently being analyzed.

The conjugation of DOTA to antibodies is not limited to NHS acitivated DOTA. The DOTA-HOBT active ester can be used in place of DOTA-NHS, as well as other activation methods known in the art, such as the use of a mixed anhydride of ethyl chloroformate or isobutyl chloroformate, p-nitrophenyl ester.

Example 2

Pharmacokinetics and Biodistribution of $^{131}$I- and $^{111}$In-labeled deJ591 and Murine J415 in Nude Mice Bearing LNCaP Human Prostate Tumors In nude mice bearing PSMA-positive human LNCaP tumors, the pharmacokinetics, biodistibution and tumor uptake of monoclonal deJ591 and murine J415 antibodies radiolabeled with $^{131}$I or $^{111}$In was analyzed. Autoradiographic studies were performed to identify intra-tumoral distribution of radiolabeled MAbs.

De J591 and J415 were labeled with $^{131}$I using the iodogen method (see Franker and Speck (1978), *Biochem Biophys Res Commun* 80:849–57) to a specific activity of 400 MBq/mg (21, 23). For $^{111}$In labeling, the J415 and deJ591 antibodies were first conjugated with 1,4,7,10-tetraazacyclododecane-N,N',N'',N'''-tetraacetic acid (DOTA) and then labeled with $^{111}$In to produce specific activities of 200 MBq/mg.

Prostate carcinoma cell lines LNCaP, DU145 and PC3 (American Type Culture Collection, Rockville, Md.) were grown in RPMI 1640, supplemented with 10% fetal calf serum, at a temperature of 37° C. in an environment containing 5% $CO_2$. Prior to use, the cells were trypsinized, counted and suspended in Matrigel (Collaborative Biomedical Products, Bedford, Mass.). Nu/Nu Balb C mice 8–10 weeks of age were inoculated, in the right and left flanks, with a suspension of 5×10$^6$ LNCaP cells in Matrigel (BD Biosciences, Bedford Mass.). After a period of 14–18 days, tumors (100–300 mg) had developed. The PSMA-negative DU145 and PC3 cells were implanted in nude mice in an identical manner.

The PSMA-positive and PSMA-negative tumor bearing mice were injected, via the tail vein, with 80 KBq of the iodinated MAb (400 MBq/mg) in 200 µL of PBS (pH 7.4, 0.2% BSA). Groups of animals (3–8/group) were sacrificed after 2, 4 or 6 days. The major organs and tumors were recovered. The tissue samples were weighed and counted, with appropriate standards in an automatic NaI(Tl) counter. These measured relative activity data (cpm) were background corrected and expressed as a percentage of the injected dose per gram (% ID/g). These data were also fitted with a least squares regression analysis (Microcal Origin, Northampton, Mass.) to determine the biological clearance of the various agents. J415, J591 and 7E11 were labeled with $^{111}$In (100 MBq/mg). 80 KBq of the $^{111}$In labeled MAbs were injected in groups of animals. The % ID/g in various organs and tumor tissues was determined at 2–6 days post injection in a similar way as described for $^{131}$I labeled MAbs.

For the imaging studies, animals were injected with 2 MBq of $^{111}$In-DOTA-J591. On days 1, 2, 3, 4 and 6 post-injection, the mice were sedated with ketamine/xylazine 100 mg/kg/10 mg/kg IP. The mice were imaged with a gamma camera (Transcam, ADAC Laboratories, Milpitas, Calif.) equipped with a pinhole collimator. The images were acquired in a 256×256 matrix for 1000 seconds using a 20% window of 245 KeV photopeak of $^{111}$In.

For several animals (n=20), harvested tumor samples were immediately cooled in liquid nitrogen and frozen in embedding medium (O.C.T. 4583, Sakura Finetec, Torrance Calif.). Twenty micron sections were cut and the tumor sections were either fixed with acetone and placed in direct contact with a sheet of photographic film (Biomax, Kodak, Rochester, N.Y.) or stained with hematoxin/eosin prior to exposure of the film. Tumors from control animals were collected and cut into 10 µm sections. These sections were soaked in tris buffer (170 mM, pH 7.4, with 2 mM $CaCl_2$ and 5 mM KCl) for 15 minutes, washed with Tris buffer (170 mM, pH 7.4) and incubated with $^{131}$I-J591 MAb for 1 hour at 4° C. Non-specific binding was determined in the presence of 100 nM J591 MAb. These sections were then washed 3 times with PBS (containing 0.2% BSA) and once with Tris buffer prior to being fixed with acetone and then exposed to photographic film.

Biodistribution of $^{131}$I Labeled MAbs

In nude mice bearing LNCaP tumors, the biodistribution and tumor uptake of $^{131}$I labeled deJ591 and J415 was compared to that of $^{131}$I-7E11. At 2 days post injection deJ591, J415, and 7E11 had similar tumor uptake and blood pool activity. On day 6, the tumor uptake of J415 (15.4±1.1) was significantly higher compared to that of deJ591 (9.58±1.1). The blood activity of both deJ591 and J415 was significantly lower compared to that of 7E11. With the $^{131}$I labeled MAbs, the tumor/blood and tumor/muscle ratios were significantly higher with J415 than with J591 or with 7E11.

In order to assess the specificity of radiolabeled MAb localization in PSMA-positive LNCaP tumors, the uptake of $^{131}$I labeled deJ591 and J415 in selected organs was compared to that of an irrelevant IgG antibody. At one day post injection, the tumor uptake (% injected dose/gram) of both J415 (12.2±3.24) and deJ591 (8.55±1.29) was significantly higher compared to that of an irrelevant antibody (4.41±0.40). The uptake in lungs, kidney, muscle was similar with all three antibodies. In a second control study, the tumor uptake of $^{131}$I-deJ591 was determined in nude mice bearing the PSMA-negative prostate tumors (PC3 and DU145). At 4 days post injection, the tumor uptake of $^{131}$I-deJ591 was only 0.66±0.07% ID/g in PC3 tumors (n=10) and 0.55±0.03% ID/g in DU145 tumors (n=6). In contrast, the tumor uptake of $^{131}$I-J591 was 11.4±1.49% ID/g in PSMA-positive LNCaP tumors, significantly greater than in PSMA-negative tumors (p<0.01).

Biodistribution of $^{111}$In Labeled MAbs

With $^{111}$In, the tumor uptake of deJ591 and J415 gradually increased with time and is quite similar to that of 7E11. The kinetics of blood clearance for both J415 and J591 is faster compared to 7E11. At 6 days post-injection, the blood activity of J415 (2.63±0.23) and deJ591 (2.52±0.16) is about 50% that of 7E11 (4.16±0.21). As a consequence, the tumor/blood ratios with J415 and deJ591 are significantly higher compared to that of 7E11. There were minor differences in the uptake of these three antibodies in liver, spleen and kidney.

The serial gamma camera images of a nude mouse clearly show the intense tumor accumulation of $^{111}$In-DOTA-deJ591. On day 1, the single tumor (ca 250 mg) on the right hind quarter, the blood pool and the liver are well visualized. But in the later images, while the activity has cleared from the blood pool, the tumor accumulation become gradually more intense compared to that of liver activity.

Autoradiography

Tumor specimens (n=20) were harvested for hematoxylin (H) and eosin (E) staining and autoradiography to study the intra-tumoral biodistribution of $^{131}$I-labeled MAbs 4 to 6 days after intravenous injection. The H and E stains reveal a considerable amount of necrosis, averaging 50% of the cross-sectional area, in all specimens studied. The autoradiographs reveal a focal, somewhat heterogeneous, distribution pattern with all three antibodies. Interestingly, the biodistribution pattern with MAbs to PSMA$_{int}$ and PSMA$_{ext}$ reveal almost reciprocal patterns. That is, 7E11 (anti-PSMA$_{int}$) distinctly favors localization to areas of necrosis whereas J415 and J591 (anti-PSMA$_{ext}$) demonstrate a distinct preferential accumulation in areas of viable tumor. Ex vivo autoradiography, where $^{131}$I-J591 was incubated directly on the tissue section, demonstrated a homogeneous binding pattern.

Conclusions

The localization of radiolabeled J591 and J415 in PSMA positive LNCaP tumors is highly specific. These results clearly demonstrate that PSMA-specific internalizing antibodies such as deJ591 and deJ415 may be the ideal MAbs for the development of novel therapeutic methods to target the delivery of beta emitting radionuclides ($^{131}$I, $^{90}$Y, $^{177}$Lu) for the treatment of PSMA-positive tumors.

MAbs to PSMA$_{ext}$ had a reciprocal pattern to 7E11, with localization concentrated in areas of viable tumor. The inability of 7E11 to target well vascularized, viable tumor sites probably explains the inability of ProstaScint® to image bone metastases as well as to explain its failure in RIT trials. By targeting viable tumors, mAbs to PSMA$_{ext}$, like deJ591 and deJ415, will have a better therapeutic effect. In addition, their ability to target viable tumor imparts better ability to localize well-vascularized sites in the bone marrow.

Example 3

Animal Studies Using $^{90}$Y-DOTA-deJ591

In in vitro and in vivo animal models, $^{90}$Y-DOTA-deJ591 has demonstrated substantial anti-tumor activity. In these studies, immunodeficient 'nude' mice were implanted intramuscularly with PSMA-expressing human prostate cancer cells (LNCaP). In some studies, the same animals were simultaneously implanted in the opposite thigh with a PSMA-absent human prostate cancer line (PC3). Cancers were allowed to 'establish' for a period of approximately 2 weeks during which time the cancer develops a blood supply allowing further growth. At the time of treatment initiation, the cancer implants average 1.0 cm in diameter (or approximately 5% of the animal's body weight).

Four groups of mice received a single injection of 1.3, 3.7, 5.55 or 7.4 MBq of $^{90}$Y-DOTA-deJ591. At a 1.3 MBq dose level, there was a mixed response with minimal reduction in tumor growth rate. However, at doses between 3.7–7.4 MBq, a clear anti-tumor dose-response relationship was observed. There was a 30, 55 and 90% reduction in mean tumor volume and a progressive dose-related delay in tumor re-growth of 10, 35 and 60 days at 3.7, 5.55, and 7.4 MBq dose levels, respectively. More than 70% of mice that received 3.7–5.55 MBq lived significantly longer than the controls and the mean survival time (MST) increased to 80–100 days compared to 40 days for controls.

Three groups of mice received 1.11, 2.22 or 3.33 MBq of $^{90}$Y-DOTA-huJ591 every 28 days for 3 doses. At the 1.11 MBq dose level, there was minimal tumor growth during a period of 75–80 days. At 2.22 and 3.33 MBq dose levels, there was a 50–70% reduction in the mean tumor size at day 60 followed by gradual increase in tumor size thereafter. The MST increased by about 200% at 1.11 and 2.22 MBq dose levels compared to control group (120 vs. 40 days).

These studies confirm significant improvement in survival of the $^{90}$Y-DOTA-deJ591 treated animals. The PSMA-absent cancers do not respond to treatment demonstrating the specificity of the treatment.

Example 4

Animal Studies Using $^{177}$Lu-DOTA-deJ591

Nude mice bearing LNCaP tumors treated with $^{177}$Lu-DOTA-deJ591 exhibited a response similar to the $^{90}$Y-DOTA-deJ591 treated animals. In this study mice with LNCaP tumors (300–400 mg) were divided into three groups. A control group received no treatment. Group-2 received 200 μCi and Group-3 received 300 μCi of $^{177}$Lu-DOTA-deJ591. $^{177}$Lu-DOTA-deJ591 was, in a dose dependent manner, able to reduce the mean tumor mass by 80–97% at the two dose levels. The control group showed a progressive increase in tumor size, which was accompanied by a steady loss of body weight and the mice were sacrificed by fifty-three days because of low body mass. The animals treated with 200 μCi $^{177}$Lu-DOTA-deJ591 had tumor shrinkage up to twenty days post injection, and thereafter tumor regrowth was seen in some animals. The same group also had a nadir in body mass of about 90% (of baseline wt) at twenty days post injection, but thereafter a steady rise in the mean body weight to 100–105% of the starting mass. At ninety days, four out of eleven mice had no palpable tumors. The mice treated with 300 μCi of $^{177}$Lu-DOTA-deJ591 had tumor shrinkage up to forty days post injection, and thereafter tumor regrowth was seen in some animals. The same group also had a nadir in body mass of about 90% at twenty days, but thereafter a steady rise in the mean body weight to 105–110% of the starting mass. At ninety days, five out of eleven mice had no palpable tumors.

Example 5

Human Trial with $^{131}$I-J591 (Murine): Phase I Clinical Trial Targeting a Monoclonal Antibody (mAb) to the Extracellular Domain of Prostate Specific Membrane Antigen (Psma$_{ext}$) in Hormone-Independent Patients Hormone-independent patients with rising PSA levels and acceptable hematologic, hepatic and renal function received a single dose of murine mAb J591. Doses are escalated (from 0.5–300 mg) in groups of three to six patients. Each dose included ≦1.0 mg J591 labeled with 10 mCi $^{131}$I iodine as a tracer plus "cold" mAb. The dose levels used ranged from 0.5 to 300.0 mg as follows: 0.5 mg, 1.0 mg, 2.0 mg, 5.0 mg, 10 mg, 25 mg, 50 mg, 100 mg, 125 mg, 150 mg, 200 mg, 250 mg, and 300 mg. Blood and urine were collected to monitor pharmacokinetics, toxicity and human anti-mouse antibody (HAMA) response. Patients were imaged on the day of injection (day 0), as well as days 2, 4 and 6 to track mAb targeting.

Thirty-three patients with hormone-independent prostate cancer were entered into the phase I biodistribution trial of trace-labeled $^{131}$I-J591. These patients received doses ranging from 0.5 to 300.0 mg, in each case conjugated with 10 mCi $^{131}$I. In approximately 80% of patients where disease sites had been imaged by conventional studies (CT/MRI and/or bone scan), known sites of prostate cancer metastases can be imaged. Both soft tissue and bony sites could be visualized on mAb scan. Targeting was specific for prostate cancer sites without apparent localization to non-cancer sites. The mean effective serum residence time of $^{131}$I-mJ591 was determined to be 44.0 hours (median 47.4 hrs). Eight out of sixteen evaluable patients developed a human anti-murine antibody (HAMA) response. That is, their immune systems recognized the foreign nature of the mouse-derived antibody. Only one patient had an adverse event related to the murine antibody. This patient had a severe allergic (anaphylactic) reaction to the murine mAb later determined to be due to prior (unknown) exposure to murine antibody used in purification of another experimental drug with which the patient had previously been treated. In sum, thirty-three patients were evaluated for targeting: twenty-seven out of thirty-three patients had positive bone scans, with twenty-four out of twenty-seven (about 90%) having positive monoclonal antibody scans; nine out of thirty-three patients had positive soft tissue (CT scans), with eight out of these nine (about 90%) having positive monoclonal antibody scans.

Development of a HAMA response, which occurs in most immunocompetent patients who receive murine antibodies, precludes repeated treatments with a foreign species, derived antibody. In order to allow for multiple treatments, murine antibody molecules can be "de-immunized" using molecular engineering techniques which remove foreign (mouse) amino acid sequences and replace them genetically with known homologous human sequences. As indicated above, murineJ591 has undergone de-immunization resulting in "deJ591".

In conclusion, mAb to PSMA$_{ext}$ targets in vivo specifically to disseminated prostate cancer sites in both bone and soft tissue with no significant 'adverse' localization and no significant toxicity.

Example 6

Single Human Patient Study Using $^{90}$Y-DOTA-deJ591

A single patient was treated with mAb deJ591. This patient had bulky, poorly differentiated prostate cancer and had failed multiple courses of external beam radiotherapy as well as multiple forms of hormonal and non-hormonal chemotherapy. The patient was treated under a single patient IND and received a total of twelve doses of deJ591 over a course of five months, ranging from 10 mg to 200 mg. Four doses (#1, 3, 6 and 11) were trace-radiolabeled with either $^{131}$Iodine or $^{111}$Indium for pharmacokinetic determinations and biodistribution. The mean effective serum residence time of $^{131}$I-deJ591 ranged from 31.9 to 51.3 hours, depending on the dose. Tumor localization to known tumor sites was excellent after each of the radiolabeled doses over the five month period. Dose twelve was radiolabeled with a therapeutic quantity of $^{90}$Yttrium (19 mCi) calculated to deliver less than a 150 rad dose to the blood. This dose was determined in consultation with the FDA and took into account prior radiotherapy delivered by external beam and by $^{131}$Iodine. No detectable human anti-deimmunized antibody (immune) response developed in this patient. The patient's platelet count dropped to 64,000 (normal: 150,000–300,000) at five weeks post $^{90}$Y-DOTA-deJ591 administration (as an anticipated result of radiation to the bone marrow) prior to spontaneously returning to normal levels. No other hematologic or non-hematologic toxicity occurred. The patient experienced no side effects. The patient's PSA declined from 63 at the time of deJ591-DOTA-$^{90}$Y administration to 36. No measurable reduction in tumor number or size occurred. This patient succumbed to his metastatic prostate cancer ten and one-half months after initiating treatment with $^{90}$Y-DOTA-deJ591.

Example 7

Human Trial with $^{111}$In-DOTA-deJ591—Phase I Trial of $^{111}$Indium Labeled Deimmunized Monoclonal Antibody (mAb) deJ591 to Prostate Specific Membrane Antigen/Extracellular Domain (PSMAext)

This example describes the results of a clinical trial of deJ591 to assess mAb targeting, toxicity, pharmacokinetics (PK) and immunogenicity (human anti-deimmunized Ab) of this genetically engineered mAb. DeJ591 is a strong mediator of antibody dependent cellular cytotoxicity (ADCC). As PSMA is expressed in tumor, but not normal, vascular endothelium of all cancers, the diagnostic and therapeutic utility of deJ591 may extend beyond prostate cancer to other cancers.

Patients with recurrent, progressing prostate cancer received four weekly doses of $^{111}$In-DOTA-deJ591. Doses were escalated in cohorts of three patients and ranged from 62.5–500 mg/m2 (total). Dose level is shown in Table 16. Each dose included 0.02–1.0 mg deJ591 trace-labeled with 0.1–5 mCi $^{111}$In via a mAb-DOTA chelate, with the remainder of the dose consisting of unlabeled deJ591. After the first dose, patients were imaged on the day of injection (day 0) and days 1, 2, 4 and 7.

TABLE 16

$^{111}$In-DOTA-deJ591 Dosage

| Dose Level | Loading Dose (mg/m$^2$) | Maintenance Dose (mg/m$^2$) | Total Dose (mg/m$^2$) |
|---|---|---|---|
| 1 | 25 | 12.5 | 62.5 |
| 2 | 50 | 25 | 125 |
| 3 | 100 | 50 | 250 |
| 4 | 200 | 100 | 500 |

1–2 mg $^{111}$In-DOTA-deJ591 (0.2–10 mCi), with the balance of the dose as "cold" deJ591.

Serum PK, immune reaction and toxicity were evaluated after each dose for a minimum of 12 weeks.

Fifteen patients were initially entered in the trial. Thirteen patients received all four planned doses; two patients received ≦1 dose. One patient became hypotensive 5 minutes into his first infusion due to a rapid infusion rate. The second patient who did not complete treatment was withdrawn from the study after one week due to rapid disease progression rendering him no longer eligible. Neither this latter patient nor the remaining thirteen patients experienced any toxicity or side effects. Ten out of the thirteen patients had positive bone scans; all ten demonstrated excellent mAb targeting to bony sites. Three patients had soft tissue disease as measured by a CT scan; two demonstrated mAb targeting to these sites, while the third patient that was $^{111}$In-DOTA-deJ591 negative had a radiated pelvic mass that had not changed size in >18 months. No mAb targeting to non-prostate cancer sites was noted. None of the patients developed an immune reaction to the antibody. Plasma half-life of deJ591 varied with dose.

In conclusion, deJ591 is non-immunogenic and targets sensitively and specifically to both bone and soft tissue.

Example 8

Human Trial with $^{111}$In-DOTA-deJ591; Targeting of Hormone Refractory Prostate Cancer This example describes the results of a clinical trial of deJ591 to assess mAb targeting, biodistribution, and pharmacokinetics and to optimize antibody dose for radioimmunotherapy with this mAb in patients exhibiting hormone refractory prostate cancer.

Twenty-six patients exhibiting hormone refractory prostate cancer were injected with a single dose of $^{111}$In-DOTA-deJ591, consisting of 20 mg deJ591 labeled with 185 MBq of $^{111}$In-DOTA. All patients underwent whole body and SPECT imaging on days 0 (the day of injection), 3, and 6 of $^{111}$In-DOTA-deJ591 injection. $^{111}$In-DOTA-deJ591 imaging results were compared with CT, MRI, and bone scan. All patients had rising PSA levels on three consecutive measurements.

Twenty-two of the twenty-six patients had imagable disease on routine imaging modalities, while four patients had no imagable disease. Imaging data revealed $^{111}$In-DOTA-deJ591 tumor targeting in sixteen of the twenty-two (72.7%) patients who had imagable disease. Targeting was best observed on day 3. No additional (unknown) sites were detected on SPECT imaging. Targeted metastatic sites were in the bone or bone marrow in twelve patients, in the soft tissue in two patients, and in both the bone and soft tissue in two patients.

$^{111}$In-DOTA-deJ591 imaging was false negative in four of the twenty-two (18%) patients who had imagable disease. Non-targeted metastatic sites were in the soft tissue in three patients and in both the bone and soft tissue in one patient.

Accumulation of $^{111}$In-DOTA-deJ591 in the, prostate gland was generally minimal in patients with intact but irradiated prostate. Among physiological sites, highest uptake was observed in the liver, with 27+/−1.7% uptake at day 6. The absorbed dose by the liver was 2.8+/−0.25 rads/mCi with $^{111}$In and 20.1+/−2.1 rads/mCi with $^{90}$Y. Plasma clearance (T1/2) of $^{111}$In-DOTA-deJ591 was 34+/−5 hours.

$^{111}$In-DOTA-deJ591 specifically targets hormone refractory prostate tumors and is an effective vehicle to target hormone refractory advanced prostate cancer with radioactivity or cytotoxins.

Example 9

Targeting of Hormone Refractory Prostate Cancer with $^{111}$In-DOTA-deJ591 or $^{177}$Lu-DOTA-deJ591

Imaging studies with $^{177}$Lu-DOTA-deJ591, like those described in Example 8 for $^{111}$In-DOTA-deJ591, have produced similar results. The following summary represents a combination of the results obtained for $^{177}$Lu and $^{111}$In.

Thirty-nine patients with hormone-refractory prostate cancer have thus far been enrolled in one of several clinical trials utilizing deJ591. Nuclear imaging with either $^{111}$In or $^{177}$Lu labeled deJ591 was performed as an initial step of each trial. $^{111}$In, which is a γ-emitter, was used either as tracer for "naked" mAb or as a surrogate imaging agent prior to the administration of $^{90}$Y (a pure β emitter which does not image on radionuclide scans). $^{177}$Lu emits both γ and β particles, allowing direct imaging, and can be used as both an imaging and a therapeutic agent. The antibody scans were compared to standard imaging studies (bone, CT or MR scans) obtained on each patient to assess the underlying sensitivity, specificity, and accuracy of deJ591 targeting to metastatic sites. Bony and soft tissue metastases were evaluated independently.

Results have been obtained for bony metastasis in twenty-three patients, and soft-tissue metastasis in twenty-five patients. Fifteen patients had bone metastases on bone scan, which were accurately targeted by deJ591 in twelve patients (80%). In these twelve patients, every cancerous lesion seen on bone scan was identified on the deJ591 scan. All seven patients with negative bone scans were negative on the deJ591 scan (100% specificity). For soft tissue metastases, eight out of nine patients with soft tissue masses on conventional imaging demonstrated accurate targeting using deJ591 (89%). The one false negative patient had retroperitoneal adenopathy measuring 8 mm not seen on mAb scan, but whose bony lesions were all targeted. Fifteen patients without documented soft tissue metastases had negative mAb scans (100%). One patient without soft tissue metastases on initial standard imaging but lesions identified on mAb scan subsequently proved positive on standard imaging. Overall, there was a 91% concordance between standard imaging and mAb scans for soft tissue and bony metastases.

DeJ591 accurately targets known bony or soft tissue metastases in the vast majority of patients. Additionally, one previously unseen metastatic site was demonstrated on mAb scan and later confirmed with CT imaging. DeJ591 is a highly sensitive and specific agent for targeting metastatic prostate cancer lesions.

Example 10

Human Trial with $^{90}$Y-DOTA-deJ591; Phase I Trial of De-immunized mAb deJ591-DOTA-$^{90}$Yttrium in Patients with Relapsed Prostate Cancer A phase I trial of escalating doses of $^{90}$Y-DOTA-deJ591 therapy of patients with recurrent/relapsing prostate cancer was conducted. Doses started at 5 mCi/m$^2$ and were escalated in increments of +2.5–5 mCi/m$^2$ for cohorts of three to six patients. The design of this study is summarized as follows: $^{111}$In-DOTA-deJ591 was administered to patients so as to determine the biodistribution of the antibody and the associated dosimetry; and $^{90}$Y-DOTA-deJ591 was administered 7–10 days later at 5.0, 10, 15, 17.5, and 20 mCi/m$^2$. All administrations were by intravenous infusion at a rate of about 5 mg/min. DeJ591-DOTA was labeled at a specific activity between 3–5 mCi-$^{90}$Y/mg antibody to reach the defined dose of $^{90}$Y, with the balance brought up to 20 mg total deJ591 with "cold" deJ591. Dosages were administered with 6–8 weeks between dose levels. Subsequent doses of $^{90}$Y-DOTA-deJ591 were allowed.

The subjects for this trial had prostate cancer that had relapsed after definitive therapy (e.g. surgery and/or radiation) and for whom no curative standard therapy exists.

The objectives of this trial are to: (1) define the toxicity and maximum tolerated dose (MTD) of repeated (fractionated) doses of de-immunized monoclonal antibody (mAb) deJ591-DOTA-$^{90}$Yttrium ($^{90}$Y) in patients who have recurrent and/or metastatic prostate cancer; (2) define the pharmacokinetics of deJ591-DOTA-$^{90}$Y; (3) define the human anti-deimmunsized antibody immune response to deJ591-DOTA-$^{90}$Y; and (4) define the preliminary efficacy (response rate) of repeated (fractionated) doses of deJ591-DOTA-$^{90}$Y.

Treatment Protocol:

Patients who developed ≧grade 2 allergic reaction as a result of $^{90}$Y-DOTA-deJ591 would not receive further DOTA-deJ591 and would be followed for toxicity.

Patients were followed for a minimum of 12 weeks after the deJ591-DOTA-$^{90}$Y administration. If the patient's disease was stable or responding at 12 weeks after his last dose, he was followed until progression.

The follow-up study consisted of gathering the information shown in Table 17, below, at the indicated times.

TABLE 17

| Follow-up Analyses | |
|---|---|
| Medical history | Day of Rx, week 1, 2, 4, 6, 8, and 12, then every 12 weeks thereafter until progression |
| Physical exam (focused) | Day of Rx, week 1, 2, 4, 6, 8, and 12, then every 12 weeks thereafter until progression |
| Performance status | Day of Rx, week 1, 2, 4, 6, 8, and 12, then every 12 weeks thereafter until progression |
| PSA, PAP, alkaline phosphatase | Day of Rx, week 1, 2, 4, 6, 8, and 12, then every 12 weeks thereafter until progression |
| Testosterone | Week 4, then every 6 months thereafter until progression |
| Human anti-deimmunized Ab | Day of Rx, week 2, 4, 8, and 12 |
| CBC, differential, platelet count | Day of Rx, week 1, 2, 2.5, 3, 3.5, 4, 4.5, 5, 5.5, 6, and 8, then every 4 weeks thereafter until stable, and then every 12 weeks until progression. Monitor qod if ANC <1000 and/or platelets <50,000 |
| Electrolytes, BUN, creatinine | Day of Rx, week 1, 2, 4, and 8, then every 4 weeks until stable, and then every 12 weeks until progression |
| Total protein, albumin, bilirubin, GGTP, AST, ALT, LDH | Day of Rx, week 1, 2, 4, and 8, then every 4 weeks until stable, and then every 12 weeks until progression |
| Urinalysis | Day of Rx, week 1, 2, and 4, then every 4 weeks unless normal or baseline |
| CT or MRI | Week 12, then every 12 weeks (if measurable or evaluable disease present at entry and/or if patient classified as a "responder") |
| Bone scan | Week 12, then every 12 weeks (if evaluable disease present at entry and/or if patient classified as a "responder") |
| CXR | Week 12, then every 12 weeks (if disease present at entry) |
| Weight | Day of Rx, week 1, 2, 4, 8, and 12, then every 12 weeks until progression |
| Appetite | Day of Rx, week 1, 2, 4, 8, and 12, then every 12 weeks until progression |
| Bone pain | Day of Rx, week 1, 2, 4, 8, and 12, then every 12 weeks until progression |
| Analgesic intake | Day of Rx, week 1, 2, 4, 8, and 12, then every 12 weeks until progression |

Pharmacokinetics:

Following injection of $^{111}$In-DOTA-deJ591, blood samples were obtained at 10 min, 1, 2, 4, 24 hours and days 2, 3, 4 and 7. The percent injected dose (% I.D.) in blood was determined by measuring an aliquot of blood along with a known $^{111}$In standard. Similar blood samples were taken at the same interval after the $^{90}$Y-DOTA-deJ591. The % I.D. in blood was determined by measuring an aliquot of blood along with a known $^{111}$In or $^{90}$Y standard.

Toxicity:

NCI CTEP Common Toxicity Criteria (CTC), version 2 (April, 1999) was utilized. Since CTEP has standardized the CTC, the NCI does not require inclusion of the CTC within this document. All treatment areas have access to a copy of the CTC version 2.0. A copy may also be downloaded from the CTEP web site.

Definition of Dose Limiting Toxicity (DLT):

Hematologic toxicity: grade 4 granulocytopenia [ANC<500/mm$^2$]; grade 4 thrombocytopenia [platelet count<10,000/mm$^2$]; or febrile neutropenia or neutropenic infection as defined by the CTC. Other toxicity: grade$\geq$3 non-hematologic toxicity attributable to $^{90}$Y-DOTA-deJ591.

Definition of Maximum Tolerated Dose (MTD):

The MTD is defined as the dose level at which 0/6 or 1/6 patients experience DLT with the next higher dose level having 2 or more patients experiencing DLT. Once the MTD has been reached, at least 6 patients should be evaluated at that dose to better determine the toxicities of the regimen and the pharmacokinetics of $^{90}$Y-DOTA-deJ591.

Allergic events will be managed as follows: rash, pruritis, urticaria and wheezing will be treated with benadryl and/or steroids as clinically appropriate. Anaphylaxis or anaphylactoid signs or symptoms can be treated with steroids and/or epinephrine as clinically indicated.

Specific Interventions Solely for the Purpose of the Study:

Other than the actual administration of deJ591 and related studies to define the pharmacokinetics and biodistribution of the mAb, the other interventions (labs, imaging studies, office visits) performed are standard procedures. Some of the lab tests would not typically be done in the setting of prostate cancer (e.g., immune reaction levels). Other lab and radiographic procedures, although standard in the management of patients with prostate cancer, may be done at greater frequency than typical.

Criteria for Therapeutic Response:

Prostate cancer progression is manifest by rising PSA levels, new lesions on bone scan, new disease-related symptoms and, less commonly, increasing size of a measurable soft tissue mass. Response is commonly assessed either biochemically (PSA change) or by change in size of a measurable lesion/s.

Biochemical (PSA) response can be determined by comparing the nadir PSA level after therapy to the baseline, pretreatment PSA determined just prior to initiating therapy. A decline of >50% has been demonstrated by numerous investigators (Petrylak, D. P. et al. (1992) *Cancer* 70:2870–78; Kelly W. K., et al. (1999) *J Clin Oncol* 11:607–15; Kantoff P. W., et al. (1999) *J Clin Oncol* 17:2506–13, 1999; Smith, D. C., et al. (1998) *J Clin Oncol* 16:1835–43) to correlate with improved survival. In addition, Scher, et al (Scher H. I., et al. (1999) *JNCI* 91:244–51) have demonstrated that a PSA which either declines or shows no increase from baseline at either 8 or 12 weeks after initiating therapy correlates with improved survival compared to patients whose PSA rises despite therapy.

In patients with measurable disease: complete response is defined as complete disappearance of all measurable lesions by physical examination or imaging studies with no appearance of new lesions for $\geq$2 months. Partial response: is defined as a 50% or greater reduction in the sum of the products of the longest perpendicular diameters of all measurable lesions. There may be no new lesions. Stable disease: patients who do not meet the criteria of partial response and who are without signs of progressive disease for $\geq$2 months. Progressive disease is defined as a greater than 25% increase in the sum of the products of the longest perpendicular diameters of the indicator lesions, the appearance of new lesions or a rise in prostate specific antigen above pre-treatment baseline.

Duration of response: typically, the first sign of progression will be a rise in serum PSA. In this trial the duration of response will be the time interval from treatment initiation ($^{90}$Y-DOTA-deJ591) until progression is documented by either a confirmed rise in PSA, enlargement of the measurable lesion/s, or new lesion/s on imaging studies. The rising PSA must be confirmed by a second, serially rising PSA and the duration will be defined as the time from initiation of treatment to the time of the first rising PSA.

Results:

Twenty patients have been treated according to this protocol, and nineteen of the twenty can currently be evaluated. All twenty patients had failed one or more forms of hormone therapy, and eleven of the twenty patients had failed at least one chemotherapy regimen. Furthermore, the patients all had increasing PSA levels and a minimum platelet count of 150,000.

Blood chemistry, hematology and PSA levels were monitored for twelve weeks or longer. No significant changes were observed in blood chemistry, or liver or kidney functions. Hematological changes in platelets and white blood cell levels were observed at all dose levels. Toxicity was dose-related and limited to reversible myelosuppression (primarily thrombocytopenia): Grade 3–4 thrombocytopenia was observed at 15–20 mCi/m$^2$. The maximum tolerated dose was estimated to be less than or equal to 20 mCi/m$^2$. $^{90}$Y-deJ591 radiation dosimetry estimates based on $^{111}$In-deJ591 imaging studies indicate that the organ dose to liver, kidney, spleen, and bone marrow are 20, 19, 18, and 1.7 rads/mCi, respectively. No patients developed an immune reaction.

Figure 13A:
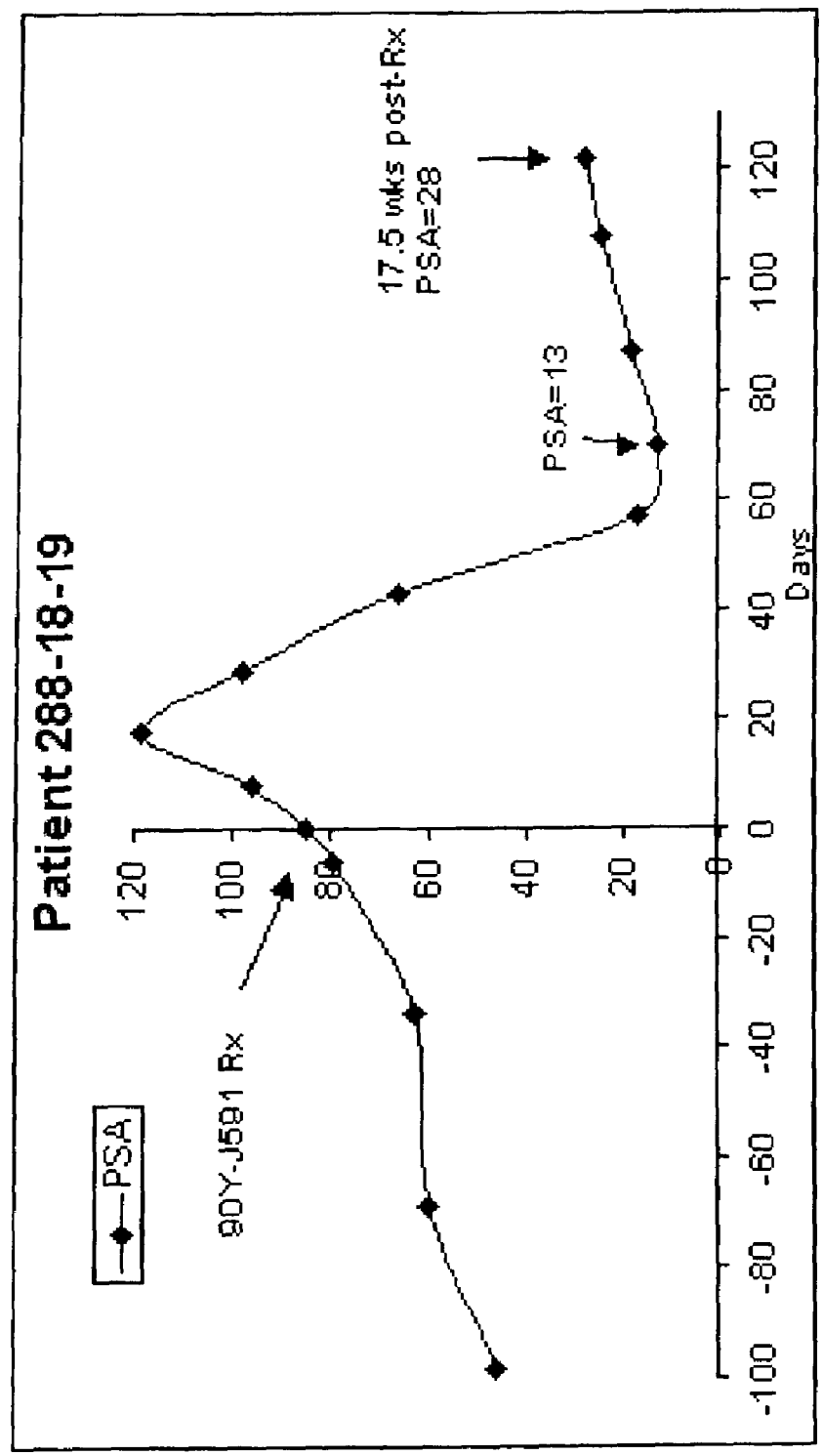
FIGS. 13A and B depict serum PSA levels as a function of time for two patients that were treated with a single dose of $^{90}$Y-DOTA-deJ591. Day 0 corresponds to the day on which the $^{90}$Y-DOTA-deJ591 was administered.

Dose-related anti-tumor effects were noted. At the first two dose levels (5 and 10 mCi/m2), five out of the eleven (45%) patients had PSA values that continued to increase despite treatment, while six out of the eleven (55%) patients achieved an average 23% reduction in PSA levels. At 15 mCi/m2, one out of the four patients (25%) progressed, while three out of the four (75%) patients achieved an average 25% reduction in PSA levels. At 20 mCi/m2, all four patients achieved an average 42% reduction in PSA levels. Two of these four patients have PSA declines of 70–85% continuing beyond 3 months, as shown in FIGS. 13A and B. Mean time to PSA nadir was 7 weeks post-treatment (range: 2–13 weeks). Measurable responses have also been seen in these patients. The patient in whom the PSA level declined by 85% had 90% shrinkage of multiple soft tissue metastases. The patient with the 70% decline in PSA had a measurable decrease in soft tissue disease of 40%.

Conclusions:

$^{90}$Y-DOTA-deJ591 is non-immunogenic (which would allow for repeated treatments) and toxicity has been limited to dose-related, reversible myelosuppression. Importantly, $^{90}$Y-DOTA-deJ591 has dose-related anti-tumor effects in patients with advanced prostate cancer. Phase I data indicates that a single administration of $^{90}$Y-DOTA-deJ591 (less than or equal to 20 mCi/m$^2$) is safe with optimal dosimetry for the treatment of prostate cancer. In addition, the radiation dosimetry estimates indicate that multiple administrations are also safe.

Example 11

Evidence of PSA Responses in Prostate Cancer Patients Receiving $^{90}$Y-deJ591

Figure 13B:
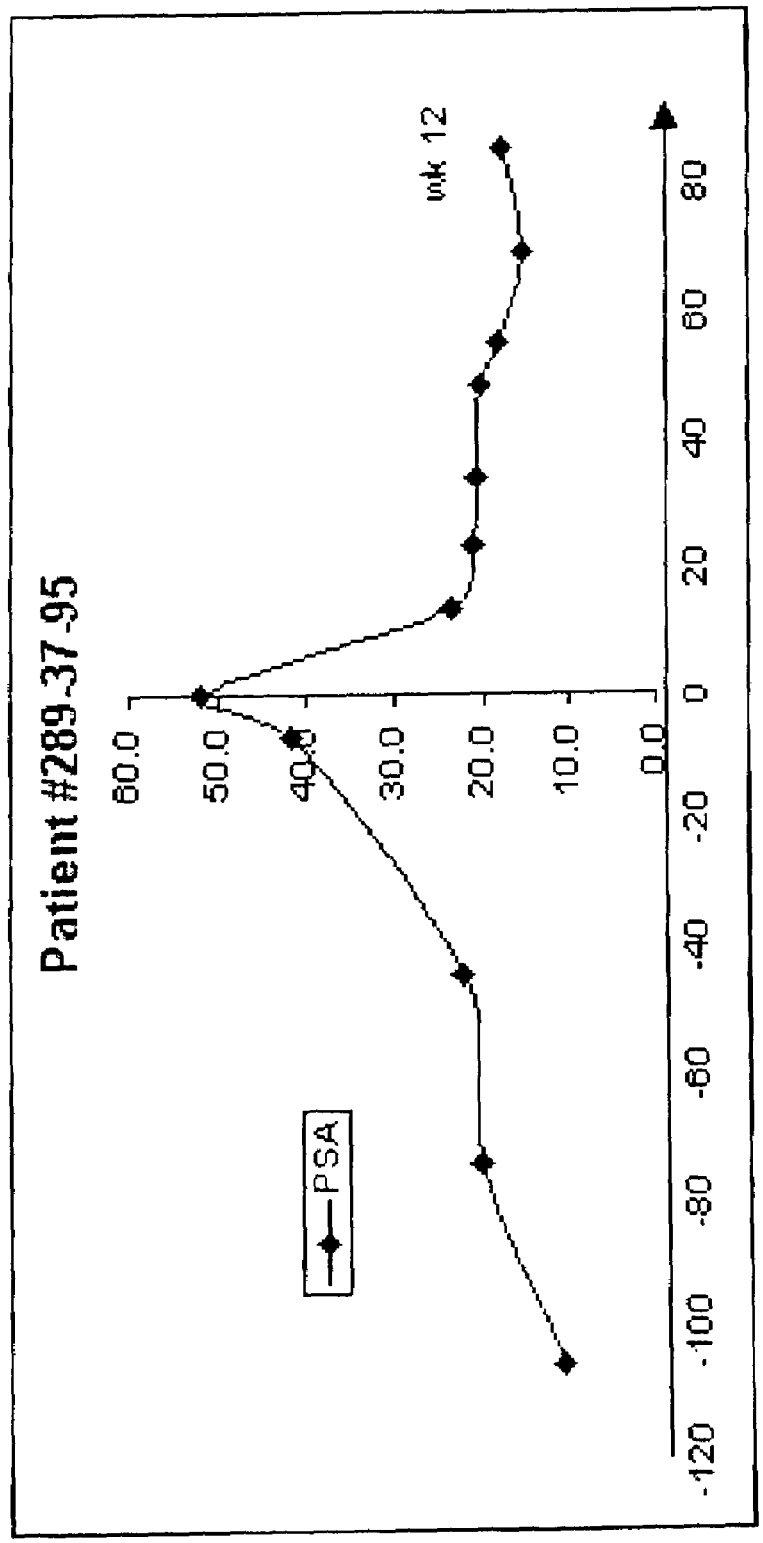

Two patients receiving $^{90}$Y-DOTA-deJ591 had rising PSA levels prior to treatment with radiolabeled J591 (see FIGS. 13A and 13B). The X-axis on the plots represents time (in days). Negative numbers on this axis indicate days prior to J591 treatment. At the "0" time point, the patients received $^{90}$Y-J591 for therapy. The graphs demonstrate that the rapidly rising PSA prior to treatment takes a sharp turn within a few weeks of treatment and becomes stable for a long period of time thereafter (at least ten weeks). The stability of the PSA level indicates that the progressive disease has stopped progressing. Higher doses of radiolabeled J591 may lead to a decrease in the disease burden and/or a prolongation of the cessation of tumor growth rate. In addition, repeated doses may also lead to absolute declines in the tumor burden as well as substantial prolongation of cessation of tumor growth rate.

Example 12

Human Trial with $^{177}$Lu-DOTA-deJ591; Phase I Trial of De-immunized mAb deJ591-DOTA-$^{177}$Lutetium in Patients with Relapsed Prostate Cancer This example describes a clinical study of subjects who have prostate cancer that has relapsed after definitive therapy (e.g., surgery and/or radiation) and/or who are hormone independent and for whom no standard therapy exists. There is currently no curative therapy for these patients. Furthermore, the example focuses on $^{177}$Lu labeled deJ591. $^{177}$Lu is a both a beta- and a gamma-emitter. As such, it can be used for both radiotherapy and imaging.

The objectives of this trial were to: (1) define the toxicity and maximum tolerated dose (MTD) of de-immunized monoclonal antibody (mAb) deJ591-DOTA-$^{177}$Lutetium ($^{177}$Lu) in patients with prostate cancer who have recurrent and/or metastatic prostate cancer (Pca); (2) define the pharmacokinetics of deJ591-DOTA-$^{177}$Lu; (3) define the biodistribution and dosimetry of deJ591-DOTA-$^{177}$Lu; (4) define the human anti-de-immunized antibody (immune) response to deJ591-DOTA-$^{177}$Lu; and (5) define the preliminary efficacy (response rate) of deJ591-DOTA-$^{177}$Lu.

Treatment Protocol:

Patients received a dose of deJ591-DOTA-$^{177}$Lu administered at an infusion rate of $\leq$5 mg/min. The total dose of deJ591 remained fixed at 10 mg/m$^2$. The $^{177}$Lu dose (in mCi/m$^2$) was escalated in cohorts of three to six patients for each dose level (see Table 15 below). DeJ591-DOTA-$^{177}$Lu was labeled at a specific activity between 3–10 mCi/mg antibody to reach the defined dose of $^{177}$Lu, with the balance brought up to 10/m$^2$ mg total deJ591 with "cold" deJ591. Dose escalation was withheld until at least three patients at the ongoing dose level had been followed for $\geq$6 weeks without serious hematologic toxicity. If any of the initial three patients at a dose level experience grade 1 or 2 hematologic toxicity by 6 weeks, escalation was withheld until recovery began or until 8 weeks of further monitoring and evaluation of toxicity had occurred. If any patient experienced grade 3 or 4 hematologic toxicity, at least six patients needed to be entered at that dose level and followed for a minimum of 8 weeks or until recovery begins prior to escalation. If, at any time, two instances of dose-limiting toxicity were observed at a given dose level, further entry at that dose level will be halted. In such a case, at least 6 patients should be entered at the prior dose level to aid in defining MTD (see "Toxicity" section below).

Patients who develop $\geq$grade 2 allergic reaction while receiving $^{177}$Lu-DOTA-deJ591 did not receive further deJ591 and were followed for toxicity.

TABLE 18

| Dose Level | Total deJ591* | $^{177}$Lu Dose |
|---|---|---|
| 1 | 10 mg/m$^2$ | 10 mCi/m$^2$ |
| 2 | 10 mg/m$^2$ | 15 mCi/m$^2$ |
| 3 | 10 mg/m$^2$ | 30 mCi/m$^2$ |
| 4 | 10 mg/m$^2$ | 45 mCi/m$^2$ |
| 5 | 10 mg/m$^2$ | 60 mCi/m$^2$ |
| 6 | 10 mg/m$^2$ | 75 mCi/m$^2$ |
| 7 | 10 mg/m$^2$ | 90 mCi/m$^2$ |
| 8 | 10 mg/m$^2$ | 105 mCi/m$^2$ |

*consisting of deJ591-DOTA-$^{177}$Lu at specific activity between 3–10 mCi/mg with the balance to 10 mg/m$^2$ total with "cold" deJ591.

Patients were followed for a minimum of 12 weeks after the deJ591-DOTA-$^{177}$Lu administration. If the patient's disease was stable or responding at 12 weeks after his treatment, he was followed until progression.

Except as noted in Table 19, follow-up was as described above in Table 14.

TABLE 16

| | |
|---|---|
| Human anti-deimmunized Ab | Day of deJ591-DOTA-$^{177}$Lu Rx, post-Rx week 1, 2, 4, 8, and 12, then every 12 weeks until progression |
| Chem-7 (including Electrolytes, BUN, creatinine, glucose) | Day of deJ591-DOTA-$^{177}$Lu Rx, post-Rx week 1, 2, 4, and 8, then every 4 weeks until stable, and then every 12 weeks until progression |
| Liver panel (including: albumin, bilirubin (tot & dir), AST, ALT, (alkaline phosphatase) | Day of deJ591-DOTA-$^{177}$Lu Rx, post-Rx week 1, 2, 4, and 8, then every 4 weeks until stable, and then every 12 weeks until progression |

TABLE 16-continued

| | |
|---|---|
| LDH | Day of deJ591-DOTA-$^{177}$Lu Rx, post-Rx week 1, 2, 3, and 8, then every 4 weeks until stable, and then every 12 weeks until progression |

$^{77}$Lu-deJ591 Imaging:

Total body images were obtained within 1 hour post-infusion (day 0) and at least 5 additional time points in the subsequent 2 weeks (e.g., days 1, 3, and 5, 10, 15). The gamma camera images were obtained using a dual head ADAC gamma camera fitted with an appropriate collimator. The percent injected dose (% I.D.) in major organs (heart, liver, spleen, kidneys, bone marrow, GI tract and bladder) was estimated by drawing regions of interest (ROI) and determining the relative counts in each organ and kinetics of wash out from each organ. SPECT studies were sometimes performed on the abdomen, pelvis and/or areas of suspected metastatic lesions. Where possible, using known standards of $^{177}$Lu, percent injected dose in tumor was estimated per gram of tumor mass.

Toxicity:

NCI CTEP Common Toxicity Criteria (CTC), version 2 (April, 1999) was utilized. Since CTEP has standardized the CTC, the NCI does not require inclusion of the CTC within this document. All treatment areas have access to a copy of the CTC version 2.0. A copy may also be downloaded from the CTEP web site.

Three to six patients were entered (or will be entered) at each dose level. Dose escalation was withheld until at least three patients at the ongoing dose level had been followed for 6 weeks without hematologic toxicity. If any of the initial three patients at a dose level experience grade 1 or 2 hematologic toxicity by 6 weeks, escalation will be withheld until 8 weeks to further evaluate toxicity. If any patient experiences grade 3 or 4 hematologic toxicity, at least six patients had to be entered at that dose level and followed for a minimum of 8 weeks prior to escalation. If, at any time, two instances of grade 3 or grade 4 toxicity were observed at a given dose level, further entry at that dose level would be terminated.

Definition of Dose Limiting Toxicity (DLT):

Hematologic toxicity: Grade 4 granulocytopenia (ANC<500/ul) for >7 days or grade 4 thrombocytopenia (platelets <10,000). Other toxicity: grade $\geq$3 non-hematologic toxicity attributable to $^{177}$Lu-DOTA-deJ591.

Adverse Event Definition:

An adverse event is defined as any untoward medical occurrence in a research patient during a clinical trial or 4 weeks-post treatment, regardless of causality. This includes clinical or laboratory findings, inter-current illness or an exacerbation or progression of a disease or a condition present at the time of entry (baseline). An adverse event is non-serious if it does not meet any of the serious criteria (see below).

Causality/Attribution:

All clinical adverse events and abnormal laboratory values were evaluated by for potential relationship to the experimental agent. The following categorizes of causality/attribution will be utilized: definite, probable, possible, unlikely, and unrelated.

Abnormal clinical laboratory values of clinical significance which were present at baseline and did not change in severity or frequency during the experimental therapy and/or which can reasonably be attributed to the underlying disease were evaluated by the investigator and recorded in the "unrelated" category. Such events, therefore, were not be considered in the evaluation of the safety of this agent.

Preexisting Conditions:

In this trial, a preexisting condition (that is, a disorder present before the adverse event reporting period started) is not reported as an adverse event unless the condition worsens or episodes increase in frequency during the adverse event reporting period.

Adverse Event Definitions:

Each adverse event was classified as serious or non-serious and/or expected or unexpected. An adverse event is classified as serious if it: it resulted in death; it was life-threatening (i.e., the encountered adverse event placed the subject at immediate risk of death; it does not apply to an adverse event which hypothetically might have caused death if it had been more severe); it required or prolonged in-patient hospitalization; it resulted in persistent or significant disability or incapacity; and it resulted in a congenital anomaly/birth defect.

Grading:

Toxicity was graded on a scale of 0–4 using either the Common Toxicity Criteria scales or the following:
(1) 0=no toxicity.
(2) 1=mild toxicity, usually transient, requiring no special treatment and generally not interfering with patient activity.
(3) 2=moderate toxicity which may be ameliorated by simple therapeutic measures; impairs usual activities.
(4) 3=severe toxicity requiring therapeutic intervention and interrupting usual activities. Hospitalization may or may not be required.
(5) 4=life threatening toxicity which requires hospitalization.
(6) 5=a fatal toxicity.

Criteria for Therapeutic Response:

Prostate cancer is manifest by rising PSA levels, new lesions on bone scan, new disease-related symptoms and, less commonly, increasing size of a measurable soft tissue mass. Response is commonly assessed either biochemically (PSA change) or by change in size of a measurable lesion/s.

Biochemical (PSA) response was determined as described above. In patients with measurable disease: Complete response is defined as complete disappearance of all measurable lesions by physical examination or imaging studies with no appearance of new lesions for >2 months. Partial response: is defined as a 50% or greater reduction in the sum of the products of the longest perpendicular diameters of all measurable lesions. There may be no new lesions. Stable disease: patients who do not meet the criteria of partial response and who are without signs of progressive disease for >2 months. Progressive disease is defined as a greater than 25% increase in the sum of the products of the longest perpendicular diameters of the immeasurable lesions, the appearance of new lesions or a rise in prostate specific antigen above pre-treatment baseline.

Duration of response: Typically, the first sign of progression will be a rise in serum PSA. In this trial the duration of response will be the time interval from treatment initiation until progression is documented by either a rise in PSA, enlargement of the measurable lesion/s, or new lesion/s on bone scan. The rising PSA must be confirmed by a second, serially rising PSA and the duration will be defined as the time from initiation of treatment to the time of the first rising PSA.

Results:

Hormone refractory patients with CT/Bone scan documented prostate cancer lesions and increasing PSA levels were enrolled in a Phase I dose-escalation (10–75 mCi/m$^2$) study. All of the patients had failed one or more forms of hormone therapy.

To date, nineteen patients (three groups of patients, 3–6/group) have received $^{177}$Lu-DOTA-deJ591 (10 mg/m$^2$). Each group received a different dose of $^{177}$Lu-DOTA-deJ591: 10, 15, 30, 45, or 60 mCi/m$^2$ (0.37, 0.74, 1.11, 1.48, or 1.85 GBq, respectively). Blood samples were obtained for two weeks, and imaging studies were performed five times during the same two weeks. Blood chemistry, hematology, and PSA levels were monitored for three months or longer.

Imaging studies showed specific tumor localization of $^{177}$Lu-DOTA-deJ591. Four patients had previously unrecognized metastatic foci demonstrated upon 177Lu-DOTA-deJ591 imaging, which was subsequently confirmed by conventional imaging. The radiation dosimetry estimates show that the liver is the critical organ receiving 7.6+/−3.3 rads/mCi. Dose to bone marrow based on blood activity is 0.7 rads/mCi. Plasma T1/2 of $^{177}$Lu-DOTA-deJ591 was 43+/−11 hours. No significant changes were observed in blood chemistry, or liver or kidney function. Hematological changes were observed at different dose levels, but even at the 60 mCi/m$^2$ dose level, no serious toxicity was observed.

The first nine patients that entered the study received a dose of $^{177}$Lu-DOTA-deJ591 at levels of 10 mCi/m$^2$ (three patients), 15 mCi/m$^2$ (three patients), and 30 mCi/m$^2$ (three patients). All patients had failed one or more forms of hormone therapy, and one (17%) patient had failed at least one chemotherapy regimen. Toxicity was minimal, with no patients having grade 2 or 3 adverse events, and limited to reversible myelosuppression, primarily thrombocytopenia. No patients developed an immune response to $^{177}$Lu-DOTA-J591.

Figure 14:
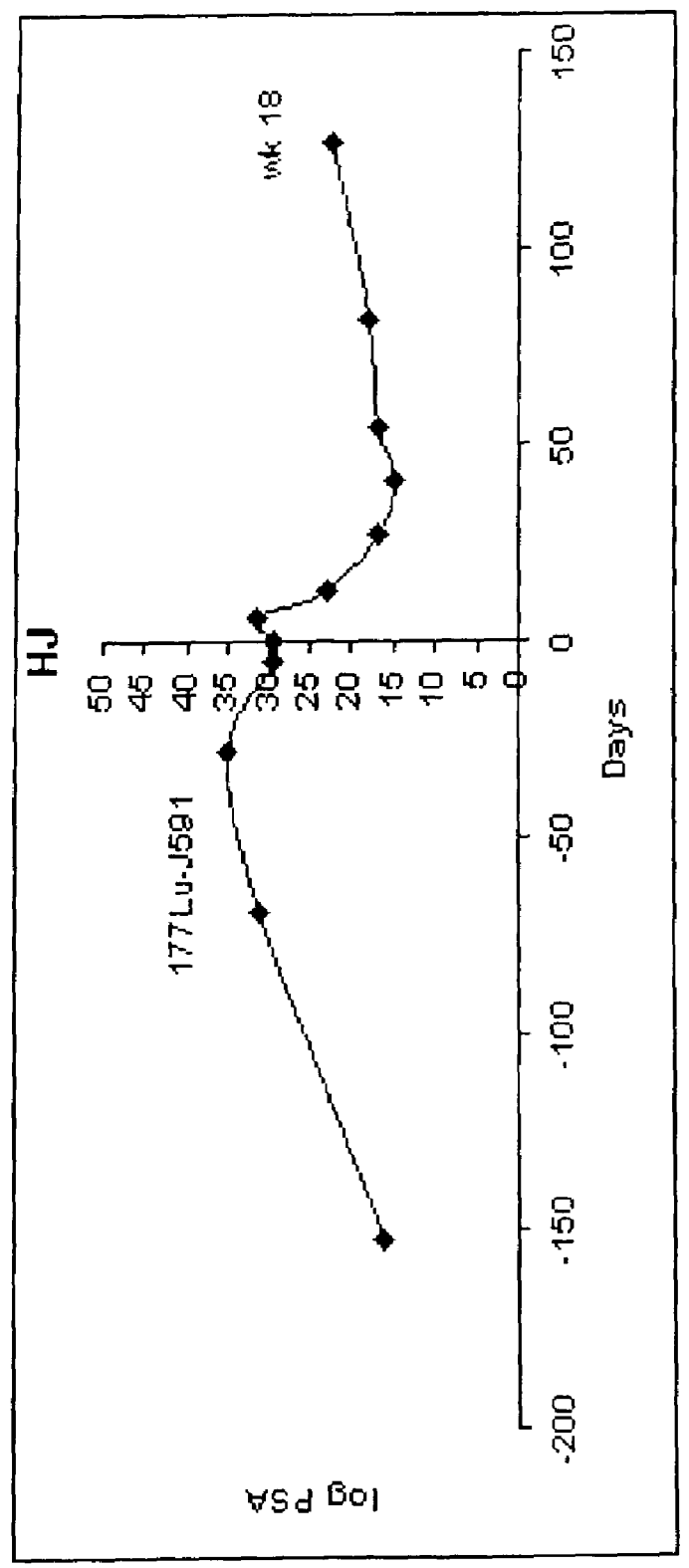
FIG. 14 depicts the serum PSA levels as a function of time for a patient that was treated with a single dose of $^{177}$Lu-DOTA-deJ591. Day 0 corresponds to the day on which the $^{177}$Lu-DOTA-deJ591 was administered.

Among these first nine patients, dose-related anti-tumor effects were noted. Following treatment at the 10 mCi/m$^2$ dose level, two patients had PSA levels that continued to rise despite treatment, while the remaining patient showed stabilization of PSA levels. At 15 mCi/m$^2$, two patients had a mean decrease of 35% in PSA levels, while one patient's PSA levels progressed despite therapy. Mean time to PSA nadir was 4 weeks post treatment (range: 2–6 weeks). One of the three patients that exhibited a decrease in PSA levels, who did not have measurable disease, continued to have 50% reduced PSA levels even at 18 weeks post-treatment (see FIG. 14). Some of these patients are currently being retreated and have received at least three doses of $^{177}$Lu-DOTA-deJ591.

Conclusions:

$^{177}$Lu-J591 is non-immunogenic (which would allow for repeated treatments) and has low toxicity at doses used thus far. It has dose-related anti-tumor effects in patients with advanced prostate cancer. In contrast to $^{90}$Y-DOTA-deJ591, which has a maximum tolerated dose estimated to be about 20 mCi/m$^2$, $^{177}$Lu-DOTA-deJ591 is safe even at a 30 mCi/m$^2$ dose level. $^{177}$Lu-DOTA-deJ591 appears to eliminate disadvantages associated with both $^{131}$I-DOTA-deJ591 (which is dehalogenated in vivo and is not ideal for mAbs that are internalized) and $^{90}$Y-DOTA-deJ591. The longer residence time of $^{177}$Lu-DOTA-deJ591 in tumor tissue may also augment the anti-tumor response.

Example 13

Imaging Non-Prostate Cancers

In addition to prostate epithelial cells, immunohistochemical studies show that PSMA is also expressed by vascular endothelial cells of numerous solid tumors, but not by normal vascular endothelium in benign tissues. As discussed above, this expression pattern of PSMA occurs in virtually all solid tumors.

An IRB approved Phase I dose escalation trial of $^{111}$In-DOTA-deJ591 was initiated to assess its value as an therapeutic agent for vasculotoxic therapy, to define its toxicity and maximum tolerated dose, to determine its pharmacokinetics and biodistribution, and to assess for immunogenicity. Eligible patients were those with refractory solid tumor malignancies whose tumor types are known to express PSMA on the neovasculature.

Fifteen patients received 5 mg (three patients), 10 mg (six patients), or 20 mg (six patients) of $^{111}$In-DOTA-deJ591, followed by a second dose 14 days later.

Patients the participated in the study included eight renal cell cancer patients, four bladder cancer patients, two colon cancer patients, and one pancreas cancer patient. All patients underwent whole body and SPECT imaging on days 0 (the day of injection), 2, 5, and 7 of $^{111}$In-DOTA-deJ591 injection. The $^{111}$In-DOTA-deJ591 imaging results were compared with CT and bone scans.

Imaging data revealed $^{111}$In-DOTA-deJ591 tumor targeting in ten of the fifteen patients (7 renal cell cancer, 2 bladder cancer, and 1 colon cancer). Targeting was best observed on days 2 and 5, and was independent of antibody mass delivered. No additional sites were detected on SPECT. Targeted metastatic sites included: lungs, femur, retroperitoneal and cervical lymph nodes. Brain metastasis in one patient (with renal cell cancer) was first detected by $^{111}$In-DOTA-deJ591 imaging and later confirmed by MRI. $^{111}$In-DOTA-deJ591 imaging was false negative in five of the fifteen patients (2 bladder cancer, 1 colon cancer, 1 pancreas cancer, and 1 renal cell cancer). Non-targeted metastatic sites included: liver, renal bed, pancreas, lungs, and celiac lymph nodes. Undetected lung lesions measured less than 1 cm in size.

No objective responses occurred, although a colon cancer patient had a 50% decline in CEA and two patients had improvement in cancer pain and performance status.

Two different patients with metastatic kidney cancer, having disease that had spread to the lungs, lymph nodes, and/or bones, were injected with deJ591 labeled with $^{111}$Indium. Images of the patients, taken within 2 days of injection, demonstrated significant uptake of the antibody in the known tumor sites in these varying tissues and organs. The extent of the uptake of antibody is both substantial and rapid.

Among physiological sites, highest uptake was observed in the liver. Plasma clearance and liver uptake were dependent upon antibody mass; lower mass resulted in faster plasma clearance and higher liver uptake (in terms of percentage uptake). Plasma clearance (T1/2) for 5 mg, 10 mg, and 20 mg of deJ591 were 21+/−11 hours, 24+/−6 hours, and 37+/−8 hours, respectively. Liver uptake for the same dose levels was 28%+/−14%, 17%+/−7%, and 13%+/−5%, respectively.

Based on these data, the protocol was revised to provide dosing for 6 consecutive weeks (10, 20, 40 and 80 mg/week dose levels) with the option for re-treatment on 8 week cycles if patients have stable or responding disease. To date, nine patients are currently receiving treatment on this schedule.

[111]In-DOTA-deJ591 specifically targets vascular endothelium of solid tumors. These trials demonstrate that deJ591 is an effective approach to targeting solid tumor vascular endothelium with radioactivity or cytotoxins.

Example 14

Phase II Trial of mAb deJ591 in Combination with Low-dose Subcutaneous Interleukin-2 in Patients with Recurrent Prostate Cancer The subjects for this trial have prostate cancer which has relapsed after definitive therapy (e.g. surgery and/or radiation) and/or who are hormone independent and for whom no standard therapy exists. There is currently no curative therapy for these patients.

The objectives of the trial are to: (1) To define the preliminary efficacy (response rate) of mAb deJ591 in combination with daily low-dose subcutaneous IL-2 in patients who have recurrent and/or metastatic prostate cancer; (2) to study the toxicity of mAb deJ591 in combination with daily low-dose subcutaneous IL-2; and (3) to measure in vitro the effect of IL-2 on the immune response.

Low-Dose IL-2 Therapy:

IL-2 promotes the proliferation and enhances the secretory capacity of all major types of lymphocytes, including T cells, B cells, and natural killer (NK) cells (Smith K. A. (1988) *Science* 240:169). The IL-2 stimulated expansion of antigen-selected T-cell and B-cell clones determines the magnitude of antigen-specific immune responses, while the quality of the response is determined by IL-2 promoted secretion of additional cytokines, cytolytic molecules and antibodies (Smith K. A (1993) *Blood* 81:1414–1423). In addition, through its effects on NK cells, IL-2 stimulates antigen-nonspecific host reactions that involve an interplay between NK cells and monocytes. As a result of these functions, it follows that IL-2 should be useful as an immune stimulant, particularly in cancer immunotherapy. The therapeutic use of IL-2, however, is made difficult because one of its major effects consists of the stimulation of secondary cytokine secretion by IL-2-responsive cells. Many of the potential beneficial effects of IL-2 can be attributed to these secondary cytokines that recruit and activate additional cell types, especially monocytes, that contribute to the total immune/inflammatory reaction. However, these same secondary cytokines, when produced in too large amounts, can also lead to severe toxicity. IL-2 was first used in very high doses for the treatment of cancer, equivalent to 150 million units (MU) of Chiron Corporation IL-2 (Rosenberg S. A (1990) *Sci. Am* 262:62–69). This high dose was determined using the dose-escalation and dose-intensification principles of chemotherapy, and was associated with significant grade 3 and 4 toxicity. IL-2 in high doses is known to cause serious side effects including fever, rigors, malaise, myalgia, nausea/vomiting, hypotension and possibly death.

In the 1990s, researchers began to examine the immunomodulatory effects and toxicities of continuous low dose IL-2 (Smith K. A (1993) *Blood* 81:1414–1423; Caligiuri et al. (1991) *J Clin Oncol* 9:2110–2119; Caligiuri et al. (1993) *J Clin Invest* 91:123–132; Bernstein et al. (1995) *Blood* 86:3287–3294). These studies demonstrated that doses of IL-2 as low as 1.2 MU daily resulted in the specific expansion of NK cells with minimal toxicity. Bernstein et al. (1995) *Blood* 86:3287–3294; Lalezari et al. (2000) HIV Clin Trials). Potential side effects include injection site reactions (usually redness at the injection site), asthenia, flu-like symptoms, nausea, diarrhea and eosinophilia. The selective expansion of human $CD3^-$, $CD56^+$ NK cells during low-dose IL-2 begins within 2 weeks of therapy and plateaus after 4–6 weeks of treatment (Smith K. A (1993) *Blood* 81:1414–1423; Fehniger et al. (2000) *J Clin Invest* 106: 117–124). NK cells can account for as many as 60%–80% of PBMCs after one month of therapy (Smith K. A (1993) supra). Recent studies suggest that increased NK cell number results from enhanced NK-cell differentiation from bone marrow progenitors, combined with a delay in IL-2 dependent NK-cell death (Fehniger et al. (2000) supra). The low-dose IL-2 regimens have been specifically designed to completely avoid toxicity.

Combination Monoclonal Antibody and IL-2 Therapy:

The combination of monoclonal antibodies and IL-2 potentially should enhance monoclonal antibody efficacy. IL-2 will function to augment the reticuloendothelial system to recognize antigen-antibody complexes by its effects on NK cells and macrophages. Thus, by stimulating NK cells to release IFN, GM-CSF, and TNF, these cytokines will increase the cell surface density of Fc receptors, as well as the phagocytic capacities of these cells. Therefore, the effector arm of both the humoral and cellular arms will be artificially enhanced. The net effect will be to improve the efficiency of monoclonal antibody therapy, so that a maximal response may be obtained. A small number of clinical trials have combined IL-2 with a monoclonal antibody (Albertini et al. (1997) *Clin Cancer Res* 3:1277–1288; Frost et al. (1997) *Cancer* 80:317–333; Kossman et al. (1999) *Clin Cancer Res* 5:2748–2755). In such studies, IL-2 was administered intravenously by either bolus or continuous infusion. Toxicity was associated with higher doses of IL-2.

IL-2 Therapy in Prostate Cancer:

A variety of studies have examined the effects of IL-2 on prostate cancer cells in vitro and in prostate cancer animal models, Moody et al. Interleukin-2-transfected prostate cancer cells generate a local antitumor effect in vivo (*Prostate*, 24: 244–251, 1994; Sokoloff et al. (1996) *Cancer*, 77: 1862–1872; Triest et al. (1998) *Clin Cancer Res*, 4: 2009–2014; Hautmann et al. (1999) *Anticancer Res*, 19: 2661–2663; Hillman et al. (1999) *Cancer Detect. Prev.* 23: 333–342), although there have been few clinical trials of IL-2 in patients with advanced prostate cancer. Hillman et al. (1999) supra; Maffezzini et al. (1996) *Prostate*, 28: 282–286; Morris et al. (2000) *Cancer*, 89: 1329–1348). A Phase II trials of I.V. intermediate dose IL-2 (dose ranging from 10–15 MU daily×4) in patients with hormone refractory prostate cancer was conducted. In six out of ten patients, a transient decline in PSA levels was observed. It is unclear if this was from anti-tumor activity, or if IL-2 affected PSA expression, as had been reported in vitro studies using LNCaP cells (Sokoloff et al. (1996) supra). No regression of measurable disease was observed in any patient. The effect of daily sub-cutaneous low-dose IL-2 in patients with progressive prostate cancer has not been examined.

Specific Aims:
(1) To define the preliminary efficacy (response rate) of mAb deJ591 in combination with daily low-dose subcutaneous IL-2 in patients who have recurrent and/or metastatic prostate cancer.
(2) To study the toxicity of mAb deJ591 in combination with daily low-dose subcutaneous IL-2.
(3) To measure the effect of IL-2 on the peripheral blood mononuclear cell (PBMC) population.
(4) To measure in vitro the effect of IL-2 activated NK cells from patients on this protocol to induce ADCC with mAb deJ591.

Treatment Protocol:

Patients receive daily low-dose subcutaneous rIL-2 ($1.2 \times 10^6$ IU/m$^2$/day) on day 1 through day 56. After three weeks of IL-2 administration, patients receive deJ591 by I.V. (25 mg/m$^2$) once a week for three consecutive weeks (on days 22, 29, and 36). IL-2 administration is continued during this period another two weeks afterwards. This 8-week regimen constitutes one cycle of therapy. Patients are evaluated for response at the end of one cycle. Patients who have responded to therapy or have stable disease are eligible for additional cycles of therapy. Additional cycles will be initiated when there is at least two consecutive rises in PSA at least 2 weeks apart. A three-week lead in with IL-2 should be sufficient to significantly increase the NK cell population. The dose of deJ591 is based on preliminary pharmacokinetic data from the Phase I $^{111}$In-labeled deJ591 trial. The dose of antibody will be adjusted based on additional data analysis of patients treated in this manner.

A single cycle of treatment has been initiated. Patients who progress by radiographic documentation after one cycle will be removed from the study. Patients who responded by radiographic documentation, or who had stable disease by imaging with >50% decline in PSA value, or who had stable disease by imaging with stable PSA levels, will be examined every 3–4 weeks. Responding or stable patients will be eligible for re-treatment (a second 8-week cycle) following 2 consecutive PSA rises at least 2 weeks apart, at the discretion of the Principal Investigator and the option of the patient. Patients who have stable disease by imaging with a rising PSA (>25% of pre-treatment value) will be examined every 3–4 weeks. Re-treatment will be at the discretion of the Principal Investigator. In order to be retreated, the patient must have a immune reaction titer <$\frac{1}{100}$ and satisfy all initial Eligibility and Exclusion criteria. Re-treatment will be at the identical dose formulation as the initial dose given to the patient.

Patient Selection:

The trial is a pilot study to ascertain if low-dose IL-2 in combination with deJ591 has activity in prostate cancer. It is possible that low-dose IL-2 may have activity in prostate cancer patients. However, it has been decided not to treat patients with IL-2 alone, or delay antibody therapy, if the PSA declines after 3 weeks of therapy on low-dose IL-2, as it will be interesting to study the combined effect of deJ591 with IL-2. If significant activity is observed, a subsequent randomized trial of IL-2 alone vs. IL-2 with deJ591 will be conducted. It is unclear which stage of patient with prostate cancer might benefit from this approach. Therefore, at least ten patients will be treated, each in the following subgroups: 1) Biochemical relapse, hormone naive: rising PSA following radical prostatectomy or radiation therapy, without evidence of metastatic disease; 2) Biochemical relapse, hormone refractory: rising PSA following hormonal therapy without prior chemotherapy (these patients may or may not have radiographic documented metastatic disease); and 3) Hormone refractory, having received prior chemotherapy. About 30–40 patients will be enrolled on this trial.

Toxicity:

Toxicity will be scored using the Cancer Therapy Evaluation Program Common Toxicity Criteria, Version 2.0 (April 1999).

IL2 Dosage Modifications:

IL-2 will be permanently discontinued for any study drug-related Grade 4 toxicity except hematologic (which can be corrected with EPO or G-CSF or blood transfusions). If at any time during the study, ALT is $\geq 20$ times the upper limit of normal, both IL-2 and mAb therapy will be permanently discontinued in that subject. Electrolyte abnormalities that can be readily corrected will not require permanent drug discontinuation.

This protocol allows for one dose level reduction of IL-2 of 25% to 0.9 mU/M$^2$. Subjects receiving IL-2 may have their IL-2 interrupted for $\geq$Grade 1 toxicity for 24–48 hours. Toxicities that may cause IL-2 to be temporarily interrupted are:

Electrolyte abnormalities Grade 1 or higher that cannot be rapidly corrected;
Grade 1 or higher respiratory toxicity;
Grade 3 local reaction or any local reaction involving ulceration;
Fever>38° C., or intolerable flu-like symptoms or rigors;
Other Grade 3 or greater toxicity, either related or unrelated to IL-2;
Fever suspected to be related to an opportunistic infection;
Grade 1 fatigue; and
Grade 2 hematologic toxicity that can be corrected with EPO, G-CSF, or blood transfusions.

Subjects who have their IL-2 interrupted can have it resumed at the same dose or at one dose level reduction within 24–48 hours of stopping drug. The dose of IL-2 for that subject may later be increased to the initial dose at the discretion of the subject and the local investigator.

MAb deJ591:

Allergic events will be managed as follows: rash, pruritis, urticaria and wheezing will be treated with benadryl and/or steroids as clinically appropriate. Anaphylaxis or anaphylactoid signs or symptoms will be treated with steroids and/or epinephrine as clinically indicated. Patients will be treated in a general clinical research center equipped for cardiopulmonary resuscitation.

Both drugs will be discontinued in patients who experience any grade 3 or 4 toxicity during the three weeks when mAb is administered. Treatment with mAb will resume at a 25% reduction in dose of mAb deJ591 after the toxicity has returned to grade I or less. If grade 3 or 4 toxicity recurs on attenuated doses, mAb treatment will be discontinued. IL-2 treatment will continue for completion of the 8-week cycle.

Criteria for Therapeutic Response:

Response will be assessed either biochemically (PSA change) and/or by change in size of a measurable lesion/s using standard response criteria for prostate cancer (Dawson N. A. (1999) *Semin Oncol* 26:174–184; Bubley, G. J., et al. (1999) *J Clin Oncol,* 17:3461–3467)

Biochemical (PSA) response will be determined as described above. Criteria for measuring the disease is as follows: Complete response is defined as complete disappearance of all measurable lesions by physical examination or imaging studies with no appearance of new lesions for $\geq 2$ months. Partial response: is defined as a 50% or greater reduction in the sum of the products of the longest perpendicular diameters of all measurable lesions. There may be no new lesions. Stable disease: patients who do not meet the criteria of partial response and who are without signs of progressive disease for >2 months. Progressive disease is defined as a greater than 25% increase in the sum of the products of the longest perpendicular diameters of the indicator lesions, the appearance of new lesions or a rise in prostate specific antigen above pre-treatment baseline.

Correlative Studies:

Immunologic Phenotyping: Immunofluorescence and phenotyping will be performed using flow cytometry to measure the PBMC population and to quantify expression of lymphocyte subsets (CD3 for T cells, CD56 for NK cells and CD14 for monocytes) as previously described (Bernstein Z. P., et al. (1995) *Blood* 86:3287–3294; Lalezari J. P., et al. (2000) *HIV Clin Trials*).

$^{51}$Cr-Release Assay For Cytolysis By NK/Lak Cells: A standard chromium release assay will be used to measure the ability of NK cells derived from PBMCs to lyse PSMA expressing target cells (Cox J. H., et al. (2000) *Mol Biotechnol* 15:147–154). NK cells will be isolated from PBMCs using a series of purifications using Ficoll-Hypaque density gradient, nylon wool columns and negative selection with immunomagnetic beads to remove T lymphocytes and residual monocytes as well as B cells, as described. (Cox J. H. (2000) supra). On the day of the cytotoxicity assay, viable LNCaP cells (target cells) are labeled with no less than 100 uCi of $^{51}$Cr for 1 hr in a 37° C., washed, and resuspend in RPMI at a concentration of $5 \times 10^4$ cells/ml, with a goal of 0.2 to 1.5 cpm per cell.

Additional Assays:

Assays to measure expression of intracellular accumulation of cytokines, such as IL-2, TNF, and IFN, are described in Pala P. et al. (2000) *J Immunol Methods* 234:107–124. Expression of these cytokines in patients PBMCs before and on therapy can be measured.

Statistical Methods:

For all outcome variable with measurements taken at various time points, a Repeated Measures Analysis of Variance (RMANOVA) will be carried out to determine any patterns of change over time. Upon finding a significant time effect, Bonferroni-adjusted painwise contrasts will be calculated to determine which time points differ from one another. To simplify the analysis for data obtained at multiple time points, one may choose to "aggregate" the measurement values taken over time. An area under the curve (AUC) analysis for the PSA levels can be carried out. Alternatively, a "slope analysis" may be carried out.

Current Status of Results:

Six patients have been entered and three have completed 8 weeks of therapy; two patients are being retreated based on PSA stabilization. A third patient had objective disease progression. Toxicities have been expected and minor including fatigue, injection site reactions and asymptomatic thyroid function abnormalities. IL-2 mediated immune modulation is being evaluated by flow cytometry on peripheral blood to quantify expression of lymphocyte subsets pre- and post-mAb treatment.

Example 15

Conjugation of deJ591 to the Maytansinoid Cytotoxin DM1

This example describes a process for the production of the deJ591-DM1 immunoconjugate. The process is based on standard methods known in the art and can therefore be generalized to other antibodies, including other antibodies of the invention such as deJ415.

The methods of conjugation are based on several small scale experiments, including one experiment performed using 5 g of deJ591 starting material (Lot 1552-60S) and three experiments performed using between 6.7 g and 7.3 g of deJ591 starting material (Lots 1552-7168, 1552-104, and 6106-036).

The steps involved in the methods of conjugation are as follows:

1) 5 g to 7.5 g of deJ591 antibody is concentrated by tangential flow filtration (10 kD NMWCO membranes) to 25–30 mg/ml and diafiltered against 5 volumes of 50 mM potassium phosphate, 2 mM EDTA, pH 6.0. The yield is, typically between 98% and 100%.

2) The concentrated antibody is filtered through a 0.2µ filter, if opalescent, and then modified with N-succinimidyl 4-(2-pyridyldithio)propionate (SPP) at a concentration of 20–22 mg/ml antibody and 7 molecules of SPP per molecule of antibody. The modification is done in 50 mM potassium phosphate, 2 mM EDTA, 5% ethanol, pH 6.0, for 2.5+/–0.5 hours. The modification vessel is a 500 ml round bottom flask.

3) The modified antibody is separated from the reaction mixture of step 2) using gel filtration chromatography and a Sephadex G-25™ column. The column load represents about 25% of the column volume and the chromatography is done in 50 mM potassium phosphate, 2 mM EDTA, pH 6.0, at a flow rate of 50 cm/hr. The modified antibody elutes between 38–75% column volume. Typically the yield of this step between 95% and 100% and the SPP to antibody ration is about 5.4 to 5.9 SPP molecule/antibody.

4) At a concentration of about 10 mg/ml, the modified antibody is conjugated with DM1 (using 1.7 molecules of DM1/molecule of SPP conjugated to the antibodies) for 20+/–4 hours. Typically, the reaction time is between 16.25 and 17.7 hours and is carried out in a 1 L round bottom glass flask equipped with a magnetic stirring bar. The conjugation reaction is done in 3% DMA, 10% sucrose (100 mg sucrose/ml of reaction). At the end of the reaction the conjugated antibody is filtered through a 2.0µ filter and a spectrophotometric reading is taken.

5) The conjugated antibody is separated from unreacted DM1 by gel filtration chromatography using a Sephadex G-25™ column. The column load represents 22–23% of the column volume and the flow rate is about 50 cm/hr. The column is equilibrated and run in 20 mM succinate, 5% sucrose (50 mg/ml), pH 5.5. The antibody conjugate elutes between about 31% and 65% of column volume, and is collected from the start of the peak elution to the start of the peak trailing edge as a single fraction, followed by fractionation of the remaining peak material in 15×2% column volume fractions. All fractions are adjusted to 100 mg/ml of sucrose (10% sucrose) through the addition of appropriate amounts of 50% sucrose. The 2% column volume fractions are assayed by analytical sizing (TSK 3000SWL) and selected fractions (fractions 1 and 2) are pooled together with the main peak. The fractions are assayed using analytical sizing with the pooling criterion being the 24 minute peak representing <20% or the total peak area. Typically the yield of this step is between 60% and 65% with the exception of run 1552-104 where there was no sucrose present in the reaction and/or purification mixture. The eluted antibody concentration ranges from 3.8 to 4.2 mg/ml and the ration of DM1/antibody ranges from 3.6 to 3.9.

6) The antibody conjugate is then concentrated to 7–10 mg/ml using a 10 kD NMWCO tangential flow filtration membrane and diafiltered against 5 volumes of 50 mM succinate, 10% sucrose, pH 5.5 (Inlet Pressure<10 psi). Following diafiltration the antibody conjugate is adjusted to 5 mg/ml. Typical yield for this step is between 92% and 100%, with the final protein concentration being between 4.85 and 5.1 mg/ml.

7) Finally, the antibody conjugate is filtered through a 0.2 m filter and aliquoted to the specified volumes. Step yield is between 90% and 100% and the final DM1-antibody ratio is 3.5 to 3.8.

The resulting deJ591-DM1 conjugates were analyzed according to appearance, concentration, DM1/antibody ratio, endotoxin, non-specific cytotoxicity, acetone extractable DM1, analytical sizing, reduced and non-reduced SDS-PAGE, pH, bioburden, specific cytotoxicity, and IEF. Selected analytical results for lots 1552-168, 1552-104, and 1552-036 are shown in Table 20, below.

Table 20

TABLE 19

| Lot No. | Amount Recovered | Concentration (mg/ml) | DM1/antibody | Process Recovery (%) |
|---|---|---|---|---|
| 1552-168 | 3.85 | 5.1 | 3.7 | 57.2 |
| 1552-104 | 2.75 | 4.85 | 3.5 | 37.8* |
| 1610-036 | 3.41 | 5.05 | 3.8 | 47.2 |
| Mean | 3.34 | 5.00 | 3.67 | 47.4 |
| Standard Dev. | 0.55 | 0.13 | 0.15 | 9.7 |
| % c.v. | 16.6 | 2.6 | 4.2 | 20.5 |

Lower recovery due partly to the lack of sucrose in the conjugation reaction and the second G-25 gel filtration run and partly to the fact that the front end of the product peak was not collected due to a malfunction in the chart recorder.

Example 16

Use of the mAbs for Targeted Delivery of Cytotoxic Drugs to Prostate Cancer Cells Anti-PSMA antibodies can be conjugated to substances with high cytotoxic potential, such as drugs of the maytansinoid class. Maytansinoids exert their cytotoxic effects by interfering with the formation and stabilization of microtubules. They have 100- to 1000-fold greater cytotoxic potential than conventional chemotherapeutic agents (such as doxorubicin, methotrexate, and Vinca alkaloids) (Chari, R. V. J. et al. (1992) *Cancer Res.* 52: 127).

Both murine and deimmunized J591 antibodies have been conjugated to the maytansinoid, DM1, via a hindered disulfide bond. This bond is cleaved intracellularly allowing release of the drug. One or more lysine residues in the constant regions of the antibodies were conjugated to a linker containing a pyridyldithio group, which was, in turn, coupled to a maytansinoid toxin. A ratio of 3 to 4 moles of maytansinoid per mole of IgG is preferred.

The process for the DM1-linked J591 antibodies starts by reacting J591 with a linker that contains both a pyridyldithio group and a N-hydroxysuccinimide leaving group. In this case, the linker was N-succinimidyl 4-(2-pyridyldithio)propionate (or SPP), although other linkers can be used. The products of the reaction include modified J591 antibodies that contain one or more linker groups (4-(2-pyridyldithio) propionone) attached to surface exposed lysine groups, with the linker groups retaining the pyridyldithio reactive groups, and N-hydroxysuccinimide leaving groups. The J591 antibodies are then separated from the reaction mixture and N-hydroxysuccinimide by gel filtration, e.g., using sephadex G25. The modified J591 antibodies are reacted with DM1, which contains a thiol group that reacts with the pyridyldithio groups now present on the surface of the modified antibody, thereby producing J591-DM1 immunoconjugates and thiopyridine. The J591-DM1 immunoconjugate is isolated from the reaction mixture and thiopyridine by size exclusion chromatography, e.g., using a sephacryl S300 column. Methods for preparing maytansinoid conjugates are described in U.S. Pat. Nos. 5,208,020; 5,475,092; 5,585,499; 5,846,545; and 6,333,410, the contents of which are incorporated by reference.

A study evaluating the efficacy, toxicity, and antigen selectivity of the murine J591-DM1 immunoconjugate in the treatment of prostate cancer cells in vivo is described below.

Experiment 1

Establish Efficacy, Toxicity, and Dose-Response Curves In-Vivo

Tumor xenografts of LNCaP cells were established in the right flank of BALB/c mice ($5\times10^6$ cells injected subcutaneously). Animals were observed until tumors were visible (7–10 mm). Animals were then treated with PBS, unconjugated mAb J591, unconjugated DM1, both mAb J591 and DM1 but unconjugated, and J591-DM1 immunoconjugate (100, 200, 300, and 400 mcg/day intraperitoneal qday×5 days). The mAb J591 was modified to introduce dithiopyridyl groups and then conjugated to DM1 via a hindered disulfide bond, as described above. Unconjugated mAb J591 and DM1 were given in equimolar concentrations.

Experiment 2

Selectivity for PSMA-positive Tumors

Tumor xenografts of both LNCaP cells ($5\times10^6$ cells injected subcutaneously in the right flank) and PC3 cells ($3\times10^6$ cells injected subcutaneously in the left flank) were established in BALB/c mice. Animals were observed until LNCaP tumors were visible (PC3 tumors were present but much smaller). Animals treated with J591-DM1 immunoconjugate: 300 mcg/day intraperitoneal qday×5 days.

Experiment 3

Determine Optimal Dosing Schedule for the Immunoconjugate

Tumor xenografts of LNCaP cells were established subcutaneously in the right flank of BALB/c mice. When tumors were visible, animals were treated with PBS, unconjugated mAb J591, J591-DM1 immunoconjugate (300 mcg/day intravenously qday×5 days; one course given), J591-DM1 immunoconjugate (400 mcg/day intravenously every other day for 5 doses in 10 days; one course given), and J591-DM1 immunoconjugate (300 mcg/day intravenously qday×5 days; two courses given for a total of 10 doses). For animals receiving 2 courses of J591-DM1 immunoconjugate, the second 5-day course was given at tumor volume nadir (typically seen on days 21–24 after completion of the first course).

All animals were photographed pre- and post-treatment and tagged for identification. Tumor volume was determined (length×width×depth) and closely followed. Animal weight was followed as a measure of toxicity.

Results: Experiment 1

All mice treated with unconjugated DM1 (either alone or with unconjugated mAb J591) died within 48 hours of treatment completion. Immunoconjugate at doses of 400 mcg/day was lethal to 50% of the mice. With doses of 300 mcg/day, significant reductions in tumor volume were noted with several complete responses and minimal toxicity. These complete responses were not durable, however, with subsequent increases in tumor size noted 2–20 days after tumor volume nadir.

Results: Experiment 2

In mice with both LNCaP and PC3 tumors, LNCaP tumor volume decreased substantially after treatment with the J591-DM1 immunoconjugate. Although complete responses were not achieved in these animals, tumor volume nadirs averaged 0.08 cm$^3$. PC3 tumor growth was not affected by the J591-DM1 immunoconjugate as noted by a steady increase in PC3 tumor volume after treatment.

Experiment 3

Although route of administration was different (intravenous vs. intraperitoneal), treatment with one course of J591-DM1 immunoconjugate paralleled the results obtained from Experiment 1. Complete responses were achieved (at days 21–24) but these results were not durable. In animals treated with every other day dosing of 400 mcg, toxicity was demonstrated (weight loss >10% of total body weight) but all animals eventually survived. Tumor volume decreased in all animals but complete responses were not achieved. All animals treated with 2 courses of J591-DM1 immunoconjugate have achieved complete responses lasting at least through day 66.

Conclusions:

Murine J591 anti-PSMA antibody can be conjugated effectively to drugs of the maytansinoid class (such as DM1). These J591-DM1 immunoconjugates provide highly selective, antigen-specific targeted delivery of this cytotoxic drug to PSMA-positive prostate cancer cells in-vivo. The greatest reduction in tumor volume with minimal toxicity was noted at a dose of 300 mcg/day. The optimal dosing schedule appears to be two 5-day courses of J591-DM1 immunoconjugate with the second course given at tumor volume nadir (day 21–24).

Example 17

Pharmacodynamics and Efficacy of the deJ591-DM1 Immuoconjuate

In parallel to the experiments described in Example 16, additional experiments were performed with the deJ591-DM1 immunoconjugate. The experiments and results obtained therefrom are described below.

In vitro Pharmacodynamics of deJ591-DM1 and DM1:

Experiment: LNCaP cells were plated into 96 well plates at an initial density of 1000 cells per well for a proliferation assay deJ591-DM1 or DM1 was added to the wells over a range of concentrations (0.01 nM to 100 nM) and left in contact with the cells for defined periods of time (0.5, 2, 8, 24, 72 and 144 hours). At the end of that period the drug containing media was removed and replaced with drug free media until a total of 144 hours elapsed from the start of the experiment. The resulting effect of drug exposure on proliferation was then determined.

Results: The pharmacodynamic analysis using the methodology developed by Kalns et al. (1995), Cancer Research 55:5315–5322, the contents of which are incorporated herein by reference, indicates that when considering the relative importance to observed effect from the variables (1) time of exposure and (2) concentration, that exposure time is more important for deJ591-DM1 compared to DM1, where concentration it the more important variable.

Serum Levels of DEJ591-DM1 in Mice After a Single IV Dose

Experiment: Mice were administered an intravenous 14.5 mg/kg dose of deJ591-DM1 and sera samples collected for analysis of the test article using an ELISA assay for human antibody. Samples were collected from groups of 3 mice at 6, 24, 48, 72 and 168 hours. Data were fit to a bi-exponential equation to determine pharmacokinetic parameters. These parameters were used to simulate serum levels after multiple dosing.

Results: Analysis of the pharmacokinetic data indicated a serum half life of deJ591-DM1 in mice as measured in the ELISA assay, to be 130 hours.

Effect of Dose Interval on Efficacy Against CWR22 Prostate Xenografts

Experiment: Male SCID mice were implanted by serial passage of CWR22 prostate tumor xenograft. When these tumors reached 200–250 mm$^3$ size (estimated from external caliper measurement), mice were randomized into treatment groups of 8 to receive vehicle only (every 7 days) or deJ591-DM1 at a dose of 14.5 mg/kg antibody conjugate (equivalent to 240 ug/kg DM1) given on one of the following schedules (every 7, 14, 21, or 28 days). All treatments were given intravenously. Tumor growth and animal health were continually monitored throughout the study with tumor growth measured every 3 days.

Results: Differences in the schedule of administration have distinct effects on the observed tumor growth for the CWR22 xenograft in SCID mice. The tumor growth can be characterized as slowed growth for the schedule of 21 or 28 day dosing interval until they reached the maximum size permitted under our IACUC regulations. For the 7 and 14 day dosing interval schedule, there is an apparent block in tumor growth with a resumption of normal growth kinetics approximately 30 days after the last dose. The results when considered with the pharmacokinetic simulation suggest a relationship between duration of exposure and maintaining a minimum effective concentration.

Efficacy of deJ591-DM1 Compared to the Unconjugated Antibody (deJ591) or the Unconjugated Tumor Inhibitory Agent (DM1)

Experiment: Male SCID mice were implanted by serial passage of CWR22 prostate tumor xenograft. When these tumors reached 200–250 mm$^3$ size (estimated from external caliper measurement), mice were randomized into treatment groups of 8 to receive vehicle only, deJ591-DM1 at a dose of 14.5 mg/kg antibody conjugate (equivalent to 240 ug/kg DM1), deJ591 at the same dose as deJ591-DM1, or DM1 given at a dose of 240 ug/kg. All treatments were given intravenously and on a schedule of every three days for 5 doses. Tumor growth and animal health were continually monitored throughout the study with tumor growth measured every 3 days.

Results: The unconjugated anti-PSMA antibody (deJ591) had no significant effect on reduction in the rate or extent of CWR22 xenograft tumor growth. DM1 administered as free drug produced some tumor growth delay, but was a minor response compared to the deJ591-DM1 administered on the same schedule with the same molar equivalent of the active DM1. The deJ591-DM1 produced a suppression of tumor growth for approximately 20 days following the last administered dose.

Efficacy of DEJ591-DM1 at Different Doses

Experiment: Male SCID mice were implanted by serial passage of CWR22 prostate tumor xenograft. When these tumors reached 200–250 mm$^3$ size (estimated from external caliper measurement), mice were randomized into treatment groups of 8 to receive vehicle only, deJ591-DM1 at a dose of 14.5 mg/kg antibody conjugate (equivalent to 240 ug/kg DM1), or a lower dose of 7.25 mg/kg. All treatments were given intravenously and on a schedule of every seven days for 5 doses. Tumor growth and animal health were continually monitored throughout the study with tumor growth measured every 3 days.

Results: A dose response relationship is evident for the CWR22 xenograft tumor growth inhibition by deJ591-DM1. This is shown on a 7 day dosing interval study for 2 different doses of deJ591-DM1. At the higher dose, there is suppression of tumor growth with some reduction from the initial tumor volume. At the lower dose there is not the same reduction from initial tumor volume and there is a more rapid return to normal growth kinetics of approximately 10 days following the last dose administered compared to the higher dose.

Example 18

Bone Marrow Involvement in Advanced Prostate Cancer Patients Demonstrated on Bone Marrow Biopsy Bone marrow involvement in advanced prostate cancer is not routinely examined. We report on the results of bone marrow biopsies performed on advanced, hormone-refractory prostate cancer patients.

Screening diagnostic studies were performed on hormone-refractory prostate cancer patients to determine eligibility for two phase I radioimmunotherapy clinical trials. Studies included serologic testing, bone scan, CT scans of the head, chest, abdomen and pelvis, and a bone marrow biopsy taken from the iliac crest. A total of Thirty-nine patients have been screened thus far.

All patients had advanced disease as determined by bony or soft tissue metastases on imaging and/or three consecutive rises in serum PSA levels. All patients had received prior hormonal therapy, and the majority had received local therapy, including radical prostatectomy (N=15), radiotherapy (N=19), and/or chemotherapy (N=19). Sixteen patients (41%) had histologic evidence of metastatic prostate cancer on bone marrow biopsy. Of the thirty-nine screened patients, thirteen (33%) had significant bone marrow involvement (>10% involvement), making them ineligible for entry into these clinical trials.

Patients with bone marrow involvement had significantly higher serum alkaline phosphatase (ALP) levels (median 374 U/L vs. 96 U/L, p<0.001) and significantly lower serum hemoglobin (median 11.6 g/dL vs. 12.7 g/dL, p=0.02). There was no difference in serum hemoglobin between patients with prior chemotherapy and/or prior radiotherapy. When the ALP was normal (<120 U/L) or elevated (>120 U/L) 0% and 75% of patients, respectively, had metastatic prostate cancer on bone marrow biopsy (p<0.0001). Patients with bone scans indicating bony metastases in three or more different anatomic sites (spine, thorax, pelvis, appendicular or calvarium) vs. two or less sites, were more likely to have bone marrow involvement (54% vs. 9%, p=0.01). Age, initial Gleason sum, serum PSA, PSA doubling time, the presence of soft-tissue metastases, prior local treatment or chemotherapy, or other hematologic parameters (WBC, platelet count) were not significantly different between the two groups.

Bone marrow involvement in advanced prostate cancer patients is not routinely examined, but is present in a large minority of cases. Current clinical staging studies may significantly underestimate bone marrow involvement, although elevation of alkaline phosphatase or depressed serum hemoglobin may be correlative. This situation should be considered in clinical trials carrying potential hematologic toxicity.

Example 19

A Novel Sandwich Enzyme-Linked Immunoassay (ELISA) for Quantification of Prostate-Specific Membrane Antigen Ideally, serum PSMA should be detectable with a simple, rapid, reproducible and quantitative ELISA assay. Our objective was to establish an ELISA assay to measure serum PSMA.

Ninety-six well plates were coated with an anti-PSMA antibody as a "capture" antibody. Dilutions of serum from males and females "spiked" with recombinant PSMA (rPSMA), semen, LNCaP lysates, as well as the standard (rPSMA range 1.6–1600 ng/ml) were then added to these wells. A noncompeting biotinylated anti-PSMA antibody (that recognizes a different epitope on PSMA) was then added as the "detection" antibody. Avidin phosphatase followed by p-nitrophenyl phosphate (substrate) was added. Optical densities were then measured.

The standard curve for the assay was linear through a range of 5–1600 ng/ml (correlation coefficient >0.99). Using this assay, PSMA was detected in LNCaP lysate, semen, and "spiked" serum.

Equivalents

Those skilled in the art will recognize, or be able to ascertain using no more than routine experimentation, many equivalents of the specific embodiments of the invention described herein. Such equivalents are intended to be encompassed by the following claims.

SEQUENCE LISTING

<160> NUMBER OF SEQ ID NOS: 128

<210> SEQ ID NO 1
<211> LENGTH: 10
<212> TYPE: PRT
<213> ORGANISM: Mus musculus

<400> SEQUENCE: 1

Gly Tyr Thr Phe Thr Glu Tyr Thr Ile His
1               5                   10

<210> SEQ ID NO 2
<211> LENGTH: 17
<212> TYPE: PRT
<213> ORGANISM: Mus musculus

<400> SEQUENCE: 2

Asn Ile Asn Pro Asn Asn Gly Gly Thr Thr Tyr Asn Gln Lys Phe Glu
1               5                   10                  15

Asp

<210> SEQ ID NO 3
<211> LENGTH: 6
<212> TYPE: PRT
<213> ORGANISM: Mus musculus

<400> SEQUENCE: 3

Gly Trp Asn Phe Asp Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Val Gly Thr Ala Val Asp
1               5                   10

<210> SEQ ID NO 5
<211> LENGTH: 7
<212> TYPE: PRT
<213> ORGANISM: Mus musculus

<400> SEQUENCE: 5

Trp Ala Ser Thr Arg His Thr
1               5

<210> SEQ ID NO 6
<211> LENGTH: 9
<212> TYPE: PRT
<213> ORGANISM: Mus musculus

<400> SEQUENCE: 6

Gln Gln Tyr Asn Ser Tyr Pro Leu Thr
1               5

<210> SEQ ID NO 7
<211> LENGTH: 82
<212> TYPE: PRT
<213> ORGANISM: Mus musculus

<400> SEQUENCE: 7

-continued

Glu Val Gln Leu Gln Gln Ser Gly Pro Glu Leu Lys Lys Pro Gly Thr
1               5                   10                  15

Ser Val Arg Ile Ser Cys Lys Thr Ser Trp Val Lys Gln Ser His Gly
            20                  25                  30

Lys Ser Leu Glu Trp Ile Gly Lys Ala Thr Leu Thr Val Asp Lys Ser
        35                  40                  45

Ser Ser Thr Ala Tyr Met Glu Leu Arg Ser Leu Thr Ser Glu Asp Ser
    50                  55                  60

Ala Val Tyr Tyr Cys Ala Ala Trp Gly Gln Gly Thr Thr Leu Thr Val
65                  70                  75                  80

Ser Ser

<210> SEQ ID NO 8
<211> LENGTH: 80
<212> TYPE: PRT
<213> ORGANISM: Mus musculus

<400> SEQUENCE: 8

Asp Ile Val Met Thr Gln Ser His Lys Phe Met Ser Thr Ser Val Gly
1               5                   10                  15

Asp Arg Val Ser Ile Ile Cys Trp Tyr Gln Gln Lys Pro Gly Gln Ser
            20                  25                  30

Pro Lys Leu Leu Ile Tyr Gly Val Pro Asp Arg Phe Thr Gly Ser Gly
        35                  40                  45

Ser Gly Thr Asp Phe Thr Leu Thr Ile Thr Asn Val Gln Ser Glu Asp
    50                  55                  60

Leu Ala Asp Tyr Phe Cys Phe Gly Ala Gly Thr Met Leu Asp Leu Lys
65                  70                  75                  80

<210> SEQ ID NO 9
<211> LENGTH: 25
<212> TYPE: PRT
<213> ORGANISM: Artificial Sequence
<220> FEATURE:
<223> OTHER INFORMATION: deimmunized heavy chain J591

<400> SEQUENCE: 9

Glu Val Gln Leu Val Gln Ser Gly Pro Glu Val Lys Lys Pro Gly Ala
1               5                   10                  15

Thr Val Lys Ile Ser Cys Lys Thr Ser
            20                  25

<210> SEQ ID NO 10
<211> LENGTH: 14
<212> TYPE: PRT
<213> ORGANISM: Artificial Sequence
<220> FEATURE:
<223> OTHER INFORMATION: deimmunized heavy chain J591

<400> SEQUENCE: 10

Trp Val Lys Gln Ala Pro Gly Lys Gly Leu Glu Trp Ile Gly
1               5                   10

<210> SEQ ID NO 11
<211> LENGTH: 32
<212> TYPE: PRT
<213> ORGANISM: Artificial Sequence
<220> FEATURE:
<223> OTHER INFORMATION: deimmunized heavy chain J591

<400> SEQUENCE: 11

```
Lys Ala Thr Leu Thr Val Asp Lys Ser Thr Asp Thr Ala Tyr Met Glu
 1               5                  10                  15

Leu Ser Ser Leu Arg Ser Glu Asp Thr Ala Val Tyr Tyr Cys Ala Ala
            20                  25                  30
```

<210> SEQ ID NO 12
<211> LENGTH: 11
<212> TYPE: PRT
<213> ORGANISM: Artificial Sequence
<220> FEATURE:
<223> OTHER INFORMATION: deimmunized heavy chain J591

<400> SEQUENCE: 12

```
Trp Gly Gln Gly Thr Leu Leu Thr Val Ser Ser
 1               5                  10
```

<210> SEQ ID NO 13
<211> LENGTH: 23
<212> TYPE: PRT
<213> ORGANISM: Artificial Sequence
<220> FEATURE:
<223> OTHER INFORMATION: deimmunized light chain J591

<400> SEQUENCE: 13

```
Asp Ile Gln Met Thr Gln Ser Pro Ser Ser Leu Ser Thr Ser Val Gly
 1               5                  10                  15

Asp Arg Val Thr Leu Thr Cys
            20
```

<210> SEQ ID NO 14
<211> LENGTH: 15
<212> TYPE: PRT
<213> ORGANISM: Artificial Sequence
<220> FEATURE:
<223> OTHER INFORMATION: deimmunized light chain J591

<400> SEQUENCE: 14

```
Trp Tyr Gln Gln Lys Pro Gly Pro Ser Pro Lys Leu Leu Ile Tyr
 1               5                  10                  15
```

<210> SEQ ID NO 15
<211> LENGTH: 32
<212> TYPE: PRT
<213> ORGANISM: Artificial Sequence
<220> FEATURE:
<223> OTHER INFORMATION: deimmunized light chain J591

<400> SEQUENCE: 15

```
Gly Ile Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Asp Tyr Tyr Cys
            20                  25                  30
```

<210> SEQ ID NO 16
<211> LENGTH: 10
<212> TYPE: PRT
<213> ORGANISM: Artificial Sequence
<220> FEATURE:
<223> OTHER INFORMATION: deimmunized light chain J591

<400> SEQUENCE: 16

```
Phe Gly Pro Gly Thr Lys Val Asp Ile Lys
 1               5                  10
```

<210> SEQ ID NO 17
<211> LENGTH: 82
<212> TYPE: PRT
<213> ORGANISM: Artificial Sequence
<220> FEATURE:
<223> OTHER INFORMATION: deimmunized heavy chain J591

<400> SEQUENCE: 17

```
Glu Val Gln Leu Val Gln Ser Gly Pro Glu Val Lys Lys Pro Gly Ala
1               5                   10                  15

Thr Val Lys Ile Ser Cys Lys Thr Ser Trp Val Lys Gln Ala Pro Gly
            20                  25                  30

Lys Gly Leu Glu Trp Ile Gly Lys Ala Thr Leu Thr Val Asp Lys Ser
        35                  40                  45

Thr Asp Thr Ala Tyr Met Glu Leu Ser Ser Leu Arg Ser Glu Asp Thr
    50                  55                  60

Ala Val Tyr Tyr Cys Ala Ala Trp Gly Gln Gly Thr Leu Leu Thr Val
65                  70                  75                  80

Ser Ser
```

<210> SEQ ID NO 18
<211> LENGTH: 80
<212> TYPE: PRT
<213> ORGANISM: Artificial Sequence
<220> FEATURE:
<223> OTHER INFORMATION: deimmunized light chain J591

<400> SEQUENCE: 18

```
Asp Ile Gln Met Thr Gln Ser Pro Ser Ser Leu Ser Thr Ser Val Gly
1               5                   10                  15

Asp Arg Val Thr Leu Thr Cys Trp Tyr Gln Gln Lys Pro Gly Pro Ser
            20                  25                  30

Pro Lys Leu Leu Ile Tyr Gly Ile Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Asp Tyr Tyr Cys Phe Gly Pro Gly Thr Lys Val Asp Ile Lys
65                  70                  75                  80
```

<210> SEQ ID NO 19
<211> LENGTH: 115
<212> TYPE: PRT
<213> ORGANISM: Mus musculus

<400> SEQUENCE: 19

```
Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110
```

```
Val Ser Ser
        115

<210> SEQ ID NO 20
<211> LENGTH: 107
<212> TYPE: PRT
<213> ORGANISM: Mus musculus

<400> SEQUENCE: 20

Asp Ile Val Met Thr Gln Ser His Lys Phe Met Ser Thr Ser Val Gly
 1               5                  10                  15

Asp Arg Val Ser Ile Ile Cys Lys Ala Ser Gln Asp Val Gly Thr Ala
             20                  25                  30

Val Asp Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Asp Tyr Phe Cys Gln Gln Tyr Asn Ser Tyr Pro Leu
                 85                  90                  95

Thr Phe Gly Ala Gly Thr Met Leu Asp Leu Lys
            100                 105

<210> SEQ ID NO 21
<211> LENGTH: 115
<212> TYPE: PRT
<213> ORGANISM: Artificial Sequence
<220> FEATURE:
<223> OTHER INFORMATION: deimmunized heavy chain J591

<400> SEQUENCE: 21

Glu Val Gln Leu Val Gln Ser Gly Pro Glu Val Lys Lys Pro Gly Ala
 1               5                  10                  15

Thr Val Lys Ile Ser Cys Lys Thr Ser Gly Tyr Thr Phe Thr Glu Tyr
             20                  25                  30

Thr Ile His Trp Val Lys Gln Ala Pro Gly Lys Gly Leu Glu Trp Ile
         35                  40                  45

Gly Asn Ile Asn Pro Asn Asn Gly Gly Thr Thr Tyr Asn Gln Lys Phe
 50                  55                  60

Glu Asp Lys Ala Thr Leu Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Leu Leu Thr
            100                 105                 110

Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: deimmunized light chain J591

<400> SEQUENCE: 22

Asp Ile Gln Met Thr Gln Ser Pro Ser Ser Leu Ser Thr Ser Val Gly
 1               5                  10                  15
```

```
Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
        35                  40                  45

Tyr Trp Ala Ser Thr Arg His Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
            100                 105

<210> SEQ ID NO 23
<211> LENGTH: 807
<212> TYPE: DNA
<213> ORGANISM: Artificial Sequence
<220> FEATURE:
<221> NAME/KEY: CDS
<222> LOCATION: (122)...(166)
<220> FEATURE:
<221> NAME/KEY: CDS
<222> LOCATION: (249)...(605)
<223> OTHER INFORMATION: deimmunized heavy chain J591

<400> SEQUENCE: 23
aagcttatga atatgcaaat cctctgaatc tacatggtaa atataggttt gtctatacca      60
caaacagaaa aacatgagat cacagttctc tctacagtta ctgagcacac aggacctcac     120 c atg gga tgg agc tgt atc atc ctc ttc ttg gta gca aca gct aca         166
  Met Gly Trp Ser Cys Ile Ile Leu Phe Leu Val Ala Thr Ala Thr
  1               5                  10                  15 ggtaagggc tcacagtagc aggcttgagg tctggacata tatatgggtg acaatgacat      226
ccactttgcc tttctctcca ca ggt gtc cac tcc gag gtc caa ctg gta cag     278
                         Gly Val His Ser Glu Val Gln Leu Val Gln
                                         20                   25 tct gga cct gaa gtg aag aag cct ggg gct aca gtg aag ata tcc tgc     326
Ser Gly Pro Glu Val Lys Lys Pro Gly Ala Thr Val Lys Ile Ser Cys
            30                  35                  40 aag act tct gga tac aca ttc act gaa tat acc ata cac tgg gtg aag     374
Lys Thr Ser Gly Tyr Thr Phe Thr Glu Tyr Thr Ile His Trp Val Lys
        45                  50                  55 cag gcc cct gga aag ggc ctt gag tgg att gga aac atc aat cct aac     422
Gln Ala Pro Gly Lys Gly Leu Glu Trp Ile Gly Asn Ile Asn Pro Asn
    60                  65                  70 aat ggt ggt acc acc tac aat cag aag ttc gag gac aag gcc aca cta     470
Asn Gly Gly Thr Thr Tyr Asn Gln Lys Phe Glu Asp Lys Ala Thr Leu
75                  80                  85 act gta gac aag tcc acc gat aca gcc tac atg gag ctc agc agc cta     518
Thr Val Asp Lys Ser Thr Asp Thr Ala Tyr Met Glu Leu Ser Ser Leu
            90                  95                 100                 105 aga tct gag gat act gca gtc tat tat tgt gca gct ggt tgg aac ttt     566
Arg Ser Glu Asp Thr Ala Val Tyr Tyr Cys Ala Ala Gly Trp Asn Phe
                110                 115                 120 gac tac tgg ggc caa ggg acc ctg ctc acc gtc tcc tca ggtgagtcct     615
Asp Tyr Trp Gly Gln Gly Thr Leu Leu Thr Val Ser Ser
            125                 130 tacaacctct ctcttctatt cagcttaaat agatttact gcatttgttg gggggaaat      675 gtgtgtatct gaatttcagg tcatgaagga ctagggacac cttgggagtc agaaagggtc    735
```

-continued

```
attgggagcc cgggctgatg cagacagaca tcctcagctc ccagacttca tggccagaga    795
tttataggat cc                                                        807

<210> SEQ ID NO 24
<211> LENGTH: 807
<212> TYPE: DNA
<213> ORGANISM: Artificial Sequence
<220> FEATURE:
<223> OTHER INFORMATION: deimmunized heavy chain J591

<400> SEQUENCE: 24
ggatcctata aatctctggc catgaagtct gggagctgag gatgtctgtc tgcatcagcc     60
cgggctccca atgacccttt ctgactccca aggtgtccct agtccttcat gacctgaaat    120
tcagatacac acatttcccc cccaacaaat gcagtaaaat ctatttaagc tgaatagaag    180
agagaggttg taaggactca cctgaggaga cggtgagcag ggtcccttgg ccccagtagt    240
caaagttcca accagctgca caataataga ctgcagtatc ctcagatctt aggctgctga    300
gctccatgta ggctgtatcg gtggacttgt ctacagttag tgtggccttg tcctcgaact    360
tctgattgta ggtggtacca ccattgttag gattgatgtt tccaatccac tcaaggccct    420 ttccagggc  ctgcttcacc cagtgtatgg tatattcagt gaatgtgtat ccagaagtct    480
tgcaggatat cttcactgta gccccaggct tcttcacttc aggtccagac tgtaccagtt    540
ggacctcgga gtggacacct gtggagagaa aggcaaagtg gatgtcattg tcacccatat    600
atatgtccag acctcaagcc tgctactgtg agccccttac ctgtagctgt tgctaccaag    660
aagaggatga tacagctcca tcccatggtg aggtcctgtg tgctcagtaa ctgtagagag    720
aactgtgatc tcatgttttt ctgtttgtgg tatagacaaa cctatattta ccatgtagat    780
tcagaggatt tgcatattca taagctt                                        807

<210> SEQ ID NO 25
<211> LENGTH: 620
<212> TYPE: DNA
<213> ORGANISM: Artificial Sequence
<220> FEATURE:
<221> NAME/KEY: CDS
<222> LOCATION: (122)...(166)
<220> FEATURE:
<221> NAME/KEY: CDS
<222> LOCATION: (249)...(581)
<223> OTHER INFORMATION: deimmunized light chain J591

<400> SEQUENCE: 25
aagcttatga atatgcaaat cctctgaatc tacatggtaa atataggttt gtctatacca     60
caaacagaaa aacatgagat cacagttctc tctacagtta ctgagcacac aggacctcac    120 c atg gga tgg agc tgt atc atc ctc ttc ttg gta gca aca gct aca        166
  Met Gly Trp Ser Cys Ile Ile Leu Phe Leu Val Ala Thr Ala Thr
  1               5                  10                  15 ggtaagggc  tcacagtagc aggcttgagg tctggacata tatatgggtg acaatgacat    226
ccactttgcc tttctctcca ca ggt gtc cac tcc gac atc cag atg acc cag    278
                         Gly Val His Ser Asp Ile Gln Met Thr Gln
                                      20                  25 tct ccc tca tcc ctg tcc aca tca gta gga gac agg gtc acc ctc acc    326
Ser Pro Ser Ser Leu Ser Thr Ser Val Gly Asp Arg Val Thr Leu Thr
             30                  35                  40 tgt aag gcc agt caa gat gtg ggt act gct gta gac tgg tat caa cag    374
Cys Lys Ala Ser Gln Asp Val Gly Thr Ala Val Asp Trp Tyr Gln Gln
         45                  50                  55
```

```
aaa cca gga cca tct cct aaa cta ctg att tat tgg gca tcc act cgg      422
Lys Pro Gly Pro Ser Pro Lys Leu Leu Ile Tyr Trp Ala Ser Thr Arg
            60                  65                  70 cac act gga atc cct agt cgc ttc tca ggc agt gga tct ggg aca gac      470
His Thr Gly Ile Pro Ser Arg Phe Ser Gly Ser Gly Ser Gly Thr Asp
 75                  80                  85 ttc act ctc acc att tct agt ctt cag cct gaa gac ttt gca gat tat      518
Phe Thr Leu Thr Ile Ser Ser Leu Gln Pro Glu Asp Phe Ala Asp Tyr
 90                  95                 100                 105 tac tgt cag caa tat aac agc tat cct ctc acg ttc ggt cct ggg acc      566
Tyr Cys Gln Gln Tyr Asn Ser Tyr Pro Leu Thr Phe Gly Pro Gly Thr
                110                 115                 120 aag gtg gac atc aaa cgtgagtaga atttaaactt tgcttcctca gttggatcc       620
Lys Val Asp Ile Lys
            125

<210> SEQ ID NO 26
<211> LENGTH: 620
<212> TYPE: DNA
<213> ORGANISM: Artificial Sequence
<220> FEATURE:
<223> OTHER INFORMATION: deimmunized light chain J591

<400> SEQUENCE: 26
ggatccaact gaggaagcaa agtttaaatt ctactcacgt ttgatgtcca ccttggtccc     60
aggaccgaac gtgagaggat agctgttata ttgctgacag taataatctg caaagtcttc   120
aggctgaaga ctagaaatgg tgagagtgaa gtctgtccca gatccactgc ctgagaagcg   180 actaggggatt ccagtgtgcc gagtggatgc ccaataaatc agtagtttag gagatggtcc   240
tggtttctgt tgataccagt ctacagcagt acccacatct tgactggcct tacaggtgag   300
ggtgaccctg tctcctactg atgtggacag ggatgaggga gactgggtca tctggatgtc   360
ggagtggaca cctgtggaga gaaaggcaaa gtggatgtca ttgtcaccca tatatatgtc   420
cagacctcaa gcctgctact gtgagcccct tacctgtagc tgttgctacc aagaagagga   480
tgatacagct ccatcccatg gtgaggtcct gtgtgctcag taactgtaga gagaactgtg   540
atctcatgtt tttctgtttg tggtatagac aaacctatat ttaccatgta gattcagagg   600
atttgcatat tcataagctt                                               620

<210> SEQ ID NO 27
<211> LENGTH: 134
<212> TYPE: PRT
<213> ORGANISM: Artificial Sequence
<220> FEATURE:
<223> OTHER INFORMATION: deimmunized heavy chain J591

<400> SEQUENCE: 27

Met Gly Trp Ser Cys Ile Ile Leu Phe Leu Val Ala Thr Ala Thr Gly
 1               5                  10                  15

Val His Ser Glu Val Gln Leu Val Gln Ser Gly Pro Glu Val Lys Lys
            20                  25                  30

Pro Gly Ala Thr Val Lys Ile Ser Cys Lys Thr Ser Gly Tyr Thr Phe
        35                  40                  45

Thr Glu Tyr Thr Ile His Trp Val Lys Gln Ala Pro Gly Lys Gly Leu
    50                  55                  60

Glu Trp Ile Gly Asn Ile Asn Pro Asn Asn Gly Gly Thr Thr Tyr Asn
65                  70                  75                  80

Gln Lys Phe Glu Asp Lys Ala Thr Leu Thr Val Asp Lys Ser Thr Asp
```

```
                        85                  90                  95
Thr Ala Tyr Met Glu Leu Ser Ser Leu Arg Ser Glu Asp Thr Ala Val
            100                 105                 110
Tyr Tyr Cys Ala Ala Gly Trp Asn Phe Asp Tyr Trp Gly Gln Gly Thr
        115                 120                 125
Leu Leu Thr Val Ser Ser
    130

<210> SEQ ID NO 28
<211> LENGTH: 126
<212> TYPE: PRT
<213> ORGANISM: Artificial Sequence
<220> FEATURE:
<223> OTHER INFORMATION: deimmunized light chain J591

<400> SEQUENCE: 28

Met Gly Trp Ser Cys Ile Ile Leu Phe Leu Val Ala Thr Ala Thr Gly
1               5                   10                  15
Val His Ser Asp Ile Gln Met Thr Gln Ser Pro Ser Ser Leu Ser Thr
            20                  25                  30
Ser Val Gly Asp Arg Val Thr Leu Thr Cys Lys Ala Ser Gln Asp Val
        35                  40                  45
Gly Thr Ala Val Asp Trp Tyr Gln Gln Lys Pro Gly Pro Ser Pro Lys
    50                  55                  60
Leu Leu Ile Tyr Cys Ala Ser Thr Arg His Thr Gly Ile Pro Ser Arg
65                  70                  75                  80
Phe Ser Gly Ser Gly Ser Gly Thr Asp Phe Thr Leu Thr Ile Ser Ser
                85                  90                  95
Leu Gln Pro Glu Asp Phe Ala Asp Tyr Tyr Cys Gln Gln Tyr Asn Ser
            100                 105                 110
Tyr Pro Leu Thr Phe Gly Pro Gly Thr Lys Val Asp Ile Lys
        115                 120                 125

<210> SEQ ID NO 29
<211> LENGTH: 10
<212> TYPE: PRT
<213> ORGANISM: Mus musculus

<400> SEQUENCE: 29

Gly Phe Thr Phe Ser Asn Tyr Trp Met Asn
1               5                   10

<210> SEQ ID NO 30
<211> LENGTH: 19
<212> TYPE: PRT
<213> ORGANISM: Mus musculus

<400> SEQUENCE: 30

Glu Ile Arg Ser Gln Ser Asn Asn Phe Ala Thr His Tyr Ala Glu Ser
1               5                   10                  15
Val Lys Gly

<210> SEQ ID NO 31
<211> LENGTH: 5
<212> TYPE: PRT
<213> ORGANISM: Mus musculus

<400> SEQUENCE: 31

Arg Trp Asn Asn Phe
1               5
```

-continued

<210> SEQ ID NO 32
<211> LENGTH: 11
<212> TYPE: PRT
<213> ORGANISM: Mus musculus

<400> SEQUENCE: 32

Lys Ala Ser Glu Asn Val Gly Thr Tyr Val Ser
1               5                   10

<210> SEQ ID NO 33
<211> LENGTH: 7
<212> TYPE: PRT
<213> ORGANISM: Mus musculus

<400> SEQUENCE: 33

Gly Ala Ser Asn Arg Phe Thr
1               5

<210> SEQ ID NO 34
<211> LENGTH: 9
<212> TYPE: PRT
<213> ORGANISM: Mus musculus

<400> SEQUENCE: 34

Gly Gln Ser Tyr Thr Phe Pro Tyr Thr
1               5

<210> SEQ ID NO 35
<211> LENGTH: 82
<212> TYPE: PRT
<213> ORGANISM: Mus musculus

<400> SEQUENCE: 35

Glu Val Lys Leu Glu Glu Ser Gly Gly Leu Val Gln Pro Gly Gly
1               5                   10                  15

Ser Met Lys Leu Ser Cys Val Ala Ser Trp Val Arg Gln Ser Pro Glu
                20                  25                  30

Lys Gly Leu Glu Trp Val Ala Arg Val Ile Ile Ser Arg Asp Asp Ser
            35                  40                  45

Lys Ser Ser Val Tyr Leu Gln Met Asn Asn Leu Arg Ala Glu Asp Thr
50                  55                  60

Gly Ile Tyr Tyr Cys Thr Arg Trp Gly Gln Gly Thr Thr Leu Thr Val
65                  70                  75                  80

Ser Ser

<210> SEQ ID NO 36
<211> LENGTH: 80
<212> TYPE: PRT
<213> ORGANISM: Mus musculus

<400> SEQUENCE: 36

Asn Ile Val Met Thr Gln Phe Pro Lys Ser Met Ser Ile Ser Val Gly
1               5                   10                  15

Glu Arg Val Thr Leu Thr Cys Trp Tyr Gln Gln Lys Pro Glu Gln Ser
                20                  25                  30

Pro Lys Met Leu Ile Tyr Gly Val Pro Asp Arg Phe Thr Gly Ser Gly
            35                  40                  45

Ser Ala Thr Asp Phe Ile Leu Thr Ile Ser Ser Val Gln Thr Glu Asp
50                  55                  60

```
Leu Val Asp Tyr Tyr Cys Phe Gly Gly Gly Thr Lys Leu Glu Met Lys
65                  70                  75                  80

<210> SEQ ID NO 37
<211> LENGTH: 25
<212> TYPE: PRT
<213> ORGANISM: Artificial Sequence
<220> FEATURE:
<223> OTHER INFORMATION: deimmunized heavy chain J415-4

<400> SEQUENCE: 37

Glu Val Lys Leu Glu Glu Ser Gly Gly Gly Leu Val Gln Pro Gly Gly
1               5                   10                  15

Ser Met Lys Ile Ser Cys Val Ala Ser
            20                  25

<210> SEQ ID NO 38
<211> LENGTH: 14
<212> TYPE: PRT
<213> ORGANISM: Artificial Sequence
<220> FEATURE:
<223> OTHER INFORMATION: deimmunized heavy chain J415-4

<400> SEQUENCE: 38

Trp Val Arg Gln Ser Pro Glu Lys Gly Leu Glu Trp Val Ala
1               5                   10

<210> SEQ ID NO 39
<211> LENGTH: 32
<212> TYPE: PRT
<213> ORGANISM: Artificial Sequence
<220> FEATURE:
<223> OTHER INFORMATION: deimmunized heavy chain J415-4

<400> SEQUENCE: 39

Arg Val Ile Ile Ser Arg Asp Asp Ser Lys Ser Ser Val Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: deimmunized heavy chain J415-4

<400> SEQUENCE: 40

Trp Gly Gln Gly Thr Thr Val Thr Val Ser Ser
1               5                   10

<210> SEQ ID NO 41
<211> LENGTH: 23
<212> TYPE: PRT
<213> ORGANISM: Artificial Sequence
<220> FEATURE:
<223> OTHER INFORMATION: deimmunized light chain J415-5

<400> SEQUENCE: 41

Asn Ile Val Met Thr Gln Phe Pro Lys Ser Met Ser Ala Ser Ala Gly
1               5                   10                  15

Glu Arg Met Thr Leu Thr Cys
            20

<210> SEQ ID NO 42
```

```
<211> LENGTH: 15
<212> TYPE: PRT
<213> ORGANISM: Artificial Sequence
<220> FEATURE:
<223> OTHER INFORMATION: deimmunized light chain J415-5

<400> SEQUENCE: 42

Trp Tyr Gln Gln Lys Pro Thr Gln Ser Pro Lys Met Leu Ile Tyr
1               5                   10                  15

<210> SEQ ID NO 43
<211> LENGTH: 32
<212> TYPE: PRT
<213> ORGANISM: Artificial Sequence
<220> FEATURE:
<223> OTHER INFORMATION: deimmunized light chain J415-5

<400> SEQUENCE: 43

Gly Val Pro Asp Arg Phe Ser Gly Ser Gly Ser Gly Thr Asp Phe Ile
1               5                   10                  15

Leu Thr Ile Ser Ser Val Gln Ala Glu Asp Leu Val Asp Tyr Tyr Cys
            20                  25                  30

<210> SEQ ID NO 44
<211> LENGTH: 10
<212> TYPE: PRT
<213> ORGANISM: Artificial Sequence
<220> FEATURE:
<223> OTHER INFORMATION: deimmunized light chain J415-5

<400> SEQUENCE: 44

Phe Gly Gly Gly Thr Lys Leu Glu Met Lys
1               5                   10

<210> SEQ ID NO 45
<211> LENGTH: 82
<212> TYPE: PRT
<213> ORGANISM: Artificial Sequence
<220> FEATURE:
<223> OTHER INFORMATION: deimmunized heavy chain J415-4

<400> SEQUENCE: 45

Glu Val Lys Leu Glu Glu Ser Gly Gly Gly Leu Val Gln Pro Gly Gly
1               5                   10                  15

Ser Met Lys Ile Ser Cys Val Ala Ser Trp Val Arg Gln Ser Pro Glu
            20                  25                  30

Lys Gly Leu Glu Trp Val Ala Arg Val Ile Ile Ser Arg Asp Asp Ser
        35                  40                  45

Lys Ser Ser Val Tyr Leu Gln Met Asn Ser Leu Arg Ala Glu Asp Thr
    50                  55                  60

Ala Val Tyr Tyr Cys Thr Arg Trp Gly Gln Gly Thr Thr Val Thr Val
65                  70                  75                  80

Ser Ser

<210> SEQ ID NO 46
<211> LENGTH: 80
<212> TYPE: PRT
<213> ORGANISM: Artificial Sequence
<220> FEATURE:
<223> OTHER INFORMATION: deimmunized light chain J415-5

<400> SEQUENCE: 46

Asn Ile Val Met Thr Gln Phe Pro Lys Ser Met Ser Ala Ser Ala Gly
1               5                   10                  15
```

```
Glu Arg Met Thr Leu Thr Cys Trp Tyr Gln Gln Lys Pro Thr Gln Ser
            20                  25                  30

Pro Lys Met Leu Ile Tyr Gly Val Pro Asp Arg Phe Ser Gly Ser Gly
            35                  40                  45

Ser Gly Thr Asp Phe Ile Leu Thr Ile Ser Ser Val Gln Ala Glu Asp
    50                  55                  60

Leu Val Asp Tyr Tyr Cys Phe Gly Gly Thr Lys Leu Glu Met Lys
65                  70                  75                  80
```

<210> SEQ ID NO 47
<211> LENGTH: 116
<212> TYPE: PRT
<213> ORGANISM: Mus musculus

<400> SEQUENCE: 47

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
            35                  40                  45

Ala Glu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Arg Trp Asn Asn Phe Trp Gly Gln Gly Thr Thr Leu
            100                 105                 110

Thr Val Ser Ser
        115
```

<210> SEQ ID NO 48
<211> LENGTH: 107
<212> TYPE: PRT
<213> ORGANISM: Mus musculus

<400> SEQUENCE: 48

```
Asn Ile Val Met Thr Gln Phe Pro Lys Ser Met Ser Ile Ser Val Gly
1               5                   10                  15

Glu Arg Val Thr Leu Thr Cys Lys Ala Ser Glu Asn Val Gly Thr Tyr
            20                  25                  30

Val Ser Trp Tyr Gln Gln Lys Pro Glu Gln Ser Pro Lys Met Leu Ile
            35                  40                  45

Tyr Gly Ala Ser Asn Arg Phe Thr Gly Val Pro Asp Arg Phe Thr Gly
    50                  55                  60

Ser Gly Ser Ala Thr Asp Phe Ile Leu Thr Ile Ser Ser Val Gln Thr
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105
```

<210> SEQ ID NO 49
<211> LENGTH: 116
<212> TYPE: PRT
<213> ORGANISM: Artificial Sequence

```
<220> FEATURE:
<223> OTHER INFORMATION: deimmunized heavy chain J415-4

<400> SEQUENCE: 49

Glu Val Lys Leu Glu Glu Ser Gly Gly Gly Leu Val Gln Pro Gly Gly
  1               5                  10                  15

Ser Met Lys Ile Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Ser Gln Ser Asn Asn Phe Ala Thr His Tyr Ala Glu
 50                  55                  60

Ser Val Lys Gly Arg Val Ile Ile Ser Arg Asp Asp Ser Lys Ser Ser
 65                  70                  75                  80

Val Tyr Leu Gln Met Asn Ser Leu Arg Ala Glu Asp Thr Ala Val Tyr
                 85                  90                  95

Tyr Cys Thr Arg Arg Trp Asn Asn Phe Trp Gly Gln Gly Thr Thr Val
                100                 105                 110

Thr Val Ser Ser
            115

<210> SEQ ID NO 50
<211> LENGTH: 107
<212> TYPE: PRT
<213> ORGANISM: Artificial Sequence
<220> FEATURE:
<223> OTHER INFORMATION: deimmunized light chain J415-5

<400> SEQUENCE: 50

Asn Ile Val Met Thr Gln Phe Pro Lys Ser Met Ser Ala Ser Ala Gly
  1               5                  10                  15

Glu Arg Met Thr Leu Thr Cys Lys Ala Ser Glu Asn Val Gly Thr Tyr
                 20                  25                  30

Val Ser Trp Tyr Gln Gln Lys Pro Thr Gln Ser Pro Lys Met Leu Ile
             35                  40                  45

Tyr Gly Ala Ser Asn Arg Phe Thr Gly Val Pro Asp Arg Phe Ser Gly
 50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
                100                 105

<210> SEQ ID NO 51
<211> LENGTH: 348
<212> TYPE: DNA
<213> ORGANISM: Artificial Sequence
<220> FEATURE:
<223> OTHER INFORMATION: deimmunized heavy chain J415-4

<400> SEQUENCE: 51
gaagtgaaac ttgaggagtc tggaggaggc ttggtgcaac ctggagggtc catgaaaatc    60
tcctgtgttg cctctggatt cactttcagt aattactgga tgaactgggt ccgccagtct   120
ccagagaagg ggcttgagtg ggttgctgaa attagatcgc aatctaataa ttttgcaaca   180
cattatgcgg agtctgtgaa agggagggtc atcatctcaa gagatgattc caagagtagt   240
gtctacctgc aaatgaacag tttgagagct gaagacactg ccgtttatta ctgtaccagg   300
```

```
cgatggaata atttctgggg ccaaggcacc actgtcacag tctcctca                    348

<210> SEQ ID NO 52
<211> LENGTH: 321
<212> TYPE: DNA
<213> ORGANISM: Artificial Sequence
<220> FEATURE:
<223> OTHER INFORMATION: deimmunized light chain J415-5

<400> SEQUENCE: 52
aacattgtaa tgacccaatt tcccaaatcc atgtccgcct cagcaggaga gaggatgacc        60
ttgacctgca aggccagtga aatgtgggt acttatgtgt cctggtatca acagaaacca       120
acacagtctc ctaagatgtt gatatacggg gcatccaacc ggttcactgg ggtcccagat      180
cgcttctccg gcagtggatc tggaacagat tcattctga ccatcagcag tgtgcaggca       240
gaagaccttg tagattatta ctgtggacag agttacacct ttccgtacac gttcggaggg      300
gggaccaagc tggaaatgaa g                                                321

<210> SEQ ID NO 53
<211> LENGTH: 810
<212> TYPE: DNA
<213> ORGANISM: Artificial Sequence
<220> FEATURE:
<223> OTHER INFORMATION: deimmunized heavy chain J415-1
<220> FEATURE:
<221> NAME/KEY: CDS
<222> LOCATION: (122)...(160)
<220> FEATURE:
<221> NAME/KEY: CDS
<222> LOCATION: (249)...(608)

<400> SEQUENCE: 53
aagcttatga atatgcaaat cctctgaatc tacatggtaa atataggttt gtctatacca        60
caaacagaaa aacatgagat cacagttctc tctacagtta ctgagcacac aggacctcac      120 c atg gga tgg agc tgt atc atc ctc ttc ttg gta gca aca gctacaggta      170
  Met Gly Trp Ser Cys Ile Ile Leu Phe Leu Val Ala Thr
  1               5                   10 agggctcac agtagcaggc ttgaggtctg acatatata tgggtgacaa tgacatccac         230 tttgccttc tctccaca ggt gtc cac tcc gaa gtg aaa ctt gag gag tct        281
                    Gly Val His Ser Glu Val Lys Leu Glu Glu Ser
                             15                  20 gga gga ggc ttg gtg caa cct gga ggg tcc atg aaa atc tcc tgt aaa       329
Gly Gly Gly Leu Val Gln Pro Gly Gly Ser Met Lys Ile Ser Cys Lys
 25                  30                  35                  40 gcc tct gga ttc act ttc agt aat tac tgg atg aac tgg gtc cgc cag       377
Ala Ser Gly Phe Thr Phe Ser Asn Tyr Trp Met Asn Trp Val Arg Gln
             45                  50                  55 act cca gag aag ggg ctt gag tgg gtt gct ctt att aga tcg caa tct       425
Thr Pro Glu Lys Gly Leu Glu Trp Val Ala Leu Ile Arg Ser Gln Ser
         60                  65                  70 aat aat ttt gca aca cat tat gcg gag tct gtg aaa ggg agg gtc atc       473
Asn Asn Phe Ala Thr His Tyr Ala Glu Ser Val Lys Gly Arg Val Ile
     75                  80                  85 atc tca aga gat gat tcc aag agt agt gtc tac ctg caa atg aac agt       521
Ile Ser Arg Asp Asp Ser Lys Ser Ser Val Tyr Leu Gln Met Asn Ser
 90                  95                 100 ttg aga gct gaa gac act gcc gtt tat tac tgt acc agg cga tgg aat       569
Leu Arg Ala Glu Asp Thr Ala Val Tyr Tyr Cys Thr Arg Arg Trp Asn
105                 110                 115                 120
```

```
aat ttc tgg ggc caa ggc acc act gtc aca gtc tcc tca ggtgagtcct    618
Asn Phe Trp Gly Gln Gly Thr Thr Val Thr Val Ser Ser
                125                 130 tacaacctct ctcttctatt cagcttaaat agattttact gcatttgttg gggggaaat    678 gtgtgtatct gaatttcagg tcatgaagga ctagggacac cttgggagtc agaaagggtc   738
attgggagcc cgggctgatg cagacagaca tcctcagctc ccagacttca tggccagaga   798
tttataggat cc                                                      810

<210> SEQ ID NO 54
<211> LENGTH: 133
<212> TYPE: PRT
<213> ORGANISM: Artificial Sequence
<220> FEATURE:
<223> OTHER INFORMATION: deimmunized heavy chain J415-1

<400> SEQUENCE: 54

Met Gly Trp Ser Cys Ile Ile Leu Phe Leu Val Ala Thr Gly Val His
 1               5                  10                  15

Ser Glu Val Lys Leu Glu Glu Ser Gly Gly Gly Leu Val Gln Pro Gly
                20                  25                  30

Gly Ser Met Lys Ile Ser Cys Lys Ala Ser Gly Phe Thr Phe Ser Asn
            35                  40                  45

Tyr Trp Met Asn Trp Val Arg Gln Thr Pro Glu Lys Gly Leu Glu Trp
        50                  55                  60

Val Ala Leu Ile Arg Ser Gln Ser Asn Asn Phe Ala Thr His Tyr Ala
65                  70                  75                  80

Glu Ser Val Lys Gly Arg Val Ile Ile Ser Arg Asp Asp Ser Lys Ser
                85                  90                  95

Ser Val Tyr Leu Gln Met Asn Ser Leu Arg Ala Glu Asp Thr Ala Val
                100                 105                 110

Tyr Tyr Cys Thr Arg Arg Trp Asn Asn Phe Trp Gly Gln Gly Thr Thr
            115                 120                 125

Val Thr Val Ser Ser
        130

<210> SEQ ID NO 55
<211> LENGTH: 810
<212> TYPE: DNA
<213> ORGANISM: Artificial Sequence
<220> FEATURE:
<223> OTHER INFORMATION: deimmunized heavy chain J415-1

<400> SEQUENCE: 55
ggatcctata atctctggc catgaagtct gggagctgag gatgtctgtc tgcatcagcc     60
cgggctccca atgacccttt ctgactccca aggtgtccct agtccttcat gacctgaaat   120
tcagatacac acatttcccc cccaacaaat gcagtaaaat ctatttaagc tgaatagaag   180
agagaggttg taaggactca cctgaggaga ctgtgacagt ggtgccttgg ccccagaaat   240
tattccatcg cctggtacag taataaacgg cagtgtcttc agctctcaaa ctgttcattt   300
gcaggtagac actactcttg gaatcatctc ttgagatgat gaccctccct ttcacagact   360
ccgcataatg tgttgcaaaa ttattagatt gcgatctaat aagagcaacc cactcaagcc   420
ccttctctgg agtctggcgg acccagttca tccagtaatt actgaaagtg aatccagagg   480
ctttacagga gattttcatg gaccctccag gttgcaccaa gcctcctcca gactcctcaa   540
gtttcacttc ggagtggaca cctgtggaga gaaaggcaaa gtggatgtca ttgtcaccca   600
```

-continued

```
tatatatgtc cagacctcaa gcctgctact gtgagcccct tacctgtagc tgttgctacc      660
aagaagagga tgatacagct ccatcccatg gtgaggtcct gtgtgctcag taactgtaga      720
gagaactgtg atctcatgtt tttctgtttg tggtatagac aaacctatat ttaccatgta      780
gattcagagg atttgcatat tcataagctt                                       810
```

```
<210> SEQ ID NO 56
<211> LENGTH: 620
<212> TYPE: DNA
<213> ORGANISM: Artificial Sequence
<220> FEATURE:
<223> OTHER INFORMATION: deimmunized light chain J415-1
<220> FEATURE:
<221> NAME/KEY: CDS
<222> LOCATION: (122)...(160)
<220> FEATURE:
<221> NAME/KEY: CDS
<222> LOCATION: (249)...(581)
```

<400> SEQUENCE: 56

```
aagcttatga atatgcaaat cctctgaatc tacatggtaa atataggttt gtctatacca      60
caaacagaaa aacatgagat cacagttctc tctacagtta ctgagcacac aggacctcac     120 c atg gga tgg agc tgt atc atc ctc ttc ttg gta gca aca gctacaggta      170
  Met Gly Trp Ser Cys Ile Ile Leu Phe Leu Val Ala Thr
   1               5                  10 agggctcac agtagcaggc ttgaggtctg acatatata tgggtgacaa tgacatccac       230 tttgccttc tctccaca ggt gtc cac tcc aac att gta atg acc caa tcc       281
                    Gly Val His Ser Asn Ile Val Met Thr Gln Ser
                         15                  20 ccc aaa tcc atg tcc gcc tca gca gga gag agg atg acc ttg acc tgc      329
Pro Lys Ser Met Ser Ala Ser Ala Gly Glu Arg Met Thr Leu Thr Cys
 25                  30                  35                  40 aag gcc agt gag aat tcc ggt act tat gtg tcc tgg tat caa cag aaa      377
Lys Ala Ser Glu Asn Ser Gly Thr Tyr Val Ser Trp Tyr Gln Gln Lys
                 45                  50                  55 cca aca cag tct cct aag atg ttg ata tac ggg gca tcc aac cgg ttc      425
Pro Thr Gln Ser Pro Lys Met Leu Ile Tyr Gly Ala Ser Asn Arg Phe
             60                  65                  70 act ggg gtc cca gat cgc ttc tcc ggc agt gga tct gga aca gat ttc      473
Thr Gly Val Pro Asp Arg Phe Ser Gly Ser Gly Ser Gly Thr Asp Phe
         75                  80                  85 att ctg acc gcc agc agt gtg cag gca gaa gac cct gta gat tat tac      521
Ile Leu Thr Ala Ser Ser Val Gln Ala Glu Asp Pro Val Asp Tyr Tyr
     90                  95                 100 tgt gga cag agt tac acc ttt ccg tac acg ttc gga ggg ggg acc aag      569
Cys Gly Gln Ser Tyr Thr Phe Pro Tyr Thr Phe Gly Gly Gly Thr Lys
105                 110                 115                 120 ctg gaa atg aag cgtgagtaga atttaaactt tgcttcctca gttggatcc           620
Leu Glu Met Lys
```

```
<210> SEQ ID NO 57
<211> LENGTH: 124
<212> TYPE: PRT
<213> ORGANISM: Artificial Sequence
<220> FEATURE:
<223> OTHER INFORMATION: deimmunized light chain J415-1
```

<400> SEQUENCE: 57

```
Met Gly Trp Ser Cys Ile Ile Leu Phe Leu Val Ala Thr Gly Val His
 1               5                  10                  15

Ser Asn Ile Val Met Thr Gln Ser Pro Lys Ser Met Ser Ala Ser Ala
```

-continued

```
                    20                  25                  30
Gly Glu Arg Met Thr Leu Thr Cys Lys Ala Ser Glu Asn Ser Gly Thr
            35                  40                  45

Tyr Val Ser Trp Tyr Gln Gln Lys Pro Thr Gln Ser Pro Lys Met Leu
    50                  55                  60

Ile Tyr Gly Ala Ser Asn Arg Phe Thr Gly Val Pro Asp Arg Phe Ser
65                  70                  75                  80

Gly Ser Gly Ser Gly Thr Asp Phe Ile Leu Thr Ala Ser Ser Val Gln
                85                  90                  95

Ala Glu Asp Pro Val Asp Tyr Tyr Cys Gly Gln Ser Tyr Thr Phe Pro
            100                 105                 110

Tyr Thr Phe Gly Gly Gly Thr Lys Leu Glu Met Lys
            115                 120
```

<210> SEQ ID NO 58
<211> LENGTH: 620
<212> TYPE: DNA
<213> ORGANISM: Artificial Sequence
<220> FEATURE:
<223> OTHER INFORMATION: deimmunized light chain J415-1

<400> SEQUENCE: 58

```
ggatccaact gaggaagcaa agtttaaatt ctactcacgc ttcatttcca gcttggtccc      60
ccctccgaac gtgtacggaa agtgtaact ctgtccacag taataatcta cagggtcttc     120
tgcctgcaca ctgctggcgg tcagaatgaa atcgttcca gatccactgc cggagaagcg     180
atctgggacc ccagtgaacc ggttggatgc ccgtatatc aacatcttag agactgtgt     240
tggtttctgt tgataccagg acacataagt accggaattc tcactggcct tgcaggtcaa    300
ggtcatcctc tctcctgctg aggcggacat ggatttgggg gattgggtca ttacaatgtt    360
ggagtggaca cctgtggaga gaaaggcaaa gtggatgtca ttgtcaccca tatatatgtc    420
cagacctcaa gcctgctact gtgagcccct tacctgtagc tgttgctacc aagaagagga    480
tgatacagct ccatcccatg gtgaggtcct gtgtgctcag taactgtaga gagaactgtg    540
atctcatgtt tttctgtttg tggtatagac aaacctatat ttaccatgta gattcagagg    600
atttgcatat tcataagctt                                                620
```

<210> SEQ ID NO 59
<211> LENGTH: 116
<212> TYPE: PRT
<213> ORGANISM: Artificial Sequence
<220> FEATURE:
<223> OTHER INFORMATION: deimmunized heavy chain J415-2

<400> SEQUENCE: 59

```
Glu Val Lys Leu Glu Glu Ser Gly Gly Gly Leu Val Gln Pro Gly Gly
1               5                   10                  15

Ser Met Lys Ile Ser Cys Val Ala Ser Gly Phe Thr Phe Ser Asn Tyr
            20                  25                  30

Trp Met Asn Trp Val Arg Gln Thr Pro Glu Lys Gly Leu Glu Trp Val
        35                  40                  45

Ala Leu Ile Arg Ser Gln Ser Asn Asn Phe Ala Thr His Tyr Ala Glu
    50                  55                  60

Ser Val Lys Gly Arg Val Ile Ile Ser Arg Asp Asp Ser Lys Ser Ser
65                  70                  75                  80

Val Tyr Leu Gln Met Asn Ser Leu Arg Ala Glu Asp Thr Ala Val Tyr
                85                  90                  95
```

```
Tyr Cys Thr Arg Arg Trp Asn Asn Phe Trp Gly Gln Gly Thr Thr Val
                100                 105                 110
Thr Val Ser Ser
        115
```

<210> SEQ ID NO 60
<211> LENGTH: 116
<212> TYPE: PRT
<213> ORGANISM: Artificial Sequence
<220> FEATURE:
<223> OTHER INFORMATION: deimmunized heavy chain J415-3

<400> SEQUENCE: 60

```
Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
                20                  25                  30

Trp Met Asn Trp Val Arg Gln Thr Pro Glu Lys Gly Leu Glu Trp Val
            35                  40                  45

Ala Glu Ile Arg Ser Gln Ser Asn Asn Phe Ala Thr His Tyr Ala Glu
        50                  55                  60

Ser Val Lys Gly Arg Val Ile Ile Ser Arg Asp Asp Ser Lys Ser Ser
 65                 70                  75                  80

Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
                100                 105                 110

Thr Val Ser Ser
        115
```

<210> SEQ ID NO 61
<211> LENGTH: 116
<212> TYPE: PRT
<213> ORGANISM: Artificial Sequence
<220> FEATURE:
<223> OTHER INFORMATION: majority sequence

<400> SEQUENCE: 61

```
Glu Val Lys Leu Glu Glu Ser Gly Gly Gly Leu Val Gln Pro Gly Gly
 1               5                  10                  15

Ser Met Lys Ile Ser Cys Val Ala Ser Gly Phe Thr Phe Ser Asn Tyr
                20                  25                  30

Trp Met Asn Trp Val Arg Gln Thr Pro Glu Lys Gly Leu Glu Trp Val
            35                  40                  45

Ala Glu Ile Arg Ser Gln Ser Asn Asn Phe Ala Thr His Tyr Ala Glu
        50                  55                  60

Ser Val Lys Gly Arg Val Ile Ile Ser Arg Asp Asp Ser Lys Ser Ser
 65                 70                  75                  80

Val Tyr Leu Gln Met Asn Ser Leu Arg Ala Glu Asp Thr Ala Val Tyr
                85                  90                  95

Tyr Cys Thr Arg Arg Trp Asn Asn Phe Trp Gly Gln Gly Thr Thr Val
                100                 105                 110

Thr Val Ser Ser
        115
```

<210> SEQ ID NO 62
<211> LENGTH: 107
<212> TYPE: PRT

```
<213> ORGANISM: Artificial Sequence
<220> FEATURE:
<223> OTHER INFORMATION: deimmunized light chain J415-2

<400> SEQUENCE: 62

Asn Ile Val Met Thr Gln Ser Pro Lys Ser Met Ser Ala Ser Ala Gly
 1               5                  10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ala Ser Ser Val Gln Ala
65                  70                  75                  80

Glu Asp Pro Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: deimmunized light chain J415-3

<400> SEQUENCE: 63

Asn Ile Val Met Thr Gln Ser Pro Lys Ser Met Ser Ala Ser Ala Gly
 1               5                  10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60

Ser Gly Ser Gly Thr Asp Phe Ile Leu Thr Ala Ser Ser Val Gln Ala
65                  70                  75                  80

Glu Asp Leu Val Asp Tyr Tyr Cys Gly Gln Ser Tyr Thr Phe Pro Tyr
                85                  90                  95

Thr Phe Gly Gly Gly Thr Lys Leu Glu Met Lys
            100                 105

<210> SEQ ID NO 64
<211> LENGTH: 107
<212> TYPE: PRT
<213> ORGANISM: Artificial Sequence
<220> FEATURE:
<223> OTHER INFORMATION: deimmunized light chain J415-4

<400> SEQUENCE: 64

Asn Ile Val Met Thr Gln Ser Pro Lys Ser Met Ser Ala Ser Ala Gly
 1               5                  10                  15

Glu Arg Met Thr Leu Thr Cys Lys Ala Ser Glu Asn Val Gly Thr Tyr
            20                  25                  30

Val Ser Trp Tyr Gln Gln Lys Pro Thr Gln Ser Pro Lys Met Leu Ile
        35                  40                  45

Tyr Gly Ala Ser Asn Arg Phe Thr Gly Val Pro Asp Arg Phe Ser Gly
    50                  55                  60
```

-continued

```
Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: deimmunized light chain J415-6

<400> SEQUENCE: 65

Asn Ile Val Met Thr Gln Phe Pro Lys Ser Met Ser Ala Ser Ala Gly
 1               5                  10                  15

Glu Arg Met Thr Leu Thr Cys Lys Ala Ser Glu Asn Val Gly Thr Tyr
                 20                  25                  30

Val Ser Trp Tyr Gln Gln Lys Pro Glu Gln Ser Pro Lys Met Leu Ile
             35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: deimmunized light chain J415-7

<400> SEQUENCE: 66

Asn Ile Val Met Thr Gln Phe Pro Lys Ser Met Ser Ala Ser Ala Gly
 1               5                  10                  15

Glu Arg Val Thr Leu Thr Cys Lys Ala Ser Glu Asn Val Gly Thr Tyr
                 20                  25                  30

Val Ser Trp Tyr Gln Gln Lys Pro Thr Gln Ser Pro Lys Met Leu Ile
             35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
 65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 67
<211> LENGTH: 107
<212> TYPE: PRT
<213> ORGANISM: Artificial Sequence
<220> FEATURE:
<223> OTHER INFORMATION: deimmunized light chain J415-8
```

```
<400> SEQUENCE: 67

Asn Ile Val Met Thr Gln Phe Pro Lys Ser Met Ser Ala Ser Ala Gly
 1               5                   10                  15

Glu Arg Met Thr Leu Thr Cys Lys Ala Ser Glu Asn Ser Gly Thr Tyr
             20                  25                  30

Val Ser Trp Tyr Gln Gln Lys Pro Glu Gln Ser Pro Lys Met Leu Ile
         35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: majority sequence

<400> SEQUENCE: 68

Asn Ile Val Met Thr Gln Phe Pro Lys Ser Met Ser Ala Ser Ala Gly
 1               5                   10                  15

Glu Arg Met Thr Leu Thr Cys Lys Ala Ser Glu Asn Val Gly Thr Tyr
             20                  25                  30

Val Ser Trp Tyr Gln Gln Lys Pro Thr Gln Ser Pro Lys Met Leu Ile
         35                  40                  45

Tyr Gly Ala Ser Asn Arg Phe Thr Gly Val Pro Asp Arg Phe Ser Gly
     50                  55                  60

Ser Gly Ser Gly Thr Asp Phe Ile Leu Thr Ile Ser Ser Val Gln Ala
65                  70                  75                  80

Glu Asp Leu Val Asp Tyr Tyr Cys Gly Gln Ser Tyr Thr Phe Pro Tyr
                 85                  90                  95

Thr Phe Gly Gly Gly Thr Lys Leu Glu Met Lys
            100                 105

<210> SEQ ID NO 69
<211> LENGTH: 123
<212> TYPE: PRT
<213> ORGANISM: Mus musculus

<400> SEQUENCE: 69

Glu Val Lys Leu Glu Glu Ser Gly Gly Gly Leu Val Gln Pro Gly Gly
 1               5                   10                  15

Ser Met Lys Leu Ser Cys Val Ala Ser Gly Phe Thr Phe Ser Asn Tyr
             20                  25                  30

Trp Met Asn Trp Val Arg Gln Ser Pro Glu Lys Gly Leu Glu Trp Val
         35                  40                  45

Ala Glu Ile Arg Leu Lys Ser Asp Asn Tyr Ala Thr His Tyr Ala Glu
     50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
```

```
                        85                  90                  95
Tyr Cys Thr Thr Gly Gly Tyr Gly Gly Arg Arg Ser Trp Phe Ala Tyr
                100                 105                 110

Trp Gly Gln Gly Thr Leu Val Thr Val Ser Ser
        115                 120
```

<210> SEQ ID NO 70
<211> LENGTH: 123
<212> TYPE: PRT
<213> ORGANISM: Artificial Sequence
<220> FEATURE:
<223> OTHER INFORMATION: majority sequence

<400> SEQUENCE: 70

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Ala Glu Ile Arg Leu Gln Ser Asp Asn Phe Ala Thr His Tyr Ala Glu
        50                  55                  60

Ser Val Lys Gly Arg Val Ile Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Thr Gly Gly Tyr Gly Gly Arg Arg Ser Trp Asn Ala Phe
                100                 105                 110

Trp Gly Gln Gly Thr Leu Val Thr Val Ser Ser
        115                 120
```

<210> SEQ ID NO 71
<211> LENGTH: 113
<212> TYPE: PRT
<213> ORGANISM: Mus musculus

<400> SEQUENCE: 71

```
Asp Ile Val Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
                100                 105                 110

Lys
```

<210> SEQ ID NO 72
<211> LENGTH: 113
<212> TYPE: PRT
<213> ORGANISM: Artificial Sequence
<220> FEATURE:

<223> OTHER INFORMATION: majority sequence

<400> SEQUENCE: 72

Asp Ile Val Met Thr Gln Ser Pro Ser Ser Leu Ala Val Ser Ala Gly
1               5                   10                  15

Glu Lys Val Thr Leu Ser Cys Lys Ala Ser Glu Ser Leu Leu Asn Val
            20                  25                  30

Gly Asn Gln Lys Thr Tyr Val Ala Trp Tyr Gln Lys Pro Gly Gln
        35                  40                  45

Ser Pro Lys Leu Leu Ile Tyr Gly Ala Ser Thr Arg Glu Ser Gly Val
50                  55                  60

Pro Asp Arg Phe Thr Gly Ser Gly Ser Gly Thr Asp Phe Ile Leu Thr
65                  70                  75                  80

Ile Ser Ser Val Gln Ala Glu Asp Leu Ala Val Tyr Tyr Cys Gly Asn
                85                  90                  95

Ser Tyr Ser Phe Pro Leu Thr Phe Gly Gly Gly Thr Lys Leu Glu Leu
            100                 105                 110

Lys

<210> SEQ ID NO 73
<211> LENGTH: 354
<212> TYPE: DNA
<213> ORGANISM: Mus musculus
<220> FEATURE:
<221> NAME/KEY: CDS
<222> LOCATION: (1)...(354)

<400> SEQUENCE: 73 gag gtc cag ctg cag cag tct gga cct gag ctg gtt aag cct ggg gct      48
Glu Val Gln Leu Gln Gln Ser Gly Pro Glu Leu Val Lys Pro Gly Ala
1               5                   10                  15 tca gtg aag atg tcc tgc aag gct tct gga tac aca ttc act ggc tat      96
Ser Val Lys Met Ser Cys Lys Ala Ser Gly Tyr Thr Phe Thr Gly Tyr
            20                  25                  30 gtt atg cac tgg gtg aag cag aag cct gga cag gtc ctt gag tgg att     144
Val Met His Trp Val Lys Gln Lys Pro Gly Gln Val Leu Glu Trp Ile
        35                  40                  45 gga tat att aat cct tac aat gat gtt act agg tat aat ggg aag ttc     192
Gly Tyr Ile Asn Pro Tyr Asn Asp Val Thr Arg Tyr Asn Gly Lys Phe
    50                  55                  60 aaa ggc aag gcc aca ctg acc tca gac aaa tat tcc agc aca gcc tac     240
Lys Gly Lys Ala Thr Leu Thr Ser Asp Lys Tyr Ser Ser Thr Ala Tyr
65                  70                  75                  80 atg gag ctc agc ggc ctg acc tct gag gac tct gcg gtc tat tac tgt     288
Met Glu Leu Ser Gly Leu Thr Ser Glu Asp Ser Ala Val Tyr Tyr Cys
                85                  90                  95 gca aga ggg gag aac tgg tac tac ttt gac tcc tgg ggc cga ggc gcc     336
Ala Arg Gly Glu Asn Trp Tyr Tyr Phe Asp Ser Trp Gly Arg Gly Ala
            100                 105                 110 act ctc aca gtc tcc tca                                             354
Thr Leu Thr Val Ser Ser
        115

<210> SEQ ID NO 74
<211> LENGTH: 118
<212> TYPE: PRT
<213> ORGANISM: Mus musculus

<400> SEQUENCE: 74

Glu Val Gln Leu Gln Gln Ser Gly Pro Glu Leu Val Lys Pro Gly Ala

```
                 1               5                  10                 15
              Ser Val Lys Met Ser Cys Lys Ala Ser Gly Tyr Thr Phe Thr Gly Tyr
                              20                  25                  30

Val Met His Trp Val Lys Gln Lys Pro Gly Gln Val Leu Glu Trp Ile
                              35                  40                  45

Gly Tyr Ile Asn Pro Tyr Asn Asp Val Thr Arg Tyr Asn Gly Lys Phe
                              50                  55                  60

Lys Gly Lys Ala Thr Leu Thr Ser Asp Lys Tyr Ser Ser Thr Ala Tyr
               65                  70                  75                  80

Met Glu Leu Ser Gly Leu Thr Ser Glu Asp Ser Ala Val Tyr Tyr Cys
                              85                  90                  95

Ala Arg Gly Glu Asn Trp Tyr Tyr Phe Asp Ser Trp Gly Arg Gly Ala
                              100                 105                 110

Thr Leu Thr Val Ser Ser
                              115
```

<210> SEQ ID NO 75
<211> LENGTH: 354
<212> TYPE: DNA
<213> ORGANISM: Mus musculus

<400> SEQUENCE: 75

```
tgaggagact gtgagagtgg cgcctcggcc ccaggagtca agtagtacc  agttctcccc      60
tcttgcacag taatagaccg cagagtcctc agaggtcagg ccgctgagct ccatgtaggc     120
tgtgctggaa tatttgtctg aggtcagtgt ggccttgcct ttgaacttcc cattatacct    180
agtaacatca ttgtaaggat taatatatcc aatccactca aggacctgtc caggcttctg    240
cttcacccag tgcataacat agccagtgaa tgtgtatcca gaagccttgc aggacatctt    300
cactgaagcc ccaggcttaa ccagctcagg tccagactgc tgcagctgga cctc          354
```

<210> SEQ ID NO 76
<211> LENGTH: 333
<212> TYPE: DNA
<213> ORGANISM: Mus musculus
<220> FEATURE:
<221> NAME/KEY: CDS
<222> LOCATION: (1)...(333)

<400> SEQUENCE: 76

```
gac att gtg ctg acc caa tct cca gct tct ttg gct gtg tct cta gga     48
Asp Ile Val Leu Thr Gln Ser Pro Ala Ser Leu Ala Val Ser Leu Gly
 1               5                  10                  15 cag agg gcc acc ata tcc tgc aga gcc agt gaa agt att gat agt tat     96
Gln Arg Ala Thr Ile Ser Cys Arg Ala Ser Glu Ser Ile Asp Ser Tyr
                20                  25                  30 gac aat act ttt atg cac tgg tac cag cag aaa cca gga cag cca ccc    144
Asp Asn Thr Phe Met His Trp Tyr Gln Gln Lys Pro Gly Gln Pro Pro
            35                  40                  45 aac ctc ctc atc ttt cgt gca tcc atc cta gaa tct ggg atc cct gcc    192
Asn Leu Leu Ile Phe Arg Ala Ser Ile Leu Glu Ser Gly Ile Pro Ala
        50                  55                  60 agg ttc agt ggc agt ggg tct ggg aca gac ttc acc ctc acc att tat    240
Arg Phe Ser Gly Ser Gly Ser Gly Thr Asp Phe Thr Leu Thr Ile Tyr
 65                  70                  75                  80 cct gtg gag gct gat gat gtt gca acc tat tac tgt cac caa agt att    288
Pro Val Glu Ala Asp Asp Val Ala Thr Tyr Tyr Cys His Gln Ser Ile
                85                  90                  95 gag gat ccg tac acg ttc gga ggg ggg acc aag ctg gaa ata aaa        333
Glu Asp Pro Tyr Thr Phe Gly Gly Gly Thr Lys Leu Glu Ile Lys
```

```
Glu Asp Pro Tyr Thr Phe Gly Gly Gly Thr Lys Leu Glu Ile Lys
            100                 105                 110
```

<210> SEQ ID NO 77
<211> LENGTH: 111
<212> TYPE: PRT
<213> ORGANISM: Mus musculus

<400> SEQUENCE: 77

```
Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Ile Asp Ser Tyr
             20                  25                  30

Asp Asn Thr Phe Met His Trp Tyr Gln Gln Lys Pro Gly Gln Pro Pro
         35                  40                  45

Asn Leu Leu Ile Phe Arg Ala Ser Ile Leu Glu Ser Gly Ile Pro Ala
     50                  55                  60

Arg Phe Ser Gly Ser Gly Ser Gly Thr Asp Phe Thr Leu Thr Ile Tyr
 65                  70                  75                  80

Pro Val Glu Ala Asp Asp Val Ala Thr Tyr Tyr Cys His Gln Ser Ile
                 85                  90                  95

Glu Asp Pro Tyr Thr Phe Gly Gly Gly Thr Lys Leu Glu Ile Lys
            100                 105                 110
```

<210> SEQ ID NO 78
<211> LENGTH: 333
<212> TYPE: DNA
<213> ORGANISM: Mus musculus

<400> SEQUENCE: 78

```
ttttatttcc agcttggtcc ccctccgaa  cgtgtacgga tcctcaatac tttggtgaca      60
gtaataggtt gcaacatcat cagcctccac aggataaatg gtgagggtga agtctgtccc     120
agacccactg ccactgaacc tggcagggat cccagattct aggatggatg cacgaaagat     180
gaggaggttg ggtggctgtc ctggtttctg ctggtaccag tgcataaaag tattgtcata     240
actatcaata ctttcactgg ctctgcagga tatggtggcc ctctgtccta gagacacagc     300
caaagaagct ggagattggg tcagcacaat gtc                                   333
```

<210> SEQ ID NO 79
<211> LENGTH: 125
<212> TYPE: PRT
<213> ORGANISM: Mus musculus

<400> SEQUENCE: 79

```
Glu Val Gln Leu Gln Gln Ser Gly Pro Glu Leu Val Lys Pro Gly Ala
  1               5                  10                  15

Ser Val Lys Ile Ser Cys Lys Ala Ser Gly Tyr Thr Phe Thr Asp Tyr
             20                  25                  30

Tyr Met Asn Asn Trp Val Lys Gln Ser Pro Gly Lys Ser Leu Glu Trp
         35                  40                  45

Ile Gly Asp Ile Asn Pro Gly Asn Gly Gly Thr Ser Tyr Asn Gln Lys
     50                  55                  60

Phe Lys Gly Lys Ala Thr Leu Thr Val Asp Lys Ser Ser Ser Thr Ala
 65                  70                  75                  80

Tyr Met Gln Leu Ser Ser Leu Thr Ser Glu Asp Ser Ala Val Tyr Tyr
                 85                  90                  95

Cys Ala Arg Gly Tyr Tyr Ser Ser Ser Tyr Met Ala Tyr Tyr Ala Phe
```

```
                    100                 105                 110
Asp Tyr Trp Gly Gln Gly Thr Thr Val Thr Val Ser Ser
            115                 120                 125
```

<210> SEQ ID NO 80
<211> LENGTH: 125
<212> TYPE: PRT
<213> ORGANISM: Artificial Sequence
<220> FEATURE:
<223> OTHER INFORMATION: majority sequence

<400> SEQUENCE: 80

```
Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Gly Tyr
            20                  25                  30

Val Met Asn Trp Val Lys Gln Ser Pro Gly Gln Val Leu Glu Trp
        35                  40                  45

Ile Gly Asp Ile Asn Pro Gly Asn Gly Thr Ser Tyr Asn Gly Lys
    50                  55                  60

Phe Lys Gly Lys Ala Thr Leu Thr Val Asp Lys Ser Ser Thr Ala
65                  70                  75                  80

Tyr Met Glu Leu Ser Gly Leu Thr Ser Glu Asp Ser Ala Val Tyr Tyr
                85                  90                  95

Cys Ala Arg Gly Glu Asn Ser Ser Tyr Met Ala Tyr Tyr Ala Phe
                100                 105                 110

Asp Ser Trp Gly Gln Gly Ala Thr Val Thr Val Ser Ser
            115                 120                 125
```

<210> SEQ ID NO 81
<211> LENGTH: 112
<212> TYPE: PRT
<213> ORGANISM: Mus musculus

<400> SEQUENCE: 81

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Asp Ala Ala Thr Tyr Tyr Cys Gln Gln Ser Asn
                85                  90                  95

Glu Asp Pro Pro Trp Thr Phe Gly Gly Gly Thr Lys Leu Glu Ile Lys
                100                 105                 110
```

<210> SEQ ID NO 82
<211> LENGTH: 112
<212> TYPE: PRT
<213> ORGANISM: Artificial Sequence
<220> FEATURE:
<223> OTHER INFORMATION: majority sequence

<400> SEQUENCE: 82

```
Asp Ile Val Leu Thr Gln Ser Pro Ala Ser Leu Ala Val Ser Leu Gly
```

```
                 1               5                  10                 15
Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
         35                  40                  45

Asn Leu Leu Ile Phe Ala Ala Ser Ile Leu Glu Ser Gly Val Pro Ala
     50                  55                  60

Arg Phe Ser Gly Ser Gly Ser Gly Thr Asp Phe Thr Leu Thr Ile His
 65                  70                  75                  80

Pro Val Glu Ala Asp Asp Ala Thr Tyr Tyr Cys Gln Gln Ser Ile
                 85                  90                  95

Glu Asp Pro Pro Tyr Thr Phe Gly Gly Gly Thr Lys Leu Glu Ile Lys
             100                 105                 110
```

<210> SEQ ID NO 83
<211> LENGTH: 363
<212> TYPE: DNA
<213> ORGANISM: Mus musculus
<220> FEATURE:
<221> NAME/KEY: CDS
<222> LOCATION: (1)...(363)

<400> SEQUENCE: 83

```
cag gtg cag cta aag gag tca gga cct ggc ctg gtg gcg tcc tca cag      48
Gln Val Gln Leu Lys Glu Ser Gly Pro Gly Leu Val Ala Ser Ser Gln
 1               5                  10                  15 agc ctg tcc atc aca tgc acc gtc tca gga ttc tca tta acc gcc tat      96
Ser Leu Ser Ile Thr Cys Thr Val Ser Gly Phe Ser Leu Thr Ala Tyr
                20                  25                  30 ggt att aac tgg gtt cgc cag cct cca gga aag ggt ctg gag tgg ctg     144
Gly Ile Asn Trp Val Arg Gln Pro Pro Gly Lys Gly Leu Glu Trp Leu
             35                  40                  45 gga gtg ata tgg cct gat gga aac aca gac tat aat tca act ctc aaa     192
Gly Val Ile Trp Pro Asp Gly Asn Thr Asp Tyr Asn Ser Thr Leu Lys
         50                  55                  60 tcc aga ctg aac atc ttc aag gac aac tcc aag aac caa gtt ttc tta     240
Ser Arg Leu Asn Ile Phe Lys Asp Asn Ser Lys Asn Gln Val Phe Leu
 65                  70                  75                  80 aaa atg agc agt ttc caa act gat gac aca gcc aga tac ttc tgt gcc     288
Lys Met Ser Ser Phe Gln Thr Asp Asp Thr Ala Arg Tyr Phe Cys Ala
                 85                  90                  95 aga gat tcg tat ggt aac ttc aag agg ggt tgg ttt gac ttc tgg ggc     336
Arg Asp Ser Tyr Gly Asn Phe Lys Arg Gly Trp Phe Asp Phe Trp Gly
             100                 105                 110 cag ggc acc act ctc aca gtc tcc tca                                 363
Gln Gly Thr Thr Leu Thr Val Ser Ser
         115                 120
```

<210> SEQ ID NO 84
<211> LENGTH: 121
<212> TYPE: PRT
<213> ORGANISM: Mus musculus

<400> SEQUENCE: 84

```
Gln Val Gln Leu Lys Glu Ser Gly Pro Gly Leu Val Ala Ser Ser Gln
 1               5                  10                  15

Ser Leu Ser Ile Thr Cys Thr Val Ser Gly Phe Ser Leu Thr Ala Tyr
                20                  25                  30

Gly Ile Asn Trp Val Arg Gln Pro Pro Gly Lys Gly Leu Glu Trp Leu
             35                  40                  45
```

```
Gly Val Ile Trp Pro Asp Gly Asn Thr Asp Tyr Asn Ser Thr Leu Lys
 50                  55                  60

Ser Arg Leu Asn Ile Phe Lys Asp Asn Ser Lys Asn Gln Val Phe Leu
 65                  70                  75                  80

Lys Met Ser Ser Phe Gln Thr Asp Asp Thr Ala Arg Tyr Phe Cys Ala
                 85                  90                  95

Arg Asp Ser Tyr Gly Asn Phe Lys Arg Gly Trp Phe Asp Phe Trp Gly
                100                 105                 110

Gln Gly Thr Thr Leu Thr Val Ser Ser
            115                 120
```

<210> SEQ ID NO 85
<211> LENGTH: 363
<212> TYPE: DNA
<213> ORGANISM: Mus musculus

<400> SEQUENCE: 85

```
tgaggagact gtgagagtgg tgccctggcc ccagaagtca aaccaacccc tcttgaagtt      60
accatacgaa tctctggcac agaagtatct ggctgtgtca tcagtttgga aactgctcat    120
ttttaagaaa acttggttct tggagttgtc cttgaagatg ttcagtctgg atttgagagt    180
tgaattatag tctgtgtttc catcaggcca tatcactccc agccactcca gacccttccc   240
tggaggctgg cgaacccagt taataccata ggcggttaat gagaatcctg agacggtgca    300
tgtgatggac aggctctgtg aggacgccac caggccaggt cctgactcct ttagctgcac    360
ctg                                                                   363
```

<210> SEQ ID NO 86
<211> LENGTH: 321
<212> TYPE: DNA
<213> ORGANISM: Mus musculus
<220> FEATURE:
<221> NAME/KEY: CDS
<222> LOCATION: (1)...(321)

<400> SEQUENCE: 86

```
aac att gtg atg acc cag tct caa aaa ttc atg tcc aca tca cca gga       48
Asn Ile Val Met Thr Gln Ser Gln Lys Phe Met Ser Thr Ser Pro Gly
  1               5                  10                  15 gac agg gtc agg gtc acc tgc aag gcc agt cag aat gtg ggt tct gat      96
Asp Arg Val Arg Val Thr Cys Lys Ala Ser Gln Asn Val Gly Ser Asp
                 20                  25                  30 gta gcc tgg tat caa gcg aaa cca gga caa tct cct aga ata ctg att     144
Val Ala Trp Tyr Gln Ala Lys Pro Gly Gln Ser Pro Arg Ile Leu Ile
             35                  40                  45 tac tcg aca tcc tac cgt tac agt ggg gtc cct gat cgc ttc aca gcc     192
Tyr Ser Thr Ser Tyr Arg Tyr Ser Gly Val Pro Asp Arg Phe Thr Ala
     50                  55                  60 tat gga tct ggg aca gat ttc act ctc acc att acc aat gtg cag tct     240
Tyr Gly Ser Gly Thr Asp Phe Thr Leu Thr Ile Thr Asn Val Gln Ser
 65                  70                  75                  80 gaa gac ttg aca gag tat ttc tgt cag caa tat aat agc tat cct ctc     288
Glu Asp Leu Thr Glu Tyr Phe Cys Gln Gln Tyr Asn Ser Tyr Pro Leu
                 85                  90                  95 acg ttc ggt gct ggg acc aag ctg gag ctg aaa                         321
Thr Phe Gly Ala Gly Thr Lys Leu Glu Leu Lys
                100                 105
```

<210> SEQ ID NO 87

<211> LENGTH: 107
<212> TYPE: PRT
<213> ORGANISM: Mus musculus

<400> SEQUENCE: 87

```
Asn Ile Val Met Thr Gln Ser Gln Lys Phe Met Ser Thr Ser Pro Gly
  1               5                  10                  15

Asp Arg Val Arg Val Thr Cys Lys Ala Ser Gln Asn Val Gly Ser Asp
             20                  25                  30

Val Ala Trp Tyr Gln Ala Lys Pro Gly Gln Ser Pro Arg Ile Leu Ile
         35                  40                  45

Tyr Ser Thr Ser Tyr Arg Tyr Ser Gly Val Pro Asp Arg Phe Thr Ala
 50                  55                  60

Tyr Gly Ser Gly Thr Asp Phe Thr Leu Thr Ile Thr Asn Val Gln Ser
 65                  70                  75                  80

Glu Asp Leu Thr Glu Tyr Phe Cys Gln Gln Tyr Asn Ser Tyr Pro Leu
             85                  90                  95

Thr Phe Gly Ala Gly Thr Lys Leu Glu Leu Lys
            100                 105
```

<210> SEQ ID NO 88
<211> LENGTH: 321
<212> TYPE: DNA
<213> ORGANISM: Mus musculus

<400> SEQUENCE: 88

```
tttcagctcc agcttggtcc cagcaccgaa cgtgagagga tagctattat attgctgaca      60
gaaatactct gtcaagtctt cagactgcac attggtaatg gtgagagtga atctgtccc     120
agatccatag gctgtgaagc gatcaggac cccactgtaa cggtaggatg tcgagtaaat     180
cagtattcta ggagattgtc ctggtttcgc ttgataccag gctacatcag aacccacatt     240
ctgactggcc ttgcaggtga ccctgaccct gtctcctggt gatgtggaca tgaattttg     300
agactgggtc atcacaatgt t                                               321
```

<210> SEQ ID NO 89
<211> LENGTH: 121
<212> TYPE: PRT
<213> ORGANISM: Mus musculus

<400> SEQUENCE: 89

```
Gln Val Gln Leu Lys Glu Ser Gly Pro Gly Leu Val Ala Ser Ser Gln
  1               5                  10                  15

Ser Leu Ser Ile Thr Cys Thr Val Ser Gly Phe Ser Leu Thr Ala Tyr
             20                  25                  30

Gly Ile Asn Trp Val Arg Gln Pro Pro Gly Lys Gly Leu Glu Trp Leu
         35                  40                  45

Gly Val Ile Trp Pro Asp Gly Asn Thr Asp Tyr Asn Ser Thr Leu Lys
 50                  55                  60

Ser Arg Leu Asn Ile Phe Lys Asp Asn Ser Lys Asn Gln Val Phe Leu
 65                  70                  75                  80

Lys Met Ser Ser Phe Gln Thr Asp Asp Thr Ala Arg Tyr Phe Cys Ala
             85                  90                  95

Arg Asp Ser Tyr Gly Asn Phe Lys Arg Gly Trp Phe Asp Phe Trp Gly
            100                 105                 110

Gln Gly Thr Thr Leu Thr Val Ser Ser
            115                 120
```

```
<210> SEQ ID NO 90
<211> LENGTH: 121
<212> TYPE: PRT
<213> ORGANISM: Artificial Sequence
<220> FEATURE:
<223> OTHER INFORMATION: majority sequence

<400> SEQUENCE: 90

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Thr Ala Tyr
            20                  25                  30

Gly Ile Asn Trp Val Arg Gln Pro Pro Gly Lys Gly Leu Glu Trp Leu
        35                  40                  45

Gly Val Ile Trp Pro Asp Gly Asn Thr Asp Tyr Asn Ser Thr Leu Lys
    50                  55                  60

Ser Arg Leu Asn Ile Phe Lys Asp Asn Ser Lys Asn Gln Val Phe Leu
65                  70                  75                  80

Lys Met Ser Ser Phe Gln Thr Asp Asp Thr Ala Arg Tyr Phe Cys Ala
                85                  90                  95

Arg Asp Ser Tyr Gly Asn Phe Lys Arg Gly Trp Phe Asp Phe Trp Gly
            100                 105                 110

Gln Gly Thr Thr Leu Thr Val Ser Ser
        115                 120

<210> SEQ ID NO 91
<211> LENGTH: 113
<212> TYPE: PRT
<213> ORGANISM: Mus musculus

<400> SEQUENCE: 91

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 92
<211> LENGTH: 115
<212> TYPE: PRT
<213> ORGANISM: Artificial Sequence
<220> FEATURE:
<223> OTHER INFORMATION: majority sequence

<400> SEQUENCE: 92

Asp Ile Val Met Thr Gln Ser Gln Ser Ser Leu Ala Val Ser Ala Gly
1               5                   10                  15

Asp Lys Val Thr Val Ser Cys Lys Ala Ser Gln Ser Leu Leu Asn Val
```

```
                  20                  25                  30
Gly Ser Asp Lys Asn Tyr Val Ala Trp Tyr Gln Ala Lys Pro Gly Gln
         35                  40                  45

Ser Pro Lys Leu Leu Ile Tyr Ser Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Phe Cys Gln Asn
                 85                  90                  95

Asp Asn Ser Tyr Pro Leu Thr Phe Gly Ala Gly Thr Lys Leu Glu Leu
            100                 105                 110

Lys Arg Ala
        115

<210> SEQ ID NO 93
<211> LENGTH: 10
<212> TYPE: PRT
<213> ORGANISM: Mus musculus

<400> SEQUENCE: 93

Gly Tyr Thr Phe Thr Gly Tyr Val Met His
 1               5                  10

<210> SEQ ID NO 94
<211> LENGTH: 17
<212> TYPE: PRT
<213> ORGANISM: Mus musculus

<400> SEQUENCE: 94

Tyr Ile Asn Pro Tyr Asn Asp Val Thr Arg Tyr Asn Gly Lys Phe Lys
 1               5                  10                  15

Gly

<210> SEQ ID NO 95
<211> LENGTH: 9
<212> TYPE: PRT
<213> ORGANISM: Mus musculus

<400> SEQUENCE: 95

Gly Glu Asn Trp Tyr Tyr Phe Asp Ser
 1               5

<210> SEQ ID NO 96
<211> LENGTH: 15
<212> TYPE: PRT
<213> ORGANISM: Mus musculus

<400> SEQUENCE: 96

Arg Ala Ser Glu Ser Ile Asp Ser Tyr Asp Asn Thr Phe Met His
 1               5                  10                  15

<210> SEQ ID NO 97
<211> LENGTH: 7
<212> TYPE: PRT
<213> ORGANISM: Mus Musculus

<400> SEQUENCE: 97

Arg Ala Ser Ile Leu Glu Ser
 1               5

<210> SEQ ID NO 98
```

```
<211> LENGTH: 9
<212> TYPE: PRT
<213> ORGANISM: Mus musculus

<400> SEQUENCE: 98

His Gln Ser Ile Glu Asp Pro Tyr Thr
 1               5

<210> SEQ ID NO 99
<211> LENGTH: 10
<212> TYPE: PRT
<213> ORGANISM: Mus musculus

<400> SEQUENCE: 99

Gly Phe Ser Leu Thr Ala Tyr Gly Ile Asn
 1               5                  10

<210> SEQ ID NO 100
<211> LENGTH: 16
<212> TYPE: PRT
<213> ORGANISM: Mus musculus

<400> SEQUENCE: 100

Val Ile Trp Pro Asp Gly Asn Thr Asp Tyr Asn Ser Thr Leu Lys Ser
 1               5                  10                  15

<210> SEQ ID NO 101
<211> LENGTH: 13
<212> TYPE: PRT
<213> ORGANISM: Mus musculus

<400> SEQUENCE: 101

Asp Ser Tyr Gly Asn Phe Lys Arg Gly Trp Phe Asp Phe
 1               5                  10

<210> SEQ ID NO 102
<211> LENGTH: 11
<212> TYPE: PRT
<213> ORGANISM: Mus musculus

<400> SEQUENCE: 102

Lys Ala Ser Gln Asn Val Gly Ser Asp Val Ala
 1               5                  10

<210> SEQ ID NO 103
<211> LENGTH: 7
<212> TYPE: PRT
<213> ORGANISM: Mus musculus

<400> SEQUENCE: 103

Ser Thr Ser Tyr Arg Tyr Ser
 1               5

<210> SEQ ID NO 104
<211> LENGTH: 9
<212> TYPE: PRT
<213> ORGANISM: Mus musculus

<400> SEQUENCE: 104

Gln Gln Tyr Asn Ser Tyr Pro Leu Thr
 1               5

<210> SEQ ID NO 105
<211> LENGTH: 25
<212> TYPE: PRT
```

<213> ORGANISM: Mus musculus

<400> SEQUENCE: 105

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 106
<211> LENGTH: 14
<212> TYPE: PRT
<213> ORGANISM: Mus musculus

<400> SEQUENCE: 106

Trp Val Lys Gln Lys Pro Gly Gln Val Leu Glu Trp Ile Gly
1               5                   10

<210> SEQ ID NO 107
<211> LENGTH: 32
<212> TYPE: PRT
<213> ORGANISM: Mus musculus

<400> SEQUENCE: 107

Lys Ala Thr Leu Thr Ser Asp Lys Tyr Ser Ser Thr Ala Tyr Met Glu
1               5                   10                  15

Leu Ser Gly Leu Thr Ser Glu Asp Ser Ala Val Tyr Tyr Cys Ala Arg
            20                  25                  30

<210> SEQ ID NO 108
<211> LENGTH: 11
<212> TYPE: PRT
<213> ORGANISM: Mus musculus

<400> SEQUENCE: 108

Trp Gly Arg Gly Ala Thr Leu Thr Val Ser Ser
1               5                   10

<210> SEQ ID NO 109
<211> LENGTH: 82
<212> TYPE: PRT
<213> ORGANISM: Mus musculus

<400> SEQUENCE: 109

Glu Val Gln Leu Gln Gln Ser Gly Pro Glu Leu Val Lys Pro Gly Ala
1               5                   10                  15

Ser Val Lys Met Ser Cys Lys Ala Ser Trp Val Lys Gln Lys Pro Gly
            20                  25                  30

Gln Val Leu Glu Trp Ile Gly Lys Ala Thr Leu Thr Ser Asp Lys Tyr
        35                  40                  45

Ser Ser Thr Ala Tyr Met Glu Leu Ser Gly Leu Thr Ser Glu Asp Ser
    50                  55                  60

Ala Val Tyr Tyr Cys Ala Arg Trp Gly Arg Gly Ala Thr Leu Thr Val
65                  70                  75                  80

Ser Ser

<210> SEQ ID NO 110
<211> LENGTH: 23
<212> TYPE: PRT
<213> ORGANISM: Mus musculus

<400> SEQUENCE: 110

```
Asp Ile Val Leu Thr Gln Ser Pro Ala Ser Leu Ala Val Ser Leu Gly
1               5                   10                  15

Gln Arg Ala Thr Ile Ser Cys
                20
```

<210> SEQ ID NO 111
<211> LENGTH: 15
<212> TYPE: PRT
<213> ORGANISM: Mus musculus

<400> SEQUENCE: 111

```
Trp Tyr Gln Gln Lys Pro Gly Gln Pro Asn Leu Leu Ile Phe
1               5                   10                  15
```

<210> SEQ ID NO 112
<211> LENGTH: 32
<212> TYPE: PRT
<213> ORGANISM: Mus musculus

<400> SEQUENCE: 112

```
Gly Ile Pro Ala Arg Phe Ser Gly Ser Gly Ser Gly Thr Asp Phe Thr
1               5                   10                  15

Leu Thr Ile Tyr Pro Val Glu Ala Asp Val Ala Thr Tyr Tyr Cys
                20                  25                  30
```

<210> SEQ ID NO 113
<211> LENGTH: 10
<212> TYPE: PRT
<213> ORGANISM: Mus musculus

<400> SEQUENCE: 113

```
Phe Gly Gly Gly Thr Lys Leu Glu Ile Lys
1               5                   10
```

<210> SEQ ID NO 114
<211> LENGTH: 80
<212> TYPE: PRT
<213> ORGANISM: Mus musculus

<400> SEQUENCE: 114

```
Asp Ile Val Leu Thr Gln Ser Pro Ala Ser Leu Ala Val Ser Leu Gly
1               5                   10                  15

Gln Arg Ala Thr Ile Ser Cys Trp Tyr Gln Gln Lys Pro Gly Gln Pro
                20                  25                  30

Pro Asn Leu Leu Ile Phe Gly Ile Pro Ala Arg Phe Ser Gly Ser Gly
            35                  40                  45

Ser Gly Thr Asp Phe Thr Leu Thr Ile Tyr Pro Val Glu Ala Asp Asp
        50                  55                  60

Val Ala Thr Tyr Tyr Cys Phe Gly Gly Gly Thr Lys Leu Glu Ile Lys
65                  70                  75                  80
```

<210> SEQ ID NO 115
<211> LENGTH: 25
<212> TYPE: PRT
<213> ORGANISM: Mus musculus

<400> SEQUENCE: 115

```
Gln Val Gln Leu Lys Glu Ser Gly Pro Gly Leu Val Ala Ser Ser Gln
1               5                   10                  15

Ser Leu Ser Ile Thr Cys Thr Val Ser
                20                  25
```

```
<210> SEQ ID NO 116
<211> LENGTH: 14
<212> TYPE: PRT
<213> ORGANISM: Mus musculus

<400> SEQUENCE: 116

Trp Val Arg Gln Pro Pro Gly Lys Gly Leu Glu Trp Leu Gly
 1               5                  10

<210> SEQ ID NO 117
<211> LENGTH: 32
<212> TYPE: PRT
<213> ORGANISM: Mus musculus

<400> SEQUENCE: 117

Arg Leu Asn Ile Phe Lys Asp Asn Ser Lys Asn Gln Val Phe Leu Lys
 1               5                  10                  15

Met Ser Ser Phe Gln Thr Asp Asp Thr Ala Arg Tyr Phe Cys Ala Arg
            20                  25                  30

<210> SEQ ID NO 118
<211> LENGTH: 11
<212> TYPE: PRT
<213> ORGANISM: Mus musculus

<400> SEQUENCE: 118

Trp Gly Gln Gly Thr Thr Leu Thr Val Ser Ser
 1               5                  10

<210> SEQ ID NO 119
<211> LENGTH: 82
<212> TYPE: PRT
<213> ORGANISM: Mus musculus

<400> SEQUENCE: 119

Gln Val Gln Leu Lys Glu Ser Gly Pro Gly Leu Val Ala Ser Ser Gln
 1               5                  10                  15

Ser Leu Ser Ile Thr Cys Thr Val Ser Trp Val Arg Gln Pro Pro Gly
            20                  25                  30

Lys Gly Leu Glu Trp Leu Gly Arg Leu Asn Ile Phe Lys Asp Asn Ser
        35                  40                  45

Lys Asn Gln Val Phe Leu Lys Met Ser Ser Phe Gln Thr Asp Asp Thr
    50                  55                  60

Ala Arg Tyr Phe Cys Ala Arg Trp Gly Gln Gly Thr Thr Leu Thr Val
65                  70                  75                  80

Ser Ser

<210> SEQ ID NO 120
<211> LENGTH: 23
<212> TYPE: PRT
<213> ORGANISM: Mus musculus

<400> SEQUENCE: 120

Asn Ile Val Met Thr Gln Ser Gln Lys Phe Met Ser Thr Ser Pro Gly
 1               5                  10                  15

Asp Arg Val Arg Val Thr Cys
            20

<210> SEQ ID NO 121
<211> LENGTH: 15
<212> TYPE: PRT
```

<213> ORGANISM: Mus musculus

<400> SEQUENCE: 121

Trp Tyr Gln Ala Lys Pro Gly Gln Ser Pro Arg Ile Leu Ile Tyr
1               5                   10                  15

<210> SEQ ID NO 122
<211> LENGTH: 32
<212> TYPE: PRT
<213> ORGANISM: Mus musculus

<400> SEQUENCE: 122

Gly Val Pro Asp Arg Phe Thr Ala Tyr Gly Ser Gly Thr Asp Phe Thr
1               5                   10                  15

Leu Thr Ile Thr Asn Val Gln Ser Glu Asp Leu Thr Glu Tyr Phe Cys
            20                  25                  30

<210> SEQ ID NO 123
<211> LENGTH: 10
<212> TYPE: PRT
<213> ORGANISM: Mus musculus

<400> SEQUENCE: 123

Phe Gly Ala Gly Thr Lys Leu Glu Leu Lys
1               5                   10

<210> SEQ ID NO 124
<211> LENGTH: 80
<212> TYPE: PRT
<213> ORGANISM: Mus musculus

<400> SEQUENCE: 124

Asn Ile Val Met Thr Gln Ser Gln Lys Phe Met Ser Thr Ser Pro Gly
1               5                   10                  15

Asp Arg Val Arg Val Thr Cys Trp Tyr Gln Ala Lys Pro Gly Gln Ser
            20                  25                  30

Pro Arg Ile Leu Ile Tyr Gly Val Pro Asp Arg Phe Thr Ala Tyr Gly
        35                  40                  45

Ser Gly Thr Asp Phe Thr Leu Thr Ile Thr Asn Val Gln Ser Glu Asp
    50                  55                  60

Leu Thr Glu Tyr Phe Cys Phe Gly Ala Gly Thr Lys Leu Glu Leu Lys
65                  70                  75                  80

<210> SEQ ID NO 125
<211> LENGTH: 348
<212> TYPE: DNA
<213> ORGANISM: Mus musculus

<400> SEQUENCE: 125
gaagtgaagc ttgaggagtc tggaggaggc ttggtgcaac ctggaggatc catgaaactc      60
tcctgtgttg cctctggatt cactttcagt aattactgga tgaactgggt ccgccagtct     120
ccagagaagg ggcttgagtg ggttgctgaa attagatcgc aatctaataa ttttgcaaca     180
cattatgcgg agtctgtgaa agggagggtc atcatctcaa gagatgattc caagagtagt     240
gtctacctgc aaatgaacaa cttgagagct gaagacactg gcatttatta ctgtaccagg     300
cgatggaata atttctgggg ccaaggcacc actctcacag tctcctca                 348

<210> SEQ ID NO 126
<211> LENGTH: 348
<212> TYPE: DNA

```
-continued

<213> ORGANISM: Mus musculus

<400> SEQUENCE: 126
tgaggagact gtgagagtgg tgccttggcc ccagaaatta ttccatcgcc tggtacagta      60
ataaatgcca gtgtcttcag ctctcaagtt gttcatttgc aggtagacac tactcttgga    120
atcatctctt gagatgatga ccctcccttt cacagactcc gcataatgtg ttgcaaaatt    180
attagattgc gatctaattt cagcaaccca ctcaagcccc ttctctggag actggcggac    240
ccagttcatc cagtaattac tgaaagtgaa tccagaggca acacaggaga gtttcatgga    300
tcctccaggt tgcaccaagc ctcctccaga ctcctcaagc ttcacttc                 348

<210> SEQ ID NO 127
<211> LENGTH: 321
<212> TYPE: DNA
<213> ORGANISM: Mus musculus

<400> SEQUENCE: 127
aacattgtaa tgacccaatt tcccaaatcc atgtccattt cagtaggaga gagggtcacc     60
ttgacctgca aggccagtga gaatgtgggt acttatgtgt cctggtatca acagaaacca    120
gaacagtctc ctaagatgtt gatatacggg gcatccaacc ggttcactgg ggtccccgat    180
cgcttcacag gcagtggatc tgcaacagat ttcattctga ccatcagcag tgtgcagact    240
gaagaccttg tagattatta ctgtggacag agttacacct ttccgtacac gttcggaggg    300
gggaccaagc tggaaatgaa g                                              321

<210> SEQ ID NO 128
<211> LENGTH: 321
<212> TYPE: DNA
<213> ORGANISM: Mus musculus

<400> SEQUENCE: 128
cttcatttcc agcttggtcc cccctccgaa cgtgtacgga aaggtgtaac tctgtccaca     60
gtaataatct acaaggtctt cagtctgcac actgctgatg gtcagaatga aatctgttgc    120
agatccactg cctgtgaagc gatcggggac cccagtgaac cggttggatg ccccgtatat    180
caacatctta ggagactgtt ctggtttctg ttgataccag gacacataag tacccacatt    240
ctcactggcc ttgcaggtca aggtgaccct ctctcctact gaaatggaca tggatttggg    300
aaattgggtc attacaatgt t                                              321
```

We claim:

1. An anti-PSMA antibody, or antigen binding fragment thereof, comprising:
   a light chain variable region comprising the amino acid sequence shown as SEQ ID NO:22, or the light chain variable region amino acid sequence of the antibody produced by the NS0 cell line having ATCC Accession Number PTA-3709; and
   a heavy chain variable region comprising the amino acid sequence shown as SEQ ID NO:21, or the heavy chain variable region amino acid sequence of the antibody produced by the NS0 cell line having ATCC Accession Number PTA-3709, wherein the antibody, or antigen-binding fragment thereof, is coupled to a maytansinoid.

2. The antibody, or antigen binding fragment thereof, of claim 1, wherein the antibody, or antigen binding fragment thereof, comprises two heavy chains and two light chains.

3. The antibody, or antigen binding fragment thereof, of claim 1, wherein the antibody further comprises a heavy chain constant region of human isotype IgG1.

4. The antibody, or antigen binding fragment thereof, of claim 1, wherein the antibody or antigen binding fragment is coupled to the maytansinoid by a linker.

5. The antibody, or antigen binding fragment thereof, of claim 4, wherein the linker is N-succinimidyl 4-(2-pyridyldithio) pentanoate (SPP).

6. The antibody, or antigen binding fragment thereof, of claim 1, wherein the maytansinoid is maytansinol or a maytansinol analogue.

7. The antibody, or antigen binding fragment thereof, of claim 1, wherein the maytansinoid is DM1.

8. The antibody, or antigen binding fragment thereof, of claim 5, wherein the maytansinoid is maytansinol or a maytansinol analogue.

9. The antibody, or antigen binding fragment thereof, of claim 5, wherein the maytansinoid is DM1.

10. The antibody, or antigen binding fragment thereof, of claim 1, wherein the antigen binding fragment is selected from the group consisting of Fab, F(ab')$_2$, Fv, and single chain Fv fragments.

11. The antibody, or antigen binding fragment thereof, of claim 1, comprising:
a light chain variable region comprising the amino acid sequence shown as SEQ ID NO:22, and
a heavy chain variable region comprising the amino acid sequence shown as SEQ ID NO:21.

12. The antibody, or antigen binding fragment thereof, of claim 1, comprising:
the light chain variable region amino acid sequence of the antibody produced by the NS0 cell line having ATCC Accession Number PTA-3709; and
the heavy chain variable region amino acid sequence of the antibody produced by the NS0 cell line having ATCC Accession Number PTA-3709.

13. The antibody, or antigen binding fragment thereof, of claim 1, comprising:
a light chain variable region comprising the amino acid sequence shown as SEQ ID NO:22; and
the heavy chain variable region amino acid sequence of the antibody produced by the NS0 cell line having ATCC Accession Number PTA-3709.

14. The antibody, or antigen binding fragment thereof, of claim 1, comprising:
the light chain variable region amino acid sequence of the antibody produced by the NS0 cell line having ATCC Accession Number PTA-3709; and
a heavy chain variable region comprising the amino acid sequence shown as SEQ ID NO:21.

15. An anti-PSMA antibody, or antigen binding fragment thereof, comprising:
a light chain variable region comprising the amino acid sequence shown as SEQ ID NO:50, or the light chain variable region amino acid sequence of the antibody produced by the NS0 cell line having ATCC Accession Number PTA-4174; and
a heavy chain variable region comprising the amino acid sequence shown as SEQ ID NO:49, or the heavy chain variable region amino acid sequence of the antibody produced by the NS0 cell line having ATCC Accession Number PTA-4174.

16. The antibody, or antigen binding fragment thereof, of claim 15, wherein the antibody, or antigen binding fragment thereof, comprises two heavy chains and two light chains.

17. The antibody, or antigen binding fragment thereof, of claim 15, wherein the antibody further comprises a heavy chain constant region of human isotype IgG1.

18. The antibody, or antigen binding fragment thereof, of claim 15, wherein the antibody, or antigen binding fragment thereof, is coupled to a cytotoxic moiety.

19. The antibody, or antigen binding fragment thereof, of claim 18, wherein the antibody, or antigen binding fragment thereof, is coupled to the cytotoxic moiety by a chelating agent or a linker.

20. The antibody, or antigen binding fragment thereof, of claim 19, wherein the chelating agent is 1,4,7,10-tetraaza-cyclododecane-N,N',N'',N'''-tetraacetic acid (DOTA).

21. The antibody, or antigen binding fragment thereof, of claim 19, wherein the linker is N-succinimidyl 4-(2-pyridyldithio) pentanoate (SPP).

22. The antibody, or antigen binding fragment thereof, of claim 18, wherein the cytotoxic moiety is a cytotoxin, a therapeutic agent or a radioactive isotope.

23. The antibody, or antigen binding fragment thereof, of claim 18, wherein the cytotoxic moiety is selected from the group consisting of: a compound that emits radiation, a molecule of plant, fungal or bacterial origin, and a biological protein.

24. The antibody, or antigen binding fragment thereof, of claim 23, wherein the cytotoxic moiety is a molecule of bacterial origin.

25. The antibody, or antigen binding fragment thereof, of claim 22, wherein the radioactive isotope is an α-emitter, a β-emitter, a γ-emitter, or a β- and γ-emitter.

26. The antibody, or antigen binding fragment thereof, of claim 22, wherein the radioactive isotope is selected from the group consisting of: iodine ($^{131}$I), iodine ($^{125}$I), yttrium ($^{90}$Y), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), and rhodium ($^{188}$Rh).

27. The antibody, or antigen binding fragment thereof, of claim 18, wherein the cytotoxic moiety is a radioactive isotope selected from the group consisting of yttrium ($^{90}$Y) or lutetium ($^{177}$Lu).

28. The antibody, or antigen binding fragment thereof, of claim 18, wherein the cytotoxic moiety is a maytansinoid.

29. The antibody, or antigen binding fragment thereof, of claim 28, wherein the maytansinoid is maytansinol or a maytansinol analogue.

30. The antibody, or antigen binding fragment thereof, of claim 28, wherein the maytansinoid is DM1.

31. The antibody, or antigen binding fragment thereof, of claim 20, wherein cytotoxic moiety is a radioactive isotope selected from the group consisting of: yttrium ($^{90}$Y) and lutetium ($^{177}$Lu).

32. The antibody, or antigen binding fragment thereof, of claim 21, wherein the cytotoxic moiety is a maytansinoid.

33. The antibody, or antigen binding fragment thereof, of claim 32, wherein the maytansinoid is maytansinol or a maytansinol analogue.

34. The antibody, or antigen binding fragment thereof, of claim 32, wherein the maytansinoid is DM1.

35. The antibody, or antigen binding fragment thereof, of claim 18, wherein the cytotoxic moiety is a taxane.

36. The antibody, or antigen binding fragment thereof, of claim 18, wherein the cytotoxic moiety is a calicheamicin.

37. The antibody, or antigen binding fragment thereof, of claim 15, wherein the antibody or antigen binding fragment thereof is coupled to a label.

38. The antibody, or antigen binding fragment thereof, of claim 37, wherein the label is selected from the group consisting of: biologically active enzymes, prosthetic groups, luminescent materials, bioluminescent materials, fluorescent materials, paramagnetic materials and radioactive ions.

39. The antibody, or antigen binding fragment thereof, of claim 37, wherein the label is a radioactive ion.

40. The antibody, or antigen binding fragment thereof, of claim 39, wherein the radioactive ion is selected from the group consisting of: indium ($^{111}$In), technetium ($^{99m}$Tc), phosporus ($^{32}$P), carbon ($^{14}$C), sulfur ($^{35}$S), tritium ($^{3}$H), chromium ($^{51}$Cr), chlorine ($^{36}$Cl), cobalt ($^{57}$Co), cobalt ($^{58}$Co), iron ($^{59}$Fe), selenium ($^{75}$Se), gallium ($^{67}$Ga), iodine ($^{131}$I), iodine ($^{125}$I), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), rhodium ($^{188}$Rh).

41. The antibody, or antigen binding fragment thereof, of claim 39, wherein the radioactive ion is selected from the group consisting of: indium ($^{111}$In), technetium ($^{99m}$Tc), phosporus ($^{32}$P), carbon ($^{14}$C), tritium ($^{3}$H), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), and rhodium ($^{188}$Rh).

42. The antibody, or antigen binding fragment thereof, of claim 39, wherein the radioactive ion is indium ($^{111}$In).

43. The antibody, or antigen binding fragment thereof, of claim 42, wherein the radioactive ion is coupled to the antibody or antigen binding fragment thereof by a chelating agent.

44. The antibody, or antigen binding fragment thereof, of claim 43, wherein the chelating agent is 1,4,7,10-tetraazacyclododecane-N,N',N'',N'''-tetraacetic acid (DOTA).

45. The antibody, or antigen binding fragment thereof, of claim 15, wherein the antigen binding fragment is selected from the group consisting of Fab, F(ab')$_2$, Fv, and single chain Fv fragments.

46. The antibody, or antigen binding fragment thereof, of claim 15, comprising:
a light chain variable region comprising the amino acid sequence shown as SEQ ID NO:50; and
a heavy chain variable region comprising the amino acid sequence shown as SEQ ID NO:49.

47. The antibody, or antigen binding fragment thereof, of claim 15, comprising:
the light chain variable region amino acid sequence of the antibody produced by the NS0 cell line having ATCC Accession Number PTA-4174; and
the heavy chain variable region amino acid sequence of the antibody produced by the NS0 cell line having ATCC Accession Number PTA-4174.

48. The antibody, or antigen binding fragment thereof, of claim 15, comprising:
a light chain variable region comprising the amino acid sequence shown as SEQ ID NO:50; and
the heavy chain variable region amino acid sequence of the antibody produced by the NS0 cell line having ATCC Accession Number PTA-4174.

49. The antibody, or antigen binding fragment thereof, of claim 15, comprising:
the light chain variable region amino acid sequence of the antibody produced by the NS0 cell line having ATCC Accession Number PTA-4174; and
a heavy chain variable region comprising the amino acid sequence shown as SEQ ID NO:49.

50. An anti-PSMA antibody, or antigen-binding fragment thereof, comprising:
a light chain variable region comprising the amino acid sequence shown as SEQ ID NO:22, or the light chain variable region amino acid sequence of the antibody produced by the NS0 cell line having ATCC Accession Number PTA-3709;
a heavy chain variable region comprising the amino acid sequence shown as SEQ ID NO:21, or the heavy chain variable region amino acid sequence of the antibody produced by the NS0 cell line having ATCC Accession Number PTA-3709; and
a heavy chain constant region of human isotype IgG1,
wherein the antibody or antigen binding fragment thereof is coupled to a maytansinoid by an N-succinimidyl 4-(2-pyridyldithio) pentanoate (SPP).

51. An anti-PSMA antibody, or antigen binding fragment thereof, comprising:
a light chain variable region comprising the amino acid sequence shown as SEQ ID NO:50, or the light chain variable region amino acid sequence of the antibody produced by the NS0 cell line having ATCC Accession Number PTA-4174;
a heavy chain variable region comprising the amino acid sequence shown as SEQ ID NO:49, or the heavy chain variable region amino acid sequence of the antibody produced by the NS0 cell line having ATCC Accession Number PTA-4174; and
a heavy chain constant region of human isotype IgG1,
wherein the antibody or antigen binding fragment thereof is coupled to a maytansinoid by an N-succinimidyl 4-(2-pyridyldithio) pentanoate (SPP).

52. The anti-PSMA antibody, or antigen binding fragment thereof, of claim 50, wherein the light chain variable region has the amino acid sequence shown in SEQ ID NO:22, and the heavy chain variable region has the amino acid sequence shown in SEQ ID NO:21.

53. The anti-PSMA antibody, or antigen binding fragment thereof, of claim 50, wherein the light chain variable region has the amino acid sequence of the antibody produced by the NS0 cell line having ATCC Accession Number PTA-3709, and the heavy chain variable region has the amino acid sequence of the antibody produced by the NS0 cell line having ATCC Accession Number PTA-3709.

54. The anti-PSMA antibody, or antigen binding fragment thereof, of any of claims 50, 52 or 53, wherein the maytansinoid is DM1.

55. The anti-PSMA antibody, or antigen binding fragment thereof, of claim 51, wherein the light chain variable region has the amino acid sequence shown in SEQ ID NO:50, and the heavy chain variable region has the amino acid sequence shown in SEQ ID NO:49.

56. The anti-PSMA antibody, or antigen binding fragment thereof, of claim 51, wherein the light chain variable region has the amino acid sequence of the antibody produced by the NS0 cell line having ATCC Accession Number PTA-4174, and the heavy chain variable region has the amino acid sequence of the antibody produced by the NS0 cell line having ATCC Accession Number PTA-4174.

57. The anti-PSMA antibody, or antigen binding fragment thereof, of any of claims 51, 55 or 56, wherein the maytansinoid is DM1.

58. A cell line having an ATCC Accession Number PTA-3709 that produces deJ591.

59. A cell line having an ATCC Accession Number PTA-4174 that produces deJ415.

60. An anti-PSMA antibody produced by the cell line of claim 59.

61. A pharmaceutical composition comprising an anti-PSMA antibody, or an antigen binding fragment thereof and a pharmaceutically acceptable carrier, wherein the antibody, or antigen binding fragment thereof, comprises:
a light chain variable region comprising the amino acid sequence shown as SEQ ID NO:22, or the light chain variable region amino acid sequence of the antibody produced by the NS0 cell line having ATCC Accession Number PTA-3709; and
a heavy chain variable region comprising the amino acid sequence shown as SEQ ID NO:21, or the heavy chain variable region amino acid sequence of the antibody produced by the NS0 cell line having ATCC Accession Number PTA-3709, and wherein the antibody or antigen-binding fragment thereof is coupled to a maytansinoid.

62. The pharmaceutical composition of claim 61, wherein the antibody, or antigen binding fragment thereof, comprises two heavy chains and two light chains.

63. The pharmaceutical composition of claim 61, wherein the antibody further comprises a heavy chain constant region of human isotype IgG1.

64. The pharmaceutical composition of claim 61, wherein the antibody, or antigen binding fragment thereof, is coupled to the maytansinoid by a linker.

65. The pharmaceutical composition of claim 64, wherein the linker is N-succinimidyl 4-(2-pyridyldithio) pentanoate (SPP).

66. The pharmaceutical composition of claim 61, wherein the maytansinoid is maytansinol or a maytansinol analogue.

67. The pharmaceutical composition of claim 61, wherein the maytansinoid is DM1.

68. The pharmaceutical composition of claim 65, wherein the maytansinoid is maytansinol or a maytansinol analogue.

69. The pharmaceutical composition of claim 65, wherein the maytansinoid is DM1.

70. The pharmaceutical composition of claim 61, wherein the antigen binding fragment is selected from the group consisting of Fab, F(ab')$_2$, Fv, and single chain Fv fragments.

71. The pharmaceutical composition of claim 61, wherein the antibody, or antigen binding fragment thereof, comprises:
    a light chain variable region comprising the amino acid sequence shown as SEQ ID NO:22, and
    a heavy chain variable region comprising the amino acid sequence shown as SEQ ID NO:21.

72. The pharmaceutical composition of claim 61, wherein the antibody, or antigen binding fragment thereof, comprises:
    the light chain variable region amino acid sequence of the antibody produced by the NS0 cell line having ATCC Accession Number PTA-3709; and
    the heavy chain variable region amino acid sequence of the antibody produced by the NS0 cell line having ATCC Accession Number PTA-3709.

73. The pharmaceutical composition of claim 61, wherein the antibody, or antigen binding fragment thereof, comprises:
    a light chain variable region comprising the amino acid sequence shown as SEQ ID NO:22; and
    the heavy chain variable region amino acid sequence of the antibody produced by the NS0 cell line having ATCC Accession Number PTA-3709.

74. The pharmaceutical composition of claim 61, wherein the antibody, or antigen binding fragment thereof, comprises:
    the light chain variable region amino acid sequence of the antibody produced by the NS0 cell line having ATCC Accession Number PTA-3709; and
    a heavy chain variable region comprising the amino acid sequence shown as SEQ ID NO:21.

75. A pharmaceutical composition comprising an anti-PSMA antibody, or an antigen binding fragment thereof and a pharmaceutically acceptable carrier, wherein the antibody or antigen binding fragment thereof comprises:
    a light chain variable region comprising the amino acid sequence shown as SEQ ID NO:50, or the light chain variable region amino acid sequence of the antibody produced by the NS0 cell line having ATCC Accession Number PTA-4174; and
    a heavy chain variable region comprising the amino acid sequence shown as SEQ ID NO:49, or the heavy chain variable region amino acid sequence of the antibody produced by the NS0 cell line having ATCC Accession Number PTA-4174.

76. The pharmaceutical composition of claim 75, wherein the antibody, or antigen binding fragment thereof, comprises two heavy chains and two light chains.

77. The pharmaceutical composition of claim 75, wherein the antibody further comprises a heavy chain constant region of human isotype IgG1.

78. The pharmaceutical composition of claim 75, wherein the antibody, or antigen binding fragment thereof, is coupled to a cytotoxic moiety.

79. The pharmaceutical composition of claim 78, wherein the antibody or antigen binding fragment thereof, is coupled to the cytotoxic moiety by a chelating agent or a linker.

80. The pharmaceutical composition of claim 79, wherein the chelating agent is 1,4,7,10-tetraazacyclododecane-N,N',N'',N'''-tetraacetic acid (DOTA).

81. The pharmaceutical composition of claim 79, wherein the linker is N-succinimidyl 4-(2-pyridyldithio) pentanoate (SPP).

82. The pharmaceutical composition of claim 78, wherein the cytotoxic moiety is a cytotoxin, a therapeutic agent or a radioactive isotope.

83. The pharmaceutical composition of claim 78, wherein the cytotoxic moiety is selected from the group consisting of: a compound that emits radiation, a molecule of plant, fungal or bacterial origin, and a biological protein.

84. The pharmaceutical composition of claim 83, wherein the cytotoxic moiety is a molecule of bacterial origin.

85. The pharmaceutical composition of claim 82, wherein the radioactive isotope is an α-emitter, a β-emitter, a γ-emitter, or a β- and γ-emitter.

86. The pharmaceutical composition of claim 82, wherein the radioactive isotope is selected from the group consisting of: iodine ($^{131}$I), iodine ($^{125}$I), yttrium ($^{90}$Y), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), and rhodium ($^{188}$Rh).

87. The pharmaceutical composition of claim 78, wherein the cytotoxic moiety is a radioactive isotope selected from the group consisting of yttrium ($^{90}$Y) or lutetium ($^{177}$Lu).

88. The pharmaceutical composition of claim 78, wherein the cytotoxic moiety is a maytansinoid.

89. The pharmaceutical composition of claim 88, wherein the maytansinoid is maytansinol or a maytansinol analogue.

90. The pharmaceutical composition of claim 88, wherein the maytansinoid is DM1.

91. The pharmaceutical composition of claim 80, wherein cytotoxic moiety is a radioactive isotope selected from the group consisting of: yttrium ($^{90}$Y) and lutetium ($^{177}$Lu).

92. The pharmaceutical composition of claim 81, wherein the cytotoxic moiety is a maytansinoid.

93. The pharmaceutical composition of claim 92, wherein the maytansinoid is maytansinol or a maytansinol analogue.

94. The pharmaceutical composition of claim 92, wherein the maytansinoid is DM1.

95. The pharmaceutical composition of claim 78, wherein the cytotoxic moiety is a taxane.

96. The pharmaceutical composition of claim 78, wherein the cytotoxic moiety is a calicheamicin.

97. The pharmaceutical composition of claim 75, wherein the antibody, or antigen binding fragment thereof, is coupled to a label.

98. The pharmaceutical composition of claim 97, wherein the label is selected from the group consisting of: biologically active enzymes, prosthetic groups, luminescent materials, bioluminescent materials, fluorescent materials, paramagnetic materials and radioactive ions.

99. The pharmaceutical composition of claim 97, wherein the label is a radioactive ion.

100. The pharmaceutical composition of claim 99, wherein the radioactive ion is selected from the group consisting of: indium ($^{111}$In), technetium ($^{99m}$Tc), phosporus ($^{32}$P), carbon ($^{14}$C), sulfur ($^{35}$S), tritium ($^{3}$H), chromium ($^{51}$Cr), chlorine ($^{36}$Cl), cobalt ($^{57}$Co), cobalt ($^{58}$Co), iron ($^{59}$Fe), selenium ($^{75}$Se), gallium ($^{67}$Ga), iodine ($^{131}$I), iodine ($^{125}$I), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), and rhodium ($^{188}$Rh).

101. The pharmaceutical composition of claim 99, wherein the radioactive ion is selected from the group consisting of: indium ($^{111}$In), technetium ($^{99m}$Tc), phosporus ($^{32}$P), carbon ($^{14}$C), tritium ($^{3}$H), lutetium ($^{177}$Lu), actinium ($^{225}$Ac), praseodymium, bismuth ($^{212}$Bi), bismuth ($^{213}$Bi), astatine ($^{211}$At), rhenium ($^{186}$Re), and rhodium ($^{188}$Rh).

102. The pharmaceutical composition of claim 99, wherein the radioactive ion is indium ($^{111}$In).

103. The pharmaceutical composition of claim 102, wherein the radioactive ion is coupled to the antibody, or antigen binding fragment thereof, by a chelating agent.

104. The pharmaceutical composition of claim 103, wherein the chelating agent is 1,4,7,10-tetraazacyclododecane-N,N',N",N'"-tetraacetic acid (DOTA).

105. The pharmaceutical composition of claim 75, wherein the antigen binding fragment is selected from the group consisting of Fab, F(ab')$_2$, Fv, and single chain Fv fragments.

106. The pharmaceutical composition of claim 75, wherein the antibody, or antigen binding fragment thereof, comprises:
a light chain variable region comprising the amino acid sequence shown as SEQ ID NO:50; and
a heavy chain variable region comprising the amino acid sequence shown as SEQ ID NO:49.

107. The pharmaceutical composition of claim 75, wherein the antibody, or antigen binding fragment thereof, comprises:
the light chain variable region amino acid sequence of the antibody produced by the NS0 cell line having ATCC Accession Number PTA-4174; and
the heavy chain variable region amino acid sequence of the antibody produced by the NS0 cell line having ATCC Accession Number PTA-4174.

108. The pharmaceutical composition of claim 75, wherein the antibody, or antigen binding fragment thereof, comprises:
a light chain variable region comprising the amino acid sequence shown as SEQ ID NO:50; and
the heavy chain variable region amino acid sequence of the antibody produced by the NS0 cell line having ATCC Accession Number PTA-4174.

109. The pharmaceutical composition of claim 75, wherein the antibody, or antigen binding fragment thereof, comprises:
the light chain variable region amino acid sequence of the antibody produced by the NS0 cell line having ATCC Accession Number PTA-4174; and
a heavy chain variable region comprising the amino acid sequence shown as SEQ ID NO:49.

110. A pharmaceutical composition comprising an anti-PSMA antibody, or an antigen-binding fragment thereof and a pharmaceutically acceptable carrier, wherein the antibody, or antigen binding fragment thereof, comprises:
a light chain variable region comprising the amino acid sequence shown as SEQ ID NO:22, or the light chain variable region amino acid sequence of the antibody produced by the NS0 cell line having ATCC Accession Number PTA-3709;
a heavy chain variable region comprising the amino acid sequence shown as SEQ ID NO:21, or the heavy chain variable region amino acid sequence of the antibody produced by the NS0 cell line having ATCC Accession Number PTA-3709; and
a heavy chain constant region of human isotype IgG1,
wherein the antibody, or antigen binding fragment thereof, is coupled to a maytansinoid by an N-succinimidyl 4-(2-pyridyldithio) pentanoate (SPP).

111. A pharmaceutical composition comprising an anti-PSMA antibody, or an antigen binding fragment thereof and a pharmaceutically acceptable carrier, wherein the antibody, or antigen binding fragment thereof, comprises:
a light chain variable region comprising the amino acid sequence shown as SEQ ID NO:50, or the light chain variable region amino acid sequence of the antibody produced by the NS0 cell line having ATCC Accession Number PTA-4174;
a heavy chain variable region comprising the amino acid sequence shown as SEQ ID NO:49, or the heavy chain variable region amino acid sequence of the antibody produced by the NS0 cell line having ATCC Accession Number PTA-4174; and
a heavy chain constant region of human isotype IgG1,
wherein the antibody, or antigen binding fragment thereof, is coupled to a maytansinoid by an N-succinimidyl 4-(2-pyridyldithio) pentanoate (SPP).

112. The pharmaceutical composition of claim 110, wherein the antibody, or antigen binding fragment thereof, comprises the light chain variable region having the amino acid sequence shown in SEQ ID NO:22, and the heavy chain variable region having the amino acid sequence shown in SEQ ID NO:21.

113. The pharmaceutical composition of claim 110, wherein the anti-PSMA antibody, or antigen binding fragment thereof, comprises the light chain variable region having the amino acid sequence of the antibody produced by the NS0 cell line of ATCC Accession Number PTA-3709, and the heavy chain variable region having the amino acid sequence of the antibody produced by the NS0 cell line of ATCC Accession Number PTA-3709.

114. The pharmaceutical composition of any of claims 110, 112 or 113, wherein the maytansinoid is DM1.

115. The pharmaceutical composition of claim 111, wherein the antibody, or antigen binding fragment thereof, comprises the light chain variable region having the amino acid sequence shown in SEQ ID NO:50, and the heavy chain variable region having the amino acid sequence shown in SEQ ID NO:49.

116. The pharmaceutical composition of claim 111, wherein the antibody, or antigen binding fragment thereof, comprises the light chain variable region having the amino acid, sequence of the antibody produced by the NS0 cell line of ATCC Accession Number PTA-4174, and the heavy chain variable region having the amino acid sequence of the antibody produced by the NS0 cell line of ATCC Accession Number PTA-4174.

117. The pharmaceutical composition of any of claims 111, 115 or 116, wherein the maytansinoid is DM1.

118. A pharmaceutical composition comprising an anti-PSMA antibody produced by the cell line of claim 59, and a pharmaceutically acceptable carrier.

119. The antibody, or antigen binding fragment thereof, of claim 23, wherein the cytotoxic moiety is a molecule of plant origin.

120. The antibody, or antigen binding fragment thereof, of claim 23, wherein the cytotoxic moiety is a molecule of fungal origin.

121. The pharmaceutical composition of claim 83, wherein the cytotoxic moiety is a molecule of plant origin.

122. The pharmaceutical composition of claim 83, wherein the cytotoxic moiety is a molecule of plant origin.

123. The antibody, or antigen binding fragment thereof, of claim 50, wherein the antibody, or antigen binding fragment thereof, comprises two heavy chains and two light chains.

124. The antibody, or antigen binding fragment thereof, of claim 51, wherein the antibody, or antigen binding fragment thereof, comprises two heavy chains and two light chains.

125. The pharmaceutical composition of claim 110, wherein the antibody, or antigen binding fragment thereof, comprises two heavy chains and two light chains.

126. The pharmaceutical composition of claim 111, wherein the antibody, or antigen binding fragment thereof, comprises two heavy chains and two light chains.

127. The antibody, or antigen binding fragment thereof, of claim 50, comprising:
a light chain variable region comprising the amino acid sequence shown as SEQ ID NO:22; and
the heavy chain variable region amino acid sequence of the antibody produced by the NS0 cell line having ATCC Accession Number PTA-3709.

128. The antibody, or antigen binding fragment thereof, of claim 50, comprising:
the light chain variable region amino acid sequence of the antibody produced by the NS0 cell line having ATCC Accession Number PTA-3709; and
a heavy chain variable region comprising the amino acid sequence shown as SEQ ID NO:21.

129. The antibody, or antigen binding fragment thereof, of claim 51, comprising:
a light chain variable region comprising the amino acid sequence shown as SEQ ID NO:50; and
the heavy chain variable region amino acid sequence of the antibody produced by the NS0 cell line having ATCC Accession Number PTA-4174.

130. The antibody, or antigen binding fragment thereof, of claim 51, comprising:
the light chain variable region amino acid sequence of the antibody produced by the NS0 cell line having ATCC Accession Number PTA-4174; and
a heavy chain variable region comprising the amino acid sequence shown as SEQ ID NO:49.

131. The pharmaceutical composition of claim 110, wherein the antibody, or antigen binding fragment thereof, comprises:
a light chain variable region comprising the amino acid sequence shown as SEQ ID NO:22; and
the heavy chain variable region amino acid sequence of the antibody produced by the NS0 cell line having ATCC Accession Number PTA-3709.

132. The pharmaceutical composition of claim 110, wherein the antibody, or antigen binding fragment thereof, comprises:
the light chain variable region amino acid sequence of the antibody produced by the NS0 cell line having ATCC Accession Number PTA-3709; and
a heavy chain variable region comprising the amino acid sequence shown as SEQ ID NO:21.

133. The pharmaceutical composition of claim 111, wherein the antibody, or antigen binding fragment thereof, comprises:
a light chain variable region comprising the amino acid sequence shown as SEQ ID NO:50; and
the heavy chain variable region amino acid sequence of the antibody produced by the NS0 cell line having ATCC Accession Number PTA-4174.

134. The pharmaceutical composition of claim 111, wherein the antibody, or antigen binding, fragment thereof, comprises:
the light chain variable region amino acid sequence of the antibody produced by the NS0 cell line having ATCC Accession Number PTA-4174; and
a heavy chain variable region comprising the amino acid sequence shown as SEQ ID NO:49.

135. The antibody, or antigen binding fragment thereof, of claim 2, 10, 11, 12, 13 or 14, wherein the antibody, or antigen binding fragment thereof, is coupled to the maytansinoid by a linker.

136. The antibody, or antigen binding fragment thereof, of claim 135, wherein the linker is N-succinimidyl 4-(2-pyridyldithio) pentanoate (SPP).

137. The antibody, or antigen binding fragment thereof, of claim 136, wherein the maytansinoid is maytansinol or a maytansinol analogue.

138. The antibody, or antigen binding fragment thereof, of claim 136, wherein the maytansinoid is DM1.

139. The pharmaceutical composition of claim 62, 70, 71, 72, 73, or 74 wherein the antibody, or antigen binding fragment thereof, is coupled to the maytansinoid by a linker.

140. The pharmaceutical composition of claim 139, wherein the linker is N-succinimidyl 4-(2-pyridyldithio) pentanoate (SPP).

141. The pharmaceutical composition of claim 139, wherein the maytansinoid is maytansinol or a maytansinol analogue.

142. The pharmaceutical composition of claim 139, wherein the maytansinoid is DM1.

* * * * *